US011090339B2

(12) United States Patent
Herzberg et al.

(10) Patent No.: US 11,090,339 B2
(45) Date of Patent: Aug. 17, 2021

(54) TREATMENT OF PAIN USING PLACENTAL STEM CELLS

(71) Applicant: Celularity Inc., Florham Park, NJ (US)

(72) Inventors: Uri Herzberg, Bridgewater, NJ (US);
Jodi P. Gurney, Park Ridge, IL (US);
Robert J. Hariri, Bernardsville, NJ (US)

(73) Assignee: Celularity Inc., Florham Park, NJ (US)

( * ) Notice: Subject to any disclaimer, the term of this patent is extended or adjusted under 35 U.S.C. 154(b) by 0 days.

(21) Appl. No.: 16/532,437

(22) Filed: Aug. 5, 2019

(65) Prior Publication Data
US 2020/0023015 A1    Jan. 23, 2020

Related U.S. Application Data

(63) Continuation of application No. 14/951,655, filed on Nov. 25, 2015, now abandoned, which is a continuation of application No. 14/692,307, filed on Apr. 21, 2015, now abandoned, which is a continuation of application No. 13/485,161, filed on May 31, 2012, now Pat. No. 9,040,035.

(60) Provisional application No. 61/594,985, filed on Feb. 3, 2012, provisional application No. 61/548,663, filed on Oct. 18, 2011, provisional application No. 61/492,314, filed on Jun. 1, 2011.

(51) Int. Cl.
*A61K 35/50* (2015.01)
*C12N 5/073* (2010.01)
*C12N 5/0775* (2010.01)

(52) U.S. Cl.
CPC ............ *A61K 35/50* (2013.01); *C12N 5/0605* (2013.01); *C12N 5/0668* (2013.01)

(58) Field of Classification Search
CPC .................................................. C12N 5/0605
See application file for complete search history.

(56) References Cited

U.S. PATENT DOCUMENTS

| | | |
|---|---|---|
| 4,458,678 A | 7/1984 | Yannas |
| 4,485,097 A | 11/1984 | Bell |
| 4,520,821 A | 6/1985 | Schmidt |
| 4,798,824 A | 1/1989 | Belzer |
| 4,829,000 A | 5/1989 | Kleinman |
| 5,004,681 A | 4/1991 | Boyse |
| 5,192,312 A | 3/1993 | Orton |
| 5,192,553 A | 3/1993 | Boyse |
| 5,197,985 A | 3/1993 | Caplan |
| 5,226,914 A | 7/1993 | Caplan |
| 5,272,071 A | 12/1993 | Chappel |
| 5,284,766 A | 2/1994 | Okano |
| 5,318,025 A | 6/1994 | Dumoulin |
| 5,356,373 A | 10/1994 | Dracker |
| 5,372,581 A | 12/1994 | Anderson |
| 5,385,901 A | 1/1995 | Kaplan |
| 5,415,665 A | 5/1995 | Hessel |
| 5,426,098 A | 6/1995 | Carlino |
| 5,437,994 A | 8/1995 | Emerson |
| 5,443,950 A | 8/1995 | Naughton |
| 5,460,964 A | 10/1995 | McGlave |
| 5,464,764 A | 11/1995 | Capecchi |
| 5,486,359 A | 1/1996 | Caplan |
| 5,487,992 A | 1/1996 | Capecchi |
| 5,516,532 A | 5/1996 | Atala |
| 5,552,267 A | 9/1996 | Stern |
| 5,580,724 A | 12/1996 | Alter |
| 5,580,777 A | 12/1996 | Bernard |
| 5,591,625 A | 1/1997 | Gerson |
| 5,605,822 A | 2/1997 | Emerson |
| 5,613,982 A | 3/1997 | Goldstein |
| 5,627,059 A | 5/1997 | Capecchi |
| 5,635,386 A | 6/1997 | Palsson |
| 5,635,387 A | 6/1997 | Fei |
| 5,643,741 A | 7/1997 | Tsukamoto |
| 5,646,043 A | 7/1997 | Emerson |
| 5,654,186 A | 8/1997 | Cerami |
| 5,654,381 A | 8/1997 | Hrkach |
| 5,665,557 A | 9/1997 | Murray |
| 5,668,104 A | 9/1997 | Nakahata |
| 5,670,147 A | 9/1997 | Emerson |
| 5,670,351 A | 9/1997 | Emerson |
| 5,672,346 A | 9/1997 | Srour |
| 5,677,139 A | 10/1997 | Johnson |
| 5,704,361 A | 1/1998 | Seward |
| 5,709,854 A | 1/1998 | Griffith-Cima |
| 5,716,616 A | 2/1998 | Prockop |
| 5,716,794 A | 2/1998 | Tjota |
| 5,716,827 A | 2/1998 | Tsukamoto |

(Continued)

FOREIGN PATENT DOCUMENTS

| | | |
|---|---|---|
| CA | 2381292 | 2/2001 |
| CN | 1407088 | 4/2003 |

(Continued)

OTHER PUBLICATIONS

Shibata et al (Diabetes. 2008; 57: 3099-3107) (Year: 2008).*
Veves et al. (Pain Medicine. 2008; 9(6): 660-674) (Year: 2008).*
Bhatia et al. (Wounds. 2008; 20(2): 29-36). (Year: 2008).*
Abbott, "ABCG2 (BCRP) Expression in Normal and Malignant Hematopoietic Cells," Hematol. Oncol. 21:115-130 (2003).
Abe, "Therapeutic Potential of Neurotrophic Factors and Neural Stem Cells Against Ischemic Brain Injury," Journal of Cerebral Blood Flow and Metabolism, Raven Press, Ltd., New York, 20(10): 1393-1408 (2000).
Abkowitz, "Can Human Hematopoietic Stem Cells Become Skin, Gut, or Liver Cells?" N. Engl. J. Med. 346(10):770-2 (2002).
Aboagye-Mathiesen et al., "Isolation and Characterization of Human Placental Trophoblast Subpopulations from First-Trimester Chorionic Villi," Clinical and Diagnostic Laboratory Immunology 3(1):14-22 (1996).

(Continued)

*Primary Examiner* — Scott Long
(74) *Attorney, Agent, or Firm* — Geoffry T. Knudsen; Celularity Inc.

(57) ABSTRACT

Provided herein are methods of treatment of an individual having pain, e.g., neuropathic pain, comprising administering to the individual a therapeutically effective amount of tissue culture plastic adherent placental stem cells (PDAC™).

15 Claims, 23 Drawing Sheets

(56) References Cited

U.S. PATENT DOCUMENTS

Figure 1:
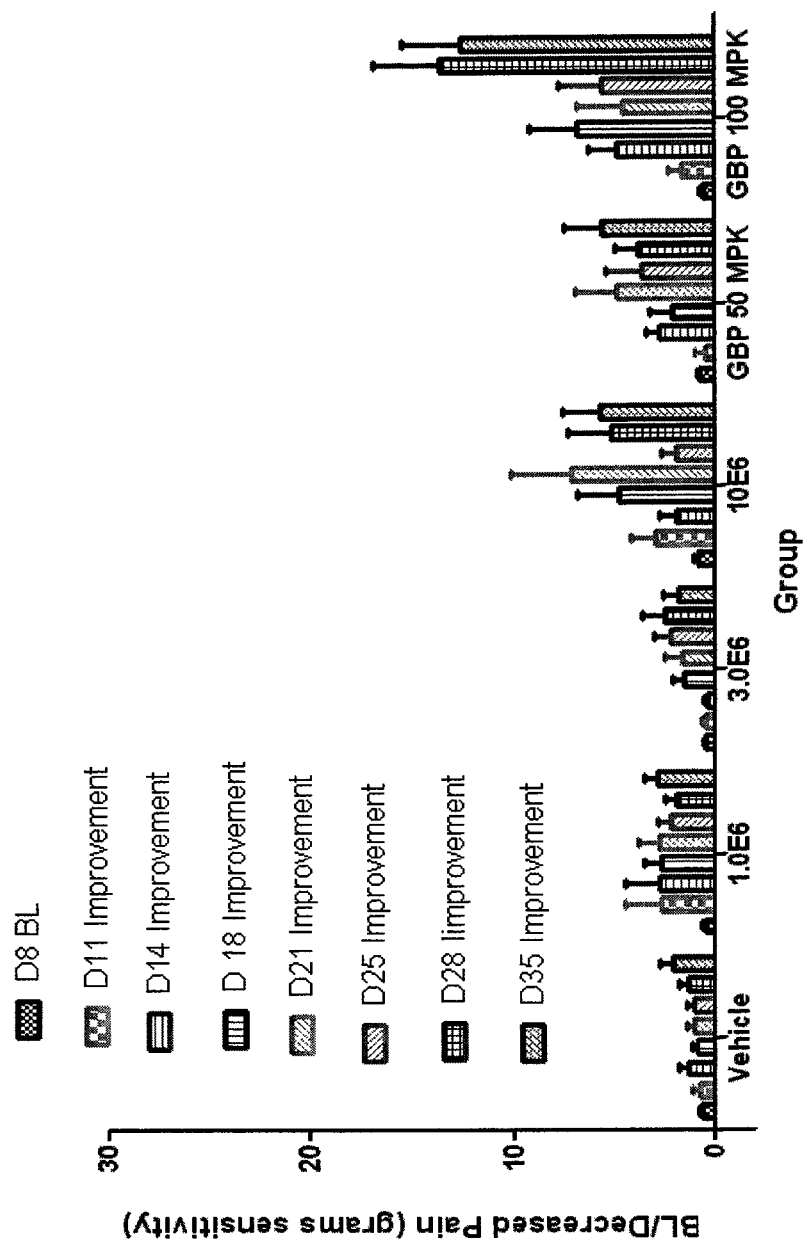

| | | |
|---|---|---|
| 5,733,541 A | 3/1998 | Taichman |
| 5,733,542 A | 3/1998 | Haynesworth |
| 5,736,396 A | 4/1998 | Bruder |
| 5,744,347 A | 4/1998 | Wagner |
| 5,744,361 A | 4/1998 | Hoffman |
| 5,750,376 A | 5/1998 | Weiss |
| 5,750,397 A | 5/1998 | Tsukamoto |
| 5,763,197 A | 6/1998 | Tsukamoto |
| 5,763,266 A | 6/1998 | Palsson |
| 5,800,539 A | 9/1998 | Waller |
| 5,806,529 A | 9/1998 | Reisner |
| 5,807,686 A | 9/1998 | Wagner |
| 5,811,094 A | 9/1998 | Caplan |
| 5,827,735 A | 10/1998 | Young |
| 5,827,740 A | 10/1998 | Pittenger |
| 5,827,742 A | 10/1998 | Scadden |
| 5,837,539 A | 11/1998 | Caplan |
| 5,840,502 A | 11/1998 | Van |
| 5,849,553 A | 12/1998 | Anderson |
| 5,851,984 A | 12/1998 | Matthews |
| 5,855,619 A | 1/1999 | Caplan |
| 5,858,782 A | 1/1999 | Long |
| 5,861,315 A | 1/1999 | Nakahata |
| 5,866,414 A | 2/1999 | Badylak |
| 5,874,301 A | 2/1999 | Keller |
| 5,877,299 A | 3/1999 | Thomas |
| 5,879,318 A | 3/1999 | Van |
| 5,879,940 A | 3/1999 | Torok-Storb |
| 5,899,936 A | 5/1999 | Goldstein |
| 5,902,741 A | 5/1999 | Purchio |
| 5,905,041 A | 5/1999 | Beug |
| 5,906,934 A | 5/1999 | Grande |
| 5,908,782 A | 6/1999 | Marshak |
| 5,908,784 A | 6/1999 | Johnstone |
| 5,914,108 A | 6/1999 | Tsukamoto |
| 5,914,268 A | 6/1999 | Keller |
| 5,916,202 A | 6/1999 | Haswell |
| 5,919,176 A | 7/1999 | Kuypers |
| 5,919,702 A | 7/1999 | Purchio |
| 5,922,597 A | 7/1999 | Verfaillie |
| 5,925,567 A | 7/1999 | Kraus |
| 5,928,214 A | 7/1999 | Rubinstein |
| 5,928,947 A | 7/1999 | Anderson |
| 5,942,225 A | 8/1999 | Bruder |
| 5,942,496 A | 8/1999 | Bonadio |
| 5,958,767 A | 9/1999 | Snyder |
| 5,962,325 A | 10/1999 | Naughton |
| 5,968,829 A | 10/1999 | Carpenter |
| 5,969,105 A | 10/1999 | Feng |
| 5,993,429 A | 11/1999 | Kuypers |
| 5,997,860 A | 12/1999 | Bauer |
| 6,001,654 A | 12/1999 | Anderson |
| 6,010,696 A | 1/2000 | Caplan |
| 6,011,000 A | 1/2000 | Perrine |
| 6,020,469 A | 2/2000 | Hershenson |
| 6,022,540 A | 2/2000 | Bruder |
| 6,022,743 A | 2/2000 | Naughton |
| 6,022,848 A | 2/2000 | Kozlov |
| 6,030,836 A | 2/2000 | Thiede |
| 6,057,123 A | 5/2000 | Craig |
| 6,059,968 A | 5/2000 | Wolf, Jr. |
| 6,077,708 A | 6/2000 | Collins |
| 6,087,113 A | 7/2000 | Caplan |
| 6,093,531 A | 7/2000 | Bjornson |
| 6,102,871 A | 8/2000 | Coe |
| 6,110,739 A | 8/2000 | Keller |
| 6,127,135 A | 10/2000 | Hill |
| 6,146,888 A | 11/2000 | Smith |
| 6,174,333 B1 | 1/2001 | Kadiyala |
| 6,179,819 B1 | 1/2001 | Haswell |
| 6,184,035 B1 | 2/2001 | Csete |
| 6,190,368 B1 | 2/2001 | Kuypers |
| 6,214,369 B1 | 4/2001 | Grande |
| 6,224,860 B1 | 5/2001 | Brown |
| 6,225,119 B1 | 5/2001 | Qasba |
| 6,227,202 B1 | 5/2001 | Matapurkar |
| 6,231,880 B1 | 5/2001 | Perrine |
| 6,239,157 B1 | 5/2001 | Mbalaviele |
| 6,248,587 B1 | 6/2001 | Rodgers |
| 6,251,383 B1 | 6/2001 | Upadhyay |
| 6,255,112 B1 | 7/2001 | Thiede |
| 6,261,549 B1 | 7/2001 | Fernandez |
| 6,280,718 B1 | 8/2001 | Kaufman |
| 6,281,012 B1 | 8/2001 | McIntosh |
| 6,291,240 B1 | 9/2001 | Mansbridge |
| 6,300,314 B1 | 10/2001 | Wallner |
| 6,306,575 B1 | 10/2001 | Thomas |
| 6,312,950 B1 | 11/2001 | Ohmura |
| 6,322,784 B1 | 11/2001 | Pittenger |
| 6,326,019 B1 | 12/2001 | Tseng |
| 6,326,198 B1 | 12/2001 | Emerson |
| 6,328,762 B1 | 12/2001 | Anderson |
| 6,328,765 B1 | 12/2001 | Hardwick |
| 6,328,960 B1 | 12/2001 | McIntosh |
| 6,333,029 B1 | 12/2001 | Vyakarnam |
| 6,335,195 B1 | 1/2002 | Rodgers |
| 6,337,387 B1 | 1/2002 | Sakano |
| 6,338,942 B2 | 1/2002 | Kraus |
| 6,355,239 B1 | 3/2002 | Bruder |
| 6,355,699 B1 | 3/2002 | Vyakarnam |
| 6,358,737 B1 | 3/2002 | Bonewald |
| 6,365,362 B1 | 4/2002 | Terstappen |
| 6,368,636 B1 | 4/2002 | McIntosh |
| 6,379,953 B1 | 4/2002 | Bruder |
| 6,384,105 B1 | 5/2002 | He |
| 6,387,367 B1 | 5/2002 | Davis-Sproul |
| 6,387,369 B1 | 5/2002 | Pittenger |
| 6,455,306 B1 | 9/2002 | Goldstein |
| 6,455,678 B1 | 9/2002 | Yin |
| 6,458,810 B1 | 10/2002 | Muller |
| 6,461,615 B1 | 10/2002 | Srivastava |
| 6,461,645 B1 | 10/2002 | Boyse |
| 6,497,875 B1 | 12/2002 | Sorrell |
| 6,528,245 B2 | 3/2003 | Sanchez-Ramos |
| 6,534,084 B1 | 3/2003 | Vyakarnam |
| 6,541,024 B1 | 4/2003 | Kadiyala |
| 6,548,299 B1 | 4/2003 | Pykett |
| 6,645,731 B2 | 11/2003 | Terstappen |
| 6,685,936 B2 | 2/2004 | McIntosh |
| 6,709,864 B1 | 3/2004 | Pittenger |
| 6,753,181 B2 | 6/2004 | Atala |
| 6,797,269 B2 | 9/2004 | Mosca |
| 6,800,480 B1 | 10/2004 | Bodnar |
| 6,835,377 B2 | 12/2004 | Goldberg |
| 6,863,900 B2 | 3/2005 | Kadiyala |
| 6,875,430 B2 | 4/2005 | McIntosh |
| 6,875,607 B1 | 4/2005 | Reubinoff |
| 6,916,655 B2 | 7/2005 | Yasumoto |
| 7,029,666 B2 | 4/2006 | Bruder |
| 7,045,148 B2 | 5/2006 | Hariri |
| 7,091,353 B2 | 8/2006 | Robarge |
| 7,147,626 B2 | 12/2006 | Goodman |
| 7,153,500 B2 | 12/2006 | Qasba |
| 7,244,759 B2 | 7/2007 | Muller |
| 7,255,879 B2 | 8/2007 | Hariri |
| 7,311,904 B2 | 12/2007 | Hariri |
| 7,311,905 B2 * | 12/2007 | Hariri .................. 424/93.1 |
| 7,410,773 B2 | 8/2008 | Abuljadayel |
| 7,455,983 B2 | 11/2008 | Xu |
| 7,468,276 B2 | 12/2008 | Hariri |
| 7,498,171 B2 | 3/2009 | Hariri |
| 7,638,141 B2 | 12/2009 | Hariri |
| 7,642,091 B2 | 1/2010 | Lee |
| 7,682,803 B2 | 3/2010 | Paludan |
| 7,700,090 B2 | 4/2010 | Heidaran |
| 7,909,806 B2 | 3/2011 | Goodman |
| 7,914,779 B2 | 3/2011 | Hariri |
| 7,928,280 B2 | 4/2011 | Hariri |
| 7,976,836 B2 | 7/2011 | Hariri |
| 7,993,918 B2 | 8/2011 | Paludan |
| 8,057,788 B2 | 11/2011 | Hariri |
| 8,057,789 B2 | 11/2011 | Hariri |
| 8,071,135 B2 | 12/2011 | Liu |
| 8,071,376 B2 | 12/2011 | Heidaran |

(56) References Cited

U.S. PATENT DOCUMENTS

| | | |
|---|---|---|
| 8,105,634 B2 | 1/2012 | Liu |
| 8,202,703 B2 * | 6/2012 | Edinger et al. ............... 435/29 |
| 8,263,065 B2 | 9/2012 | Hariri |
| 8,293,223 B2 | 10/2012 | Hariri |
| 8,367,409 B2 | 2/2013 | Abbot |
| 8,435,788 B2 | 5/2013 | Hariri |
| 8,455,250 B2 | 6/2013 | Heidaran |
| 8,460,650 B2 | 6/2013 | Edinger |
| 2001/0005591 A1 | 6/2001 | Qasba |
| 2001/0038836 A1 | 11/2001 | During |
| 2001/0044124 A1 | 11/2001 | Bacus |
| 2002/0022676 A1 | 2/2002 | He |
| 2002/0028510 A1 | 3/2002 | Sanberg |
| 2002/0045643 A1 | 4/2002 | Muller |
| 2002/0059106 A1 | 5/2002 | Tani |
| 2002/0061300 A1 | 5/2002 | Gokcen |
| 2002/0086005 A1 | 7/2002 | Chiu |
| 2002/0102239 A1 | 8/2002 | Koopmans |
| 2002/0103542 A1 | 8/2002 | Bilbo |
| 2002/0110544 A1 | 8/2002 | Goldberg |
| 2002/0123141 A1 | 9/2002 | Hariri |
| 2002/0132343 A1 | 9/2002 | Lum |
| 2002/0160510 A1 | 10/2002 | Hariri |
| 2003/0007954 A1 | 1/2003 | Naughton |
| 2003/0032179 A1 | 2/2003 | Hariri |
| 2003/0044976 A1 | 3/2003 | Dominko |
| 2003/0044977 A1 | 3/2003 | Sakuragawa |
| 2003/0045552 A1 | 3/2003 | Robarge |
| 2003/0059414 A1 | 3/2003 | Ho |
| 2003/0068306 A1 | 4/2003 | Dilber |
| 2003/0096841 A1 | 5/2003 | Robarge |
| 2003/0109042 A1 | 6/2003 | Wu |
| 2003/0152558 A1 | 8/2003 | Luft |
| 2003/0161818 A1 | 8/2003 | Weiss |
| 2003/0178031 A1 | 9/2003 | Du Pen |
| 2003/0180269 A1 | 9/2003 | Hariri |
| 2003/0187515 A1 | 10/2003 | Hariri |
| 2003/0235090 A1 | 12/2003 | Lee |
| 2003/0235563 A1 | 12/2003 | Strom |
| 2003/0235909 A1 | 12/2003 | Hariri |
| 2004/0018617 A1 | 1/2004 | Hwang |
| 2004/0019289 A1 | 1/2004 | Ross |
| 2004/0028660 A1 | 2/2004 | Hariri |
| 2004/0048372 A1 | 3/2004 | Hariri |
| 2004/0048796 A1 | 3/2004 | Hariri |
| 2004/0107453 A1 | 6/2004 | Furcht |
| 2004/0136967 A1 | 7/2004 | Weiss |
| 2004/0161419 A1 | 8/2004 | Strom |
| 2004/0166097 A1 | 8/2004 | Prockop |
| 2004/0171147 A1 | 9/2004 | Hariri |
| 2004/0176434 A1 | 9/2004 | Bennett |
| 2004/0180040 A1 | 9/2004 | Phillips |
| 2004/0219136 A1 | 11/2004 | Unknown |
| 2004/0229351 A1 | 11/2004 | Rodriguez |
| 2004/0241144 A1 | 12/2004 | Kaps |
| 2004/0267099 A1 | 12/2004 | McMahon |
| 2005/0019865 A1 | 1/2005 | Kihm |
| 2005/0019908 A1 | 1/2005 | Hariri |
| 2005/0032209 A1 | 2/2005 | Messina |
| 2005/0037491 A1 | 2/2005 | Mistry |
| 2005/0042595 A1 | 2/2005 | Haas |
| 2005/0054093 A1 | 3/2005 | Haas |
| 2005/0054098 A1 | 3/2005 | Mistry |
| 2005/0058629 A1 | 3/2005 | Harmon |
| 2005/0058630 A1 | 3/2005 | Harris |
| 2005/0058631 A1 | 3/2005 | Kihm |
| 2005/0058641 A1 | 3/2005 | Siemionow |
| 2005/0074435 A1 | 4/2005 | Casper |
| 2005/0085543 A1 | 4/2005 | Wallimann |
| 2005/0089513 A1 | 4/2005 | Sakuragawa |
| 2005/0112104 A1 | 5/2005 | Pittenger |
| 2005/0118147 A1 | 6/2005 | Oh |
| 2005/0118712 A1 | 6/2005 | Tsai |
| 2005/0118715 A1 | 6/2005 | Hariri |
| 2005/0124003 A1 | 6/2005 | Atala |
| 2005/0142118 A1 | 6/2005 | Wernet |
| 2005/0143420 A1 | 6/2005 | Moutouh-De |
| 2005/0148034 A1 | 7/2005 | Hariri |
| 2005/0148074 A1 | 7/2005 | Davies |
| 2005/0176139 A1 | 8/2005 | Chen |
| 2005/0181502 A1 | 8/2005 | Furcht |
| 2005/0186182 A1 | 8/2005 | Deisher |
| 2005/0233452 A1 | 10/2005 | Ho |
| 2005/0239897 A1 | 10/2005 | Pittenger |
| 2005/0266391 A1 | 12/2005 | Bennett |
| 2005/0272148 A1 | 12/2005 | Hariri |
| 2005/0276792 A1 | 12/2005 | Kaminski |
| 2005/0282272 A1 | 12/2005 | Bhatia |
| 2005/0283844 A1 | 12/2005 | Furcht |
| 2006/0004043 A1 | 1/2006 | Bhagwat |
| 2006/0008450 A1 | 1/2006 | Verfaillie |
| 2006/0024280 A1 | 2/2006 | West |
| 2006/0060494 A1 | 3/2006 | Goodman |
| 2006/0078993 A1 | 4/2006 | Phan |
| 2006/0122179 A1 | 6/2006 | Zeldis |
| 2006/0128012 A1 | 6/2006 | Arinzeh |
| 2006/0153816 A1 | 7/2006 | Brown |
| 2006/0153817 A1 | 7/2006 | Kihm |
| 2006/0153818 A1 | 7/2006 | Dhanaraj |
| 2006/0154366 A1 | 7/2006 | Brown |
| 2006/0154367 A1 | 7/2006 | Kihm |
| 2006/0166361 A1 | 7/2006 | Seyda |
| 2006/0171930 A1 | 8/2006 | Seyda |
| 2006/0188983 A1 | 8/2006 | Harris |
| 2006/0205771 A1 | 9/2006 | Noble |
| 2006/0222634 A1 | 10/2006 | Clarke |
| 2006/0223177 A1 | 10/2006 | Harris |
| 2006/0233765 A1 | 10/2006 | Messina |
| 2006/0233766 A1 | 10/2006 | Messina |
| 2006/0234376 A1 | 10/2006 | Mistry |
| 2006/0263337 A1 | 11/2006 | Maziarz |
| 2006/0281178 A1 | 12/2006 | Sakuragawa |
| 2007/0009494 A1 | 1/2007 | Mistry |
| 2007/0014771 A1 | 1/2007 | Mistry |
| 2007/0020225 A1 | 1/2007 | Abramson |
| 2007/0021704 A1 | 1/2007 | Hariri |
| 2007/0021762 A1 | 1/2007 | Liu |
| 2007/0031384 A1 | 2/2007 | Atala |
| 2007/0036767 A1 | 2/2007 | Mistry |
| 2007/0038298 A1 | 2/2007 | Sulner |
| 2007/0041954 A1 | 2/2007 | Ichim |
| 2007/0043328 A1 | 2/2007 | Goodman |
| 2007/0053888 A1 | 3/2007 | Hariri |
| 2007/0060616 A1 | 3/2007 | Bennett |
| 2007/0077652 A1 | 4/2007 | Peled |
| 2007/0092497 A1 | 4/2007 | Hariri |
| 2007/0092967 A1 | 4/2007 | Han |
| 2007/0116682 A1 | 5/2007 | Atala |
| 2007/0122903 A1 | 5/2007 | Rezania |
| 2007/0134210 A1 | 6/2007 | Heidaran |
| 2007/0141700 A1 | 6/2007 | Harmon |
| 2007/0160588 A1 | 7/2007 | Kihm |
| 2007/0190034 A1 | 8/2007 | Paludan |
| 2007/0190042 A1 | 8/2007 | Edinger |
| 2007/0190649 A1 | 8/2007 | Gage |
| 2007/0224174 A1 | 9/2007 | Kang |
| 2007/0243172 A1 | 10/2007 | Ra |
| 2007/0253931 A1 | 11/2007 | Varney |
| 2007/0258963 A1 | 11/2007 | Danilkovitch |
| 2007/0264269 A1 | 11/2007 | Harmon |
| 2007/0275362 A1 | 11/2007 | Edinger |
| 2007/0287176 A1 | 12/2007 | Rezania |
| 2007/0292399 A1 | 12/2007 | Heidaran |
| 2008/0032401 A1 | 2/2008 | Edinger |
| 2008/0044392 A1 | 2/2008 | Kues |
| 2008/0044848 A1 | 2/2008 | Heidaran |
| 2008/0050347 A1 | 2/2008 | Ichim |
| 2008/0050814 A1 | 2/2008 | Allickson |
| 2008/0064098 A1 | 3/2008 | Allickson |
| 2008/0069895 A1 | 3/2008 | Liu |
| 2008/0095749 A1 | 4/2008 | Aggarwal |
| 2008/0131410 A1 | 6/2008 | Hariri |
| 2008/0131522 A1 | 6/2008 | Liu |
| 2008/0131966 A1 | 6/2008 | Hariri |

(56) References Cited

U.S. PATENT DOCUMENTS

| | | |
|---|---|---|
| 2008/0145934 A1 | 6/2008 | Harris |
| 2008/0152624 A1 | 6/2008 | Paludan |
| 2008/0152629 A1 | 6/2008 | Edinger |
| 2008/0159998 A1 | 7/2008 | Ichim |
| 2008/0166328 A1 | 7/2008 | Harmon |
| 2008/0175824 A1 | 7/2008 | Heidaran |
| 2008/0181935 A1 | 7/2008 | Bhatia |
| 2008/0181967 A1 | 7/2008 | Liu |
| 2008/0206343 A1 | 8/2008 | Edinger |
| 2008/0208158 A1 | 8/2008 | Goodman |
| 2008/0213227 A1 | 9/2008 | Aggarwal |
| 2008/0213228 A1 | 9/2008 | Edinger |
| 2008/0226595 A1 | 9/2008 | Edinger |
| 2008/0226612 A1 | 9/2008 | Treves |
| 2008/0248005 A1 | 10/2008 | Phan |
| 2008/0254005 A1 | 10/2008 | Riordan |
| 2008/0254538 A1 | 10/2008 | Messina |
| 2008/0260694 A1 | 10/2008 | Gronthos |
| 2008/0260703 A1 | 10/2008 | Riordan |
| 2008/0260704 A1 | 10/2008 | Riordan |
| 2008/0274087 A1 | 11/2008 | Li |
| 2008/0279956 A1 | 11/2008 | Lin |
| 2008/0286249 A1 | 11/2008 | Varney |
| 2008/0286267 A1 | 11/2008 | Sing |
| 2008/0292597 A1 | 11/2008 | Steenblock |
| 2008/0299090 A1 | 12/2008 | Weiss |
| 2008/0305148 A1 | 12/2008 | Fu |
| 2008/0311087 A1 | 12/2008 | Gosiewska |
| 2009/0004738 A1 | 1/2009 | Merchav |
| 2009/0016999 A1 | 1/2009 | Cohen |
| 2009/0053182 A1 | 2/2009 | Ichim |
| 2009/0053805 A1 | 2/2009 | Hariri |
| 2009/0074728 A1 | 3/2009 | Gronthos |
| 2009/0074731 A1 | 3/2009 | Librach |
| 2009/0075381 A1 | 3/2009 | Clarke |
| 2009/0081171 A1 | 3/2009 | Fu |
| 2009/0092653 A1 | 4/2009 | Colter |
| 2009/0104158 A1 | 4/2009 | Young |
| 2009/0104163 A1 | 4/2009 | Deans |
| 2009/0104164 A1 | 4/2009 | Zhang |
| 2009/0123437 A1 | 5/2009 | Takebe |
| 2009/0124007 A1 | 5/2009 | Cho |
| 2009/0124573 A1 | 5/2009 | Mazmanian |
| 2009/0136457 A1 | 5/2009 | Sing |
| 2009/0136471 A1 | 5/2009 | Heidaran |
| 2009/0142831 A1 | 6/2009 | Hariri |
| 2009/0149371 A1 | 6/2009 | Mistry |
| 2009/0169522 A1 | 7/2009 | Danilkovitch |
| 2009/0169597 A1 | 7/2009 | Brown |
| 2009/0170200 A1 | 7/2009 | Yeh |
| 2009/0186006 A1 | 7/2009 | Murphy |
| 2009/0202479 A1 | 8/2009 | Shi |
| 2009/0208463 A1 | 8/2009 | Pittenger |
| 2009/0214484 A1 | 8/2009 | Mironov |
| 2009/0214493 A1 | 8/2009 | Pittenger |
| 2009/0220464 A1 | 9/2009 | Aggarwal |
| 2009/0226406 A1 | 9/2009 | Hariri |
| 2009/0232781 A1 | 9/2009 | Fu |
| 2009/0232782 A1 | 9/2009 | Fu |
| 2009/0238801 A1 | 9/2009 | Woodbury |
| 2009/0252710 A1 | 10/2009 | Zhang |
| 2009/0257989 A1 | 10/2009 | Vanguri |
| 2009/0263361 A1 | 10/2009 | Lee |
| 2009/0274665 A1 | 11/2009 | Akabutu |
| 2009/0280093 A1 | 11/2009 | Friedlander |
| 2009/0285842 A1 | 11/2009 | Davies |
| 2009/0291061 A1 | 11/2009 | Riordan |
| 2009/0304639 A1 | 12/2009 | Yokoo |
| 2009/0305406 A1 | 12/2009 | Pytlik |
| 2009/0311223 A1 | 12/2009 | Ichim |
| 2009/0311782 A1 | 12/2009 | Chiou |
| 2009/0324609 A1 | 12/2009 | Lodie |
| 2010/0008890 A1 | 1/2010 | Mays |
| 2010/0008992 A1 | 1/2010 | Ichim |
| 2010/0015705 A1 | 1/2010 | Vodyanyk |
| 2010/0015712 A1 | 1/2010 | Skuragawa |
| 2010/0021434 A1 | 1/2010 | Melamed |
| 2010/0028306 A1 | 2/2010 | Clarke |
| 2010/0028346 A1 | 2/2010 | Lutz |
| 2010/0028997 A1 | 2/2010 | Lin |
| 2010/0047213 A1 | 2/2010 | Zeitlin |
| 2010/0047214 A1 | 2/2010 | Abramson |
| 2010/0047351 A1 | 2/2010 | Zeitlin |
| 2010/0105132 A1 | 4/2010 | Totey |
| 2010/0120015 A1 | 5/2010 | Hariri |
| 2010/0143312 A1 | 6/2010 | Hariri |
| 2010/0172830 A1 | 7/2010 | Heidaran |
| 2010/0183571 A1 | 7/2010 | Paludan |
| 2010/0291679 A1 | 11/2010 | Edinger |
| 2010/0297689 A1 | 11/2010 | Edinger |
| 2010/0311036 A1 | 12/2010 | He |
| 2010/0323446 A1 | 12/2010 | Barnett |
| 2011/0003387 A1 | 1/2011 | Abbot |
| 2011/0206645 A1 | 8/2011 | Zhang |
| 2011/0217271 A1 | 9/2011 | Hariri |
| 2011/0217272 A1 | 9/2011 | Hariri |
| 2011/0223141 A1 | 9/2011 | Hariri |
| 2011/0250182 A1 | 10/2011 | Abbot |
| 2011/0250185 A1 | 10/2011 | Paludan |
| 2011/0280843 A1 | 11/2011 | Edinger |
| 2011/0280845 A1 | 11/2011 | Edinger |
| 2011/0280849 A1 | 11/2011 | Zhang |
| 2011/0311491 A1 | 12/2011 | Edinger |
| 2011/0318401 A1 | 12/2011 | Hariri |
| 2012/0020936 A1 | 1/2012 | Hariri |
| 2012/0034195 A1 | 2/2012 | Hariri |
| 2012/0121550 A1 | 5/2012 | Heidaran |
| 2012/0148553 A1 | 6/2012 | Hariri |
| 2012/0171160 A1 | 7/2012 | Johnson |
| 2012/0171161 A1 | 7/2012 | Abramson |
| 2012/0171180 A1* | 7/2012 | Abramson et al. ........ 424/93.72 |
| 2012/0171295 A1 | 7/2012 | Abramson |
| 2012/0230959 A1 | 9/2012 | Abbot |
| 2012/0328583 A1 | 12/2012 | Herzberg |
| 2013/0022581 A1 | 1/2013 | Edinger |
| 2013/0028871 A1 | 1/2013 | Edinger |
| 2013/0071362 A1 | 3/2013 | Bhatia |
| 2013/0071393 A1 | 3/2013 | Seehra |
| 2013/0172531 A1 | 7/2013 | Bhatia |
| 2013/0184821 A1 | 7/2013 | Hariri |

FOREIGN PATENT DOCUMENTS

| | | |
|---|---|---|
| CN | 1548529 A | 11/2004 |
| CN | 1597937 | 3/2005 |
| CN | 1786154 A | 6/2006 |
| CN | 100344757 C | 6/2006 |
| CN | 1810959 | 8/2006 |
| CN | 101210232 A | 7/2008 |
| CN | 101270349 | 9/2008 |
| EP | 0333328 | 9/1989 |
| EP | 0529421 | 3/1993 |
| EP | 0529751 | 3/1993 |
| EP | 0552380 | 7/1993 |
| EP | 1110957 A1 | 6/2001 |
| EP | 1264877 | 12/2002 |
| EP | 1288293 A1 | 3/2003 |
| EP | 1364775 A1 | 1/2004 |
| EP | 1405649 | 4/2004 |
| EP | 1535994 A1 | 6/2005 |
| EP | 1775341 A1 | 4/2007 |
| EP | 1974013 | 10/2008 |
| JP | 2000516616 | 12/2000 |
| JP | 3934539 | 8/2003 |
| JP | 2003235549 | 8/2003 |
| JP | 2003323558 A | 11/2003 |
| JP | 2004528021 A | 9/2004 |
| JP | 2005151907 | 6/2005 |
| JP | 2005517402 A | 6/2005 |
| JP | 2005522215 A | 7/2005 |
| JP | 2005528105 A | 9/2005 |
| KR | 20040024170 | 3/2004 |
| WO | 8904168 | 5/1989 |
| WO | 9011354 | 10/1990 |

(56) References Cited

FOREIGN PATENT DOCUMENTS

| | | |
|---|---|---|
| WO | 9101140 | 2/1991 |
| WO | 9106666 | 5/1991 |
| WO | 9106667 | 5/1991 |
| WO | 1991016062 | 10/1991 |
| WO | 9304169 | 3/1993 |
| WO | 9522611 | 8/1995 |
| WO | 9634035 | 10/1996 |
| WO | 1996032905 | 10/1996 |
| WO | 9639101 | 12/1996 |
| WO | 9837903 A1 | 9/1998 |
| WO | 9854170 A1 | 12/1998 |
| WO | 9903973 | 1/1999 |
| WO | 9964566 | 12/1999 |
| WO | 1999065470 | 12/1999 |
| WO | 0017325 | 3/2000 |
| WO | 0027999 | 5/2000 |
| WO | 2000027995 | 5/2000 |
| WO | 0038762 | 7/2000 |
| WO | 2000069355 | 11/2000 |
| WO | 0073421 | 12/2000 |
| WO | 0121767 A2 | 3/2001 |
| WO | 0193909 A2 | 12/2001 |
| WO | 0246373 A1 | 6/2002 |
| WO | 02063962 | 8/2002 |
| WO | 02064755 | 8/2002 |
| WO | 20020059106 | 8/2002 |
| WO | 20020064083 | 8/2002 |
| WO | 20020066450 | 8/2002 |
| WO | 20020097052 | 12/2002 |
| WO | 03042405 | 5/2003 |
| WO | 03068937 | 8/2003 |
| WO | 03080822 A1 | 10/2003 |
| WO | 03086373 | 10/2003 |
| WO | 03087333 | 10/2003 |
| WO | 03087392 | 10/2003 |
| WO | 03089619 | 10/2003 |
| WO | 03102151 | 12/2003 |
| WO | 2004035064 A1 | 4/2004 |
| WO | 2004047770 | 6/2004 |
| WO | 2004071283 | 8/2004 |
| WO | 2004087896 | 10/2004 |
| WO | 2005042703 | 5/2005 |
| WO | 2005055929 | 6/2005 |
| WO | 2005097190 | 10/2005 |
| WO | 2005105992 A1 | 11/2005 |
| WO | 2006015214 | 2/2006 |
| WO | 2006111706 A1 | 10/2006 |
| WO | 2006117889 | 11/2006 |
| WO | 2006133128 | 12/2006 |
| WO | 2007024441 | 3/2007 |
| WO | 2007047465 A1 | 4/2007 |
| WO | 2007047468 A2 | 4/2007 |
| WO | 2007056578 | 5/2007 |
| WO | 2007059007 A2 | 5/2007 |
| WO | 2007071048 | 6/2007 |
| WO | 2007073552 | 6/2007 |
| WO | 2007076522 A2 | 7/2007 |
| WO | 2007079183 A2 | 7/2007 |
| WO | 2007079184 A2 | 7/2007 |
| WO | 2007079185 A2 | 7/2007 |
| WO | 2007087292 | 8/2007 |
| WO | 2007087293 | 8/2007 |
| WO | 2007124594 | 11/2007 |
| WO | 2007136673 | 11/2007 |
| WO | 2008019148 | 2/2008 |
| WO | 2008036374 A2 | 3/2008 |
| WO | 2008036447 | 3/2008 |
| WO | 2008051568 A2 | 5/2008 |
| WO | 2008060541 | 5/2008 |
| WO | 2008100497 A1 | 8/2008 |
| WO | 2008100498 | 8/2008 |
| WO | 2008148105 | 12/2008 |
| WO | 2008152640 | 12/2008 |
| WO | 2008156659 | 12/2008 |
| WO | 2009007979 | 1/2009 |
| WO | 2009028870 | 3/2009 |
| WO | 2009035612 | 3/2009 |
| WO | 2009037690 A1 | 3/2009 |
| WO | 2009045360 | 4/2009 |
| WO | 2009046346 | 4/2009 |
| WO | 2009046377 | 4/2009 |
| WO | 2009052132 | 4/2009 |
| WO | 2009134532 | 11/2009 |
| WO | 2009144720 | 12/2009 |
| WO | 2010021714 | 2/2010 |
| WO | 2010026574 | 3/2010 |
| WO | 2011094181 | 8/2011 |
| WO | 2012009422 | 1/2012 |
| WO | 2013012698 A2 | 1/2013 |

OTHER PUBLICATIONS

Addison, et al., 'Metabolism of Prednisolone by the Isolated Perfused Human Placental Lobule,' J. Ster. Biochem. Mol. Biol., 39(1):83-90 (1991).

Aerbajinai, et al., "Thalidomide Induces gamma-Globin Gene Expression through Increased Reactive Oxygen Species-Mediated p38 MAPK Signaling and Histone H4 Acetylation in Adult Erythropoicsis," Blood 110(8)2864-2871 (2007).

Aggarwal, et al., "Human Mesenchymal Stem Cells Modulate Allogeneic Immune Cell Responses," Blood 105(4)1 815-22 (2005).

Alviano Francesco et al, "Term amniotic membrane is a high throughput source for multipotent mesenchymal stem cells with the ability to differentiate into endothelial cells in vitro", BMC Developmental Biology, Biomed Central Ltd., London, GB, (20070221), vol. 7, No. 1, ISSN 1471-213X, p. 11, XP021021998.

Anker In'T P, et al., "Isolation of Mesenchymal Stem Cells of Fetal or Maternal Origin from Human Placenta," Stem Cells 22(7): 1338-45 (2004).

Anseth et al., 2002, "In situ forming degradable networks and their application in tissue engineering and drug delivery," J. Control Release, 78(1-3): 199-209.

Aplin, "Implantation, trophoblast Differentiation and Haemochorial Placentation: Mechanistic Evidence in vivo and in vitro," Journal of Cell Science 99:681-692 (1991).

Ashihara et al., "Successful Peripheral Blood Stem Cell Transplantation for Myelodysplastic Syndrome," Bone Marrow Transplantation 24(12): 1343-1345 (1999).

Bailo, et al., "Engraftment Potential of Human Amnion and Chorion Cells Derived from Term Placenta," Transplantation 78:1439-1448 (2004).

Ballin, et al., "Autologous Umbilical Cord Blood Transfusion," Arch. Dis. Child Fetal Neonatal. Ed. 73(3):F181-F183 (1995).

Barlogie et al., "High-dose therapy immunomodulatory drugs in multiple myeloma," Seminars in Oncology, 29 (6):26-33 (2002).

Barry et al., "The Monoclonal Antibody SH-2, Raised Against Human Mesenchymal Stem Cells, Recognizes an Epitope onEndoglin (CD105)," Osiris Therapeutics Inc., (2001) Aliceanna Street, Baltimore, MD 21231, Biochemical and Biophysical Research Communications 265:134-139 (1999).

Barry, "Where Do All the Placentas Go?" Canadian Journal of Infection Control 9(1):8-10 (1994).

Battula et al., "Prospective Isolation and Characterization of Mesenchymal Stem Cells from Human Placenta Using a Firzzled-9-Specific Monoclonal Antibody," Differentiation 76:326-336 (2008).

Beltrami, et al., "Adult Cardiac Stem Cells Are Multipotent and Support Myocardial Regeneration!," 114:763-776 (2003).

Belvedere Ornella et al., "Increased blood volume and CD34+CD38- progenitor cell recovery using a novel umbilical cord blood collection system", STEM CELLS (MIAMISBURG), (2000), vol. 18, No. 4, ISSN 1066-5099, pp. 245-251, XP002552170.

Bersinger et al., "Effect of Late Pregnancy Serum on the Synthesis and Release of Pregnancy Proteins by the Perfused Human Term Placenta," Reprod. Fertil. Dev. 4:585-588 (1992).

Berlolini, et al. "Retrovirus-Mediated Transfer of the Multidrug Resistance Gene into Human Haemopoietic Progenitor Cells." Haemolotol. 88:318-324 (1994).

(56) References Cited

OTHER PUBLICATIONS

Bloxam et al., "Culture of Syncytiotrophoblast for the Study of Human Placental Transfer. Part I: Isolation and Purification of Cytotrophoblast," Placenta 18:93-98 (1997).
Bloxam, "Human Placental Trophoblast Culture: One-Sided and Two-Sided Models," Proceedings of the Nutrition Society 50:349-354 (1991).
Bullen et al., "Two-Sided Culture of Human Placental Trophoblast, Morphologyimmunocytochemistry and Permeability Properties," Placenta 11:431-450 (1990).
Burger et al., 1999, "Development of an infusible-grade solution for non-cryopreserved hematopoietic cell storage", Cytotherapy, 1(2):123-133.
Campagnoli, et al., "Identification of Mesenchymal Stem/Progenitor Cells in Human First-Trimester Fetal Blood, Liverand Bone Marrow." Blood 98(8):2396-402 (2001).
Caniggia et al., "Oxygen and Placental Development During the First Trimester: Implications for the Pathophysiology of Pre-Eclampsia," PubMed, Placenta 21(Suppl A):S25-30 (2000).
Caplan, "The Mesengenic Process," ClinPlast Surg (1994) 21(3):429-435.
Cardoso et al. "Release from Quiescence of CD34+ CD38-Human Umbilical Cord Blood Cells Reveals Their Potentiality to Engraft Adults," Proc. Natl. Acad. Sci, USA Sep. 15, 1993, vol. 90, No. 18, pp. 8707-8708.
Carter et al., "Characterization of MSC Potential to Treat GVHD Using Molecular Markers Linked to MSC-Mediated Immunosuppression in Vitro," Blood, 106(11) part 2, Abstract No. 4322, 160B (2005).
Cester et al., "Cation Transport Across Cultured Trophoblast Membrane in Preeclampsia," Clin. and Exper. Hyper. In Pregnancy, B11(1):59-69 (1992).
Chan, et al., "Placental Mesenchymal Stem Cells," Am. J. Obstet. Gynecol. 196(2):e18-e19 (2007).
Chang, et al., "Placenta-Derived Multipotent Cells Exhibit Immunosuppressive Properties That Are Enhanced in the Presence of Interferon-gamma," Stem Cells 24:2466-2477 (2006).
Chao, et al., "Stem Cell Transplantation (Cord Blood Transplants)." American Society of Hematology pp. 354-371 (2004).
Chen et al., "The Potential for the Use of Mononuclear Cells from Human Umbilical Cord Blood in the Treatment of Amyotrophic Lateral Sclerosis is SOD1 Mice," J. Med. 31(1-2):21-30 (2000).
Chen, et al. "Intravaneous Administration of Human Umbilical Cord Reduces Behavioral Deficits after Stroke in Rats," Stroke 32(11): 2682-2688 (2001).
Chen, et al., "Therapeutic Benefit of Intravenous Administration of Bone Marrow Stromal Cells after Cerebral Ischemia in Rats," Stroke, 32(4):1005-11 (2001).
Chien, "Red Cell Deformability and Its Relevance to Blood Flow," Ann. Rev. Physiol. 49:177-192 (1987).
Chies et al., "Sickle Cell Disease: A Chronics Inflammatory Condition," Medical Hypotheses 57(1):46-50 (2001).
Chin, et al., "Enhanced Interferon Production and Lymphokine-Activated Cytotoxicity of Human Placental Cells," Cellular Immunology 113:1-9 (1988).
Clark, et al., "Placental Trophoblast from Successful Human Pregnancies Expresses the Tolerance Signaling Molecule, CD200 (OX-2)" Am. J. Reprod. Immunol., 50(3):187-195 (2003).
Conget et al. "Phenotypical and functional properties of human bone marrow mesenchymal progenitor cells" Journal of Cellular Physiology 181:67-73 (1999).
Contractor et al., "A comparison of the effects of different perfusion regimens on the structure of the isolated human placental lobule," Cell Tissue Res. 237:609-617 (1984).
Cord Blood Stem Cell, Mesh Term Database, 2003.
Cosma, et al., "Use and Application of Stem Cells in Toxicology," SOT 2003 Annual Meeting, p. 4, Abstract # 19.

Cotte et al., "Preparation of Highly Purified Cytotrophoblast from Human Placenta with Subsequent Modulation to Form Syncytiotrophoblast in Monolayer Cultures," In Vitro 16(8):639-646 (1980).
Czarneski et al., "Effects of Cord Blood Transfer on the Hematopoietic Recovery Following Sublethal Irradiation in MRL 1pr/1pr Mice," Proc. Soc. Exp. Biol. Med. 220(2):79-87 (1999).
Dallas, et al., "Enhanced T Cell Reconstitution by Hematopoietic Progenitors Expanded ex vivo Using The Notch Ligand Delta1," Blood 109:3579-3587 (2007).
Davani, et al., "Mesenchymal Progenitor Cells Differentiate into an Endothelial Phenotype, Enhance Vascular Densityand Improve Heart Function in a Rat Cellular Cardiomyoplasty Model," Circulation 108[suppl II]:II-253-II-258 (2003).
Davies et al., "Thalidomide and Immunomodulatory Derivatives Augment Natural Killer Cell Cytotoxicity in Multiple Myeloma," Blood 98(1):210-216 (2001).
Davies, et al., "Engraftment and Survival After Unrelated-Donor Bone Marrow Transplantation: a Report from the National Marrow Donor Program," Blood, 96(13): 4096-4102(2000).
Davila, et al., "Use and Application of Stem Cells in Toxicology," Toxicological Sciences 79:214-223 (2004).
De Coppi et al., "Amniotic Fluid and Chorionic Villi Derived Human Stem Cells for the Engineering of Tissues in Vivo," The Journal of Urology, vol. 171, No. 4, Supplement, Saturday, May 8, 2004, p. 21, Abstract # 81.
De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93.
De Coppi, et al., "Pluripotent Stem Cells Derived from Human Chorionic Villi and Amniotic Fluid for Tissue Engineering Applications." Experimental Biology/IUPS Meeting Abstracts, A1366, Abstract #781.7 (2005).
De Coppi, et al., "Human fetal stem cell isolation from amniotic fluid for tissue reconstruction," J. Urology 167(4 Supp.) 85 (Abstract # 338) (2002).
De Filippo, et al., "Total Penile Urethra Replacement with Autologous Cell-Seeded Collagen Matrices." Urology and Reproductive Surgery, vol. 195, No. 3S, Sep. 2002, p. S95.
De Wynter, et al., "CD34+AC133+ Cells Isolated from Cord Blood are Highly Enriched in Long-Term Culture-Initiating Cells, NOD/SCID-Repopulating Cells and Dendritic Cell Progenitors," Stem Cells 16(6):387-396 (1998).
Denison et al., "Cytokine Secretion by human fetal membranesdecidua and placenta at term" Human Reproduction 13(12):3560-3565 (1998).
Dominici, et al., "Minimal Criteria for Defining Multipotent Mesenchymal Stromal Cells. The International Society for Cellular Therapy Position Statement" Cytotherapy 8(4):315-317 (2006).
Dorrel, "Expansion of Human Cord Blood CD34+CD38-Cells in ex vivo Culture during Retroviral Transduction without a Corresponding Increase in SCID Repopulation cell (SRC) Frequency: Dissociation of SRC Phenotype and Function," Blood 95(1): 102-110 (2000).
Drake, et al., "Human Placental Cytotrophoblasts Attract Monocytes and CD56 (Bright) Natural Killer Cells Via the Actions of Monocyte Inflammatory Protein 1 Alpha," J. Exp. Med. 193(10):1199-1212 (2001).
Dubick et al, "Issues of Concern Regarding the Use of Hypertonic/Hyperoncotic Fluid Resuscitation of Hemorrhagic Hypotension," Shock 25(4):321-328 (2006).
Dubick, et al., "Small-volume Fluid Resuscitation for the Far-Forward Combat Environment: Current Concepts." J. Trauma. 54(5):S43-S45 (2003).
Dushnik-Levinson, et al., "Embryogenesis in Vitro: Study of Differentiation of Embryonic Stem Cells." Biol. Neonate. 67(2):77-83, 1995.
Elchalal et al., "Postpartum Umbilical Cord Blood Collection for Transplantation: a Comparison of Three Methods," Am. J. of Obstetrics & Gyn. 182(1 Pt 1):227-232 (2000).

(56) References Cited

OTHER PUBLICATIONS

Emerson, et al., "Ex vivo Expansion of Hematopoietic Precursors, Progenitors and Stem Cells: the Next Generation of Cellular Therapeutics," Blood 87(8):3082-3088 (1996).
Ende et al., "Hemapoetic Transplantation by Means of Fetal (Cord) Blood: A New Method," Va. Med. Mon. 99:276-280 (1972).
Ende et al., "Human Umbilical Cord Blood Cells Ameliorate Huntington's Disease in Transgenic Mice," J. Med. 32(3-4):231-240 (2001).
Ende et al., "Parkinson's Disease Mice and Human Umbilical Cord Blood," Journal of Medicine 33(1-4):173-180 (2002).
Ende et al., "Pooled Umbilical Cord Blood as a Possible Universal Donor for Marrow Reconstitution and Use in Nuclear Accidents," Life Sci. 69:1531-1539 (2001).
Ende et al., "The Effect of Human Cord Blood on SJL/J Mice After Chemoablation and Irradiation and Its Possible Clinical Significance," Immunol. Invest. 24(6):999-1012 (1995).
Ende, et al. "Collection of Umbilical Cord Blood for Transplantation." Blood 80(6): 1623-1624 (1992).
Ende, et al., "Human Umbilical Cord Blood Cells Amerliorate Alzheimer's Disease in Transgenic Mice," J. Med. 32(3-4):241-7 (2001).
Ende, et al., "Human Umbilical Cord Blood Effect on SOD Mice (Amyotrophic Lateral Sclerosis)," Life Sci. 67(1):53-59 (2000).
Ende, N., "Berashis Cells in Human Umbilical Cord Blood vs. Embryonic Stem Cells," Journal of Medicine (2002) 33(1-4):167-171.
Ende, N., et al., "The Feasibility of Using Blood Bank-Stored (4 Degrees C) Cord Blood, Unmatched for HLA for Marrow Transplantation," Am. J. Clin. Pathol. (1999) 111(6)773-81.
Erices, et al., "Mesenchymal Progenitor Cells in Human Umbilical Cord Blood," Br. J. Haemotol. 109(1):235-242 Abstract (2000).
Ernst, et al., "Blood Rheology in Patients with Transient Ischemic Attacks," Stroke 19:634-636 (1988).
Evans, "Stem Cell Therapy: Moving towards Reality," Am. J. Obstet. Gynecol. 194:662-663 (2006).
Fasouliotis, et al., "Human umbilical cord blood banking and transplantation: a state of the art," Eur. J. Obstet. Gynecol. Reprod. Biol. 90(1):13-25 (2000).
Fassas, et al., "Autologous Stem Cell Transplantation in Progressive Multiple Sclerosis--an Interim Analysis of Efficacy," J. Clin. Immunol., 20(1):24-30 (2000).
Fisher et al., "Adhesive and Degradatie Properties of Human Placental Cytotrophoblast Cells In Vitro," Journal of Cell Biology 109:891-902 (1989).
Frank H G et al., "Cell culture models of human trophoblast: primary culture of trophoblast-a workshop report." Placenta Apr. 2001, (Apr. 2001), vol. 22, Suppl A, ISSN 0143-4004, pp. S107-S109, XP002443188.
Genbacev et al., "Regulation of Human Placental Development by Oxygen Tension," 277(5332):1669-1672 (1997).
Gerlach, et al., "Current State of Stem Cell Research for the Treatment of Parkinson's Disease"J. Neurol. (Suppl 3):III/33-III/35 (2002).
Gerlach, et al., "Use of Primary Human Liver Cells Originating from Discarded Grafts in a Bioreactor for Liver Support Therapy and the Prospects of Culturing Adult Liver Stem Cells in Bioreactors—a Morphologica Study," Transplantation 76(5):781-786 (2003).
Giarratana, et al., "Ex vivo Generation of Fully Mature Human Red Blood Cells from Hematopoietic Stem Cells," Nat. Biotech. 23:69-74 (2005).
Gluckman et al., "Results of Unrelated Umbilical Cord Blood Hematipoietic Stem Cell Transplant," Transfusion Clinique el Biologique 8(3):146-154 (2001).
Gluckman et al., "Cord Blood Heamatopoietic Stem Cells: Biology and Transplantation," In: Hematology, American Society of Hematology Education Program Book p. 1-14. (1998).
Graham, 1998, "Hydrogels: Their Future, Part I," Med. Device Tech., 9(1):18-22.

Greenwood et al., "Membrane Potential Difference and Intracellular Cation Concentrations in Human Placental Trophoblast Cells in Culture," Journal of Physiology 492.3:629-640 (1996).
Hadjantonakis, et al., "The Stem Cells of Early Embryos," Differentiation 68:159-166 (2001).
Hamada, et al., "Mesenchymal Stem Cells (MSC) as Therapeutic Cytoreagents for Gene Therapy," Cancer Sci 96:149-156 (2005).
Hansen et al., "Differential Alteration by Thalidomide of the Glutathione Content of Rat vs. Rabbit Conceptuses in Vitro," Reprod Toxicol13: 547-554 (1999).
Harbacheuski, et al., "Placenta Derived Adherent Cells (PDACs) Supress Tumor Cells of Diverse Origin." Blood, vol. 108, No. 11, Part 2, Nov. 2006 (Nov. 2006), p. 288b. Abstract # 4813.
Harun et al., "Cytotrophoblast Stem Cell Lines Derived from Human Embyonic Stem Cells and Their Capacity to Mimic Invasive Implantation Events," Human Reproduction, Oxford University Press, pp. 1-10 (2006).
Hattori et al., "Molecular Cloning of Adipocyte-Derived Leucine Aminopeptidase Highly Related to Placental Leucine Aminopeptidase/Oxytocinase," J. Biochem. 125(5):931-938 (1999).
Hatzopoulos et al. "Isolation and characterization of endothelial progenitor cells from mouse embryos," Development. 125(8):1457-68 (1998).
Heidaran, Disclosure Document No. 457045 for "A Method or Process for the Treatment of Degenerative Conditions or Cancer Employing Custom Fabricated Organ Tissue Grafts Using Cells Isolated, Expanded, and Stored at Birth", 15 pages, stamped by OIPE on May 28, 1999, paper dated May 13, 1999.
Herrera, et al., "Mesenchymal Stem Cells Contribute to the Renal Repair of Acute Tubular Epithelial Injury," Int. J. Mol. Med., 14(6): 1035-41 (2004).
Himori et al., "Chemotherapeutic Susceptibility of Human Bone Marrow Progenitor Cells and Human Myelogenous Leukemia Cells (HL-60) in Co-Culture: Preliminary Report," Int. J. Cell Cloning, 2(4):254-262 (1984).
Hirano et al., "CD9 is Expressied in Extravillous Trophoblasts in Association with Integrin alpha3 and integrin alpha5," Molecular Human Reproduction 5(2):162-167 (1999).
Hirashima et al., "Maturation of embryonic stem cells into endothelial cells in an in vitro model of vasculogenesis," Blood. 93(4):1253-63 (1999).
Hoek R M,et al, "Down-regulation of the macrophage lineage through interaction with OX2 (CD200)", Science, American Association for the Advancement of Science, (20001201), vol. 290, No. 5497, doi:10.1126/science.290.5497.1768, ISSN 0036-8075, pp. 1768-1771, XP002263649.
Hows, "Status of Umbilical Cord Blood Transplantation in the Year 2001," J Clin Pathol 54(6):428-434(2001).
Hoynowski, et al., "Characterization and Differentiation of Equine Umbilical Cord-Derived Matrix Cells," Biochemical and Biophysical Research Communications; 362:347-53 (2007).
Hsieh et al. "Effects of glucose on placental hormones in the human term placenta in vitro" J. Formos. Med. Assoc. 96:309-313 (1997).
Huss et al., "Perspectives on the Morphology and Biology of CD34-Negative Stem Cells," J. Hematotherapy Stem Cell Res., 9(6):783-793 (2000).
Huss, "Isolation of Primary and Immortalized CD34-Hematopoietic and Mesenchymal Stem Cells from Various Sources," Stem Cells 18:1-9 (2000).
Igura, et al., "Isolation and Characterization of Mesencymal Progenitor Cells from Chorionic Villi of Human Placenta," Cytotherapy 6(6): 543-553 (2004).
Ilan E et al, "The hepatitis B virus-trimera mouse: a model for human HBV infection and evaluation of anti-HBV therapeutic agents.", Hepatology, (Feb. 1999), vol. 29, No. 2, ISSN 0270-9139, pp. 553-562, XP009000359 [XY] 7-17 * the whole document.
Ilan E et al, "The hepatitis C virus (HCV)-Trimera mouse: a model for evaluation of agents against HCV.", The Journal of Infectious Diseases, (Jan. 15, 2002), vol. 185, No. 2, ISSN 0022-1899, pp. 153-161, XP008025444 [XY] 7-17 * the whole document *.
Ilancheran, et al., "Stem Cells Derived from Human Fetal Membranes Display Muttilineage Differentiation Potential," Biology of Reproduction, 77, 577-588 (2007).

(56) References Cited

OTHER PUBLICATIONS

Ino et al., "Expression of Placental Leucine Aminopeptidase and Adipoctye-Derived Leucine Aminopeptidase in Human Normal and Malignant Invasive Trophoblastic Cells" Laboratory Investigation 83(12):1799-1809 (2003).
Iwasaki, "Recent Advances in the Treatment of Graft-Versus-Host Disease," Clin. Med. Res. 2(4):243-52 (2004).
Jaiswal, et al., "Osteogenic Differentiation of Purified, Culture-Expanded Human Mesenchymal Stem Cells in vitro," J. Cell Biochem. 64(2):295-312 (1997).
James et al., "Cytotrophobast Differentiation in the First Trimester of Pregnancy: Evidence for Separate Progenitros of Extravillous Trophoblasts and Syncytiotrophoblast," Reproduction 130:95-130 (2005).
Jaroscak et al., "Preliminary characterization of the surface staining of placental derived adherent cells: a potential new source of stroma for umbilical cord blood (UCB) expansion," Blood 96(11, Pt 2) (2000) Abstract # 4348 p150b.
Jiang et al., "Hypoxia Prevents Induction of Aromatase Expression in Human Trophoblast Cells in Culture: Potential Nihibitory Role of the Hypoxia-Inducible Transcription Factor Mash-2 (Mammalian Achaete-Scute Homologous Protein-20," Molecular Endocrinology 14(10):1661-1673 (2010).
Jing, et al. "Blood Progenitor Cell Separation from Clinical Leukapheresis Product by Magnetic Nanoparticle Binding and Magnetophoresis," Biotechnol. Bioeng. 96(6):1139-1154 (2007).
Jones et al., "Isolation and Characterization of Bone Marrow Multipotential Mesenchymal Progenitor Cells," Arthritis Rheum. 46(12):3349-3360 (2002).
Jones et al., "Ultrastructure of the Normal Human Placenta," Electron Microsc. 4:129-178 (1991).
Kameneva et al., "Mechanisms of Red Blood Cell Trauma in Assisted Circulation. Rheologic Similarities of Red Blood Cell Transformations due to Natural Aging and Mechanical Stress," ASAIO J. 41:457-460 (1995).
Kameneva, et al., "Heparin Effect on Red Blood Cell Aggregation," Biorheology, 31(3):297-304 (1994).
Kameneva, et al., "Mechanical Trauma to Blood," In: Handbook of Hemorheology and Hemodynamics 206-227 (IOS Press, 2007).
Kameneva, et al., "Red Blood Cell Aging and Risk of Cardiovascular Diseases," Clin. Hemorheol. Microcirc. 8:67-74 (1998).
Kameneva, et al., "Rheologic Dissimilarities in Female and Male Blood: Potential Link to Development of Cardiovascular Diseases," Advances in Experimental Medicine and Biology 530:689-696 (2003).
Kao et al., "The Human Villous Cytotrophoblast: Interactions with Extracellular Matrix Proteins, Endocrine Function, and Cytoplasmic Differentiation in the Absence of Syncytium Formation," Developmental Biology 130:693-702 (1988).
Kato et al., "Discordant Secretion of Placental Protein Hormones in Differentiating Trophoblasts in Vitro," Journal of Clinical Endocrinology and Metabolism 68(4):814-820 (1989).
Kaufmann et al., "Extravillous Trophoblast in the Human Placenta," Trophoblast Research 10:21-65 (1997).
Kawata et al., "Transcriptional Control of HLA-A,B,C Antigen in Human Placental Cytotrophoblast Isolated Using Trophoblast-and HLA-Specific Monoclonal Antibodies and the Fluorescence-Activated Cell Sorter," J. Exp. Med. 160(3):633-51 (1984).
Kliman et al., "Purification, Characterization, and In Vitro Differentiation of Cytotropholblasts from Human Term Placentae," Endocrinology 118(4):1567-1582 (1986).
Koc, et al., "Rapid Hematopoietic Recovery After Coinfusion of Autologous-Blood Stem Cells and Culture-Expanded Marrow Mesenchymal Stem Cells in Advanced Breast Cancer Patients Receiving High-Dose Chemotherapy," J Clin Oncol 18:307-316 (2000).
Koh, et al., "Parthenolgenetically Derived Stem Cells for Urologic Reconstruction." The Journal of Urology, vol. 171, No. 4, Supplement, Saturday, May 8, 2004, p. 21, Abstract 82.

Kolf, et al., "Biology of adult mesenchymal stem cells: regulation of niche, self-renewal and differentiation," Arthritis Research & Therapy 2007, 9:204.
Korbling et al., "Hepatocytes and Epithelial Cells of Donor Origin in Recipients of Peripheral-Blood Stem Cells," N. Engl. J. Med. 346(10):738-746 (2002).
Korbling, et al., "Peripheral Blood Stem Cell Versus Bone Marrow Marrow Allotransplantation: Does the Source of Hematapoietic Stem Cells Matter?" Blood 98(10):2900-2908 (2001).
Kucia et al., "Bone Marrow as a Home of Heterogenous Populations of Non Hematopoietic Stem Cells," Leukemia vol. 19: 1118-1127(2005).
Kurtzberg, "Placental Blood as a Source of Hematopoietic Stem Cells for Transplantation into Unrelated Recipients," N. Engl. J. Med. 335:157-166 (1996).
Landon et al., "The Effects of Ethanol Methotrexate and Diphenylhydantoin on [14C] Leucine Incorporation by Human Trophoblasst Cells Cultured In Vitro," British Journal of Obstetrics and Gynaecology 94:252-255 (1987).
Lazarus, et al., "Cotransplantation of HLA-Identical Sibling Culture-Expanded Mesenchymal Stem Cells and Hematopoietic Stem Cells in Hematologic Malignancy Patients, Biol Blood Marrow Transplant," 11(5):389-398 (2005).
Le Blanc, et al., "Treatment of Severe Acute Graft-Versus-Host Disease With Third Party Haploidentical Mesenchvmal Stem Cells," Lancet; 363(9419):1439-41 (2004).
Lebkowski, et al., "Serum and Plasma Levels of FGF-2 and VEGF in Healthy Blood Donors," Cancer J. 7(Suppl 2):583-593 (2001).
Leonard, et al., "The Role of ABC Transporters in Clinical Practice," Oncologist. 8:411-424 (2003).
Li et al., "Mesenchymal Stem Cells Derived from Human Placenta Suppress Allogenic Umbilical Cord Blood Lymphocyte Proliferation." Cell Res. 15(7): 539-547 (2005).
Li Xin et al, "Human Placenta-Derived Adherent Cells Prevent Bone loss, Stimulate Bone formation, and Suppress Growth of Multiple Myeloma in Bone", Stem Cells, (Miamisburg), (Nov. 23, 2010), vol. 29, No. 2, ISSN 1066-5099, pp. 263-273, XP002631698.
Lin, et al. "Murine CD200(+)CK7(+) trophoblasts in a poly (LC)-induced embryo resorption model." Reproduction (Cambridge), vol. 130, No. 4, pp. 529-537, XP002443406 ISSN: 1470-1626 (Oct. 2005).
Lindberg et al., "Apoptosis in Refractory Anaemia With Ringed Sideroblasts Is Initiated a the Stem Cell Level and Associated With Increased Activation of Caspases," British Journal of Haematoloty 112(3):714-726 (2001).
Lipinski et al., "Human Trophoblast Cell-Surface Antigen Defined By Monoclonal Antibodies," Proc. Natl. Acad. Sci. USA, Medical Sciences 78(8):5147-5150 (1981).
Loke et al., "Identification of Cytotrophoblast Colonies in Cultures of Human Placental Cells Using Monoclonal Antibodies," Placenta 7:221-231 (1986).
Lorkowski, et al., "ABCG Subfamily of Human ATP-Binding Cassette Proteins," Pure Appl. Chem. 74(11):2057-2081 (2002).
Lowy et al., "Isolation of transforming DNA: cloning the hamster aprt gene," Cell. 22(3):817-23 (1980).
Ma et al., "Developement of an in vitro Human Placenta Model by the Cultivation of Human Trophoblasts in a Fiber-Based Bioreactor System," Tissue Engineering 5, 91-102 (1999).
Ma et al., "Human Umbilical Cord Wharton's Jelly-Derived Mesenchymal Stem Cells Differentiation into Nerve-Like Cells," Chinese Med. Jour., 118(23):1987-1993 (2005).
Mackay, et al., "Chondrogenic Differentiation of Cultured Human Mesenchymal Stem Cells from Marrow," Tissue Engineering; 4(4):415-28 (1998).
Madri et al., "Capillary Endothelial Cell Cultures: Phenotypic Modulation by Matrix Components," J. Cell Biol. 97:153-165 (1983).
Magatti et al., "Human Amnion Mesenchyme Harbors Cells with Allogeneic T-Cell Suppression and Stimulation Capabilities," Stem Cells 26:182-192 (2008).
Malek et al., "Lack of transport of erythropoietin across the human placenta as studied by an in vitro perfusion system," European Journal of Physiology 427:157-161 (1994).

(56) References Cited

OTHER PUBLICATIONS

Malik et al, "An in vitro Model of Human Red Blood Cell Production from Hematopoietic Progenitor Cells," Blood 91:2664-2671 (1998).
Marascalco, et al., "Development of Standard Tests to Examine Viscoelastic Properties of Blood of Experimental Animals for Pediatric Mechanical Support Device Evaluation," ASAIO J. 52:567-574 (2006).
Marmont, "New Horizons in the Treatment of Autoimmune Diseases: Immunoablation and Stem Cell Transplantation," Ann. Rev. Medicine 51:115-134 (2000).
McMaster, M. et al, "Human Placental HLA-G Expression is Restricted to Differentiated Cytotrophoblasts," Journal ofImmunology, The Williams and Wilkins Co. (1995) 154(8): 3771-3778.
Melchner, et al., "Human placental conditioned medium reverses apparent commitment to differentiation of human promyelocytic leukemia cells (HL60)," Blood. (1985) 66(6): 1469-72.
Melnik, et al., "Evaluation of Eluants from Batch Separations of CD34(+) Cells from Human Cord Blood Using a CommerciaIImmunomagnetic Cell Separation System," Biotechnol. Prog. 17(5):907-916 (2001).
Melville, et al., "Direct Magnetic Separation of Red Cells from Whole Blood," Nature 255:706 (1975).
Meng et al., J. Biomaterials Sci., Polymer Edition 18(1):81-94 (2007).
Miki et al., "Isolation of Multipotent Stem Cells from Placenta." AASLD Abstracts, Hepatology, Abstract # 279, p. 290A (Oct. 2003).
Miki et al., "Stem Cell Characteristics of Amniotic Epithelial Cells," Stem Cells Express, published online Aug. 9, 2005; doi:10.1634/stemcells.2004-0357, pp. 1-32.
Miki, et al., "Production of Hepatocytes from Human Amniotic Stem Cells." Hepatology, Abstract # 20, vol. 36, No. 4, Pt. 2 (2002) 171A.
Minguell, et al., "Mesenchymal Stem Cells," Exp. Biol. Med. 226:507-520 (2001).
Moore et al., "A Simple Perfusion Technique for Isolation of Maternal Intervillous Blood Mononuclear Cells from Human Placentae," J. Immunol. Methods 209(1):93-104 (1997).
Moreau et al., "Myofibroblastic Stromal Cells Isolated From Human Bone Marrow Indue the Proliferation of Both Early Myeloid and B-Lymphoid Cells," Blood 82:2396-2405 (1993).
Morgan et al., "Human Placental Cell Culture," Biochemical Society Transactions 12: 317-318 (1984).
Morgan et al., "Long-Term Culture of Human Trophoblast Cells," British Journal of Obstetrics and Gynaecology 92:84-92 (1985).
Morigi, et al., "Mesenchymal Stem Cells are Renotropic, Helping to Repair the Kidney and Improve Function in Acute Renal Failure," J. Am. Soc. Nephrol., 15(7): 1794-1804 (2004).
Morishima, et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," Blood, 2002; 99(11):4200-06.
Morrish et al., "Epidermal Growth Factor Induces Differentiation and Secretion of Human Choronic Gonadotropin and Placental Lactogen in Normal Human Placenta," Journal of Clinical Endocrinology and Metabolism 65(6):1282-1290 (1987).
Morrish et al., "In Vitro Cultured Human Term Cytotrophoblast: A Model for Normal Primary Epitehlial Cells Demonstrating a Spontaneous Differentiation Programme that Requires EGF for Extensive Development of Syncytium," Placenta 18: 577-585 (1997).
Muhlemann et al., "Cytomegalovirus in the Perfused Human Term Placenta In Vitro," Placenta (1995) 16:367-373.
Myllynen, "In Search of Models for Hepatic and Placental Pharmacokinetics" Dissertation, Univeristy of Oulu (2003).
Nadkarni et al., "Effect of Retinoic Acid on Bone-Marrow Committed Stem Cells (CFU-c) from Chronic myeloid Leukemia Patients," Tumori. 70(6):503-505 (1984).

Nagayama et al., "Immunological reconstitution after cord blood transplantation for an adult patient", Bone Marrow Transplantation 24: 211-213 (1999).
Nguyen et al., 2002, "Photopolymerizable Hydrogels for Tissue Engineering Applications," Biomaterials, 23(22):4307-4314.
Ninichuk, et al., "Multipotent Mesenchymal Stem Cells Reduce Interstitial Fibrosis but do not Delay Progression of Chronic Kidney Disease in Collagen4a3-Deficient Mice," Kidney Int.; 70(1):121-29 (2006).
Nishishita, et al., "A Potential Pro-Angiogenic Cell Therapy with Human Placenta-Derived Mesenchymal Cells," Biochem. Biophys. Res. Commun. 325(1):24-31 (2004).
Noort et al., "Mesenchymal Stem Cells Promote Engraftment of Human Umbilical Cord Blood-Derived CD34+ Cells in NOD/SCID Mice," Experimental Hematology 30(8):870-878 (2002).
Notice of Opposition by Farmindustria S.A. to corresponding claims filed in Peru; English translation Jan. 18, 2008.
Ordi, et al., "Massive Chronic Intervilllositis of the Placenta Associated with Malaria Infection," Am. J. Surg. Pathol. 8:1006-1011 (1998).
Paludan, et al., "Immune Suppression by Placenta Derived Adherent Cells (PDAC) Correlate with Monocyte Chemoattractant Protein-1 and 1 L-2 Secretion," Blood 108(11) Part II, p. 48B (2006) (abstract #3883).
Paludan, et al., "Placental Derived Stem Cells (PDAC) Suppress the Allo-MLR and the EBV Regression Assay," http://www.call4abstract.com/hem/finalpreview.php?absnum=552996 (2006). Abstract# 1737.
Pande et al., "Isolation and Culture of Hamster Ectoplacental Cone Trophoblasts: an In Vitro Study on the Cell Types and Their Growth Pattern," Cell Prolif. 29:163-171 (1996).
Panepucci et al., "Comparison of Gene Expression of Umbilical Cord Vein and Bone Marrow-Derived Mesenchymal Stem Cells," Stem Cells 22(7): 1263-78 (2004).
Papaioannou et al., "Stem Cells from Early Mammalian Embryos" Stem Cells Handbook:19-31 (2004).
Parolini O et al, "Concise Review: Isolation and Characterization of Cells from Human Term Placenta: Outcome of the First International Workshop on Placenta Derived Stem Cells", Stem Cells, Alphamed Press, Dayton, OH, US LNKD-DOI:10.1634/Stemcells.2007-0594, vol. 26, No. 2, ISSN 1066-5099, (Feb. 1, 2008), pp. 300-311, (Nov. 1, 2007), XP002567088.
Pauling, et al., "The Magnetic Properties and Structure of the Hemochromogens and Related Substances," Proc. Natl. Acad. Sci. USA 22:159-163 (1936).
Pellegrini, et al., "FADD and Caspase-8 Are Required for Cytokine-Induced Proliferation of Hemopoietic Progenitor Cells," Blood 106(5):1581-1589 (2005).
Peppas et al., 2000, "Hydrogels in Pharmaceutical Formulations," Eur. J. Pharm. Biopharm., 50(1):27-46.
Pera, et al., "Human Embryonic Stem Cells," J. Cell. Sci. 113:5-10 (2000).
Pesce, et al., "Oct. 4: Gatekeeper in the Beginnings of Mammalian Development," Stem Cells 19:271-278 (2001).
Petroff et al., "Isolation and Culture of Term Human Trophoblast Cells," Methods in Molecular Medicine, Placenta and Trophoblast, 1(16):203-217 (2006).
Pittenger, et al., "Multilineage Potential of Adult Human Mesenchymal Stem Cells." Science, American Association of Science, vol. 284, No. 5411, Apr. 2, 1999, pp. 143-147.
Pluchino et al., "Neural Stem Cells and Their Use as Therapeutic Tool in Neurological Disorders," Brain Res Brain Res. Rev. 48(2):211-219 (2005).
Ponticiello et al., "Gelatin-Based Resorbable Sponge as a Carrier Matrix for Human Mesenchymal Stem Cells in Cartilage Regeneration Therapy" Journal of Biomedical Materials Research 52:246-255 (2000).
Portmann-Lanz, et al., "Placental Mesenchymal Stem Cells as Potential Autologous Graft for Pre-and Perinatal Neuroregeneration" Am. J. Obstet Gynecol. 194:664-673 (2006).
Potgens et al., "Human Trophoblast Contains an Intracellular Protein Reactive with and Antibody against CD133—A Novel Marker for Trophoblast," Placenta 22:639-645 (2001).

(56) References Cited

OTHER PUBLICATIONS

Potgens et al., "Monoclonal Antibody CD133-2 (AC141) Against Hematopoeietic Stem Cell Antigen CD133 Shows Crossactivity with Cytokeratin 18," Journal of Histochemistry & Cytochemistry 50(8):1131-1134 (2002).
Pountos, et al., "Mesenchymal Stem Cell Tissue Engineering: Techniques for Isolation, Expansion and Application," Injury Int. J. Care Injured; 38(Supp. 4):523-33 (2007).
Quinn et al., "Mouse Trophoblast Stem Cells," Methods in Molecular Medicine 121(1):125-148 (2005).
Rachmilewitz et al., "Intermediate Cells During Cytottphoblast Differentiation in Vitro," Cell Growth & Differentiation 4:395-402 (1993).
Reubinoff, "Neural Progenitors from Human Embryonic Stem Cells," Nature Biotech. 19(12):1134-1140 (2001).
Reyes et al., Origin of endothelial progenitors in human postnatal bone marrow. J Clin Invest. 109(3):337-46 (2002).
Reyes, et al., "Purification and ex vivo Expansion of Postnatal Human Marrow Mesodermanl Progenitor Cells," Blood 98(9):2615-2625 (2001).
Rielland et al., "Trophoblast Stem Cell Derivation, Cross-species Comparison and Use of Nuclear Transfer: New Tools to Study Trophoblast Growth and Differentiation," Developmental Biology 322:1-10 (2008).
Ringler et al., "In Vitro Systems for the Study of Human Placental Endocrine Function," Endocrine Reviews 11(1):105-123 (1990).
Rong-Hao et al., "Establishment and Characterization of a Cytotrophoblast Cell Line From Normal Placenta of Human Origin," Human Reproduction 11(6):1328-1333 (1996).
Roth, I., et al. "Human Placental Cytotrophoblats Produce the Immunosuppressive Cytokine Interliukin 10," The Journal of Experimental Medicine (1996) 184(2): 539-548.
Rubinstein, et al., "Processing and Cryopreservation of Placental/Umbilical Cord Blood for Unrelated Bone Marrow Re constitution," Proc. Natl. Acad. Sci. USA 92:10119-10122 (1995).
Rudel, "Caspase Inhibitors in Prevention of Apoptosis," Herz 24:236-41 (1999).
Russo, "Fighting Darwin's Battles. Symposium Marks Evolutionist Victory, Anti-Evolution Growth" The Scientist 15:6 (2001).
Sakabe et al., "Functional Differences Between Subpopulations of Mobilized Peripheral Blood-Derived CD34+ Cells Expressing Different Levels of HLA-DR, CD33, CD38 and c-kit Antigens," Stem Cells 15(11):73-81 (1997).
Sakuragawa et al., "Human amniotic epithelial cells are promising transgene carriers for allogeneic cell transplantation into liver," J. Hum. Genet. 45:171-176 (2000).
Saric et al., "An IFN-y-induced Aminopeptidase in the ER, ERAP I, Trims Precursors to MHC Class I-presented Peptides," Nature Immunology 3(12):1169-1176 (2002).
Savicki, et al., "Magnetic Susceptibility of Oxy-and Carbonmonoxyhemoglobins," Proc. Natl. Acad. Sci. USA 81:5417-5419 (1984).
Schulz et al., "Human Embryonic Stem Cells as Models for Trophoblast Differentiation," Placenta 29(Suppl A):S10-S16 (2008).
Schutz, et al., "Isolation and Cultivation of Endothelial Cells Derived from Human Placenta," Eur. J. Cell Biol. 395-401 (1996).
Semenov et al. "Multipotent mesenchymal stem cells from human placenta: critical parameters for isolation and maintenance of sternness after isolation" American Journal of Obstetrics & Gynecolocy 202:193.e1-13 (2010).
Serafini, et al., "Pluripotency in Adult Stem Cells: State of the Art," Semi. Reprod. Med. 24:379-388 (2006).
Shah et al., 1999, "Synthesis and enantiomeric separation of 2-phthalimidino-glutaric acid analogues: potent inhibitors of tumor metastasis," J. Med. Chem. 42:3014-3017.
Shamblott et al., "Derivation of Pluripotent Stem Cells from Cultured human Primordial Germ Cells," Proc. Natl. Acad. Sci. USA 95(23):13726-13731 (1998).
Shani, 1985, Nature 314:283.
Sherley, "Asymmetric Cell Kinetics Genes: The Key to Expansion of Adult Stem Cells in Culture", Stem Cell 20:561-72 (2002).
Shi et al., "BAX and Caspase Activity Limit Adult Neural Stem Cell Persistence," Society for Neuroscience Abstract Viewer and Itinerary Planner, vol. 2003, Abstract No. 356-7, & 33rd Annual Meeting of the Society of Neuroscience; New Orleans, LA, USA, Nov. 8-12, 2003.
Shibata et al (Diabetes. 2008; 57: 3099-3107).
Shimazawa et al., "Antiangiogenic activity of tumor necrosis factor-alpha production regulators derived from thalidomide," Biol. Pharm. Bull. 22(2): 224-226 (1999).
Shuto, et al., "Dexamethasone Stimulates Osteoclast-Like Cell Formation by Inhibiting Granulocyte-Macrophage Colony-Stimulating Factor Production in Mouse Bone Marrow Cultures," Endocrinology 134:1121-1126 (1994).
Sikkema-Raddatz, "Four Years' Cytogenetic Experience with the Culture of Chorionic Villi," Prenatal Diagnosis 20:950-955 (2000).
Sirchia, et al., "Placental/Umbilical Cord Blood Transplantation," Haematologica 84:738-747 (1999).
Skelhorne et al., 2002, "Hydrogel Adhesives for Wound-Care Applications," Med. Device Tech., 13(9):19-20 & 22-23.
Slager, Transforming growth factor-beta in the early mouse embryo: implications for the regulation of muscle formation and implantation. Dev Genet. 14(3):212-24 (1993).
Snowden, et al, "Long-term Outcome of Autoimmune Disease Following Allogeneic Bone Marrow Transplantation," American College of Rheumatology, vol. 41:453-459 (1998).
Soma, "Human Trophoblast in Tissue Culture," Obstetrics and Gynaecology 18(6):704-718 (1961).
Soncini et al., "Isolation and Characterization of Mesenchymal Cells from Human Fetal Membranes," J Tissue Eng Regen. Med (2007) 1:296-305.
Southard et al., "Important contents of the UW solution," Transplantation 49(2):251-257 (1990).
Srour et al., "Ex vivo expansion of hematopoietic stem and progenitor cells: are we ther yet?", The Journal of Hematotherapy, (1999), vol. 8, pp. 93-102, XP002909283.
Stanworth, et al., "Stem Cells: Progress in Research and Edging towards the Clinical Setting," Clin. Med. 1(5):378-382 (2001).
Stromberg et al., "Isolation of Functional Human Trophoblast Cells and Their Partial Characterization in Primary Cell Culture," In Vitro 14(7):631-638 (1978).
Stromberg et al., "Methods in Cell Biology, Chapter 10: The Human Placenta in Cell and Organ Culture," 21:227-252 (1980).
Studeny et al., "Bone Marrow-derived Mesenchymal Stem Cells as Vehicles for Interferon-B Delivery into Tumors," Cancer Res. 62:3603-3608 (2002).
Sudo et al., "Mesenchymal Progenitors Able to Differentiate into Osteogenic, Chondrogenic, and/or Adipogenic Cells In Vitro Are Present in Most Primary Fibroblast-Like Cell Populations," Stem Cells, 25: 1610-1617, Publically available Mar. 29, 2007 (2007).
Sunderland et al., "HLA A, B, C Antigens Are Expressed on Nonvillous Trophoblast of the Early Human Placenta," Journal of Immunology 127(6):2614-2615 (1981).
Takahashi E et al, "Induction of CD16(+) CD56(bright) NK cells with antitumour cytotoxicity not only from CD16(-) CD56(bright) NK cells but also from CD16(-) CD56(dim) NK cells", Scandinavian Journal of Immunology, (200702), vol. 65, No. 2, ISSN 0300-9475, pp. 126-138, XP002528954.
Tarrade et al., "Characterization of Human Villous and Extravillous Trophoblasts Isolated from First Trimester Placenta," Laboratory Investigation 81(9):1199-1211 (2001).
Thomson, et al., Embryonic stem cell lines derived from human blastocysts. Science. 282 (5391): 1145-1147 (1998).
Toma et al., "Human Mesenchymal Stem Cells Differentiate to a Cardiomyocyte Phenotype in the Adult Murine Heart," Circulation 105:93-98 (2002).
Travis, "Advances in Therapeutic Approaches to Ulcerative Colitis and Crohn's Disease," Current Gastroenterology Reports 7(6):475-484 (2005).
Truman et al., "Human Placental Cytotrophoblast Cells: Identification and Culture," Arch Gynecol. Obstet. 246:39-49 (1989).

(56) References Cited

OTHER PUBLICATIONS

Truman et al., "The Effects of Substrate and Epidermal Growth Factor on Human Placental Trophoblast Cells in Culture," In Vitro Cellular & Developmental Biology 22(9):525-528 (1986).
Tsai et al., "Functional network analysis of the transcriptomes of mesenchymal stem cells derived from amniotic fluid, amniotic membrane, cord blood, and bone marrow", Stem Cells 25:2511-2523 (2007).
Tse et al., "Suppression of Allogeneic T-Cell Proliferation by Human Marrow Stromal Cells: Implications in Transplantation", Transplantation 75(3):389-397 (2003).
Turner et al., "A modified Harvest Technique for Cord Blood Hematopoietic Stem Cells," Bone Marrow Transplantation 10:89-91 (1992). Abstract.
U.S. Appl. No. 13/584,612, filed Aug. 13, 2012, Hariri et al.
U.S. Appl. No. 13/650,803, filed Oct. 12, 2012, Heidaran et al.
U.S. Appl. No. 13/654,191, filed Oct. 17, 2012 Heidaran et al.
U.S. Appl. No. 13/727,217, filed Dec. 26, 2012, Hariri et al.
U.S. Appl. No. 13/777,391, filed Feb. 26, 2013, Bhatia et al.
U.S. Appl. No. 13/863,308, filed Apr. 15, 2013, Hariri.
U.S. Appl. No. 13/875,650, filed May 2, 2013, Heidaran et al.
Uchida et al., Direct Isolation of Human Central Nervous System Stem Cells, Proc. Natl. Acad. Sci. Usa 97(26): 14720-5 (2000).
Ulloa-Montoya, et al., "Culture Systems for Pluripotent Stem Cells," Journal of Bioscience and Bioengineering; 100(1):12-27 (2005).
Vacanti, et al. "Selective Cell Transportation Using Bioabsorbable Artifical Polymers As Matrices," J. Pediatric Surg. (1998) 23:3.
Vacca et al., 1999, "Bone marrow neovascularization, plasma cell angiogenic potential, and matrix metalloproteinase-2 secretion parallel progression of human multiple myeloma," Blood 93(9):3064-3073.
Van Bekkum, "The Pluripotent Hemopoietic Stem Cell: It's Identification and Applications," Verh. Dtsch. Ges. Patol. 74:19-24 (1990).
Vawda et al., "Stem Cell Therapies for Perinatal Brain Injuries", Seminars in Fetal and Neonatal Medicine, Elsevier, GB 12(4):259-272 (2007).
Veves et al. (Diabetes Care. Oct. 1994; 17(10): 1200-1202) (Year: 1994).
Veves et al. (Pain Medicine. 2008; 9(6): 660-674).
Viacord, Umblicical cord blood can save lives (Informational brochure), Boston: ViaCell CENTR-BRO R1 Oct. 1, 2001.
Wang et al., "Enhanced Recovery of Hematopoietic Progenitor and Stem Cells from Cultivated, Postpartum Human Placenta," Blood 98(11/1): 183a Abstract # 769 (2001).
Wang et al., "Mesenchymal Stem/Progenitor Cells in Human Cord Blood as Support for Ex Vivo Expansion of CD34+ Hematopoietic Stem Cells and for Chondrogenic Differentiation," Haematologica 89(7):837-844 (2004).
Wang et al., Biomaterials 24(22):3969-3980 (2003).
Watanabe, et al, "Multilineage Potential of Human Placenta-Derived Mesenchymal Cells," Blood 100(11):517a, Abstract # 2022 (2002).
Weber et al., "A multicenter, randomized, parallel-group, double-blind, placebo-controlled study of lenalidomide plus dexamethasone versus dexamethasone alone in previously treated subjects with multiple myeloma," Abstract # PO.738, International Multiple Myeloma Workshop, Apr. 10-14, 2005.
Weber, "Thalidomide and Its Derivatives: New Promise for Multiple Myeloma," Cancer Control, vol. 10, No. 5, 375-383, 2003.
Wiesmann et al., "Effects of Caspase Inhibitors on Hematopoietic Engraftment After Short-Term Culture," Cell. Transplant. 11(4):351-358 (2002).
Wiesmann, et al., "no. Reduction of TGF-Beta Induced Apoptosis on Hematopoietic Stem and Progenitor Cells in Vitro by Caspase Inhibitors," Blood 98(11) Part 2, p. 141 b (2001), abstract considered.

Wikipedia: Organ 2010.
Woods et al., "Osomometric and permeability characteristics of human placental/umbilical cord blood CD34+ cells and their application to cryopreservation," J. Hemather. Stem Cell Res. 9(2):161-173 (2000).
Wulf et al. Mesengenic Progenitor Cells Derived from Human Placenta. Tissue Engineering, 2004, vol. 10, pp. 1136-1147.
Xu et al. "Feeder-free growth of undifferentiated human embryonic stem cells" Nature Biotechnology 19:971-974 (2001).
Xu et al., "High Sensitivity of Megakaryocyte Progenitor Cells Contained in Placental/Umbilical Cord Blood to the Stresses During Cryopreservation," Bone Marrow Transplantation 34: 537-543 (2004).
Xu et al., "BMP4 Initiates Human Embryonic Stem Cell Differentiation to Trophoblast," Nature Biology 20:1261-1264 (2002).
Xu et al., 2004, "Aligned biodegradable nanofibrous structure: a potential scaffold for blood vessel engineering," Biomaterials 25:877-886.
Xu et al., Tissue Engineering 10(7): 1160-1168 (2004).
Yan et al., Retinoic acid promotes differentiation of trophoblast stem cells to a giant cell fate. Dev. Biol. 235(2): 422-32 (2001).
Ye et al., "Novel IMiD drugs enhance expansion and regulate differentiation of human cord blood CD34+ cells with cytokines," Blood, Abstract #4099, American Society of Hematology (Dec. 6-10, 2002).
Ye et al., "Recovery of Placental-Derived Adherent Cells with Mesenchymal Stem Cell Characteristics," Blood 98(11/1 ):147b Abstract # 4260 (2001).
Yeger et al., "Enzymatic Isolation of Human Trophoblast and Culture on Various Substrates: Comparison of First Trimester with Term Trophoblast," Placenta 10:137-151 (1989).
Yen et al, "Isolation of multipotent cells from human term placenta" Stem Cells (Dayton, Ohio) 2005, vol. 23(1):3-9, XP002443187 ISSN: 1065-5099 (Jan. 2005).
Yin et al., "AC133, A Novel Marker for Human Hematopoietic Stem and Progenitor Cells," Blood 90(12):5002-5012 (1997).
Young, et al., "Use of Mesenchymal Stem Cells in a Collagen Matrix for Achilles Tendon Repair," 16:4:406-413 (1998).
Young, et al., "Human Pluripotent and Progenitor Cells Display Cell Surface Cluster Differentiation Markers CD10, CD13, CD56, and MHC class-I," Proc Soc Exp Biol Med. 221(1):63-71 (1999).
Yui et al., "Functional, Long-term Cultures of Human Term Trophoblasts Purified by Column-elimination of CD9 Expressing Cells," Placenta 15:231-246 (1994).
Zhang, et al., "Human Placenta-Derived Mesenchymal Progenitor Cells Support Culture Expansion of Long-Term Culture-Initiating Cells from Cord Blood CD34+ Cells." Exp. Hematol. 32(7): 657-664 (2004).
Zhang, et al., "Comparison of Mesenchymal Stem Cells from Human Placenta and Bone Marrow," Chinese Medical Journal, 117(6):882-87 (2004).
Zhang, et al., "Efficient Adena-Associated Virus-Mediated Gene Expression in Human Placenta-Derived Mesenchvmal Cells," Microbiol. Immunol., 47(1):109-16 (2003).
Zhao et al., "Transplanted Human Bone Marrow-Derived Adult Stem Cells Survive and Improve Functional Outcome in a Rat Model of Cortical Ischemic Brain Injury," Experimental Neurology, Academic Press, New York, 164(2):465-466, XP001159669 (2000).
Zhao, et al., "Human Bone Marrow Stem Cells Exhibit Neural Phenotypes After Transplantation and Ameliorate Neurological Deficits with Ischemic Brain Injury in Rats," Abstract of the Annual Meeting of the Society for Neuroscience, Society of Neuroscience, Washington, DC, 26(1/02):860.01, XP001159670 (2000).
Zhao, et al., "Microscopic Investigation of Erythrocyte Deformation Dynamics," Biorheology 43(6):747-65 (2006).
Zhu, et al., "Mesenchymal Stem Cells Derived from Bone Marrow Favor Tumor Cell Growth in vivo," Exp Mol Pathol. 80(3):267-274 (2006).

\* cited by examiner

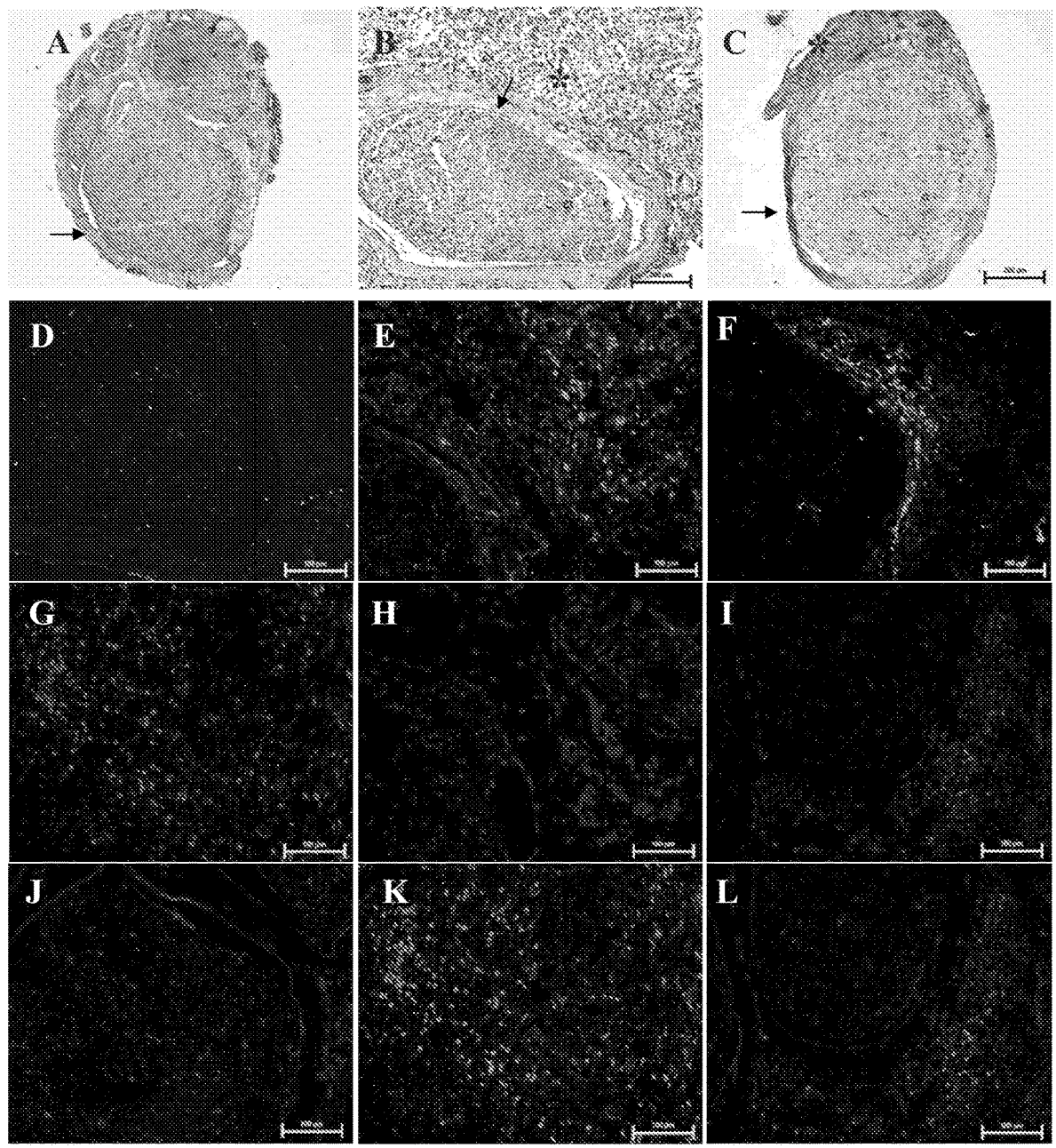
FIG. 8A-L

TREATMENT OF PAIN USING PLACENTAL STEM CELLS

This application claims priority to U.S. Provisional Patent Application No. 61/492,314, filed Jun. 1, 2011, U.S. Provisional Patent Application No. 61/548,663, filed Oct. 18, 2011, and U.S. Provisional Patent Application No. 61/594,985, filed Feb. 3, 2012, the disclosures of each of which are herein incorporated by reference in their entireties.

1. FIELD

Provided herein are methods of ameliorating pain, and of treating individuals having pain, using isolated placental stem cells.

2. BACKGROUND

Because mammalian placentas are plentiful and are normally discarded as medical waste, they represent a unique source of medically-useful stem cells. There is a need in the medical field for improved compositions and methods of suppressing pain. As such, provided herein are placental stem cells, and compositions comprising placental stem cells, useful in the treatment of pain, and methods of using the same to treat pain.

3. SUMMARY

In one aspect, provided herein is a method of treating pain, or abnormal sensory conditions such as dysaesthesia, allodynia and hyperalgesia, in an individual, comprising administering to the individual a therapeutically effective amount of placental stem cells, or culture medium conditioned by placental stem cells, wherein the therapeutically effective amount is an amount sufficient to cause a detectable improvement in said pain. In a specific embodiment, said method comprises identifying an individual in need of pain relief, or an individual suffering from pain. In another specific embodiment, said method additionally comprises determining one or more first levels of pain in said individual prior to administration of said placental stem cells, and determining one or more second levels of pain in said individual after administration of said placental stem cells, wherein said therapeutically effective amount of placental stem cells reduces said one or more second levels of said pain as compared to said one or more first level of pain. In a more specific embodiment, said therapeutically effective amount of placental stem cells results in a detectable improvement in said pain that is greater than, or more long-lasting than, improvement due to administration of a placebo. In a more specific embodiment, said one or more first levels of pain and said one or more second levels of pain are determined by a pain assessment scale. In a more specific embodiment, said pain assessment scale is the Numeric Pain Intensity Scale; the Pain Quality Assessment Scale; the Simple Descriptive Pain Intensity Scale; the Visual Analog Scale; the Wong-Baker FACES Pain Rating Scale; the FLACC scale; the CRIES scale; or the COMFORT scale.

In another specific embodiment, said method additionally comprises determining a first level of one or more physiological indicia of pain in said individual prior to administration of said placental stem cells, and determining a second level of one or more physiological indicia of pain in said individual after administration of said placental stem cells, wherein said therapeutically effective amount of placental stem cells reduces said second level as compared to said first level. In a more specific embodiment, said physiological indicium of pain is heart rate in the individual. In a more specific embodiment, said heart rate in said individual is lower after said administration compared to said heart rate in said individual before said administration. In another more specific embodiment, said physiological indicium of pain is the systolic of said individual. In a more specific embodiment, said systolic of said individual is lower after said administration compared to said systolic in said individual before said administration. In another more specific embodiment, said physiological indicium of pain is the diastolic of said individual. In a more specific embodiment, said diastolic of said individual is lower after said administration compared to said diastolic in said individual before said administration.

In another embodiment of the method of treating pain, said pain is neuropathic pain. In a specific embodiment, said neuropathic pain is caused by diabetic neuropathy. In another specific embodiment, said neuropathic pain is caused by injury to a nerve in said individual. In another specific embodiment, said neuropathic pain is caused by a drug. In certain specific embodiments, said drug is or comprises a platinum-containing anticancer drug, e.g., oxaliplatin, carboplatin or cisplatin, or another chemotherapeutic drug such as paclitaxel or vincristine. In another embodiment, the neuropathic pain is caused by a virus, e.g., a viral disease such as varicella zoster, herpes (e.g., herpes simplex) or human immunodeficiency virus (HIV). Yet in another embodiment the pain is cause by radiation injury, e.g., radiation injury that is part of cancer treatment. In another specific embodiment, said neuropathic pain is caused by inflammation, e.g., neuroinflammation, neuritis.

In another embodiment of the method of treating pain, said pain is inflammatory pain. In another embodiment, said pain is bone pain. In a specific embodiment, said bone pain is associated with or caused by cancer. In another embodiment, said pain is caused by cancer. In another embodiment, said pain is caused by or associated with vulvodynia. In another embodiment, said pain is caused by or associated with interstitial cystitis. In another embodiment, said pain is unresponsive to steroid therapy. In another embodiment, said pain is unresponsive to nonsteroidal anti-inflammatory therapy. In another embodiment, said pain is unresponsive to opioid therapy. In another embodiment, said pain is unresponsive to opiate therapy.

In another aspect, provided herein is a therapeutically effective amount of placental stem cells, or culture medium conditioned by placental stem cells, for use in treating pain in an individual, wherein the therapeutically effective amount is an amount sufficient to cause a detectable improvement in said pain. In one embodiment, said level of pain in said individual before said use and said level of pain in the individual after said use are determined by a pain assessment scale, e.g., the Numeric Pain Intensity Scale; the Pain Quality Assessment Scale; the Simple Descriptive Pain Intensity Scale; the Visual Analog Scale; the Wong-Baker FACES Pain Rating Scale; the FLACC scale; the CRIES scale; or the COMFORT scale. In another embodiment, said level of pain in said individual before said use and said level of pain in the individual after said use are determined by one or more physical indicia of pain. In a specific embodiment, said physiological indicium of pain is heart rate in the individual, e.g., said heart rate in said individual is lower after said use than before said use. In another specific embodiment, said physiological indicium of pain is the systolic of said individual, e.g., said systolic in said individual is lower after said use than before said use. In another specific embodiment, said physiological indicium of pain is diastolic of said individual, e.g., said diastolic in said individual is lower after said use than before said use. In certain embodiments, said pain is neuropathic pain. In a more specific embodiment, said neuropathic pain is caused by diabetic neuropathy. In a more specific embodiment, said neuropathic pain is caused by injury to a nerve in said individual. In another more specific embodiment, said neuropathic pain is caused by inflammation. In another more specific embodiment, said neuropathic pain is caused by a drug. In a more specific embodiment, said drug is or comprises a platinum-containing anticancer drug, e.g., platinum-containing anticancer drug is or comprises oxaliplatin, carboplatin or cisplatin. In another specific embodiment, said drug is or comprises paclitaxel. In other specific embodiments, said pain is inflammatory pain, bone pain (e.g., bone pain is associated with or caused by cancer), pain caused by cancer, pain caused by or associated with vulvodynia, pain caused by or associated with interstitial cystitis, or pain caused by degenerative joint disease such as osteoarthritis. In certain embodiments, said pain is unresponsive to steroid therapy. In certain other embodiments, said pain is unresponsive to nonsteroidal anti-inflammatory therapy. In certain other embodiments, said pain is unresponsive to opioid therapy. In certain other embodiments, said pain is unresponsive to non-specific or mixed mu/delta opioids therapy.

In a specific embodiment of any of the above embodiments, said placental stem cells are $CD10^+$, $CD34^-$, and $CD105^+$. In a more specific embodiment, said placental stem cells are additionally $CD200^+$, e.g., the placental stem cells are $CD10^+$, $CD34^-$, $CD105^+$, and $CD200^+$. In a more specific embodiment, said placental stem cells are additionally $CD45^-$ and $CD90^+$. In a more specific embodiment, said placental stem cells are additionally $CD80^-$ and $CD86^-$. In other specific embodiments, said placental stem cells express CD200 and do not express HLA-G; or express CD73, CD105, and CD200; or express CD200 and OCT-4; or express CD73 and CD105 and do not express HLA-G. In a specific embodiment of any of the placental stem cells described herein, said placental stem cells are $HLA-A,B,C^+$. In specific embodiments of any of the embodiments herein, said placental stem cells are additionally $OCT-4^+$. In certain embodiments, said placental stem cells are formulated to be administered locally. In certain other embodiments, said placental stem cells are formulated to be administered systemically, e.g., intravenously or intraarterially.

3.1 Definitions

As used herein, the term "about," when referring to a stated numeric value, indicates a value within plus or minus 10% of the stated numeric value.

As used herein, the term "derived" means isolated from or otherwise purified. For example, placental derived adherent cells are isolated from placenta. The term "derived" encompasses cells that are cultured from cells isolated directly from a tissue, e.g., the placenta, and cells cultured or expanded from primary isolates.

As used herein, "immunolocalization" means the detection of a compound, e.g., a cellular marker, using an immune protein, e.g., an antibody or fragment thereof in, for example, flow cytometry, fluorescence-activated cell sorting, magnetic cell sorting, in situ hybridization, immunohistochemistry, or the like.

As used herein, the term "SH2" refers to an antibody that binds an epitope on the marker CD105. Thus, cells that are referred to as $SH2^+$ are $CD105^+$.

As used herein, the terms "SH3" and "SH4" refer to antibodies that bind epitopes present on the marker CD73. Thus, cells that are referred to as $SH3^+$ and/or $SH4^+$ are $CD73^+$.

As used herein, a stem cell is "isolated" if at least 50%, 60%, 70%, 80%, 90%, 95%, or at least 99% of the other cells with which the stem cell is naturally associated are removed from the stem cell, e.g., during collection and/or culture of the stem cell. A population of "isolated" cells means a population of cells that is substantially separated from other cells of the tissue, e.g., placenta, from which the population of cells is derived. In some embodiments, a population of, e.g., stem cells is "isolated" if at least 50%, 60%, 70%, 80%, 90%, 95%, or at least 99% of the cells with which the population of stem cells are naturally associated are removed from the population of stem cells, e.g., during collection and/or culture of the population of stem cells.

As used herein, the term "placental stem cell" refers to a stem cell or progenitor cell that is derived from, e.g., isolated from, a mammalian placenta, regardless of the number of passages after a primary culture, which adheres to a tissue culture substrate (e.g., tissue culture plastic or a fibronectin-coated tissue culture plate). The term "placental stem cell" as used herein does not, however, refer to a trophoblast, a cytotrophoblast, embryonic germ cell, or embryonic stem cell, as those cells are understood by persons of skill in the art. A cell is considered a "stem cell" if the cell retains at least one attribute of a stem cell, e.g., a marker or gene expression profile associated with one or more types of stem cells; the ability to replicate at least 10-40 times in culture; multipotency, e.g., the ability to differentiate, either in vitro, in vivo or both, into cells of one or more of the three germ layers; the lack of adult (i.e., differentiated) cell characteristics, or the like. The terms "placental stem cell" and "placenta-derived stem cell" may be used interchangeably. Unless otherwise noted herein, the term "placental" includes the umbilical cord. The placental stem cells disclosed herein are, in certain embodiments, multipotent in vitro (that is, the cells differentiate in vitro under differentiating conditions), multipotent in vivo (that is, the cells differentiate in vivo), or both.

As used herein, a stem cell is "positive" for a particular marker when that marker is detectable. For example, a placental stem cell is positive for, e.g., CD73 because CD73 is detectable on placental stem cells in an amount detectably greater than background (in comparison to, e.g., an isotype control or an experimental negative control for any given assay). A cell is also positive for a marker when that marker can be used to distinguish the cell from at least one other cell type, or can be used to select or isolate the cell when present or expressed by the cell.

As used herein, "immunomodulation" and "immunomodulatory" mean causing, or having the capacity to cause, a detectable change in an immune response, and the ability to cause a detectable change in an immune response.

4. BRIEF DESCRIPTION OF THE FIGURES

FIG. 1 depicts the efficacy of $CD10^+$, $CD34^-$, $CD105^+$, $CD200^+$ placental stem cells, vehicle or gabapentin (GBP) in the reduction of pain in a neuropathic pain model. X axis: conditions; Y axis: improvement in sensitivity (allodynia)

according to the Von Frey Filament Assortment assay. "D": Day. GBP: gabapentin. MPK: milligrams per kilogram. BL: baseline.

Figure 2:
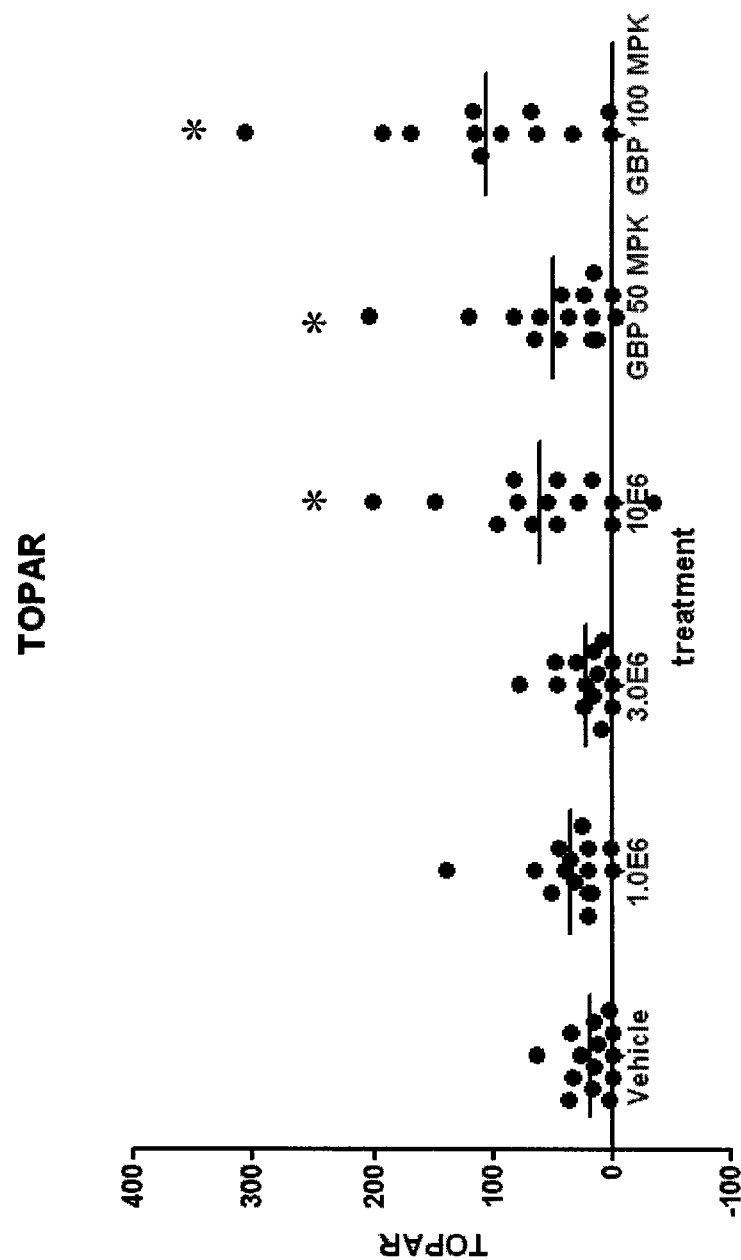

FIG. 2 depicts the degree of total pain relief (TOPAR) produced by administration of CD10$^+$, CD34$^-$, CD105$^+$, CD200$^+$ placental stem cells (1×10$^6$, 3×10$^6$ or 10×10$^6$ cells/administration), vehicle or gabapentin (GBP) in the neuropathic pain animal model. Asterisks indicate significant results compared to vehicle administration alone.

FIGS. 3A-3D depict the effect of CD10$^+$, CD34$^-$, CD105$^+$, CD200$^+$ placental stem cells on mechanical allodynia measured by 26 g force of Von Frey fiber (A): hind paw withdrawal frequency at ipsi-lateral limb following administration of 4×10$^6$ placental stem cells (squares) and vehicle (diamonds). (B): hind paw withdrawal frequency at contra-lateral limb following administration of 4×10$^6$ placental stem cells (squares) and vehicle (straight line). (C): dose-dependent effect of placental stem cells on reduction of mechanical allodynia at ipsi-lateral limb. (D): dose-dependent effect of placental stem cells on the percentage of pain reduction responders. *P<0.05; **p<0.01 vs vehicle. For FIGS. 3C and 3D, the first bar (leftmost) represents the vehicle; the second bar represents 4×10$^6$ placental stem cells; the third bar represents 1×10$^6$ placental stem cells; and the fourth bar (rightmost) represents 4×10$^5$ placental stem cells.

Figure 4A:
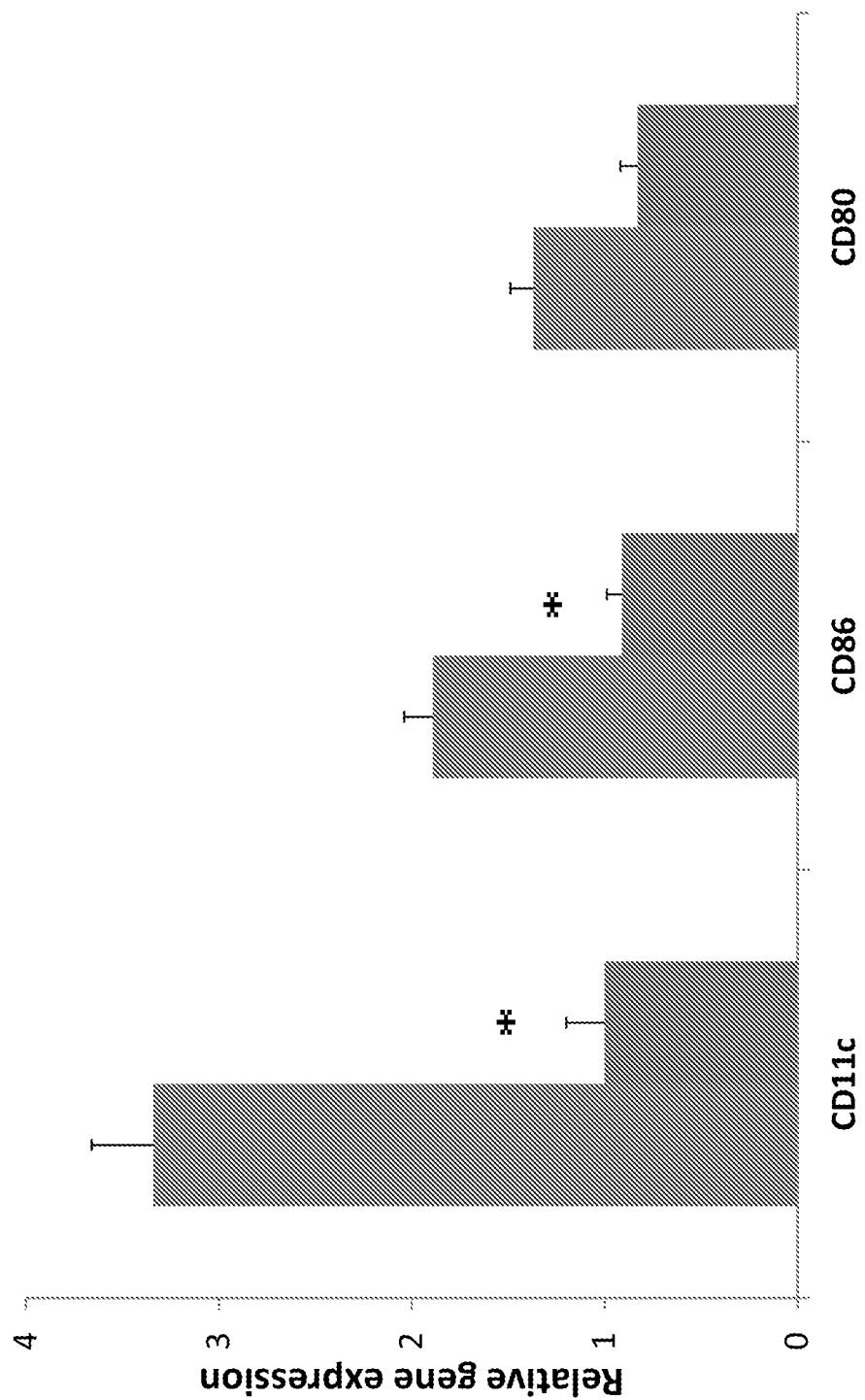
Figure 4B:
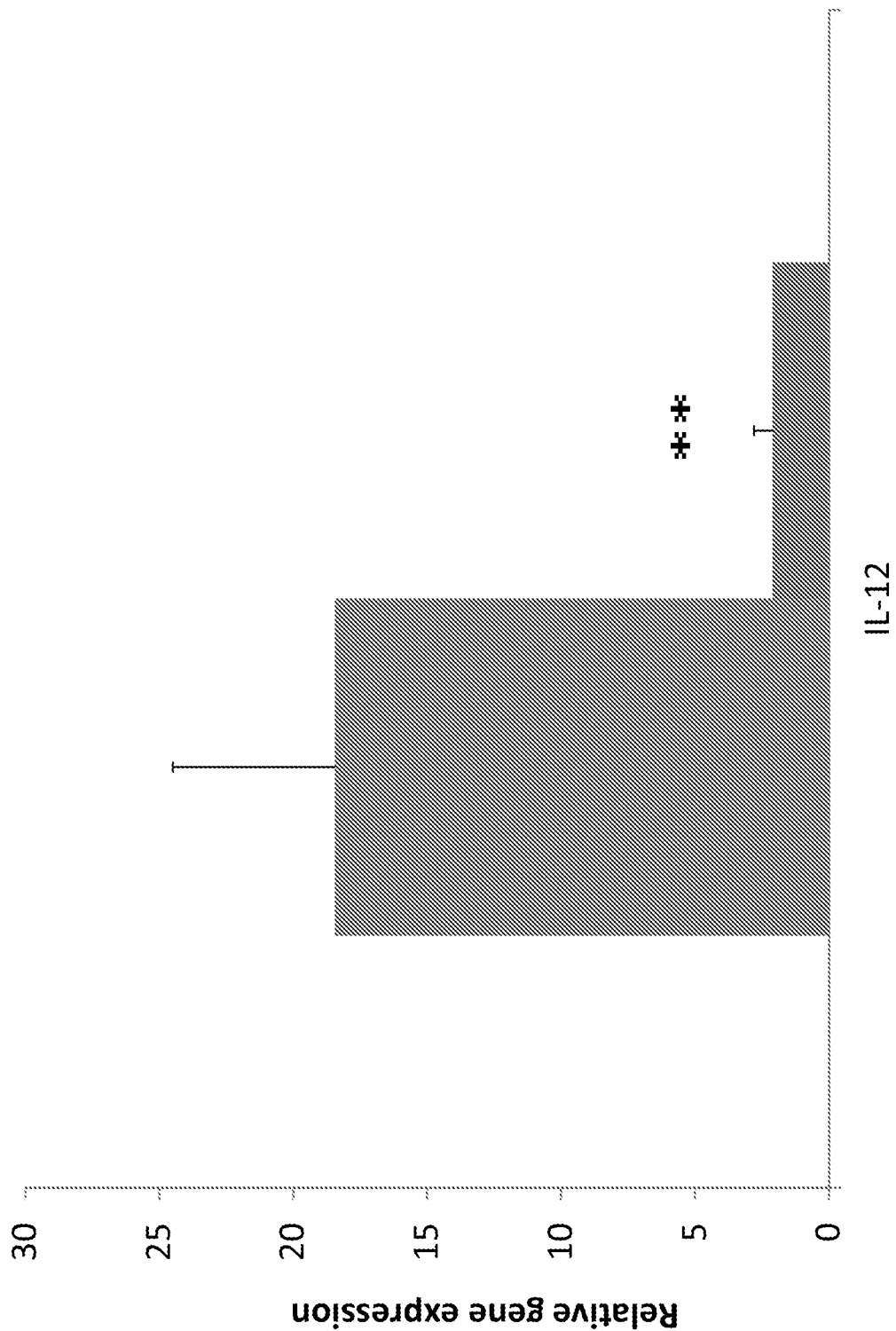

FIGS. 4A-4B demonstrate that CD10$^+$, CD34$^-$, CD105$^+$, CD200$^+$ placental stem cells suppress dendritic cells recruitment, activation, and differentiation at draining lymph nodes at Day 4. (A): The placental stem cell treated group had lower CD11c, CD86 and CD80 gene expression. (B): The placental stem cell treated group had lower IL-12 gene expression. *P<0.05; **p<0.01 vs vehicle. For FIGS. 4A and 4B, the first bar (leftmost) represents the vehicle; the second bar (rightmost) represents placental stem cells.

Figure 5A:
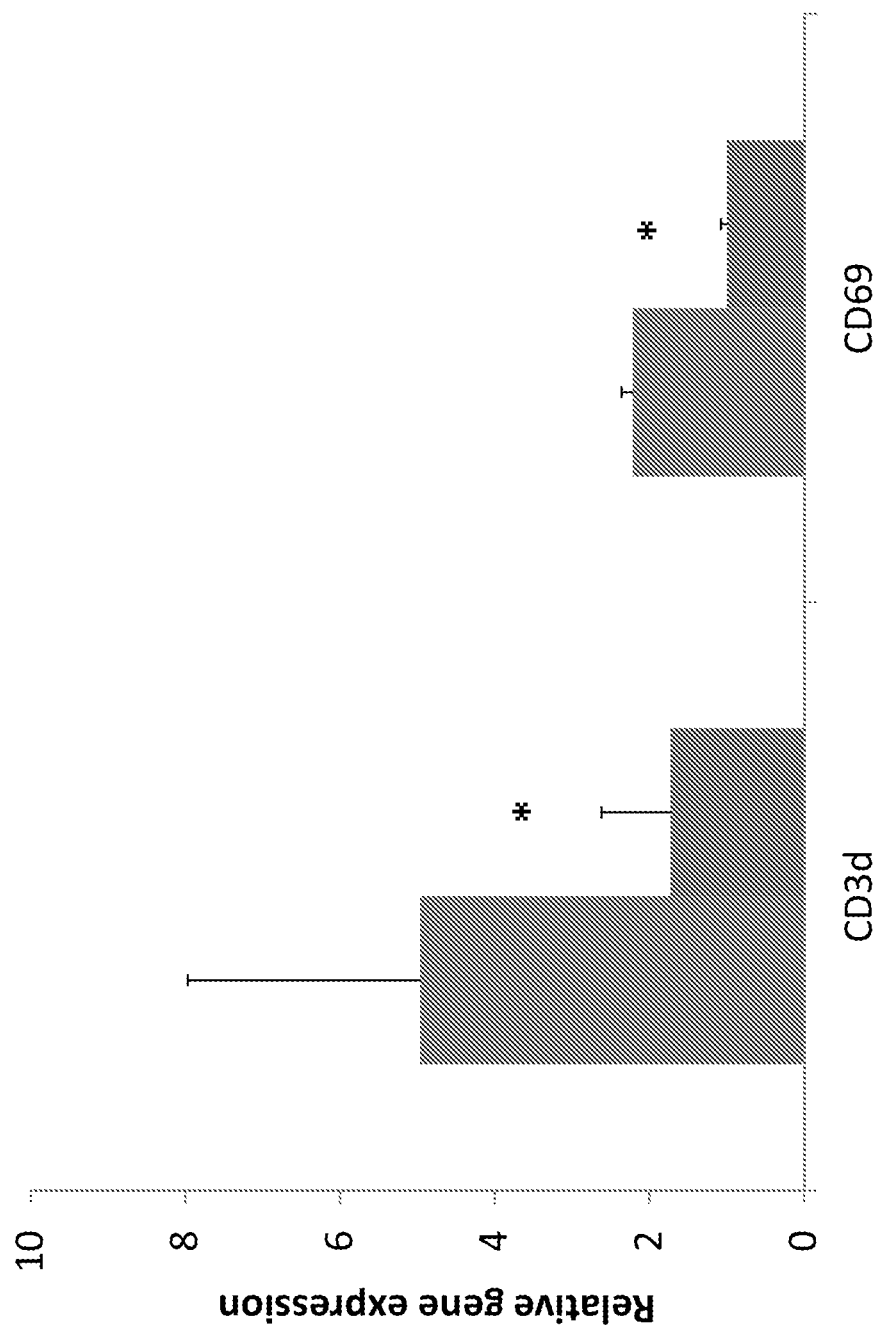
Figure 5B:
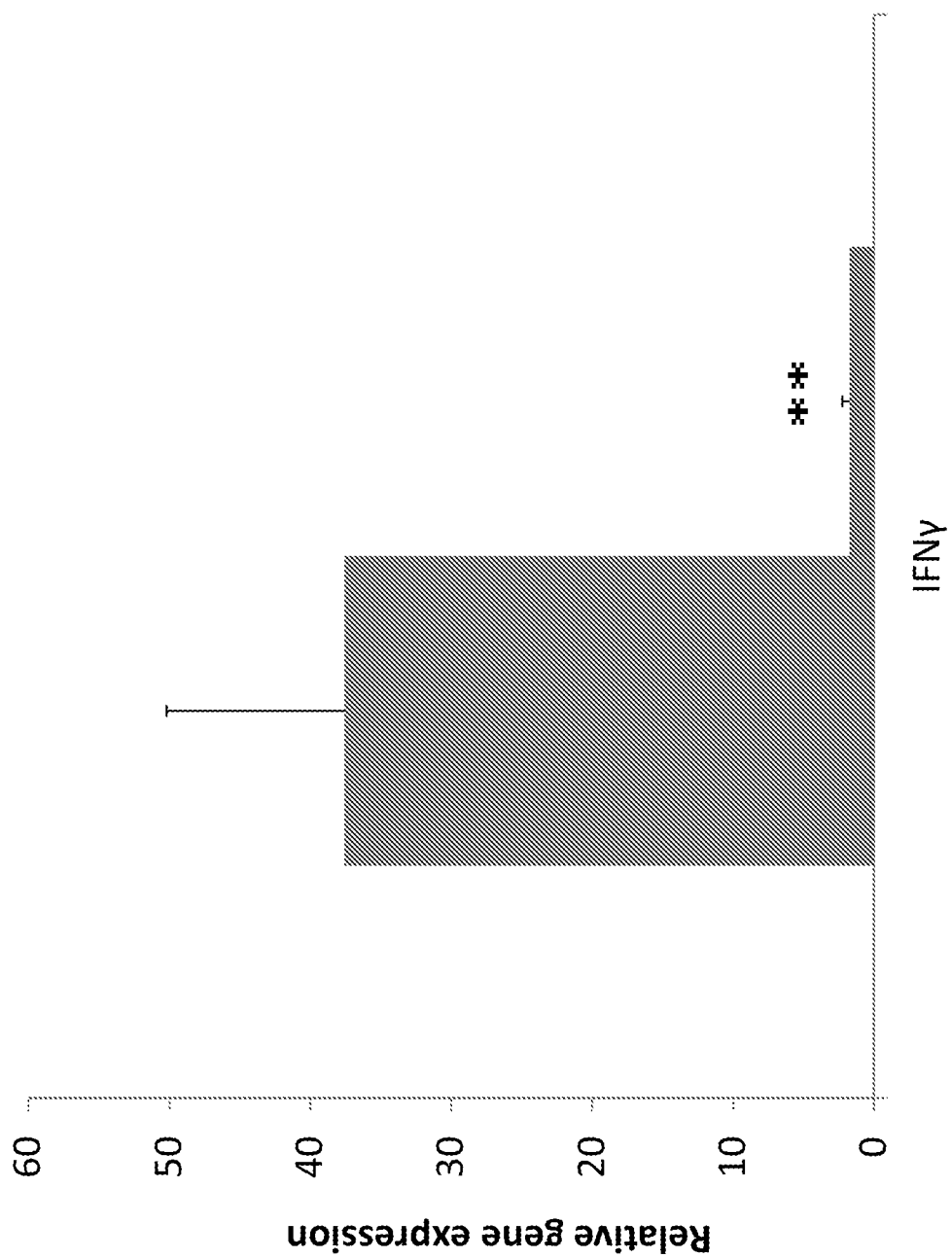
Figure 5C:
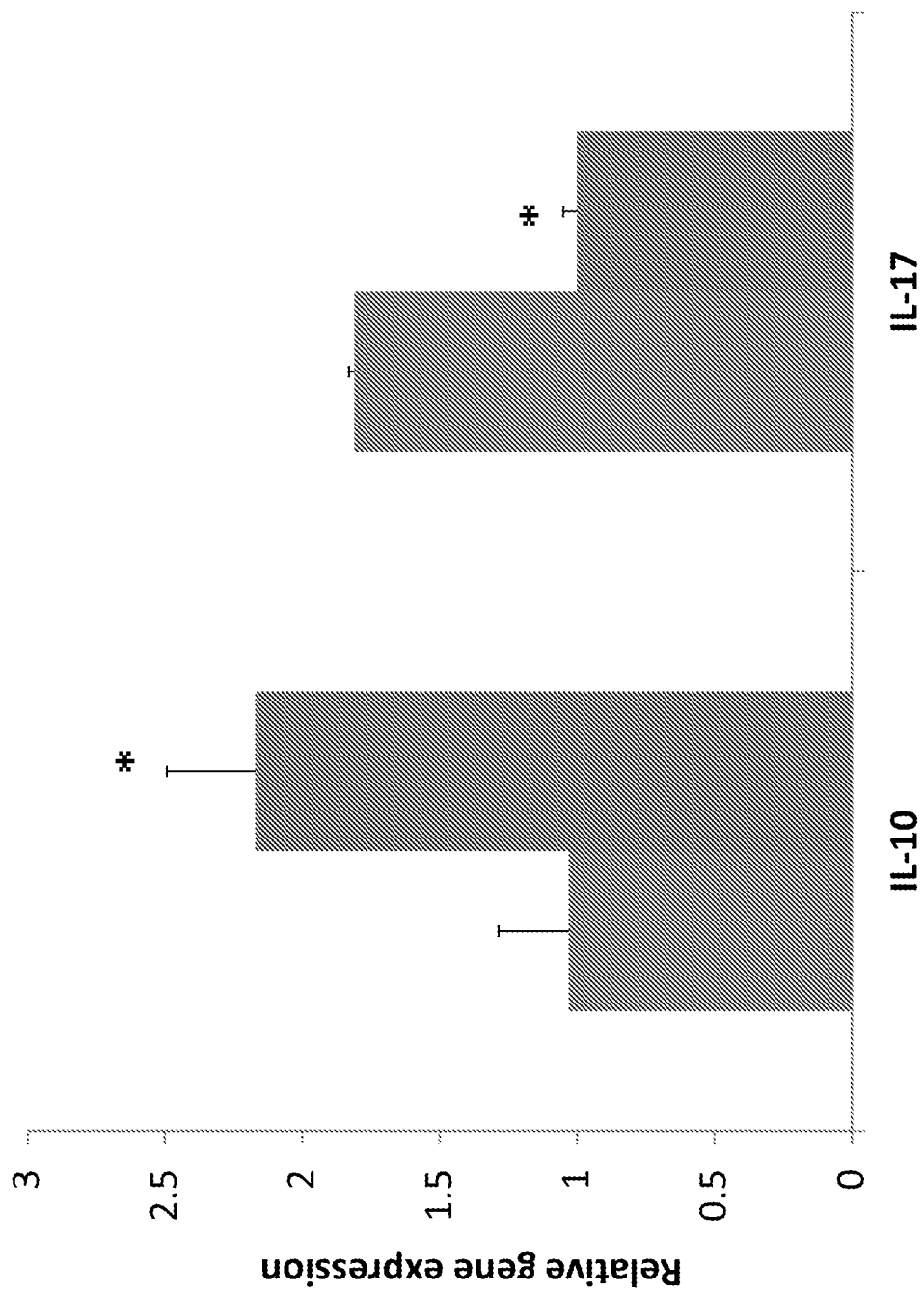

FIGS. 5A-5C demonstrate that CD10$^+$, CD34$^-$, CD105$^+$, CD200$^+$ placental stem cells suppress T-cell activation, modulated T-cell differentiation and cytokine profile. (A): The placental stem cell treated group had lower CD3 and CD69 gene expression at draining lymph node at Day 4. (B) The placental stem cell treated group had significantly lower IFNγ gene expression at draining lymph node at Day 4. (C): The placental stem cell treated group had higher IL-10, but lower IL-17 gene expression at draining lymph node at Day 4. *P<0.05; **p<0.01 vs vehicle. For FIGS. 5A, 5B, and 5C, the first bar (leftmost) represents the vehicle; the second bar (rightmost) represents placental stem cells.

Figure 6A:
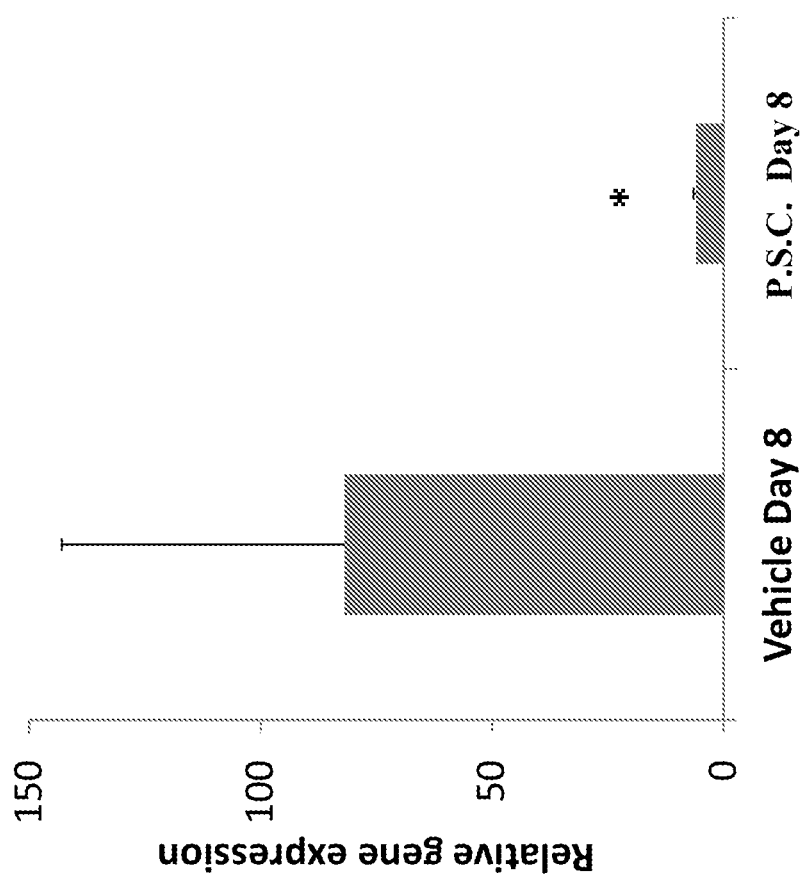
Figure 6B:
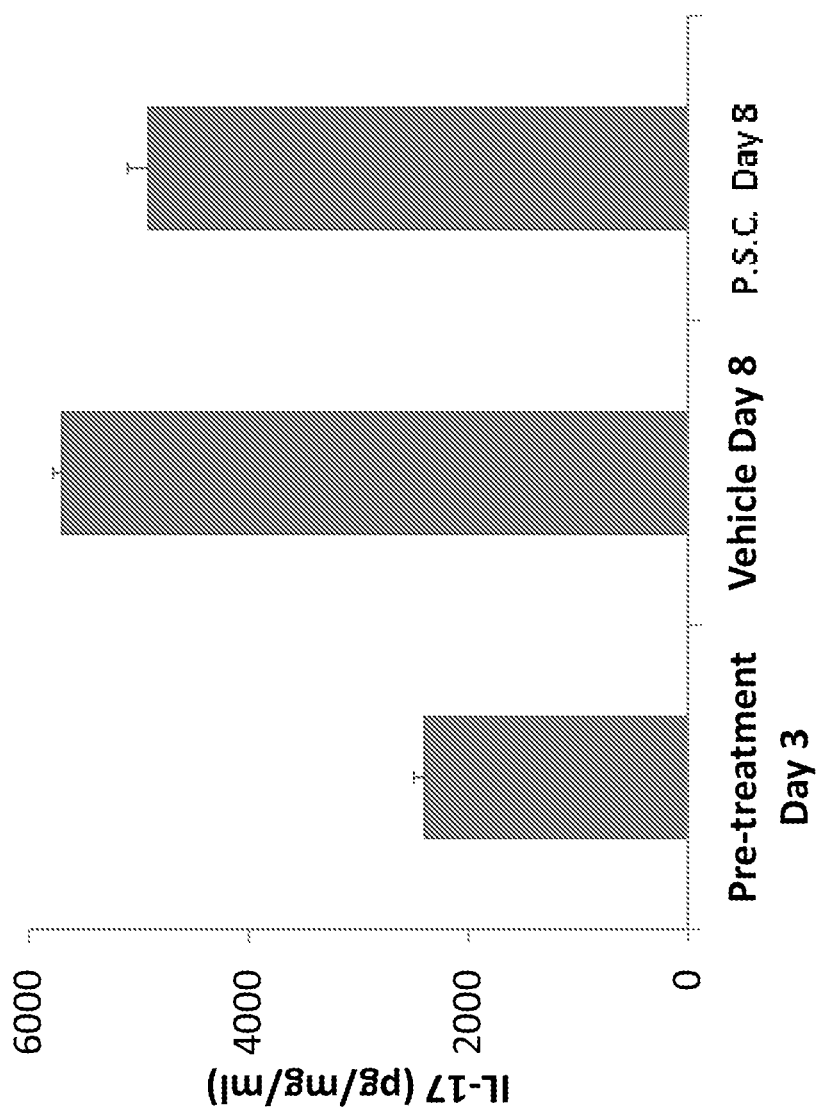

FIGS. 6A-6B demonstrate that CD10$^+$, CD34$^-$, CD105$^+$, CD200$^+$ placental stem cells (PSC) suppress IL-17 mRNA (A) and protein (B) expression in ipsi-lateral sciatic nerve at Day 8. *P<0.05 vs vehicle.

FIGS. 7A-7D demonstrate that CD10$^+$, CD34$^-$, CD105$^+$, CD200$^+$ placental stem cells suppress immune cell infiltration into ipsi-lateral sciatic nerve at Day 8. (A): Placental stem cells suppressed macrophage infiltration (Emr1) and activation (CD68). (B): Placental stem cells suppressed dendritic cell infiltration (CD11c) and activation (CD80, IL-12b). (C): Placental stem cells suppressed T-cell infiltration (CD3d) and activation (CD69). (D): Flow cytometry analysis of sciatic nerve single cell suspension showed that placental stem cells suppressed T-cell (CD3) and macrophage (ED2) infiltration. *P<0.05 vs vehicle. For FIGS. 7A, 7B, and 7C, the first bar (leftmost) represents the vehicle; the second bar (rightmost) represents placental stem cells. For FIG. 7D, the first bar (leftmost) represents the naive cells; the middle bar represents the vehicle; and the third bar (rightmost) represents placental stem cells.

FIGS. 8A-8L demonstrate that CD10$^+$, CD34$^-$, CD105$^+$, CD200$^+$ placental stem cells suppress inflammatory infiltrates into Ipsi-lateral sciatic nerve at Day 8. H&E staining (A-C), CD68 (D-F), CD8 (G-I), and CD4 (J-L) in normal, vehicle and placental stem cell-treated animals. Arrows indicate perineurium in A, B, and C; asterisks indicate epineurium. Magnification 100×, scale bar 200 mM.

Figure 9:
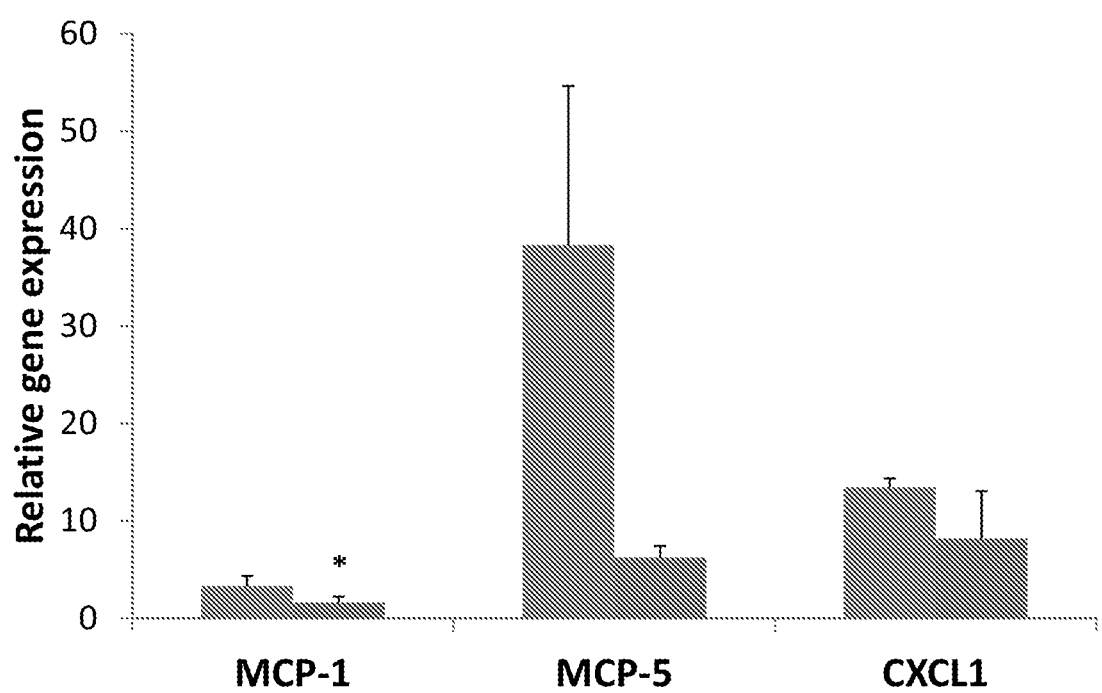

FIG. 9 demonstrates that CD10$^+$, CD34$^-$, CD105$^+$, CD200$^+$ placental stem cells suppress mRNA expression of CCL2, CCL12, and CXCL1 in ipsi-lateral sciatic nerve at Day 8. The first bar (leftmost) represents the vehicle; the second bar (rightmost) represents placental stem cells.

FIGS. 10A-10D depict the number of responses to 26 g stimuli to the rats' paw at baseline, following the nerve injury procedure (D6), and following treatment (D10, D16, D25 and D30). (A) A significant pain reduction was observed following CD10$^+$, CD34$^-$, CD105$^+$, CD200$^+$ placental stem cell administration on pain induced by CCI. (C) A significant pain reduction following CD10$^+$, CD34$^-$, CD105$^+$, CD200$^+$ placental stem cell administration on pain induced by CCI was observed. (B, D) The effect on the contralateral paw is depicted.

Figure 11A:
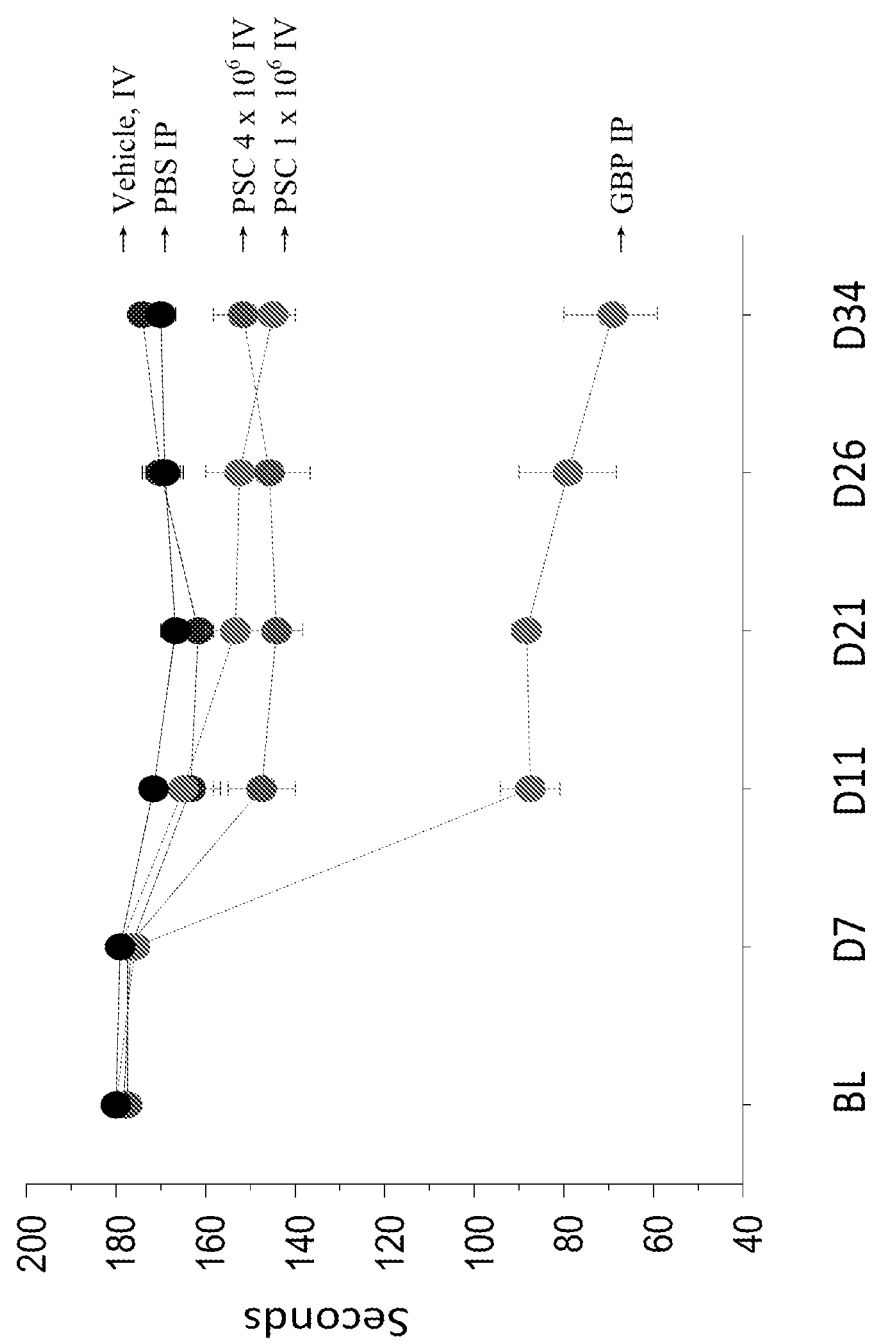
Figure 11B:
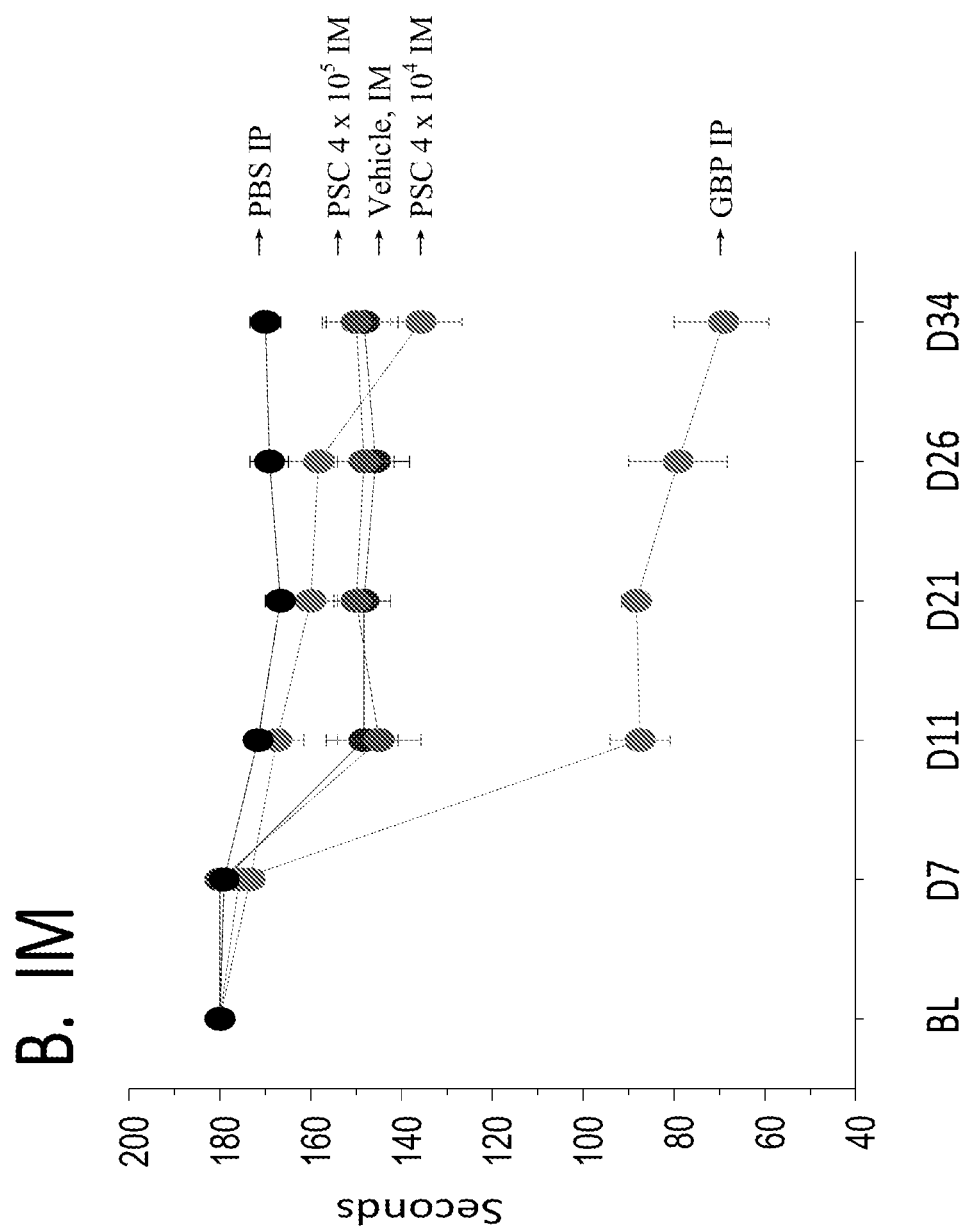

FIGS. 11A-11B depict the duration rats were able to remain on a rotating rod (up to 180 second), at baseline (BL), following the nerve injury procedure (D7) and following treatment (D11, D21, D26 and D34). (A) CD10$^+$, CD34$^-$, CD105$^+$, CD200$^+$ placental stem cell intravenous (IV) treated and control groups. (B) CD10$^+$, CD34$^-$, CD105$^+$, CD200$^+$ placental stem cell intramuscular (IM) treated and control groups.

5. DETAILED DESCRIPTION

5.1 Methods of Treatment of Pain

Described herein are methods of treating pain comprising the administration of placental-derived cells, e.g., placental stem cells, e.g., the placental stem cells described in Section 5.4, below, or prepared as described in Example 7, below. In specific embodiments, the placental stem cells used in the methods for treating pain described herein are CD10$^+$, CD34$^-$, CD105$^+$, and CD200$^+$. In other specific embodiments, the placental stem cells used in the methods for treating pain described herein express the ELOVL2, ST3GAL6, ST6GALNAC5, and/or SLC12A8 gene at a detectably higher level than the expression of said gene by an equivalent number of BM-MSCs. In certain embodiments, the placental stem cells used in the methods described herein express the CPA4, TCF21, and/or VTN gene at a detectably higher level than the expression of said gene by an equivalent number of BM-MSCs. In certain embodiments, the placental stem cells used in the methods described herein express the B4GALT6, FLJ10781, and/or NUAK1 gene at a detectably higher level than the expression of said gene by an equivalent number of BM-MSCs. In a specific embodiment, said placental stem cells further express the C11orf9 gene at a detectably higher level than the expression of said gene by an equivalent number of BM-MSCs.

5.1.1 Methods of Treating Pain

Pain is generally defined as an unpleasant sensory and emotional experience associated with actual or potential tissue damage or described in terms of such damage. Merskey H, Bogduk N, eds., Classification of Chronic Pain, International Association for the Study of Pain (IASP) Task Force on Taxonomy, IASP Press: Seattle, 209-214, 1994. Because the perception of pain is highly subjective, it is one of the most difficult pathologies to diagnose and treat effectively.

In one aspect, provided herein is a method of treating an individual having pain, comprising administering to the individual a therapeutically effective amount of placental stem cells, or culture medium conditioned by placental stem cells, wherein the therapeutically effective amount is an amount sufficient to cause a detectable improvement in said pain or a symptom associated with said pain. In one embodiment, said method additionally comprises determining a first level of pain in said individual prior to administration of said placental stem cells, and determining a second level of pain in said individual after administration of said placental stem cells, wherein said therapeutically effective amount of placental stem cells reduces said second level of said pain as compared to said first level of pain.

In certain embodiments, the therapeutically effective amount of placental stem cells, when administered, results in greater, or more long-lasting, improvement of pain in the individual as compared to administration of a placebo.

In certain embodiments, the pain is nociceptive pain. Nociceptive pain is typically elicited when noxious stimuli such as inflammatory chemical mediators are released following tissue injury, disease, or inflammation and are detected by normally functioning sensory receptors (nociceptors) at the site of injury. See, e.g., Koltzenburg, M. Clin. J. of Pain 16:S131-S138 (2000). Examples of causes of nociceptive pain include, but are not limited to, chemical or thermal burns, cuts and contusions of the skin, osteoarthritis, rheumatoid arthritis, tendonitis, and myofascial pain. In certain embodiments, nociceptive pain is stimulated by inflammation.

In certain other embodiments, the pain is neuropathic pain. Neuropathic pain reflects injury or impairment of the nervous system, and has been defined as "pain initiated or caused by a primary lesion or dysfunction in the nervous system." Merskey H, Bogduk N, eds., Classification of Chronic Pain, International Association for the Study of Pain (IASP) Task Force on Taxonomy, IASP Press: Seattle, 209-214, 1994. In a specific embodiment, the neuropathic pain is characterized by altered excitability of peripheral neurons. In other specific embodiments, the neuropathic pain includes, but is not limited to, pain associated with diabetic neuropathy, postherpetic neuralgia, trigeminal neuralgia, inflammation (e.g., neuroinflammation, neuritis), and post-stroke pain. In certain embodiments, the neuropathic pain is continuous, episodic, and is described as, e.g., burning, tingling, prickling, shooting, electric-shock-like, jabbing, squeezing, deep aching, or spasmodic. In certain other embodiments, the individual having neuropathic pain additionally experiences partial or complete sensory deficit, abnormal or unfamiliar unpleasant sensations (dysaesthesia), pain resulting from non-noxious stimuli, or disproportionate perception of pain in response to supra-threshold stimuli (hyperalgesia).

In another specific embodiment, the neuropathic pain is complex regional pain syndrome (CRPS). In a specific embodiment, CRPS affects the extremities in the absence of a nerve injury (CRPS type I). In a more specific embodiment, said CRPS type I includes reflex sympathetic dystrophy (RSD). In a more specific embodiment, said RSD is stage I RSD, or "early RSD". In early RSD, pain is more severe than would be expected from the injury, and it has a burning or aching quality. It may be increased by dependency of the limb, physical contact, or emotional upset. The affected area typically becomes edematous, may be hyperthermic or hypothermic, and may show increased nail and hair growth. Radiographs may show early bony changes. In another more specific embodiment, said RSD is stage II RSD, or "established RSD". In a more specific embodiment, said established RSD comprises, in addition to pain, induration of edematous tissue; hyperhidrosis of skin with livedo reticularis or cyanosis; hair loss; ridging, cracking or brittling of nails; development of dry hands; and/or noticeable atrophy of skin and subcutaneous tissues. Pain remains the dominant feature. In another more specific embodiment, said RSD is stage III RSD, or "late RSD". In a more specific embodiment, said late RSD comprises pain that spreads proximally; irreversible tissue damage; thin, shiny skin; and bone demineralization visible on radiographs.

In another specific embodiment, the neuropathic pain is pain caused by a drug, e.g., a chemotherapeutic drug or anti-cancer drug. In specific embodiments, the drug is or comprises a platinum-containing drug, a taxane, an epothilone, a plant alkaloid, or a thalidomide. In more specific embodiments, the drug is or comprises bortezomib, carboplatin (e.g., PARAPLATIN®), cisplatinum (e.g., PLATINOL®), cytarabine (e.g., CYTOSAR®, Ara-C), docetaxel (e.g., TAXOTERE®), etoposide/VP-16 (VEPESID®), gemcitibine (e.g., GEMZAR®), HALAVEN® (eribulin mesylate), hexamethylmelamine (e.g., HEXALIN®), paclitaxel (e.g., TAXOL®; ABRAXANE™), oxaliplatin (e.g., ELOXATIN®), suramin, thalidomide (e.g., THALOMID®), vinblastine (e.g., VELBAN®; ALKABAN-AQ®), vincristine (e.g., ONCOVIN®, VINCASAR PFS®, Vincrex), or vinorelbine (NAVELBINE®).

In certain other specific embodiments, the drug is an antibiotic. In certain other embodiments, the drug is a statin.

In certain other specific embodiments, the drug is or comprises amlodipine (e.g., NORVASC®, Lotril or Lotrel), atorvastatin (e.g., LIPITOR®), duloxetine (e.g., CYMBALTA®), pregabalin (LYRICA®), allopurinol (e.g., LOPURIM®, ZYLOPRIM®), aminodipinberglate, amiodarone (e.g., CORDERONE®, PACERONE®), amiodipine, amitriptyline (e.g., ELAVIL™, ENDEP™, VANATRIP™), metronidazole (e.g., FLAGYL®, METROGEL™), nitrofurantoin (e.g., FURADANTIN®, MACROBID®, MACRODANTIN®, NITRO MACRO), perhexiline, VYTORIN®, ciprofloxacin (e.g., CIPRO®, PROQUIN®), disulfiram (e.g., ANTABUSE), zolpidem (e.g., AMBIEN®), buspirone (e.g., BUSPAR), clonazepam (e.g., KLONOPIM, CEBERKLON, VALPAX), alaprazolam (e.g., XANAX®), phenytoin (DILANTIN®), citalopram (e.g., CELEXA), duloxetine (e.g., CYMBALTA®), venlaxafine (e.g., EFFEXOR, EFFEXOR XR®), nortriptyline (e.g., AVENTYL HCL, PAMELOR), sertraline (e.g., ZOLOFT®), paroxetine (e.g., PAXIL, PAXIL CR®), atenolol (e.g., TENORMIN, SENORMIN), perindopril (e.g., ACEON), altace (e.g., RAMIPRIL®), losartan (e.g., COZAAR®, HYZAAR®), hydralazine (e.g., APRESOLINE®), hydrochlorothiazide (e.g., HYDRODIURIL™, EZIDE™, HYDRO-PAR™, MICROZIDE™), lisinopril (e.g., PRINOVIL®, ZESTRIL®), telmisartan (e.g., MICARDIS™), perhexiline, prazosin (e.g., MINIPRESS®), lisinopril (e.g., PRINIVIL®, ZESTRIL®), lovastatin (e.g., ALTOCOR®, MEVACOR®), CADUET®, rosuvatatin (e.g., CRESTOR®), fluvastatin (e.g., LESCOL®, LESCOL® XL), simvastatin (e.g., ZOCOR®), cerivastatin (e.g., LIPOBAY™), gemfibrozil (e.g., LOPID®), pravastatin (e.g., PRAVACHOL®, PRAVIGARD PAC™), d4T (stavudine, e.g., ZERIT®), ddC (zalcitibine; e.g., HIVID®), ddI (didanosine, e.g., VIDEX® EC), isoniazid (e.g., TUBIZID®), diaminodiphenylsulfone (DDS, dapsone)

In certain embodiments, the neuropathic pain is not pain caused by a drug, e.g., a chemotherapeutic drug or anticancer drug. In specific embodiments, the neuropathic pain is not pain caused by a platinum-containing drug, a taxane, an epothilone, a plant alkaloid, or a thalidomide. In more specific embodiments, the neuropathic pain is not pain caused by bortezomib, carboplatin (e.g., PARAPLATIN®), cisplatinum (e.g., PLATINOL®), cytarabine (e.g., CYTOSAR®, Ara-C), docetaxel (e.g., TAXOTERE®), etoposide/VP-16 (VEPESID®), gemcitibine (e.g., GEMZAR®), HALAVEN® (eribulin mesylate), hexamethylmelamine (e.g., HEXALIN®), paclitaxel (e.g., TAXOL®; ABRAXANE™), oxaliplatin (e.g., ELOXATIN®), suramin, thalidomide (e.g., THALOMID®), vinblastine (e.g., VELBAN®; ALKABAN-AQ®), vincristine (e.g., ONCOVIN®, VINCASAR PFS®, Vincrex), or vinorelbine (NAVELBINE®).

In another specific embodiment, said CRPS affects the extremities in the presence of a nerve injury (CRPS type II). In a more specific embodiment, said CRPS II includes causalgia. In another specific embodiment, said CRPS includes sympathetic maintained pain syndrome. In certain embodiments, symptoms of CRPS include but are not limited to pain, autonomic dysfunction, edema, movement disorder, dystrophy, atrophy, burning pain, allodynia (pain with light touch). In certain embodiments, CRPS-related pain is accompanied by swelling and joint tenderness, increased sweating, sensitivity to temperature, and/or color change of the skin.

In certain other specific embodiments, the neuropathic pain is neuropathic pain caused by or related to a dietary deficiency. In a more specific embodiment, the dietary deficiency is vitamin B12 (cobalamin, cyanocobalamin) deficiency. In another more specific embodiment, the dietary deficiency is vitamin B6 (pyridoxine, pyridoxal phosphate) deficiency. In another more specific embodiment, the dietary deficiency is vitamin B1 (thiamine) deficiency. In another specific embodiment, the individual having neuropathic pain, caused by nutritional deficiency, has had bariatric surgery. In another specific embodiment, the neuropathic pain is caused by or is related to alcoholism or consumption of alcohol by the individual having pain.

In certain embodiments, the pain is caused by or associated with vulvodynia. Vulvodynia is pain of the vulva, e.g., pain unexplained by vulvar or vaginal infection or skin disease. In one embodiment, the pain of vulvodynia is localized to the vulvar region, e.g., in the vestibular region such as vulvar vestibulitis or vestibulodynia. In another embodiment, the pain of vulvodynia may extend into the clitoris, e.g., clitorodynia. Example of causes of vulvodynia include, but are not limited to, dyspareunia, injury to or irritation of the nerves that innervate the vulva, genetic predisposition to inflammation, allergy, autoimmune disorders (e.g., lupus erythematosus or Sjogren's Syndrome), infection (e.g., yeast infections, HPV or bacterial vaginosis), and neuropathy. Exemplary symptoms of vulvodynia include without limitation, diffuse pain or burning sensation on or around the vulva, the labia majora, labia minor, or the vestibule.

In certain embodiments, the pain is caused by or associated with interstitial cystitis. Interstitial cystitis, also known as bladder pain syndrome, is a chronic condition, often characterized by, e.g., pain or pressure associated with the bladder, pain associated with urination, irritative voiding, urinary frequency, urgency, or pain or pressure in pelvis. The pathology and pathogenesis of interstitial cystitis is not clearly understood. However, several possible causes have been proposed, e.g., vascular obstruction, autoimmunity, inflammation, leaky bladder lining, mast cells, stress, and genetic, neurogenic and endocrine causes. In one embodiment, diagnosis of interstitial cystitis can be done by, e.g., the Pelvic Pain Urgency/Frequency (PUF) Patient Survey or the KCl test, also known as the potassium sensitivity test.

In certain other embodiments, the pain is visceral pain.

In certain other embodiments, the pain is post-operative pain, such as that resulting from trauma to tissue caused during surgery.

In certain other embodiments, the pain is mixed pain, e.g., is chronic pain that has nociceptive and neuropathic components. In specific embodiments, said mixed pain is cancer pain or low back pain.

In certain other embodiments, the pain is migraine pain or pain from headache, e.g., vascular headache, cluster headache or toxic headache.

In specific embodiments, said symptoms associated with pain include, but are not limited to, one or more of autonomic dysfunction, inability to initiate movement, weakness, tremor, muscle spasm, dystonia, dystrophy, atrophy, edema, stiffness, joint tenderness, increased sweating, sensitivity to temperature, light touch (allodynia), color change to the skin, hyperthermic or hypothermic, increased nail and hair growth, early bony changes, hyperhidrotic with livedo reticularis or cyanosis, lost hair, ridged, cracked or brittle nails, dry hand, diffuse osteoporosis, irreversible tissue damage, thin and shiny skin, joint contractures, and marked bone demineralization.

In certain embodiments, the administration of placental stem cells to an individual in accordance with the methods described herein results in a reduction in pain in the individual without an accompanying side effect that is associated with one or more drugs indicated/used for treatment of pain, e.g., gabapentin. In a specific embodiment, the use of placental stem cells in accordance with the methods described herein results in reduction of pain in an individual to whom the placental stem cells are administered, but does not result in sensory and/or motor coordination deficiency in said individual.

5.1.2 Pain Assessment Scales

In one embodiment, the therapeutically effective amount of placental stem cells administered to the individual having pain is an amount that results in a detectable reduction in the pain in the individual. The reduction can be detectable to the individual, detectable to an observer, or both. In certain embodiments of the methods of treatment provided herein, the level of pain in the individual is assessed by the individual, e.g., as guided by a medical doctor, or as part of a pre-treatment workup, according to one or more individual pain scales. In certain other embodiments, the level of pain in the individual is assessed by an observer using one or more observer pain scales. Where levels of pain are assessed according to the method before and after administration of placental stem cells, the same scale is preferably used for each assessment. Pain in the individual can be assessed once or more than once, e.g., 2, 3, 4, or 5 times, before administration of placental stem cells, and once or more than once, e.g., 2, 3, 4, or 5 times, after administration of placental stem cells.

In one embodiment, pain in the individual is assessed by the 0-10 Numeric Pain Intensity Scale. In this scale, zero equals no pain, and 10 equals the worst pain. In certain embodiments, e.g., the Pain Quality Assessment Scale, the pain is broken down into more than one numeric descriptor, e.g., 0-10 for how "hot" the pain feels, 0-10 for how "intense" the pain feels, 0-10 for how "sharp" the pain feels, 0-10 for how "dull" the pain feels, 0-10 for how "cold" the pain feels, 0-10 for how "sensitive" the pain feels, 0-10 for how "tender" the pain feels, 0-10 for how "itchy" the pain feels, 0-10 for how "shooting" the pain feels, 0-10 for how "numb" the pain feels, 0-10 for how "tingling" the pain feels, 0-10 for how "electrical" the pain feels, 0-10 for how "cramping" the pain feels, 0-10 for how "throbbing" the pain feels, 0-10 for how "radiating" the pain feels, 0-10 for how "aching" the pain feels, 0-10 for how "heavy" the pain feels, and/or 0-10 for how "unpleasant" the pain feels.

In another embodiment, pain in the individual is assessed by the Simple Descriptive Pain Intensity Scale. In this scale, pain is described as, e.g., "no pain", "mild pain", "moderate pain", "severe pain", "very severe pain" or "worst possible pain".

In another embodiment, pain in the individual is assessed by the Visual Analog Scale. In the Visual Analog Scale, the individual is presented with a graph consisting of a vertical line; one end of the line is labeled "no pain" and the other end is labeled "worst possible pain". The individual is asked to mark the line at a point between the two ends indicating the level of pain perceived by the individual.

In another embodiment, pain in the individual is assessed by the Wong-Baker FACES Pain Rating Scale. In the FACES Pain Rating Scale, the level of pain is indicated by a series of cartoon faces, typically six faces, appearing happy to progressively more unhappy. In a specific embodiment, the faces are subtexted with phrases such as "no hurt", "hurts little bit" "hurts little more", "hurts even more", "hurts whole lot" and "hurts worst". In another specific embodiment, the faces are subtexted with phrases such as "no pain", "mild, annoying pain", "nagging, uncomfortable, troublesome pain", "distressing, miserable pain", "intense, dreadful, horrible pain" and "worst possible, unbearable, excruciating pain", either alone or accompanied by a numeric 0 to 10 scale.

In certain embodiments, pain in the individual is assessed by the FLACC (Face, Legs, Activity, Cry and Consolability) scale. In specific embodiments, each of the five characteristics is rated from, e.g., 0 to 2, with 2 indicating pain and 0 indicating no pain. The scores may be used separately or totaled.

In certain other embodiment, pain in the individual is assessed by the CRIES (Crying, Requires $O_2$ for $SaO_2$ (hemoglobin saturation), Increased vital signs (blood pressure and heart rate, Expression and Sleepless) scale. In specific embodiments, each of the five characteristics is rated from, e.g., 0 to 2, with 2 indicating pain and 0 indicating no pain. The scores may be used separately or totaled.

In certain embodiment, pain in the individual is assessed by the COMFORT scale, which assesses nine different characteristics (alertness, calmness, respiratory distress, crying, physical movement, muscle tone, facial tension, blood pressure and heart rate), each rated on a scale of 1-5, with 1 indicating no or least pain, and 5 most pain. The scores may be used individually or totaled.

5.1.3 Physiological Indicia of Pain

As used herein, "treatment of pain" and the like can comprise completely eliminating pain; noticeable reduction of pain by the individual suffering the pain; detectable reduction of pain or indicia of pain by objective criteria (e.g., heart rate, blood pressure, muscle tone, or the like); or a combination of any two or all three. In certain other embodiments, pain in the individual can be assessed, either before or after administration of placental stem cells, or both, by physiological criteria, e.g., physiological criteria of stress. Such physiological criteria can include objectively measurable criteria such as heart rate or blood pressure, e.g., elevated heart rate or blood pressure as compared to a non-pain state in the individual, or as compared to an expected norm (e.g., 120 systolic and 80 diastolic; 60 beats per minute). Such physiological criteria can also, or instead, include subjectively measurable criteria such as facial expressions, muscle tensioning (muscle tone), sweating, trembling, and the like.

Thus, in certain embodiments, the therapeutically effective amount of placental stem cells, administered to the individual having pain, results in a detectable reduction in heart rate in the individual, e.g., a 5%, 10%, 15%, 20%, 25%, 30%, 35%, 40%, 45% or 50% reduction; a reduction of heart rate from 120 beats per minute (bpm) or above to below 110 bpm; a reduction from 110 bpm or above to below 100 bpm; a reduction from 100 bpm or above to below 90 bpm; a reduction from 90 bpm or above to below 80 bpm; a reduction from 120 bpm or above to below 100 bpm; a reduction from above to below 90 bpm; a reduction from 100 bpm above to below 80 bpm; a reduction from 130 bpm above to below 100 bpm; a reduction from 120 bpm above to below 90 bpm; a reduction from 110 bpm to below 80 bpm; or a reduction from 120 bpm or above to below 80 bpm.

In certain other embodiments, the therapeutically effective amount of placental stem cells, when administered to the individual having pain, results in a detectable reduction in blood pressure in the individual, e.g., a reduction of 5%, 10%, 15%, 20%, 25%, 30%, 35%, 40%, 45% or 50% reduction in the individual's systolic, diastolic, or both; a reduction in the individual's systolic from 200 or above to under 190; a reduction in the systolic from 190 or above to under 180; a reduction in the systolic from 180 or above to under 170; a reduction in the systolic from 170 or above to under 160; a reduction in the systolic from 160 or above to under 150; a reduction in the systolic from 150 or above to under 140; a reduction in the systolic from 140 or above to under 130; a reduction in the systolic from 200 or above to under 180; a reduction in the systolic from 190 or above to under 170; a reduction in the systolic from 180 or above to under 160; a reduction in the systolic from 170 or above to under 150; a reduction in the systolic from 160 or above to under 140; a reduction in the systolic from 150 or above to under 130; a reduction in the systolic from 200 or above to under 170; a reduction in the systolic from 190 or above to under 160; a reduction in the systolic from 180 or above to under 150; a reduction in the systolic from 170 or above to under 140; a reduction in the systolic from 160 or above to under 130; a reduction in the systolic from 200 or above to under 160; a reduction in the systolic from 190 or above to under 150; a reduction in the systolic from 180 or above to under 140; a reduction in the systolic from 200 or above to under 130; a reduction in the systolic from 200 or above to under 150; a reduction in the systolic from 190 or above to under 140; a reduction in the systolic from 180 or above to under 130; a reduction in the systolic from 200 or above to under 140; a reduction in the systolic from 190 or above to under 130; or a reduction in the systolic from 200 or above to under 130; a reduction in the individual's diastolic from 140 or above to under 130; a reduction in the diastolic from 130 or above to under 120; a reduction in the diastolic from 120 or above to under 110; a reduction in the diastolic from 110 or above to under 100; a reduction in the diastolic from 100 or above to under 90; a reduction in the diastolic from 140 or above to under 120; a reduction in the diastolic from 110 or above to below 90; a reduction in the diastolic from 140 or above to below 110; a reduction in the diastolic from 130 or above to under 100; a reduction in the diastolic from 120 or above to under 90; a reduction in the diastolic from 140 or above to below 100; a reduction in the diastolic from 130 or above to below 90; or a reduction in the diastolic from 140 or above to below 90.

In certain embodiments, the therapeutically effective amount of placental stem cells, when administered to the individual having pain, results in a detectable reduction in the amount of one or more cytokines (e.g., pro-inflammatory cytokines) in the individual. In a specific embodiment, administration of placental stem cells to individual having pain in accordance with the methods described herein results in a decrease in the amount of IL-2, IL-6, IL-12, IL-17, and/or interferon-γ, or any combination thereof, in the individual. Assessment of decreases in cytokines in the individual can be accomplished using any method known in the art, e.g., the cytokine levels in the blood plasma of the individual can be measured using, e.g., ELISA.

In certain embodiments, the therapeutically effective amount of placental stem cells, when administered to the individual having pain, results in a detectable increase in one or more cytokines in the individual. In a specific embodiment, administration of placental stem cells to individual having pain in accordance with the methods described herein results in an increase in the amount of IL-10 in the individual. Assessment of increases in cytokine levels in the individual can be accomplished using any method known in the art, e.g., the cytokine levels in the blood plasma of the individual can be measured using, e.g., ELISA.

In certain embodiments, the therapeutically effective amount of placental stem cells, when administered to the individual having pain, results in a detectable reduction in the amount of one or more chemokines in the individual. In a specific embodiment, administration of placental stem cells to individual having pain in accordance with the methods described herein results in a decrease in the amount of CCL2, CCL12, and/or CXCL1, or any combination thereof, in the individual. Assessment of chemokines in the individual can be accomplished using any method known in the art, e.g., the chemokine levels in the blood plasma of the individual can be measured using, e.g., ELISA.

In certain embodiments, the therapeutically effective amount of placental stem cells, when administered to the individual having pain, results in a detectable reduction in the activation and/or differentiation in one or more cell types in the individual. In a specific embodiment, administration of placental stem cells to individual having pain in accordance with the methods described herein results in a decrease in the activation and/or differentiation of dendritic cells, T cells, and/or macrophages, or any combination thereof, in the individual. Assessment of the activation and/or differentiation of specific cell types in the individual can be accomplished using any method known in the art, e.g., measurement of specific cell markers present in specific areas of the individual, e.g., measurement/assessment of specific cell markers associated with cells of the blood, or associated with cells found in specific tissues/organs.

5.2 Suppression of an Inflammatory Response Associated with, or Causative of, Pain Inflammation is not a sole source of pain. However, in certain embodiments, placental stem cells can be used to ameliorate pain related to, or caused by, inflammation. In one embodiment, provided herein is a method for the amelioration of pain in an individual comprising contacting immune cell(s) in the individual with an effective amount of placental stem cells, wherein said effective amount is an amount that (1) detectably suppresses an immune response in said individual, and (2) detectably reduces pain in said individual. In specific embodiments, said placental stem cells detectably suppress T cell proliferation in a mixed lymphocyte reaction (MLR) assay or a regression assay. The contacting can be accomplished by, e.g., administering the placental stem cells to the individual, e.g., locally, systemically, or regionally (or by a combination of such). Thus, provided herein is a method for the amelioration of pain in an individual comprising contacting immune cell(s) in the individual with an effective amount of placental stem cells, wherein said effective amount is an amount that (1) detectably modulates, e.g., suppresses, an immune and/or inflammatory response in said individual, and (2) detectably reduces pain in said individual. In a specific embodiment, contacting immune cell(s) in the individual with an effective amount of placental stem cells results in a decrease in the amount of IL-2, IL-6, IL-12, IL-17, and/or interferon-γ, or any combination thereof, in the individual. In another specific embodiment, contacting immune cell(s) in the individual with an effective amount of placental stem cells results in a decrease in the amount of CCL2, CCL12, and/or CXCL1, or any combination thereof, in the individual. In another specific embodiment, contacting immune cell(s) in the individual with an effective amount of placental stem cells results in an increase in the amount of IL-10 in the individual.

In another embodiment, provided herein is a method for the amelioration of pain in an individual comprising administering an effective amount of placental stem cells to the individual, wherein said effective amount is an amount that (1) detectably modulates, e.g., suppresses, an immune and/or inflammatory response in said individual, and (2) detectably reduces pain in said individual. In specific embodiments, said placental stem cells detectably suppress T cell proliferation in a mixed lymphocyte reaction (MLR) assay or a regression assay. The administering can be performed locally, systemically, or regionally (or by a combination of such). In a specific embodiment, administering an effective amount of placental stem cells to the individual results in a decrease in the amount of IL-2, IL-6, IL-12, IL-17, and/or interferon-γ, or any combination thereof, in the individual. In another specific embodiment, administering an effective amount of placental stem cells to the individual results in a decrease in the amount of CCL2, CCL12, and/or CXCL1, or any combination thereof, in the individual. In another specific embodiment, administering an effective amount of placental stem cells to the individual results in an increase in the amount of IL-10 in the individual.

An "immune cell" in the context of this method means any cell of the immune system (adaptive or innate), particularly T cells and NK (natural killer) cells, dendritic cells, and macrophages. Thus, in various embodiments of the method, placental stem cells are contacted with a plurality of immune cells, wherein the plurality of immune cells are, or comprises, a plurality of T cells (e.g., a plurality of CD3$^+$ T cells, CD4$^+$ T cells and/or CD8$^+$ T cells) and/or natural killer cells. An "immune response" in the context of the method can be any response by an immune cell to a stimulus normally perceived by an immune cell, e.g., a response to the presence of an antigen. In various embodiments, an immune response can be the proliferation of T cells (e.g., CD3$^+$ T cells, CD4$^+$ T cells and/or CD8+ T cells) in response to a foreign antigen, such as an antigen present in a transfusion or graft, or to a self-antigen, as in an autoimmune disease. The immune response can also be a proliferation of T cells contained within a graft. The immune response can also be any activity of a natural killer (NK) cell, the maturation of a dendritic cell, the differentiation of T cells, skewing macrophages into the M1 or M2 lineage, or the like.

Placental stem cells used for reduction or amelioration of pain, e.g., by reduction of inflammation, can also be derived from a single species, e.g., the species of the intended recipient or the species of the immune cells the function of which is to be reduced or suppressed, or can be derived from multiple species.

In various embodiments, said contacting is sufficient to suppress an immune function (e.g., T cell proliferation in response to an antigen) or inflammation in an individual afflicted with pain by at least 50%, 60%, 70%, 80%, 90% or 95%, compared to the immune function in the absence of the placental stem cells. Such suppression in an in vivo context can be determined in an in vitro assay (see below) using, e.g., a sample of T cells from the individual; that is, the degree of suppression in the in vitro assay can be extrapolated, for a particular number of placental stem cells and a number of immune cells in a recipient individual, to a degree of suppression in the individual.

Placental stem cells can be tested, e.g., in an MLR comprising combining CD4+ or CD8+ T cells, dendritic cells (DC) and placental stem cells in a ratio of about 10:1:2, wherein the T cells are stained with a dye such as, e.g., CFSE that partitions into daughter cells, and wherein the T cells are allowed to proliferate for about 6 days. The T cells and/or DC cells can be obtained from the individual to be treated, e.g., can be autologous to the individual, or can be allogeneic to the individual. The placental stem cells are immunosuppressive if the T cell proliferation at 6 days in the presence of placental stem cells is detectably reduced compared to T cell proliferation in the presence of DC and absence of placental stem cells. In one embodiment of an MLR, for example, placental stem cells can be either thawed or harvested from culture. About 20,000 placental stem cells are resuspended in 100 μl of medium (RPMI 1640, 1 mM HEPES buffer, antibiotics, and 5% pooled human serum), and allowed to attach to the bottom of a well for 2 hours. CD4+ and/or CD8+ T cells are isolated from whole peripheral blood mononuclear cells Miltenyi magnetic beads. The cells are CFSE stained, and a total of 100,000 T cells (CD4+ T cells alone, CD8+ T cells alone, or equal amounts of CD4+ and CD8+ T cells) are added per well. The volume in the well is brought to 200 μl, and the MLR is allowed to proceed.

In certain embodiments, the anti-inflammatory activity (i.e., immunosuppressive activity) of the placental stem cells is determined prior to administration to the individual suffering pain. This can be accomplished, for example, by determining the immunosuppressive activity of a sample of the placental stem cells to be administered for the amelioration of pain. Such an activity can be determined, for example, by testing a sample of the placental stem cells or placental stem cells in, e.g., an MLR or regression assay. In one embodiment, an MLR is performed with the sample, and a degree of immunosuppression demonstrated by the sample placental stem cells in the assay is determined. The degree of pain amelioration is expected to correlate with the immunosuppressive activity of the sampled placental stem cells. Thus, the MLR can be used as a method of determining the absolute and relative ability of a particular population of placental stem cells or placental stem cells to ameliorate pain attributable to inflammation.

The parameters of the MLR can be varied to provide more data or to best determine the capacity of a sample of placental stem cells or placental stem cells to immunosuppress, and therefore ameliorate pain. For example, because immunosuppression by placental stem cells appears to increase roughly in proportion to the number of placental stem cells present in the assay, the MLR can be performed with, in one embodiment, two or more numbers of placental stem cells, e.g., $1\times10^3$, $3\times10^3$, $1\times10^4$ and/or $3\times10^4$ placental stem cells per reaction. The number of placental stem cells relative to the number of T cells in the assay can also be varied. For example, placental stem cells and T cells in the assay can be present in any ratio of, e.g. about 10:1 to about 1:10, preferably about 1:5, though a relatively greater number of placental stem cells or T cells can be used.

The regression assay or BTR assay can be used in similar fashion.

Placental stem cells can be administered to an individual in a ratio, with respect to a known or expected number of immune cells, e.g., T cells, in the individual, of from about 10:1 to about 1:10, preferably about 1:5. However, placental stem cells can be administered to an individual in a ratio of, in non-limiting examples, about 10,000:1, about 1,000:1, about 100:1, about 10:1, about 1:1, about 1:10, about 1:100, about 1:1,000 or about 1:10,000. Generally, about $1\times10^5$ to about $1\times10^8$ placental stem cells per recipient kilogram, preferably about $1\times10^6$ to about $1\times10^7$ placental stem per recipient kilogram can be administered to effect immunosuppression. In various embodiments, placental stem cells administered to an individual or subject comprise at least, about, or no more than, $1\times10^5$, $3\times10^5$, $1\times10^6$, $3\times10^6$, $1\times10^7$, $3\times10^7$, $1\times10^8$, $3\times10^8$, $1\times10^9$, $3\times10^9$ placental stem cells, or more.

The placental stem cells can also be administered with one or more second types of stem cells, e.g., mesenchymal stem cells from bone marrow. Such second stem cells can be administered to an individual with said placental stem cells in a ratio of, e.g., between about 1:10 to about 10:1.

To facilitate contacting, or proximity of, placental stem cells and immune cells in vivo, the placental stem cells can be administered to an individual by any route sufficient to bring the placental stem cells and immune cells into contact with each other. For example, the placental stem cells can be administered to the individual, e.g., intravenously, intramuscularly, intraperitoneally, intraocularly, parenterally, intrathecally, subcutaneously, or directly into an organ, e.g., pancreas. The placental stem cells can be administered to an area of an individual suffering pain at the site of pain, or at a site of nerve damage causing the pain. For in vivo administration, the placental stem cells can be formulated as a pharmaceutical composition, as described in Section 5.8.1.2, below.

In another aspect, the placental stem cells administered to the individual suffering from pain have been genetically engineered to express one or more anti-inflammatory cytokines. In a specific embodiment, said anti-inflammatory cytokines comprise IL-10.

5.3 Second Therapeutic Compositions and Second Therapies

In any of the above methods of treatment of pain in an individual, the method can comprise the administration of a second therapeutic composition or second therapy, e.g., an anti-pain medication or therapy. In a preferred embodiment, the second active agents are capable of relieving pain, inhibiting or modulating inflammatory reactions, providing a sedative effect or an antineuralgic effect, or ensuring patient comfort.

In certain embodiments, the second therapeutic compositions comprise, but are not limited to, opioid analgesics, non-narcotic analgesics, antiinflammatories, cox-2 inhibitors, alpha-adrenergic receptor agonists or antagonists, ketamine, anesthetic agents, NMDA antagonists, immunomodulatory agents, immunosuppressive agents, antidepressants, anticonvulsants, antihypertensives, anxiolytics, calcium channel blockers, muscle relaxants, corticosteroids, hyperbaric oxygen, JNK inhibitors, other therapeutics known to relieve pain, and pharmaceutically acceptable salts, solvates, hydrates, stereoisomers, clathrates, prodrugs and pharmacologically active metabolites thereof.

In certain embodiments, the second therapeutic composition is an opioid. Opioids can be used, e.g., to treat severe pain. Examples of opioid analgesics include, but are not limited to, oxycodone (e.g., OXYCONTIN®), morphine sulfate (e.g., MS CONTIN®, DURAMORPH®, and/or ASTRAMORPH®), meperidine (e.g., DEMEROL®), and fentanyl transdermal patch (e.g., DURAGESIC®) and other known conventional medications. Oxycodone (e.g., OXYCONTIN®) is a long-acting form of an opioid and may be used, e.g., in initial and later stages of CRPS.

Non-narcotic analgesics and anti-inflammatories may be used, e.g., for treatment of pain during pregnancy and breastfeeding. Non-steroidal anti-inflammatory drugs (NSAIDs) may be used, e.g., in the early stage of pain syndrome. Examples of anti-inflammatories include, but are not limited to, salicylic acid acetate (e.g., aspirin), ibuprofen (e.g., MOTRIN®, ADVIL®, or the like), ketoprofen (e.g., ORUVAIL®), rofecoxib (e.g., VIOXX®), naproxen sodium (e.g., ANAPROX®, NAPRELAN®, NAPROSYN®, or the like), ketorolac (e.g., ACULAR®), or other known conventional medications. A specific cox-2 inhibitor is celecoxib (e.g., CELEBREX).

Examples of second therapeutic compounds that are antidepressants include, but are not limited to, nortriptyline (PAMELOR®), amitriptyline (ELAVIL®), imipramine (TOFRANIL®), doxepin (SINEQUAN®), clomipramine (ANAFRANIL®), fluoxetine (PROZAC®), sertraline (ZOLOFT®), nefazodone (SERZONE®), venlafaxine (EFFEXOR®), trazodone (DESYREL®), bupropion (WELLBUTRIN®) and other known conventional medications. See, e.g., Physicians' Desk Reference, 329, 1417, 1831 and 3270 (57th ed., 2003).

Examples of second therapeutic compounds that are anticonvulsant drugs include, but are not limited to, carbamazepine, oxcarbazepine, gabapentin (NEURONTIN®), phenyloin, sodium valproate, clonazepam, topiramate, lamotrigine, zonisamide, and tiagabine. See, e.g., Physicians' Desk Reference, 2563 (57th ed., 2003).

Other second therapeutic compounds include, but are not limited to, corticosteroids (e.g., prednisone, dexamethasone or hydrocortisone), orally active class Ib anti-arrhythmic agents (e.g., mexiletine), calcium channel blockers (e.g., nifedipine), beta-blockers (e.g., propranolol), alpha-blocker (e.g., phenoxybenzamine), and alpha2-adrenergic agonists (e.g., clonidine) can also be used in combination with an immunomodulatory compound. See, e.g., Physicians' Desk Reference, 1979, 2006 and 2190 (57th ed., 2003).

In another specific embodiment, said second therapy comprises an immunomodulatory compound, wherein the immunomodulatory compound is 3-(4-amino-1-oxo-1,3-dihydroisoindol-2-yl)-piperidine-2,6-dione; 3-(4'aminoisolindoline-1'-one)-1-piperidine-2,6-dione; 4-(Amino)-2-(2,6-dioxo(3-piperidyl))-isoindoline-1,3-dione; or α-(3-aminophthalimido) glutarimide. In a more specific embodiment, said immunomodulatory compound is a compound having the structure

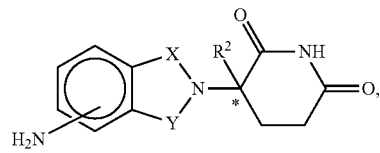

wherein one of X and Y is C=O, the other of X and Y is C=O or $CH_2$, and $R^2$ is hydrogen or lower alkyl, or a pharmaceutically acceptable salt, hydrate, solvate, clathrate, enantiomer, diastereomer, racemate, or mixture of stereoisomers thereof. In another more specific embodiment, said immunomodulatory compound is a compound having the structure

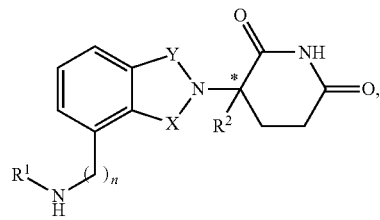

wherein one of X and Y is C=O and the other is $CH_2$ or C=O;

$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(S)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(O)NHR^3$, $C(S)NHR^3$, $C(O)NR^3R^{3'}$, $C(S)NR^3R^{3'}$ or $(C_1-C_8)$alkyl-$O(CO)R^5$;

$R^2$ is H, F, benzyl, $(C_1-C_8)$alkyl, $(C_2-C_8)$alkenyl, or $(C_2-C_8)$alkynyl; $R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;

$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$(C_1-C_6)$heterocycloalkyl, or $(C_0-C_4)$alkyl-$(C_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_8)$heteroaryl, or $(C_0-C_8)$alkyl-$C(O)O$—$R^5$ or the $R^6$ groups can join to form a heterocycloalkyl group;

n is 0 or 1; and

* represents a chiral-carbon center;

or a pharmaceutically acceptable salt, hydrate, solvate, clathrate, enantiomer, diastereomer, racemate, or mixture of stereoisomers thereof. In another more specific embodiment, said immunomodulatory compound is a compound having the structure

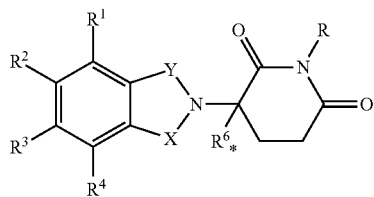

wherein:
one of X and Y is C=O and the other is CH$_2$ or C=O;
R is H or CH$_2$OCOR';
(i) each of R$^1$, R$^2$, R$^3$, or R$^4$, independently of the others, is halo, alkyl of 1 to 4 carbon atoms, or alkoxy of 1 to 4 carbon atoms or (ii) one of R, R$^2$, R$^3$, or R$^4$ is nitro or —NHR$^5$ and the remaining of R$^1$, R$^2$, R$^3$, or R$^4$ are hydrogen;
R$^5$ is hydrogen or alkyl of 1 to 8 carbons
R$^6$ hydrogen, alkyl of 1 to 8 carbon atoms, benzo, chloro, or fluoro;
R' is R$^7$—CHR$^{10}$—N(R$^8$R$^9$);
R$^7$ is m-phenylene or p-phenylene or —(C$_n$H$_{2n}$)— in which n has a value of 0 to 4;
each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$_1$CH$_2$CH$_2$— in which X$_1$ is —O—, —S—, or —NH—;
R$^{10}$ is hydrogen, alkyl of to 8 carbon atoms, or phenyl; and
* represents a chiral-carbon center;
or a pharmaceutically acceptable salt, hydrate, solvate, clathrate, enantiomer, diastereomer, racemate, or mixture of stereoisomers thereof. In specific embodiments, the second therapeutic compound is lenalidomide or pomalidomide.

Any combination of the above therapeutic agents can be administered. Such therapeutic agents can be administered in any combination with the placental stem cells, at the same time or as a separate course of treatment.

It should be noted that some of the second therapeutic compounds listed above (e.g., fluoxetine), though having a beneficial effect, may themselves as a side effect cause neuropathic pain in a small number of recipients. Generally, such compounds are considered safe to administer; however, one of ordinary skill in the art (e.g., a physician) will be able to determine the relative benefit of administering such a second therapeutic compound compared to the risk of further neuropathic pain.

Placental stem cells can be administered to the individual suffering from pain in the form of a pharmaceutical composition, e.g., a pharmaceutical composition suitable for intravenous, intramuscular or intraperitoneal injection. Placental stem cells can be administered to the individual in a single dose, or in multiple doses. Where placental stem cells are administered in multiple doses, the doses can be part of a therapeutic regimen designed to relieve the pain, or can be part of a long-term therapeutic regimen designed to treat the underlying cause of the pain. In embodiments in which placental stem cells are administered with a second therapeutic agent, or with a second type of stem cell, the placental stem cells and second therapeutic agent and/or second type of stem cell can be administered at the same time or different times, e.g., the administrations can take place within 1, 2, 3, 4, 5, 6, 7, 8, 9 10, 20, 30, 40, or 50 minutes of each other, or 1, 2, 3, 4, 5, 6, 7, 8, 9, 10, 12, 14, 16, 18, 20, or 22 hours of each other, or within 1, 2, 3, 4, 5, 6, 7 8, 9 or 10 days or more of each other.

5.4 Placental Stem Cells and Placental Stem Cell Populations

The methods of treating an individual having pain, or ameliorating pain in an individual, provided herein comprise administering placental stem cells to the individual suffering pain. In certain embodiments, the placental stem cells also have, in sufficient numbers, the capacity to detectably suppress an immune function, e.g., proliferation of CD4$^+$ and/or CD8$^+$ T cells in a mixed lymphocyte reaction assay or regression assay.

Placental stem cells can be either fetal or maternal in origin (that is, can have the genotype of either the mother or fetus). Populations of placental stem cells, or populations of cells comprising placental stem cells, can comprise placental stem cells that are solely fetal or maternal in origin, or can comprise a mixed population of placental stem cells of both fetal and maternal origin. The placental stem cells, and populations of cells comprising the placental stem cells, can be identified and selected by the morphological, marker, and culture characteristics discussed below.

5.4.1 Physical and Morphological Characteristics

The placental stem cells used as described herein, when cultured in primary cultures or in cell culture, adhere to the tissue culture substrate, e.g., tissue culture container surface (e.g., tissue culture plastic). Placental stem cells in culture assume a generally fibroblastoid, stellate appearance, with a number of cyotplasmic processes extending from the central cell body. The placental stem cells are, however, morphologically differentiable from fibroblasts cultured under the same conditions, as the placental stem cells exhibit a greater number of such processes than do fibroblasts. Morphologically, placental stem cells are also differentiable from hematopoietic stem cells, which generally assume a more rounded, or cobblestone, morphology in culture.

5.4.2 Cell Surface, Molecular and Genetic Markers

The isolated placental stem cells, e.g., isolated multipotent placental stem cells, and populations of such isolated placental stem cells, useful in the methods disclosed herein, e.g., the methods of treatment of pain, are tissue culture plastic-adherent human placental stem cells that have characteristics of multipotent cells or stem cells, and express a plurality of markers that can be used to identify and/or isolate the cells, or populations of cells that comprise the stem cells. The isolated placental stem cells, and placental cell populations (e.g, two or more isolated placental stem cells) described herein include placental stem cells and placental cell-containing cell populations obtained directly from the placenta, or any part thereof (e.g., chorion, placental cotyledons, or the like). Isolated placental cell populations also include populations of (that is, two or more) isolated placental stem cells in culture, and a population in a container, e.g., a bag. The isolated placental stem cells described herein are not bone marrow-derived mesenchymal cells, adipose-derived mesenchymal stem cells, or mesenchymal cells obtained from umbilical cord blood, placental blood, or peripheral blood. Placental stem cells, e.g., placental multipotent cells and placental stem cells, useful in the methods and compositions described herein are described herein and, e.g., in U.S. Pat. Nos. 7,311,904; 7,311,905; and 7,468,276; and in U.S. Patent Application Publication No. 2007/0275362, the disclosures of which are hereby incorporated by reference in their entireties.

In certain embodiments, the isolated placental stem cells are CD34$^-$, CD10$^+$ and CD105$^+$ as detected by flow cytometry. In another specific embodiment, the isolated CD34$^-$, CD10$^+$, CD105$^+$ placental stem cells have the potential to differentiate into cells of a neural phenotype, cells of an osteogenic phenotype, and/or cells of a chondrogenic phenotype. In another specific embodiment, the isolated CD34$^-$, CD10$^+$, CD105$^+$ placental stem cells are additionally CD200$^+$, i.e., the placental stem cells are CD10+, CD34−, CD105+, and CD200+. In another specific embodiment, the isolated CD34$^-$, CD10$^+$, CD105$^+$ placental stem cells are additionally CD45 or CD90$^+$. In another specific embodiment, the isolated CD34$^-$, CD10$^+$, CD105$^+$ placental stem cells are additionally CD45$^-$ and CD90$^+$, as detected by flow cytometry. In another specific embodiment, the isolated CD34$^-$, CD10$^+$, CD105$^+$, CD200$^+$ placental stem cells are additionally CD90$^+$ or CD45$^-$, as detected by flow cytometry. In another specific embodiment, the isolated CD34$^-$, CD10$^+$, CD105$^+$, CD200$^+$ placental stem cells are additionally CD90$^+$ and CD45$^-$, as detected by flow cytometry, i.e., the cells are CD34$^-$, CD10$^+$, CD45$^-$, CD90$^+$, CD105$^+$ and CD200$^+$. In another specific embodiment, said CD34$^-$, CD10$^+$, CD45$^-$, CD90$^+$, CD105$^+$, CD200$^+$ placental stem cells are additionally CD80$^-$ and CD86$^-$. In certain specific embodiments of any of the embodiments herein, the placental stem cells are additionally OCT-4$^+$.

Isolated placental stem cells generally do not express alpha smooth muscle actin (uSMA). Isolated placental stem cells generally express MHC Class I molecules, e.g., HLA-A,B,C.

In certain embodiments, said placental stem cells are CD34$^-$, CD10$^+$, CD105$^+$ and CD200$^+$, and one or more of CD38$^-$, CD45$^-$, CD80$^-$, CD86$^-$, CD133$^-$, MHC Class II$^-$ (e.g., HLA-DR,DP,DQ$^-$), SSEA3$^-$, SSEA4$^-$, CD29$^+$, CD44$^+$, CD73$^+$, CD90$^+$, CD105$^+$, HLA-A,B,C$^+$, PDL1$^+$, ABC-p$^+$, and/or OCT-4$^+$, as detected by flow cytometry. In other embodiments, any of the CD34$^-$, CD10$^+$, CD105$^+$ placental stem cells described above are additionally one or more of CD29$^+$, CD38$^-$, CD44$^+$, CD54$^+$, SH3$^+$ or SH4$^+$. In another specific embodiment, the placental stem cells are additionally CD44$^+$. In another specific embodiment of any of the isolated CD34$^-$, CD10$^+$, CD105$^+$ placental stem cells above, the cells are additionally one or more of CD117$^-$, CD133$^-$, KDR$^-$ (VEGFR2$^-$), HLA-A,B,C$^+$, HLA-DP,DQ, DR$^-$, or Programmed Death-1 Ligand (PDL1)$^+$, or any combination thereof.

In another embodiment, the CD34$^-$, CD10$^+$, CD105$^+$ placental stem cells are additionally one or more of CD13$^+$, CD29$^+$, CD33$^+$, CD38$^-$, CD44$^+$, CD45$^-$, CD54$^+$, CD62E$^-$, CD62L$^-$, CD62P$^-$, SH3$^+$ (CD73$^+$), SH4$^+$ (CD73$^+$), CD80$^-$, CD86$^-$, CD90$^+$, SH2$^+$ (CD105$^+$), CD106/VCAM$^+$, CD117$^-$, CD144/VE-cadherin$^{low}$, CD184/CXCR4$^-$, CD200$^+$, CD133$^-$, OCT-4$^+$, SSEA3$^-$, SSEA4$^-$, ABC-p$^+$, KDR$^-$ (VEGFR2$^-$), HLA-A,B,C$^+$, HLA-DP,DQ,DR$^-$, HLA-G$^-$, or Programmed Death-1 Ligand (PDL1)$^+$, or any combination thereof. In another embodiment, the CD34$^-$, CD10$^+$, CD105$^+$ placental stem cells are additionally CD13$^+$, CD29$^+$, CD33$^+$, CD38$^-$, CD44$^+$, CD45$^-$, CD54/ICAM$^+$, CD62E$^-$, CD62L$^-$, CD62P$^-$, SH3$^+$ (CD73$^+$), SH4$^+$ (CD73$^+$), CD80$^-$, CD86$^-$, CD90$^+$, SH2$^+$ (CD105$^+$), CD106/VCAM$^+$, CD117$^-$, CD144/VE-cadherin$^{low}$, CD184/CXCR4$^-$, CD200$^+$, CD133$^-$, OCT-4$^+$, SSEA3$^-$, SSEA4$^-$, ABC-p$^+$, KDR$^-$ (VEGFR2$^-$), HLA-A,B,C$^+$, HLA-DP,DQ, DR$^-$, HLA-G$^-$, and Programmed Death-1 Ligand (PDL1)$^+$.

In another specific embodiment, any of the placental stem cells described herein are additionally ABC-p$^+$, as detected by flow cytometry, or OCT-4$^+$ (POU5F1$^+$), as determined by reverse-transcriptase polymerase chain reaction (RT-PCR), wherein ABC-p is a placenta-specific ABC transporter protein (also known as breast cancer resistance protein (BCRP) or as mitoxantrone resistance protein (MXR)), and OCT-4 is the Octamer-4 protein (POU5F1). In another specific embodiment, any of the placental stem cells described herein are additionally SSEA3$^-$ or SSEA4$^-$, as determined by flow cytometry, wherein SSEA3 is Stage Specific Embryonic Antigen 3, and SSEA4 is Stage Specific Embryonic Antigen 4. In another specific embodiment, any of the placental stem cells described herein are additionally SSEA3$^-$ and SSEA4$^-$.

In another specific embodiment, any of the placental stem cells described herein are, or are additionally, one or more of MHC-I$^+$ (e.g., HLA-A,B,C$^+$), MHC-II$^-$ (e.g., HLA-DP,DQ, DR$^-$) or HLA-G$^-$. In another specific embodiment, any of the placental stem cells described herein are additionally MHC-I$^+$ (e.g., HLA-A,B,C$^+$), MHC-II$^-$ (e.g., HLA-DP,DQ, DR$^-$) and HLA-G$^-$.

Also provided herein are populations of the isolated placental stem cells, or populations of cells, e.g., populations of placental cells, comprising, e.g., that are enriched for, the isolated placental stem cells, that are useful in the methods and compositions disclosed herein. Preferred populations of cells are those comprising the isolated placental stem cells, wherein the populations of cells comprise, e.g., at least 10%, 15%, 20%, 25%, 30%, 35%, 40%, 45%, 50%, 55%, 60%, 65%, 70%, 75%, 80%, 85%, 90%, 95% or 98% isolated CD10$^+$, CD105 and CD34$^-$ placental stem cells; that is, at least 10%, 15%, 20%, 25%, 30%, 35%, 40%, 45%, 50%, 55%, 60%, 65%, 70%, 75%, 80%, 85%, 90%, 95% or 98% of cells in said population are isolated CD10$^+$, CD105$^+$ and CD34$^-$ placental stem cells. In a specific embodiment, the isolated CD34$^-$, CD10$^+$, CD105$^+$ placental stem cells are additionally CD200$^+$. In another specific embodiment, the isolated CD34$^-$, CD10$^+$, CD105$^+$, CD200$^+$ placental stem cells are additionally CD90$^+$ or CD45$^-$, as detected by flow cytometry. In another specific embodiment, the isolated CD34$^-$, CD10$^+$, CD105$^+$, CD200$^+$ placental stem cells are additionally CD90$^+$ and CD45$^-$, as detected by flow cytometry. In another specific embodiment, any of the isolated CD34$^-$, CD10$^+$, CD105$^+$ placental stem cells described above are additionally one or more of CD29$^+$, CD38$^-$, CD44$^+$, CD54$^+$, SH3$^+$ or SH4$^+$. In another specific embodiment, the isolated CD34$^-$, CD10$^+$, CD105$^+$ placental stem cells, or isolated CD34$^-$, CD10$^+$, CD105$^+$, CD200$^+$ placental stem cells, are additionally CD44$^+$. In a specific embodiment of any of the populations of cells comprising isolated CD34$^-$, CD10$^+$, CD105$^+$ placental stem cells above, the isolated placental stem cells are additionally one or more of CD13$^+$, CD29$^+$, CD33$^+$, CD38$^-$, CD44$^+$, CD45$^-$, CD54$^+$, CD62E$^-$, CD62L$^-$, CD62P$^-$, SH3$^+$ (CD73$^+$), SH4$^+$ (CD73$^+$), CD80$^-$, CD86$^-$, CD90$^+$, SH2$^+$ (CD105$^+$), CD106/VCAM$^+$, CD117$^-$, CD144/VE-cadherin$^{low}$, CD184/CXCR4$^-$, CD200$^+$, CD133$^-$, OCT-4$^+$, SSEA3$^-$, SSEA4$^-$, ABC-p$^+$, KDR$^-$ (VEGFR2$^-$), HLA-A,B,C$^+$, HLA-DP,DQ, DR$^-$, HLA-G$^-$, or Programmed Death-1 Ligand (PDL1)$^+$, or any combination thereof. In another specific embodiment, the CD34$^-$, CD10$^+$, CD105$^+$ placental stem cells are additionally CD13$^+$, CD29$^+$, CD33$^+$, CD38$^-$, CD44$^+$, CD45$^-$, CD54/ICAM$^+$, CD62E$^-$, CD62L$^-$, CD62P$^-$, SH3$^+$ (CD73$^+$), SH4$^+$ (CD73$^+$), CD80$^-$, CD86$^-$, CD90$^+$, SH2$^+$ (CD105$^+$), CD106/VCAM$^+$, CD117$^-$, CD144/VE-cadherin$^{low}$, CD184/CXCR4$^-$, CD200$^+$, CD133$^-$, OCT-4$^+$, SSEA3$^-$, SSEA4$^-$, ABC-p$^+$, KDR$^-$ (VEGFR2$^-$), HLA-A,B,C$^+$, HLA-DP,DQ, DR$^-$, HLA-G$^-$, and Programmed Death-1 Ligand (PDL1)$^+$.

In certain embodiments, the isolated placental stem cells in said population of cells are one or more, or all, of CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3$^-$, SSEA4$^-$, OCT-4$^+$, and ABC-p$^+$, wherein said isolated placental stem cells are obtained by physical and/or enzymatic disruption of placental tissue. In a specific embodiment, the isolated placental stem cells are OCT-4$^+$ and ABC-p$^+$. In another specific embodiment, the isolated placental stem cells are OCT-4$^+$ and CD34$^-$, wherein said isolated placental stem cells have at least one of the following characteristics: CD10$^+$, CD29$^+$, CD44$^+$, CD45$^-$, CD54$^+$, CD90$^+$, SH3$^+$, SH4$^+$, SSEA3$^-$, and SSEA4$^-$. In another specific embodiment, the isolated placental stem cells are OCT-4$^+$, CD34$^-$, CD10$^+$, CD29$^+$, CD44$^+$, CD45$^-$, CD54$^+$, CD90$^+$, SH3$^+$, SH4$^+$, SSEA3$^-$, and SSEA4$^-$. In another embodiment, the isolated placental stem cells are OCT-4$^+$, CD34$^-$, SSEA3$^-$, and SSEA4$^-$. In another specific embodiment, the isolated placental stem cells are OCT-4$^+$ and CD34$^-$, and are either SH2$^+$ or SH3$^+$. In another specific embodiment, the isolated placental stem cells are OCT-4$^+$, CD34$^-$, SH2$^+$, and SH3$^+$. In another specific embodiment, the isolated placental stem cells are OCT-4$^+$, CD34$^-$, SSEA3$^-$, and SSEA4$^-$, and are either SH2$^+$ or SH3$^+$. In another specific embodiment, the isolated placental stem cells are OCT-4$^+$ and CD34$^-$, and either SH2$^+$ or SH3$^+$, and are at least one of CD10$^+$, CD29$^+$, CD44$^+$, CD45$^-$, CD54$^+$, CD90$^+$, SSEA3$^-$, or SSEA4$^-$. In another specific embodiment, the isolated placental stem cells are OCT-4$^+$, CD34$^-$, CD10$^+$, CD29$^+$, CD44$^+$, CD45$^-$, CD54$^+$, CD90$^+$, SSEA3$^-$, and SSEA4$^-$, and are either SH2$^+$ or SH3$^+$.

In another embodiment, the isolated placental stem cells are SH2$^+$, SH3$^+$, SH4$^+$ and OCT-4$^+$. In another specific embodiment, the isolated placental stem cells are CD10$^+$, CD29$^+$, CD44$^+$, CD54$^+$, CD90$^+$, CD34$^-$, CD45$^-$, SSEA3$^-$, or SSEA4$^-$. In another embodiment, the isolated placental stem cells are SH2$^+$, SH3$^+$, SH4$^+$, SSEA3$^-$ and SSEA4$^-$. In another specific embodiment, the isolated placental stem cells are SH2$^+$, SH3$^+$, SH4$^+$, SSEA3$^-$ and SSEA4$^-$, CD10$^+$, CD29$^+$, CD44$^+$, CD54$^+$, CD90$^+$, OCT-4$^+$, CD34$^-$ or CD45.

In another embodiment, the isolated placental stem cells useful in the methods and compositions disclosed herein are CD10$^+$, CD29$^+$, CD34$^-$, CD44$^+$, CD45$^-$, CD54$^+$, CD90$^+$, SH2$^+$, SH3$^+$, and SH4$^+$; wherein said isolated placental stem cells are additionally one or more of OCT-4$^+$, SSEA3$^-$ or SSEA4$^-$.

In certain embodiments, isolated placental stem cells are CD200$^+$ or HLA-G$^-$. In a specific embodiment, the isolated placental stem cells are CD200$^+$ and HLA-G$^-$. In another specific embodiment, the isolated placental stem cells are additionally CD73$^+$ and CD105$^+$. In another specific embodiment, the isolated placental stem cells are additionally CD34$^-$, CD38$^-$ or CD45$^-$. In another specific embodiment, the isolated placental stem cells are additionally CD34$^-$, CD38$^-$ and CD45$^-$. In another specific embodiment, said placental stem cells are CD34$^-$, CD38$^-$, CD45$^-$, CD73$^+$ and CD105$^+$. In another specific embodiment, said isolated CD200$^+$ or HLA-G$^-$ placental stem cells facilitate the formation of embryoid-like bodies in a population of placental cells comprising the isolated placental stem cells, under conditions that allow the formation of embryoid-like bodies. In another specific embodiment, the isolated placental stem cells are isolated away from placental cells that are not said placental stem cells. In another specific embodiment, said isolated placental stem cells are isolated away from placental cells that do not display this combination of markers.

In another embodiment, a cell population useful in the methods and compositions described herein is a population of cells comprising, e.g., that is enriched for, CD200$^+$, HLA-G$^-$ placental stem cells. In a specific embodiment, said population is a population of placental cells. In various embodiments, at least about 10%, at least about 20%, at least about 30%, at least about 40%, at least about 50%, or at least about 60% of cells in said cell population are isolated CD200$^+$, HLA-G$^-$ placental stem cells. Preferably, at least about 70% of cells in said cell population are isolated CD200$^+$, HLA-G$^-$ placental stem cells. More preferably, at least about 90%, 95%, or 99% of said cells are isolated CD200$^+$, HLA-G$^-$ placental stem cells. In a specific embodiment of the cell populations, said isolated CD200$^+$, HLA-G$^-$ placental stem cells are also CD73$^+$ and CD105$^+$. In another specific embodiment, said isolated CD200$^+$, HLA-G$^-$ placental stem cells are also CD34$^-$, CD38$^-$ or CD45$^-$. In another specific embodiment, said isolated CD200$^+$, HLA-G$^-$ placental stem cells are also CD34$^-$, CD38$^-$, CD45$^-$, CD73$^+$ and CD105$^+$. In another embodiment, said cell population produces one or more embryoid-like bodies when cultured under conditions that allow the formation of embryoid-like bodies. In another specific embodiment, said cell population is isolated away from placental cells that are not placental stem cells. In another specific embodiment, said isolated CD200$^+$, HLA-G$^-$ placental stem cells are isolated away from placental cells that do not display these markers.

In another embodiment, the isolated placental stem cells useful in the methods and compositions described herein are CD73$^+$, CD105$^+$, and CD200$^+$. In another specific embodiment, the isolated placental stem cells are HLA-G$^-$. In another specific embodiment, the isolated placental stem cells are CD34$^-$, CD38$^-$ or CD45$^-$. In another specific embodiment, the isolated placental stem cells are CD34$^-$, CD38$^-$ and CD45$^-$. In another specific embodiment, the isolated placental stem cells are CD34$^-$, CD38$^-$, CD45$^-$, and HLA-G$^-$. In another specific embodiment, the isolated CD73$^+$, CD105$^+$, and CD200$^+$ placental stem cells facilitate the formation of one or more embryoid-like bodies in a population of placental cells comprising the isolated placental stem cells, when the population is cultured under conditions that allow the formation of embryoid-like bodies. In another specific embodiment, the isolated placental stem cells are isolated away from placental cells that are not the isolated placental stem cells. In another specific embodiment, the isolated placental stem cells are isolated away from placental cells that do not display these markers.

In another embodiment, a cell population useful in the methods and compositions described herein is a population of cells comprising, e.g., that is enriched for, isolated CD73$^+$, CD105$^+$, CD200$^+$ placental stem cells. In various embodiments, at least about 10%, at least about 20%, at least about 30%, at least about 40%, at least about 50%, or at least about 60% of cells in said cell population are isolated CD73$^+$, CD105$^+$, CD200$^+$ placental stem cells. In another embodiment, at least about 70% of said cells in said population of cells are isolated CD73$^+$, CD105$^+$, CD200$^+$ placental stem cells. In another embodiment, at least about 80%, 90%, 95% or 99% of cells in said population of cells are isolated CD73$^+$, CD105$^+$, CD200$^+$ placental stem cells. In a specific embodiment of said populations, the isolated placental stem cells are HLA-G$^-$. In another specific embodiment, the isolated placental stem cells are additionally CD34$^-$, CD38$^-$ or CD45$^-$. In another specific embodiment, the isolated placental stem cells are additionally CD34⁻, CD38⁻ and CD45⁻. In another specific embodiment, the isolated placental stem cells are additionally CD34⁻, CD38⁻, CD45⁻, and HLA-G⁻. In another specific embodiment, said population of cells produces one or more embryoid-like bodies when cultured under conditions that allow the formation of embryoid-like bodies. In another specific embodiment, said population of placental stem cells is isolated away from placental cells that are not placental stem cells. In another specific embodiment, said population of placental stem cells is isolated away from placental cells that do not display these characteristics.

In certain other embodiments, the isolated placental stem cells are one or more of CD10⁺, CD29⁺, CD34⁻, CD38⁻, CD44⁺, CD45⁻, CD54⁺, CD90⁺, SH2⁺, SH3⁺, SH4⁺, SSEA3⁻, SSEA4⁻, OCT-4⁺, HLA-G⁻ or ABC-p⁺. In a specific embodiment, the isolated placental stem cells are CD10⁺, CD29⁺, CD34⁻, CD38⁻, CD44⁺, CD45⁻, CD54⁺, CD90⁺, SH2⁺, SH3⁺, SH4⁺, SSEA3⁻, SSEA4⁻, and OCT-4⁺. In another specific embodiment, the isolated placental stem cells are CD10⁺, CD29⁺, CD34⁻, CD38⁻, CD45⁻, CD54⁺, SH2⁺, SH3⁺, and SH4⁺. In another specific embodiment, the isolated placental stem cells are CD10⁺, CD29⁺, CD34⁻, CD38⁻, CD45⁻, CD54⁺, SH2⁺, SH3⁺, SH4⁺ and OCT-4⁺. In another specific embodiment, the isolated placental stem cells are CD10⁺, CD29⁺, CD34⁻, CD38⁻, CD44⁺, CD45⁻, CD54⁺, CD90⁺, HLA-G⁻, SH2⁺, SH3⁺, SH4⁺. In another specific embodiment, the isolated placental stem cells are OCT-4⁺ and ABC-p⁺. In another specific embodiment, the isolated placental stem cells are SH2⁺, SH3⁺, SH4⁺ and OCT-4⁺. In another embodiment, the isolated placental stem cells are OCT-4⁺, CD34⁻, SSEA3⁻, and SSEA4⁻. In a specific embodiment, said isolated OCT-4⁺, CD34⁻, SSEA3⁻, and SSEA4⁻ placental stem cells are additionally CD10⁺, CD29⁺, CD34⁻, CD44⁺, CD45⁻, CD54⁺, CD90⁺, SH2⁺, SH3⁺, and SH4⁺. In another embodiment, the isolated placental stem cells are OCT-4⁺ and CD34⁻, and either SH3⁺ or SH4⁺. In another embodiment, the isolated placental stem cells are CD34⁻ and either CD10⁺, CD29⁺, CD44⁺, CD54⁺, CD90⁺, or OCT-4⁺.

In another embodiment, isolated placental stem cells are CD200⁺ and OCT-4⁺. In a specific embodiment, the isolated placental stem cells are CD73⁺ and CD105⁺. In another specific embodiment, said isolated placental stem cells are HLA-G⁻. In another specific embodiment, said isolated CD200⁺, OCT-4⁺ placental stem cells are CD34⁻, CD38⁻ or CD45⁻. In another specific embodiment, said isolated CD200⁺, OCT-4⁺ placental stem cells are CD34⁻, CD38⁻ and CD45⁻. In another specific embodiment, said isolated CD200⁺, OCT-4⁺ placental stem cells are CD34⁻, CD38⁻, CD45⁻, CD73⁺, CD105⁺ and HLA-G⁻. In another specific embodiment, the isolated CD200⁺, OCT-4⁺ placental stem cells facilitate the production of one or more embryoid-like bodies by a population of placental cells that comprises the placental stem cells, when the population is cultured under conditions that allow the formation of embryoid-like bodies. In another specific embodiment, said isolated CD200⁺, OCT-4⁺ placental stem cells are isolated away from placental cells that are not said placental stem cells. In another specific embodiment, said isolated CD200⁺, OCT-4⁺ placental stem cells are isolated away from placental cells that do not display these characteristics.

In another embodiment, a cell population useful in the methods and compositions described herein is a population of cells comprising, e.g., that is enriched for, CD200⁺, OCT-4⁺ placental stem cells. In various embodiments, at least about 10%, at least about 20%, at least about 30%, at least about 40%, at least about 50%, or at least about 60% of cells in said cell population are isolated CD200⁺, OCT-4⁺ placental stem cells. In another embodiment, at least about 70% of said cells are said isolated CD200⁺, OCT-4⁺ placental stem cells. In another embodiment, at least about 80%, 90%, 95%, or 99% of cells in said cell population are said isolated CD200⁺, OCT-4⁺ placental stem cells. In a specific embodiment of the isolated populations, said isolated CD200⁺, OCT-4⁺ placental stem cells are additionally CD73⁺ and CD105⁺. In another specific embodiment, said isolated CD200⁺, OCT-4⁺ placental stem cells are additionally HLA-G⁻. In another specific embodiment, said isolated CD200⁺, OCT-4⁺ placental stem cells are additionally CD34⁻, CD38⁻ and CD45⁻. In another specific embodiment, said isolated CD200⁺, OCT-4⁺ placental stem cells are additionally CD34⁻, CD38⁻, CD45⁻, CD73⁺, CD105⁺ and HLA-G⁻. In another specific embodiment, the cell population produces one or more embryoid-like bodies when cultured under conditions that allow the formation of embryoid-like bodies. In another specific embodiment, said cell population is isolated away from placental cells that are not isolated CD200⁺, OCT-4⁺ placental cells. In another specific embodiment, said cell population is isolated away from placental cells that do not display these markers.

In another embodiment, the isolated placental stem cells useful in the methods and compositions described herein are CD73⁺, CD105⁺ and HLA-G⁻. In another specific embodiment, the isolated CD73⁺, CD105⁺ and HLA-G⁻ placental stem cells are additionally CD34⁻, CD38⁻ or CD45⁻. In another specific embodiment, the isolated CD73⁺, CD105⁺, HLA-G⁻ placental stem cells are additionally CD34⁻, CD38⁻ and CD45⁻. In another specific embodiment, the isolated CD73⁺, CD105⁺, HLA-G⁻ placental stem cells are additionally OCT-4⁺. In another specific embodiment, the isolated CD73⁺, CD105⁺, HLA-G⁻ placental stem cells are additionally CD200⁺. In another specific embodiment, the isolated CD73⁺, CD105⁺, HLA-G⁻ placental stem cells are additionally CD34⁻, CD38⁻, CD45⁻, OCT-4⁺ and CD200⁺. In another specific embodiment, the isolated CD73⁺, CD105⁺, HLA-G⁻ placental stem cells facilitate the formation of embryoid-like bodies in a population of placental cells comprising said placental stem cells, when the population is cultured under conditions that allow the formation of embryoid-like bodies. In another specific embodiment, said the isolated CD73⁺, CD105⁺, HLA-G⁻ placental stem cells are isolated away from placental cells that are not the isolated CD73⁺, CD105⁺, HLA-G⁻ placental stem cells. In another specific embodiment, said the isolated CD73⁺, CD105⁺, HLA-G⁻ placental stem cells are isolated away from placental cells that do not display these markers.

In another embodiment, a cell population useful in the methods and compositions described herein is a population of cells comprising, e.g., that is enriched for, isolated CD73⁺, CD105⁺ and HLA-G⁻ placental stem cells. In various embodiments, at least about 10%, at least about 20%, at least about 30%, at least about 40%, at least about 50%, or at least about 60% of cells in said population of cells are isolated CD73⁺, CD105⁺, HLA-G⁻ placental stem cells. In another embodiment, at least about 70% of cells in said population of cells are isolated CD73⁺, CD105⁺, HLA-G⁻ placental stem cells. In another embodiment, at least about 90%, 95% or 99% of cells in said population of cells are isolated CD73⁺, CD105⁺, HLA-G⁻ placental stem cells. In a specific embodiment of the above populations, said isolated CD73⁺, CD105⁺, HLA-G⁻ placental stem cells are additionally CD34⁻, CD38⁻ or CD45⁻. In another specific embodiment, said isolated CD73⁺, CD105⁺, HLA-G⁻ placental stem cells are additionally CD34⁻, CD38⁻ and CD45⁻. In another specific embodiment, said isolated CD73⁺, CD105⁺, HLA-G⁻ placental stem cells are additionally OCT-4⁺. In another specific embodiment, said isolated CD73⁺, CD105⁺, HLA-G⁻ placental stem cells are additionally CD200⁺. In another specific embodiment, said isolated CD73⁺, CD105⁺, HLA-G⁻ placental stem cells are additionally CD34⁻, CD38⁻, CD45⁻, OCT-4⁺ and CD200⁺. In another specific embodiment, said cell population is isolated away from placental cells that are not CD73⁺, CD105⁺, HLA-G⁻ placental stem cells. In another specific embodiment, said cell population is isolated away from placental cells that do not display these markers.

In another embodiment, the isolated placental stem cells are CD73⁺ and CD105⁺ and facilitate the formation of one or more embryoid-like bodies in a population of isolated placental cells comprising said CD73⁺, CD105⁺ cells when said population is cultured under conditions that allow formation of embryoid-like bodies. In another specific embodiment, said isolated CD73⁺, CD105⁺ placental stem cells are additionally CD34⁻, CD38⁻ or CD45⁻. In another specific embodiment, said isolated CD73⁺, CD105⁺ placental stem cells are additionally CD34⁻, CD38⁻ and CD45⁻. In another specific embodiment, said isolated CD73⁺, CD105⁺ placental stem cells are additionally OCT-4⁺. In another specific embodiment, said isolated CD73⁺, CD105⁺ placental stem cells are additionally OCT-4⁺, CD34⁻, CD38⁻ and CD45⁻. In another specific embodiment, said isolated CD73⁺, CD105⁺ placental stem cells are isolated away from placental cells that are not said cells. In another specific embodiment, said isolated CD73⁺, CD105⁺ placental stem cells are isolated away from placental cells that do not display these characteristics.

In another embodiment, a cell population useful in the methods and compositions described herein is a population of cells comprising, e.g., that is enriched for, isolated placental stem cells that are CD73⁺, CD105⁺ and facilitate the formation of one or more embryoid-like bodies in a population of isolated placental cells comprising said cells when said population is cultured under conditions that allow formation of embryoid-like bodies. In various embodiments, at least about 10%, at least about 20%, at least about 30%, at least about 40%, at least about 50%, or at least about 60% of cells in said population of cells are said isolated CD73⁺, CD105⁺ placental stem cells. In another embodiment, at least about 70% of cells in said population of cells are said isolated CD73⁺, CD105⁺ placental stem cells. In another embodiment, at least about 80%, 90%, 95% or 99% of cells in said population of cells are said isolated CD73⁺, CD105⁺ placental stem cells. In a specific embodiment of the above populations, said isolated CD73⁺, CD105⁺ placental stem cells are additionally CD34⁻, CD38⁻ or CD45⁻. In another specific embodiment, said isolated CD73⁺, CD105⁺ placental stem cells are additionally CD34⁻, CD38⁻ and CD45⁻. In another specific embodiment, said isolated CD73⁺, CD105⁺ placental stem cells are additionally OCT-4⁺. In another specific embodiment, said isolated CD73⁺, CD105⁺ placental stem cells are additionally CD200⁺. In another specific embodiment, said isolated CD73⁺, CD105⁺ placental stem cells are additionally CD34⁻, CD38⁻, CD45⁻, OCT-4⁺ and CD200⁺. In another specific embodiment, said cell population is isolated away from placental cells that are not said isolated CD73⁺, CD105⁺ placental stem cells. In another specific embodiment, said cell population is isolated away from placental cells that do not display these markers.

In another embodiment, the isolated placental stem cells are OCT-4⁺ and facilitate formation of one or more embryoid-like bodies in a population of isolated placental cells comprising said placental stem cells when said population of cells is cultured under conditions that allow formation of embryoid-like bodies. In a specific embodiment, said isolated OCT-4⁺ placental stem cells are additionally CD73⁺ and CD105⁺. In another specific embodiment, said isolated OCT-4⁺ placental stem cells are additionally CD34⁻, CD38⁻, or CD45⁻. In another specific embodiment, said isolated OCT-4⁺ placental stem cells are additionally CD200⁺. In another specific embodiment, said isolated OCT-4⁺ placental stem cells are additionally CD73⁺, CD105⁺, CD200⁺, CD34⁻, CD38⁻, and CD45⁻. In another specific embodiment, said isolated OCT-4⁺ placental stem cells are isolated away from placental cells that are not OCT-4⁺ placental cells. In another specific embodiment, said isolated OCT-4⁺ placental stem cells are isolated away from placental cells that do not display these characteristics.

In another embodiment, a cell population useful in the methods and compositions described herein is a population of cells comprising, e.g., that is enriched for, isolated placental stem cells that are OCT-4⁺ and facilitate the formation of one or more embryoid-like bodies in a population of isolated placental cells comprising said cells when said population is cultured under conditions that allow formation of embryoid-like bodies. In various embodiments, at least about 10%, at least about 20%, at least about 30%, at least about 40%, at least about 50%, or at least about 60% of cells in said population of cells are said isolated OCT-4⁺ placental stem cells. In another embodiment, at least about 70% of cells in said population of cells are said isolated OCT-4⁺ placental stem cells. In another embodiment, at least about 80%, 90%, 95% or 99% of cells in said population of cells are said isolated OCT-4⁺ placental stem cells. In a specific embodiment of the above populations, said isolated OCT-4⁺ placental stem cells are additionally CD34⁻, CD38⁻ or CD45⁻. In another specific embodiment, said isolated OCT-4⁺ placental stem cells are additionally CD34⁻, CD38⁻ and CD45⁻. In another specific embodiment, said isolated OCT-4⁺ placental stem cells are additionally CD73⁺ and CD105⁺. In another specific embodiment, said isolated OCT-4⁺ placental stem cells are additionally CD200⁺. In another specific embodiment, said isolated OCT-4⁺ placental stem cells are additionally CD73⁺, CD105⁺, CD200⁺, CD34⁻, CD38⁻, and CD45⁻. In another specific embodiment, said cell population is isolated away from placental cells that are not said placental stem cells. In another specific embodiment, said cell population is isolated away from placental cells that do not display these markers.

In another embodiment, the isolated placental stem cells useful in the methods and compositions described herein are isolated HLA-A,B,C⁺, CD45⁻, CD133⁻ and CD34⁻ placental stem cells. In another embodiment, a cell population useful in the methods and compositions described herein is a population of cells comprising isolated placental stem cells, wherein at least about 70%, at least about 80%, at least about 90%, at least about 95% or at least about 99% of cells in said population of cells are isolated HLA-A,B,C⁺, CD45⁻, CD133⁻ and CD34⁻ placental stem cells. In a specific embodiment, said isolated placental cell or population of isolated placental cells is isolated away from placental cells that are not HLA-A,B,C⁺, CD45⁻, CD133⁻ and CD34⁻ placental stem cells. In another specific embodiment, said isolated placental stem cells are non-maternal in origin. In another specific embodiment, said population of isolated placental stem cells are substantially free of maternal components; e.g., at least about 40%, 45%, 50%, 55%, 60%, 65%, 70%, 75%, 80%, 85%, 90%, 95%, 98% or 99% of said cells in said population of isolated placental stem cells are non-maternal in origin.

In another embodiment, the isolated placental stem cells useful in the methods and compositions described herein are isolated $CD10^+$, $CD13^+$, $CD33^+$, $CD45^-$, $CD117^-$ and $CD133^-$ placental stem cells. In another embodiment, a cell population useful in the methods and compositions described herein is a population of cells comprising isolated placental stem cells, wherein at least about 70%, at least about 80%, at least about 90%, at least about 95% or at least about 99% of cells in said population of cells are isolated $CD10^+$, $CD13^+$, $CD33^+$, $CD45^-$, $CD117^-$ and $CD133^-$ placental stem cells. In a specific embodiment, said isolated placental stem cells or population of isolated placental stem cells is isolated away from placental cells that are not said isolated placental stem cells. In another specific embodiment, said isolated $CD10^+$, $CD13^+$, $CD33^+$, $CD45^-$, $CD117^-$ and $CD133^-$ placental stem cells are non-maternal in origin, i.e., have the fetal genotype. In another specific embodiment, at least about 40%, 45%, 50%, 55%, 60%, 65%, 70%, 75%, 90%, 85%, 80%, 95%, 98% or 99% of said cells in said population of isolated placental stem cells, are non-maternal in origin. In another specific embodiment, said isolated placental stem cells or population of isolated placental stem cells are isolated away from placental cells that do not display these characteristics.

In another embodiment, the isolated placental stem cells are isolated $CD10^+$ $CD33^-$, $CD44^+$, $CD45^-$, and $CD117^-$ placental cells. In another embodiment, a cell population useful for the in the methods and compositions described herein is a population of cells comprising, e.g., enriched for, isolated placental cells, wherein at least about 70%, at least about 80%, at least about 90%, at least about 95% or at least about 99% of cells in said population of cells are isolated $CD10^+$ $CD33^-$, $CD44^+$, $CD45^-$, and $CD117^-$ placental cells. In a specific embodiment, said isolated placental cell or population of isolated placental cells is isolated away from placental cells that are not said cells. In another specific embodiment, said isolated placental cells are non-maternal in origin. In another specific embodiment, at least about 40%, 45%, 50%, 55%, 60%, 65%, 70%, 75%, 80%, 85%, 90%, 95%, 98% or 99% of said placental stem cells in said cell population are non-maternal in origin. In another specific embodiment, said isolated placental stem cells or population of isolated placental stem cells is isolated away from placental cells that do not display these markers.

In another embodiment, the isolated placental stem cells useful in the methods and compositions described herein are isolated $CD10^+$ $CD13^-$, $CD33^-$, $CD45^-$, and $CD117^-$ placental stem cells. In another embodiment, a cell population useful in the methods and compositions described herein is a population of cells comprising, e.g., enriched for, isolated $CD10^+$, $CD13^-$, $CD33^-$, $CD45^-$, and $CD117^-$ placental stem cells, wherein at least about 70%, at least about 80%, at least about 90%, at least about 95% or at least about 99% of cells in said population are CD10+ $CD13^-$, $CD33^-$, $CD45^-$, and $CD117^-$ placental stem cells. In a specific embodiment, said isolated placental stem cells or population of isolated placental stem cells are isolated away from placental cells that are not said placental stem cells. In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin. In another specific embodiment, said isolated placental stem cells or population of isolated placental stem cells is isolated away from placental cells that do not display these characteristics.

In another embodiment, the isolated placental stem cells useful in the methods and compositions described herein are HLA A,B,C+, $CD45^-$, $CD34^-$, and $CD133^-$, and are additionally $CD10^+$, $CD13^+$, $CD38^+$, $CD44^+$, $CD90^+$, $CD105^+$, $CD200^+$ and/or HLA-G$^-$, and/or negative for CD117. In another embodiment, a cell population useful in the methods and compositions described herein is a population of cells comprising isolated placental stem cells, wherein at least about 20%, 25%, 30%, 35%, 40%, 45%, 50%, 55%, 60%, 65%, 70%, 75%, 80%, 85%, 90%, 95%, 98% or about 99% of the cells in said population are isolated placental stem cells that are HLA A,B,C$^-$, $CD45^-$, $CD34^-$, $CD133^-$, and that are additionally positive for CD10, CD13, CD38, CD44, CD90, CD105, CD200, and/or negative for CD117 and/or HLA-G. In a specific embodiment, said isolated placental stem cells or population of isolated placental stem cells are isolated away from placental cells that are not said placental stem cells. In another specific embodiment, said isolated placental stem cells are non-maternal in origin. In another specific embodiment, at least about 40%, 45%, 50%, 55%, 60%, 65%, 70%, 75%, 90%, 85%, 90%, 95%, 98% or 99% of said placental stem cells in said cell population are non-maternal in origin. In another specific embodiment, said isolated placental stem cells or population of isolated placental stem cells are isolated away from placental cells that do not display these characteristics.

In another embodiment, the isolated placental stem cells are isolated placental stem cells that are $CD200^+$ and $CD10^+$, as determined by antibody binding, and $CD117^-$, as determined by both antibody binding and RT-PCR. In another embodiment, the isolated placental stem cells are isolated placental stem cells that are $CD10^+$, $CD29$, $CD54^+$, $CD200^+$, HLA-G$^-$, MHC class I$^+$ and $\beta$-2-microglobulin$^+$. In another embodiment, isolated placental stem cells useful in the methods and compositions described herein are placental stem cells wherein the expression of at least one cellular marker is at least two-fold higher than in an equivalent number of mesenchymal stem cells, e.g., bone marrow-derived mesenchymal stem cells. In another specific embodiment, said isolated placental stem cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin.

In another embodiment, the isolated placental stem cells are isolated placental stem cells that are one or more of $CD10^+$, $CD29^+$, $CD44^+$, $CD45^-$, CD54/ICAM$^+$, CD62E$^-$, CD62L$^-$, CD62P$^-$, CD80$^-$, CD86$^-$, CD103$^-$, CD104$^-$, CD105$^+$, CD106/VCAM$^+$, CD144/VE-cadherin$^{low}$, CD184/CXCR4$^-$, $\beta$2-microglobulin$^{low}$, MHC-I$^{low}$, MHC-II$^-$, HLA-G$^{low}$, and/or PDL1$^{low}$. In a specific embodiment, the isolated placental stem cells are at least $CD29^+$ and $CD54^+$. In another specific embodiment, the isolated placental stem cells are at least $CD44^+$ and $CD106^+$. In another specific embodiment, the isolated placental stem cells are at least $CD29^+$.

In another embodiment, a cell population useful in the methods and compositions described herein comprises isolated placental stem cells, and at least 50%, 60%, 70%, 80%, 90%, 95%, 98% or 99% of the cells in said cell population are isolated placental stem cells that are one or more of $CD10^+$, $CD29^+$, $CD44^+$, $CD45^-$, CD54/ICAM$^+$, CD62-E$^-$, CD62-L$^-$, CD62-P$^-$, CD80$^-$, CD86$^-$, CD103$^-$, CD104$^-$, CD105$^+$, CD106/VCAM$^+$, CD144/VE-cadherin$^{dim}$, CD184/CXCR4$^-$, $\beta$2-microglobulin$^{dim}$, HLA-I$^{dim}$, HLA-II$^-$, HLA- $G^{dim}$, and/or $PDL1^{dim}$ placental stem cells. In another specific embodiment, at least 50%, 60%, 70%, 80%, 90%, 95%, 98% or 99% of cells in said cell population are $CD10^+$, $CD29^+$, $CD44^+$, $CD45^-$, $CD54/ICAM^+$, $CD62-E^-$, $CD62-L^-$, $CD62-P^-$, $CD80^-$, $CD86^-$, $CD103^-$, $CD104^-$, $CD105^+$, $CD106/VCAM^+$, $CD144/VE$-cadherin$^{dim}$, $CD184/CXCR4^-$, $\beta 2$-microglobulin$^{dim}$, $MHC-I^{dim}$, $MHC-II^-$, $HLA-G^{dim}$, and $PDL1^{dim}$ placental stem cells. In certain embodiments, the placental stem cells express HLA-II markers when induced by interferon gamma (IFN-γ).

In another embodiment, the isolated placental stem cells useful in the methods and compositions described herein are isolated placental stem cells that are one or more, or all, of $CD10^+$, $CD29^+$, $CD34^-$, $CD38^-$, $CD44^+$, $CD45^-$, $CD54^+$, $CD90^+$, $SH2^+$, $SH3^+$, $SH4^+$, $SSEA3^-$, $SSEA4^-$, $OCT-4^+$, and $ABC-p^+$, where ABC-p is a placenta-specific ABC transporter protein (also known as breast cancer resistance protein (BCRP) or as mitoxantrone resistance protein (MXR)), wherein said isolated placental stem cells are obtained by perfusion of a mammalian, e.g., human, placenta that has been drained of cord blood and perfused to remove residual blood.

In another specific embodiment of any of the above embodiments, expression of the recited cellular marker(s) (e.g., cluster of differentiation or immunogenic marker(s)) is determined by flow cytometry. In another specific embodiment, expression of the marker(s) is determined by RT-PCR.

Gene profiling confirms that isolated placental stem cells, and populations of isolated placental stem cells, are distinguishable from other cells, e.g., mesenchymal stem cells, e.g., bone marrow-derived mesenchymal stem cells. The isolated placental stem cells described herein can be distinguished from, e.g., bone marrow-derived mesenchymal stem cells on the basis of the expression of one or more genes, the expression of which is significantly higher in the isolated placental stem cells in comparison to bone marrow-derived mesenchymal stem cells. In particular, the isolated placental stem cells, useful in the methods of treatment provided herein, can be distinguished from bone marrow-derived mesenchymal stem cells on the basis of the expression of one or more genes, the expression of which is significantly higher (that is, at least twofold higher) in the isolated placental stem cells than in an equivalent number of bone marrow-derived mesenchymal stem cells, wherein the one or more genes are ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, ZC3H12A, or a combination of any of the foregoing, when the cells are grown under equivalent conditions. See, e.g., U.S. Patent Application Publication No. 2007/0275362, the disclosure of which is incorporated herein by reference in its entirety. In certain specific embodiments, said expression of said one or more genes is determined, e.g., by RT-PCR or microarray analysis, e.g., using a U133-A microarray (Affymetrix).

In another specific embodiment, said isolated placental stem cells express said one or more genes when cultured for a number of population doublings, e.g., anywhere from about 3 to about 35 population doublings, in a medium comprising DMEM-LG (e.g., from Gibco); 2% fetal calf serum (e.g., from Hyclone Labs.); 1× insulin-transferrin-selenium (ITS); 1× linoleic acid-bovine serum albumin (LA-BSA); $10^{-9}$ M dexamethasone (e.g., from Sigma); $10^{-4}$ M ascorbic acid 2-phosphate (e.g., from Sigma); epidermal growth factor 10 ng/mL (e.g., from R&D Systems); and platelet-derived growth factor (PDGF-BB) 10 ng/mL (e.g., from R&D Systems). In another specific embodiment, the isolated placental cell-specific gene is CD200.

Specific sequences for these genes can be found in GenBank at accession nos. NM_001615 (ACTG2), BC065545 (ADARB1), (NM_181847 (AMIGO2), AY358590 (ARTS-1), BC074884 (B4GALT6), BC008396 (BCHE), BC020196 (C11orf9), BC031103 (CD200), NM_001845 (COL4A1), NM_001846 (COL4A2), BC052289 (CPA4), BC094758 (DMD), AF293359 (DSC3), NM_001943 (DSG2), AF338241 (ELOVL2), AY336105 (F2RL1), NM_018215 (FLJ10781), AY416799 (GATA6), BC075798 (GPR126), NM_016235 (GPRC5B), AF340038 (ICAM1), BC000844 (IER3), BC066339 (IGFBP7), BC013142 (IL1A), BT019749 (IL6), BC007461 (IL18), (BC072017) KRT18, BC075839 (KRT8), BC060825 (LIPG), BC065240 (LRAP), BC010444 (MATN2), BC011908 (MEST), BC068455 (NFE2L3), NM_014840 (NUAK1), AB006755 (PCDH7), NM_014476 (PDLIM3), BC126199 (PKP-2), BC090862 (RTN1), BC002538 (SERPINB9), BC023312 (ST3GAL6), BC001201 (ST6GALNAC5), BC126160 or BC065328 (SLC12A8), BC025697 (TCF21), BC096235 (TGFB2), BC005046 (VTN), and BC005001 (ZC3H12A) as of March 2008.

In certain specific embodiments, said isolated placental stem cells express each of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A at a detectably higher level than an equivalent number of bone marrow-derived mesenchymal stem cells, when the cells are grown under equivalent conditions.

In a specific embodiment, the placental stem cells used in the methods described herein express the ELOVL2 gene at a detectably higher level than the expression of said gene by an equivalent number of bone marrow-derived mesenchymal stem cells (BM-MSCs). In another specific embodiment, the placental stem cells used in the methods described herein express the ST3GAL6 gene at a detectably higher level than the expression of said gene by an equivalent number of BM-MSCs. In another specific embodiment, the placental stem cells used in the methods described herein express the ST6GALNAC5 gene at a detectably higher level than the expression of said gene by an equivalent number of BM-MSCs. In another specific embodiment, the placental stem cells used in the methods described herein express the SLC12A8 gene at a detectably higher level than the expression of said gene by an equivalent number of BM-MSCs. In certain embodiments, said placental stem cells express the ARTS-1, IER3, IL6, KRT18, LRAP, MEST, NFE2L3, or TGFB2 gene at a detectably higher level than the expression of said gene by an equivalent number of BM-MSCs. In certain embodiments, said placental stem cells express all of, or express a combination of any of, the ARTS-1, IER3, IL6, KRT18, LRAP, MEST, NFE2L3, and TGFB2 genes at a detectably higher level than the expression of said genes by an equivalent number of BM-MSCs. In certain embodiments, said placental stem cells are additionally $CD10^+$, $CD34^-$, $CD105^+$, and $CD200^+$. In certain embodiments, at least 70% of said placental stem cells are non-maternal in origin.

In a specific embodiment, the placental stem cells used in the methods described herein express all of, or express a combination of any of, the ELOVL2, ST3GAL6, ST6GALNAC5, and SLC12A8 genes at a detectably higher level than the expression of said gene by an equivalent number of BM-MSCs. In certain embodiments, said placental stem cells express the ARTS-1, IER3, IL6, KRT18, LRAP, MEST, NFE2L3, or TGFB2 gene at a detectably higher level than the expression of said gene by an equivalent number of BM-MSCs. In certain embodiments, said placental stem cells express all of, or express a combination of any of, the ARTS-1, IER3, IL6, KRT18, LRAP, MEST, NFE2L3, and TGFB2 genes at a detectably higher level than the expression of said genes by an equivalent number of BM-MSCs. In certain embodiments, said placental stem cells are additionally $CD10^+$, $CD34^-$, $CD105^+$, and $CD200^+$. In certain embodiments, at least 70% of said placental stem cells are non-maternal in origin.

In certain embodiments, the placental stem cells used in the methods described herein express the CPA4, TCF21, or VTN gene at a detectably higher level than the expression of said gene by an equivalent number of BM-MSCs. In a specific embodiment, the placental stem cells used in the methods described herein express all of, or express a combination of any of, the CPA4, TCF21, and VTN genes at a detectably higher level than the expression of said gene by an equivalent number of BM-MSCs. In certain embodiments, said placental stem cells are additionally $CD10^+$, $CD34^-$, $CD105^+$, and $CD200^+$. In certain embodiments, at least 70% of said placental stem cells are non-maternal in origin.

In certain embodiments, the placental stem cells used in the methods described herein express the B4GALT6, FLJ10781, or NUAK1 gene at a detectably higher level than the expression of said gene by an equivalent number of BM-MSCs. In a specific embodiment, said placental stem cells further express the C11orf9 gene at a detectably higher level than the expression of said gene by an equivalent number of BM-MSCs. In certain embodiments, said placental stem cells are additionally $CD10^+$, $CD34^-$, $CD105^+$, and $CD200^+$. In certain embodiments, at least 70% of said placental stem cells are non-maternal in origin.

In a specific embodiment, the placental stem cells used in the methods described herein express all of, or express a combination of any of, the B4GALT6, FLJ10781, and NUAK1 genes at a detectably higher level than the expression of said gene by an equivalent number of BM-MSCs. In another specific embodiment, said placental stem cells further express the C11orf9 gene at a detectably higher level than the expression of said gene by an equivalent number of BM-MSCs. In a specific embodiment, the placental stem cells used in the methods described herein express all of, or express a combination of any of, the B4GALT6, FLJ10781, NUAK1, and C11orf9 genes at a detectably higher level than the expression of said gene by an equivalent number of BM-MSCs. In certain embodiments, said placental stem cells are additionally $CD10^+$, $CD34^-$, $CD105^+$, and $CD200^+$. In certain embodiments, at least 70% of said placental stem cells are non-maternal in origin.

In specific embodiments, the placental stem cells express CD200 and ARTS1 (aminopeptidase regulator of type 1 tumor necrosis factor); ARTS-1 and LRAP (leukocyte-derived arginine aminopeptidase); IL6 (interleukin-6) and TGFB2 (transforming growth factor, beta 2); IL6 and KRT18 (keratin 18); IER3 (immediate early response 3); MEST (mesoderm specific transcript homolog) and TGFB2; CD200 and IER3; CD200 and IL6; CD200 and KRT18; CD200 and LRAP; CD200 and MEST; CD200 and NFE2L3 (nuclear factor (erythroid-derived 2)-like 3); or CD200 and TGFB2 at a detectably higher level than an equivalent number of bone marrow-derived mesenchymal stem cells wherein said bone marrow-derived mesenchymal stem cells have undergone a number of passages in culture equivalent to the number of passages said isolated placental stem cells have undergone. In other specific embodiments, the placental stem cells express ARTS-1, CD200, IL6 and LRAP; ARTS-1, IL6, TGFB2, IER3, KRT18 and MEST; CD200, IER3, IL6, KRT18, LRAP, MEST, NFE2L3, and TGFB2; ARTS-1, CD200, IER3, IL6, KRT18, LRAP, MEST, NFE2L3, and TGFB2; or IER3, MEST and TGFB2 at a detectably higher level than an equivalent number of bone marrow-derived mesenchymal stem cells, wherein said bone marrow-derived mesenchymal stem cells have undergone a number of passages in culture equivalent to the number of passages said isolated placental stem cells have undergone.

Expression of the above-referenced genes can be assessed by standard techniques. For example, probes based on the sequence of the gene(s) can be individually selected and constructed by conventional techniques. Expression of the genes can be assessed, e.g., on a microarray comprising probes to one or more of the genes, e.g., an Affymetrix GENECHIP® Human Genome U133A 2.0 array, or an Affymetrix GENECHIP® Human Genome U133 Plus 2.0 (Santa Clara, Calif.). Expression of these genes can be assessed even if the sequence for a particular GenBank accession number is amended because probes specific for the amended sequence can readily be generated using well-known standard techniques.

The level of expression of these genes can be used to confirm the identity of a population of isolated placental stem cells, to identify a population of cells as comprising at least a plurality of isolated placental stem cells, or the like. Populations of isolated placental stem cells, the identity of which is confirmed, can be clonal, e.g., populations of isolated placental stem cells expanded from a single isolated placental stem cells, or a mixed population of placental stem cells, e.g., a population of cells comprising isolated placental stem cells that are expanded from multiple isolated placental stem cells, or a population of cells comprising isolated placental stem cells, as described herein, and at least one other type of cell.

The level of expression of these genes can be used to select populations of isolated placental stem cells. For example, a population of cells, e.g., clonally-expanded placental stem cells, may be selected if the expression of one or more of the genes listed above is significantly higher in a sample from the population of cells than in an equivalent population of bone marrow-derived mesenchymal stem cells. Such selecting can be of a population from a plurality of isolated placental stem cells populations, from a plurality of cell populations, the identity of which is not known, etc.

Isolated placental stem cells can be selected on the basis of the level of expression of one or more such genes as compared to the level of expression in said one or more genes in, e.g., a bone marrow-derived mesenchymal stem cell control. In one embodiment, the level of expression of said one or more genes in a sample comprising an equivalent number of bone marrow-derived mesenchymal stem cells is used as a control. In another embodiment, the control, for isolated placental stem cells tested under certain conditions, is a numeric value representing the level of expression of said one or more genes in bone marrow-derived mesenchymal stem cells under said conditions.

The isolated placental stem cells described herein display the above characteristics (e.g., combinations of cell surface markers and/or gene expression profiles) in primary culture, or during proliferation in medium comprising, e.g., DMEM-LG (Gibco), 2% fetal calf serum (FCS) (Hyclone Laboratories), 1× insulin-transferrin-selenium (ITS), 1× linoleic-acid-bovine-serum-albumin (LA-BSA), $10^{-9}$ M dexamethasone (Sigma), $10^{-4}$ M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin.

In certain embodiments of any of the placental stem cells disclosed herein, the cells are human. In certain embodiments of any of the placental cells disclosed herein, the cellular marker characteristics or gene expression characteristics are human markers or human genes.

In another specific embodiment of the isolated placental stem cells or populations of cells comprising the isolated placental stem cells, said cells or population have been expanded, for example, passaged at least, about, or no more than, 1, 2, 3, 4, 5, 6, 7, 8, 9, 10, 11, 12, 13, 14, 15, 16, 17, 18, 19, or 20 times, or proliferated for at least, about, or no more than, 1, 2, 3, 4, 5, 6, 7, 8, 9, 10, 12, 14, 16, 18, 20, 22, 24, 26, 28, 30, 32, 34, 36, 38 or 40 population doublings. In another specific embodiment of said isolated placental stem cells or populations of cells comprising the isolated placental stem cells, said cells or population are primary isolates. In another specific embodiment of the isolated placental stem cells, or populations of cells comprising isolated placental stem cells, that are disclosed herein, said isolated placental stem cells are fetal in origin (that is, have the fetal genotype).

In certain embodiments, said isolated placental stem cells do not differentiate during culturing in growth medium, i.e., medium formulated to promote proliferation, e.g., during proliferation in growth medium. In another specific embodiment, said isolated placental stem cells do not require a feeder layer in order to proliferate. In another specific embodiment, said isolated placental stem cells do not differentiate in culture in the absence of a feeder layer, solely because of the lack of a feeder cell layer.

In another embodiment, the isolated placental cells are positive for aldehyde dehydrogenase (ALDH), as assessed by an aldehyde dehydrogenase activity assay. Such assays are known in the art (see, e.g., Bostian and Betts, *Biochem. J.,* 173, 787, (1978)). In a specific embodiment, said ALDH assay uses ALDEFLUOR® (Aldagen, Inc., Ashland, Oreg.) as a marker of aldehyde dehydrogenase activity. In a specific embodiment, between about 3% and about 25% of placental stem cells are positive for ALDH. In another embodiment, said isolated placental stem cells show at least three-fold, or at least five-fold, higher ALDH activity than a population of bone marrow-derived mesenchymal stem cells having about the same number of cells and cultured under the same conditions.

In certain embodiments of any of the populations of cells comprising the isolated placental stem cells described herein, the placental stem cells in said populations of cells are substantially free of cells having a maternal genotype; e.g., at least 40%, 45%, 50%, 55%, 60%, 65%, 70%, 75%, 80%, 85%, 90%, 95%, 98% or 99% of the placental stem cells in said population have a fetal genotype. In certain other embodiments of any of the populations of cells comprising the isolated placental stem cells described herein, the populations of cells comprising said placental stem cells are substantially free of cells having a maternal genotype; e.g., at least 40%, 45%, 50%, 55%, 60%, 65%, 70%, 75%, 80%, 85%, 90%, 95%, 98% or 99% of the cells in said population have a fetal genotype.

In a specific embodiment of any of the above isolated placental stem cells or cell populations comprising isolated placental stem cells, the karyotype of the cells, e.g., all of the cells, or at least about 95% or about 99% of the cells in said population, is normal. In another specific embodiment of any of the above placental stem cells or populations or placental stem cells, the placental stem cells are non-maternal in origin.

In a specific embodiment of any of the embodiments of placental cells disclosed herein, the placental cells are genetically stable, displaying a normal diploid chromosome count and a normal karyotype.

Isolated placental stem cells, or populations of isolated placental stem cells, bearing any of the above combinations of markers, can be combined in any ratio. Any two or more of the above isolated placental stem cells populations can be combined to form an isolated placental stem cell population. For example, a population of isolated placental stem cells can comprise a first population of isolated placental stem cells defined by one of the marker combinations described above, and a second population of isolated placental stem cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described isolated placental stem cells or isolated placental stem cell populations can be combined.

Isolated placental stem cells useful in the methods and compositions described herein can be obtained, e.g., by disruption of placental tissue, with or without enzymatic digestion (see Section 5.3.3) or perfusion (see Section 5.3.4). For example, populations of isolated placental stem cells can be produced according to a method comprising perfusing a mammalian placenta that has been drained of cord blood and perfused to remove residual blood; perfusing said placenta with a perfusion solution; and collecting said perfusion solution, wherein said perfusion solution after perfusion comprises a population of placental cells that comprises isolated placental stem cells; and isolating said placental stem cells from said population of cells. In a specific embodiment, the perfusion solution is passed through both the umbilical vein and umbilical arteries and collected after it exudes from the placenta. In another specific embodiment, the perfusion solution is passed through the umbilical vein and collected from the umbilical arteries, or passed through the umbilical arteries and collected from the umbilical vein.

In various embodiments, the isolated placental stem cells, contained within a population of cells obtained from perfusion of a placenta, are at least 50%, 60%, 70%, 80%, 90%, 95%, 99% or at least 99.5% of said population of placental stem cells. In another specific embodiment, the isolated placental stem cells collected by perfusion comprise fetal and maternal cells. In another specific embodiment, the isolated placental stem cells collected by perfusion are at least 50%, 60%, 70%, 80%, 90%, 95%, 99% or at least 99.5% fetal cells.

In another specific embodiment, provided herein is a composition comprising a population of the isolated placental stem cells, as described herein, collected (isolated) by perfusion, wherein said composition comprises at least a portion of the perfusion solution used to isolate the placental stem cells.

Populations of the isolated placental stem cells described herein can be produced by digesting placental tissue with a tissue-disrupting enzyme to obtain a population of placental cells comprising the placental stem cells, and isolating, or substantially isolating, a plurality of the placental stem cells from the remainder of said placental cells. The whole, or any part of, the placenta can be digested to obtain the isolated placental stem cells described herein. In specific embodiments, for example, said placental tissue can be a whole placenta (e.g., including an umbilical cord), an amniotic membrane, chorion, a combination of amnion and chorion, or a combination of any of the foregoing. In other specific embodiments, the tissue-disrupting enzyme is trypsin or collagenase. In various embodiments, the isolated placental stem cells, contained within a population of cells obtained from digesting a placenta, are at least 50%, 60%, 70%, 80%, 90%, 95%, 99% or at least 99.5% of said population of placental cells.

The populations of isolated placental stem cells described above, and populations of isolated placental stem cells generally, can comprise about, at least, or no more than, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more of the isolated placental stem cells. Populations of isolated placental stem cells useful in the methods of treatment described herein comprise at least 50%, 55%, 60%, 65%, 70%, 75%, 80%, 85%, 90%, 95%, 98%, or 99% viable isolated placental stem cells, e.g., as determined by, e.g., trypan blue exclusion.

For any of the above placental stem cells, or populations of placental stem cells, the cells or population of placental stem cells are, or can comprise, cells that have been passaged at least 1, 2, 3, 4, 5, 6, 7, 8, 9, 10, 12, 14, 16, 18, or 20 times, or more, or expanded for 1, 2, 3, 4, 5, 6, 7, 8, 9, 10, 12, 14, 16, 18, 20, 22, 24, 26, 28, 30, 32, 34, 36, 38 or 40 population doublings, or more.

In a specific embodiment of any of the above placental stem cells or placental stem cells populations, the karyotype of the cells, or at least about 95% or about 99% of the cells in said population, is normal. In another specific embodiment of any of the above placental stem cells or placental stem cells populations, the cells, or cells in the population of cells, are non-maternal in origin.

Isolated placental stem cells, or populations of isolated placental stem cells, bearing any of the above combinations of markers, can be combined in any ratio. Any two or more of the above placental stem cells populations can be isolated, or enriched, to form a placental stem cells population. For example, a population of isolated placental stem cells comprising a first population of placental stem cells defined by one of the marker combinations described above can be combined with a second population of placental stem cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described placental stem cells or placental stem cells populations can be combined.

In a specific embodiment of the above-mentioned placental stem cells, the placental stem cells constitutively secrete IL-6, IL-8 and monocyte chemoattractant protein (MCP-1).

The populations of placental cells described above can comprise about, at least, or no more than, $1\times10^5$, $5\times10^5$, $1\times10^6$, $5\times10^6$, $1\times10^7$, $2\times10^7$, $2.5\times10^7$, $3\times10^7$, $3.5\times10^7$, $4\times10^7$, $4.5\times10^7$, $5\times10^7$, $5.5\times10^7$, $6\times10^7$, $6.5\times10^7$, $7\times10^7$, $7.5\times10^7$, $8\times10^7$, $8.5\times10^7$, $9\times10^7$, $9.5\times10^7$, $1\times10^8$, $5\times10^8$, $1\times10^9$, $5\times10^9$, $1\times10^{10}$, $5\times10^{10}$, $1\times10^{11}$ or more placental stem cells. In certain embodiments, the populations of placental cells described above can comprise about $1\times10^5$ to about $1\times10^6$, about $1\times10^5$ to about $1\times10^7$, about $1\times10^6$ to about $1\times10^7$, about $1\times10^6$ to about $1\times10^8$, about $1\times10^7$ to about $1\times10^8$, about $1\times10^7$ to about $1\times10^9$, about $1\times10^8$ to about $1\times10^{10}$, about $1\times10^9$ to about $1\times10^{10}$, or about $1\times10^{10}$ to about $1\times10^{11}$ placental stem cells.

In certain embodiments, the placental stem cells useful in the methods provided herein, do not express CD34, as detected by immunolocalization, after exposure to 1 to 100 ng/mL VEGF for 4 to 21 days. In a specific embodiment, said placental stem cells are adherent to tissue culture plastic. In another specific embodiment, said placental stem cells induce endothelial cells to form sprouts or tube-like structures, e.g., when cultured in the presence of an angiogenic factor such as vascular endothelial growth factor (VEGF), epithelial growth factor (EGF), platelet derived growth factor (PDGF) or basic fibroblast growth factor (bFGF), e.g., on a substrate such as MATRIGEL™.

In another aspect, the placental stem cells provided herein, or a population of cells, e.g., a population of placental stem cells, or a population of cells wherein at least about 50%, 60%, 70%, 80%, 90%, 95% or 98% of cells in said population of cells are placental stem cells, secrete one or more, or all, of VEGF, HGF, IL-8, MCP-3, FGF2, follistatin, G-CSF, EGF, ENA-78, GRO, IL-6, MCP-1, PDGF-BB, TIMP-2, uPAR, or galectin-1, e.g., into culture medium in which the cell, or cells, are grown. In another embodiment, the placental stem cells express increased levels of CD202b, IL-8 and/or VEGF under hypoxic conditions (e.g., less than about 5% $O_2$) compared to normoxic conditions (e.g., about 20% or about 21% $O_2$).

In another embodiment, any of the placental stem cells or populations of cells comprising placental stem cells described herein can cause the formation of sprouts or tube-like structures in a population of endothelial cells in contact with said placental stem cells. In a specific embodiment, the placental stem cells are co-cultured with human endothelial cells, which form sprouts or tube-like structures, or support the formation of endothelial cell sprouts, e.g., when cultured in the presence of extracellular matrix proteins such as collagen type I and IV, and/or angiogenic factors such as vascular endothelial growth factor (VEGF), epithelial growth factor (EGF), platelet derived growth factor (PDGF) or basic fibroblast growth factor (bFGF), e.g., in or on a substrate such as placental collagen or MATRIGEL™ for at least 4 days. In another embodiment, any of the populations of cells comprising placental stem cells, described herein, secrete angiogenic factors such as vascular endothelial growth factor (VEGF), hepatocyte growth factor (HGF), platelet derived growth factor (PDGF), basic fibroblast growth factor (bFGF), or Interleukin-8 (IL-8) and thereby can induce human endothelial cells to form sprouts or tube-like structures when cultured in the presence of extracellular matrix proteins such as collagen type I and IV e.g., in or on a substrate such as placental collagen or MATRIGEL™.

In another embodiment, any of the above populations of cells comprising placental stem cells secretes angiogenic factors. In specific embodiments, the population of cells secretes vascular endothelial growth factor (VEGF), hepatocyte growth factor (HGF), platelet derived growth factor (PDGF), basic fibroblast growth factor (bFGF), and/or interleukin-8 (IL-8). In other specific embodiments, the population of cells comprising placental stem cells secretes one or more angiogenic factors and thereby induces human endothelial cells to migrate in an in vitro wound healing assay. In other specific embodiments, the population of cells comprising placental stem cells induces maturation, differentiation or proliferation of human endothelial cells, endothelial progenitors, myocytes or myoblasts.

5.4.3 Selecting and Producing Placental Cell Populations

In certain embodiments, populations of placental stem cells can be selected, wherein the population is immunosuppressive. In one embodiment, for example, immunosuppressive placental stem cells can be selected from a plurality of placental cells, comprising selecting a population of placental cells wherein at least 10%, at least 20%, at least 30%, at least 40%, at least 50% at least 60%, at least 70%, at least 80%, at least 90%, or at least 95% of said cells are CD10$^+$, CD34$^-$, CD105$^+$ placental stem cells, CD10', CD34$^-$, CD200$^+$ placental stem cells, or CD10$^+$, CD34$^-$, CD105$^+$, CD200$^+$ placental stem cells, and wherein said placental stem cells detectably suppresses T cell proliferation in a mixed lymphocyte reaction (MLR) assay. In a specific embodiment, said selecting comprises selecting placental stem cells that are also CD45$^-$ and CD90$^+$.

In another embodiment, provided herein is a method of selecting a plurality of immunosuppressive placental stem cells from a plurality of placental cells, comprising selecting a population of placental stem cells wherein at least 10%, at least 20%, at least 30%, at least 40%, at least 50% at least 60%, at least 70%, at least 80%, at least 90%, or at least 95% of said cells are CD200$^+$, HLA-G$^-$ placental stem cells, and wherein said placental stem cells detectably suppresses T cell proliferation in a mixed lymphocyte reaction (MLR) assay. In a specific embodiment, said selecting comprises selecting placental stem cells that are also CD73$^+$ and CD105$^+$. In another specific embodiment, said selecting comprises selecting placental stem cells that are also CD34$^-$, CD38$^-$ or CD45$^-$. In another specific embodiment, said selecting comprises selecting placental stem cells that are also CD34$^-$, CD38$^-$, CD45$^-$, CD73$^+$ and CD105$^+$. In another specific embodiment, said selecting also comprises selecting a plurality of placental cells, e.g., the placental stem cells described above, that forms one or more embryoid-like bodies when cultured under conditions that allow the formation of embryoid-like bodies.

In another embodiment, provided herein is a method of selecting a plurality of immunosuppressive placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD73$^+$, CD105$^+$, CD200$^+$ placental stem cells, and wherein said placental cells detectably suppresses T cell proliferation in a mixed lymphocyte reaction (MLR) assay. In a specific embodiment, said selecting comprises selecting placental stem cells that are also HLA-G$^-$. In another specific embodiment, said selecting comprises selecting placental stem cells that are also CD34$^-$, CD38$^-$ or CD45$^-$. In another specific embodiment, said selecting comprises selecting placental stem cells that are also CD34$^-$, CD38$^-$ and CD45$^-$. In another specific embodiment, said selecting comprises selecting placental stem cells that are also CD34$^-$, CD38$^-$, CD45$^-$, and HLA-G$^-$. In another specific embodiment, said selecting additionally comprises selecting a population of placental stem cells that produces one or more embryoid-like bodies when the population is cultured under conditions that allow the formation of embryoid-like bodies.

In another embodiment, also provided herein is a method of selecting a plurality of immunosuppressive placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD200$^+$, OCT-4$^+$ placental stem cells, and wherein said placental cells detectably suppresses T cell proliferation in a mixed lymphocyte reaction (MLR) assay. In a specific embodiment, said selecting comprises selecting placental stem cells that are also CD73$^+$ and CD105$^+$. In another specific embodiment, said selecting comprises selecting placental stem cells that are also HLA-G$^-$. In another specific embodiment, said selecting comprises selecting placental stem cells that are also CD34$^-$, CD38$^-$ and CD45$^-$. In another specific embodiment, said selecting comprises selecting placental stem cells that are also CD34$^-$, CD38$^-$, CD45$^-$, CD73$^+$, CD105$^+$ and HLA-G$^-$.

In another embodiment, provided herein is a method of selecting a plurality of immunosuppressive placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD73$^+$, CD105$^+$ and HLA-G$^-$ placental stem cells, and wherein said placental cells detectably suppresses T cell proliferation in a mixed lymphocyte reaction (MLR) assay. In a specific embodiment, said selecting comprises selecting placental stem cells that are also CD34$^-$, CD38$^-$ or CD45$^-$. In another specific embodiment, said selecting comprises selecting placental stem cells that are also CD34$^-$, CD38$^-$ and CD45$^-$. In another specific embodiment, said selecting comprises selecting placental stem cells that are also CD200$^+$. In another specific embodiment, said selecting comprises selecting placental stem cells that are also CD34$^-$, CD38$^-$, CD45$^-$, OCT-4$^+$ and CD200$^+$.

In another embodiment, also provided herein is provides a method of selecting a plurality of immunosuppressive placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD73$^+$, CD105$^+$ placental stem cells, and wherein said plurality forms one or more embryoid-like bodies under conditions that allow formation of embryoid-like bodies. In a specific embodiment, said selecting comprises selecting placental stem cells that are also CD34$^-$, CD38$^-$ or CD45$^-$. In another specific embodiment, said selecting comprises selecting placental stem cells that are also CD34$^-$, CD38$^-$ and CD45$^-$. In another specific embodiment, said selecting comprises selecting placental stem cells that are also OCT-4$^+$. In a more specific embodiment, said selecting comprises selecting placental stem cells that are also OCT-4$^+$, CD34$^-$, CD38$^-$ and CD45$^-$.

In another embodiment, provided herein is a method of selecting a plurality of immunosuppressive placental stem cells from a plurality of placental cells, comprising selecting a plurality of placental stem cells wherein at least 10%, at least 20%, at least 30%, at least 40%, at least 50% at least 60%, at least 70%, at least 80%, at least 90%, or at least 95% of said isolated placental cells are OCT4$^+$ placental stem cells, and wherein said plurality forms one or more embryoid-like bodies under conditions that allow formation of embryoid-like bodies. In a specific embodiment, said selecting comprises selecting placental stem cells that are also CD73$^+$ and CD10$^5$. In another specific embodiment, said selecting comprises selecting placental stem cells that are also CD34$^-$, CD38$^-$, or CD45$^-$. In another specific embodiment, said selecting comprises selecting placental stem cells that are also CD200$^+$. In a more specific embodiment, said selecting comprises selecting placental stem cells that are also CD73$^+$, CD105$^+$, CD200$^+$, CD34$^-$, CD38$^-$, and CD45$^-$.

Immunosuppressive populations, or pluralities, of placental cells can be produced according to the methods provided herein. For example, provided herein is method of producing a cell population, comprising selecting any of the pluralities of placental stem cells described above, and isolating the plurality of placental cells from other cells, e.g., other placental cells. In a specific embodiment, provided herein is a method of producing a cell population comprising selecting placental stem cells, wherein said placental stem cells (a) adhere to a substrate, (b) express CD200 and do not express HLA-G; or express CD73, CD105, and CD200; or express CD200 and OCT-4; or express CD73, CD105, and do not express HLA-G; or express CD73 and CD105 and facilitate the formation of one or more embryoid-like bodies in a population of placental cells that comprise the placental stem cells, when said population is cultured under conditions that allow formation of embryoid-like bodies; or express OCT-4 and facilitate the formation of one or more embryoid-like bodies in a population of placental cells that comprise the placental stem cells, when said population is cultured under conditions that allow formation of embryoid-like bodies; and (c) detectably suppress CD4$^+$ or CD8$^+$ T cell proliferation in an MLR (mixed lymphocyte reaction) or regression assay; and selecting said placental stem cells, or isolating said placental stem cells from other cells to form a cell population.

In a more specific embodiment, immunosuppressive placental stem cells populations can be produced by a method comprising selecting placental stem cells that (a) adhere to a substrate, (b) express CD200 and do not express HLA-G, and (c) detectably suppress CD4$^+$ or CD8$^+$ T cell proliferation in an MLR (mixed lymphocyte reaction); and isolating said placental stem cells from other cells to form a cell population. In another specific embodiment, the method comprises selecting placental stem cells that (a) adhere to a substrate, (b) express CD73, CD105, and CD200, and (c) detectably suppress CD4$^+$ or CD8$^+$ T cell proliferation in an MLR; and isolating said placental stem cells from other cells to form a cell population. In another specific embodiment, provided herein is a method of producing a cell population comprising selecting placental stem cells that (a) adhere to a substrate, (b) express CD200 and OCT-4, and (c) detectably suppress CD4$^+$ or CD8$^+$ T cell proliferation in an MLR; and isolating said placental stem cells from other cells to form a cell population. In another specific embodiment, provided herein is a method of producing a cell population comprising selecting placental stem cells that (a) adhere to a substrate, (b) express CD73 and CD105, (c) form embryoid-like bodies when cultured under conditions allowing the formation of embryoid-like bodies, and (d) detectably suppress CD4$^+$ or CD8$^+$ T cell proliferation in an MLR; and isolating said placental stem cells from other cells to form a cell population. In another specific embodiment, the method comprises selecting placental stem cells that (a) adhere to a substrate, (b) express CD73 and CD105, and do not express HLA-G, and (c) detectably suppress CD4$^+$ or CD8$^+$ T cell proliferation in an MLR; and isolating said placental stem cells from other cells to form a cell population. In another specific embodiment, the method comprises selecting placental stem cells that (a) adhere to a substrate, (b) express OCT-4, (c) form embryoid-like bodies when cultured under conditions allowing the formation of embryoid-like bodies, and (d) detectably suppress CD4$^+$ or CD8$^+$ T cell proliferation in an MLR; and isolating said placental cells from other cells to form a cell population.

In a specific embodiment of the methods of producing an immunosuppressive placental stem cells population, said T cells and said placental stem cells are present in said MLR at a ratio of about 5:1. The placental stem cells used in the method can be derived from the whole placenta, or primarily from amnion, or amnion and chorion. In another specific embodiment, the placental stem cells suppress CD4$^+$ or CD8$^+$ T cell proliferation by at least 50%, at least 75%, at least 90%, or at least 95% in said MLR compared to an amount of T cell proliferation in said MLR in the absence of said placental stem cells. The method can additionally comprise the selection and/or production of a placental stem cells population capable of immunomodulation, e.g., suppression of the activity of, other immune cells, e.g., an activity of a natural killer (NK) cell.

5.4.4 Pain Models

In certain embodiments, the placental stem cells described herein are characterized by their ability to reduce or ameliorate pain, e.g., in an animal pain model. For example, where a batch or lot of placental stem cells is produced, a sample of the batch or lot can be tested using one or more animal models of pain. Placental stem cells, from which samples that produce acceptable reductions in pain in a pain assay have been obtained, can then be selected for further use, e.g., for amelioration of any type of pain, or for amelioration of a specific type of pain. It should be understood that the placental stem cells tested need only be tested in, and/or show efficacy in one assay to be considered therapeutically effective; testing in multiple, or all, animal models of pain is not necessary. In certain embodiments, the sample placental stem cells can be tested in a pain assay that is relevant to one or more related types of pain, or pain relevant to treating a particular patient population.

In certain embodiments, the placental stem cells can be tested in, for example, an acetic acid-induced model of visceral pain. Such a study can be conducted, e.g., by administering acetic acid intraperitoneally in a dose volume of about 10 mL/kg to mice, with vehicle or placental stem cells (e.g., 1×10$^6$ to 1×10$^8$) administered prior to acetic acid administration. The number of writhings are recorded for the subsequent 20 minutes after discarding the first the 5 minutes. Each experiment contains the following groups: vehicle+2-5 doses of placental stem cells+positive control; n=10/group.

In certain other embodiments, a sample of placental stem cells can be tested using the Chung spinal nerve ligation model which L5 and L6 spinal nerves are tightly ligated, resulting in a stable and long-lasting neuropathic pain.

In certain other embodiments, a sample of placental stem cells can be tested using a taxol assay of peripheral neuropathy in which pain develops over time in the rat after the administration of a series of Taxol injections.

In certain other embodiments, a sample of placental stem cells can be tested using the Bennet Model of neuropathic pain (allodynia), in which pain, induced by application of loose ligatures around one of the sciatic nerves, is shown by the sharp withdrawal of affected hind paw to light mechanical stimuli.

In certain other embodiments, a sample of placental stem cells can be tested using a carrageenan administration-induced model of pain.

In certain other embodiments, a sample of placental stem cells can be tested using a Complete Freund's Adjuvant model of neuropathic pain (e.g., allodynia). For example, five rats can be used per group, with an initial dose of, e.g., $1 \times 10^6$ to $1 \times 10^7$ i.v., with efficacy determined by reduction of CFA-induced hind paw hyperalgesia. Unpaired Student's t test is applied for comparison between vehicle control and treated groups. Other pain medications can be used as positive controls (mg/kg per os), e.g., aspirin >100; cyclosporine A >100; dexamethasone >30; gabapentin ~200; indomethacin >10; or morphine 30.

In certain other embodiments, a sample of placental stem cells can be tested using phenylquinone (PQ) as a pain-engendering compound, e.g., using five mice per condition, an initial dose of, e.g., $1 \times 10^6$ to $1 \times 10^7$ i.v., 1 hr pretreatment, followed by determination of reduction of PQ (2 mg/kg i.p.)-induced writhing during a 5 min observation period.

In certain other embodiments, a sample of placental stem cells can be tested using a hind paw incision model of, e.g., postoperative pain.

In certain other embodiments, a sample of placental stem cells can be tested using a tail flick model, in which response to tail flick pain stimulus is assessed before and after administration of the placental stem cells.

The pain assays provided herein are non-limiting examples only; other assays known in the art may be used as well.

5.4.5 Growth in Culture

The growth of the placental cells, e.g., the placental stem cells described herein, as for any mammalian cell, depends in part upon the particular medium selected for growth. Under optimum conditions, placental stem cells typically double in number in 3-5 days. During culture, the placental stem cells provided herein adhere to a substrate in culture, e.g. the surface of a tissue culture container (e.g., tissue culture dish plastic, fibronectin-coated plastic, and the like) and form a monolayer.

Populations of isolated placental cells that comprise the placental stem cells provided herein, when cultured under appropriate conditions, can form embryoid-like bodies, that is, three-dimensional clusters of cells grow atop the adherent stem cell layer. Cells within the embryoid-like bodies express markers associated with very early stem cells, e.g., OCT-4, Nanog, SSEA3 and SSEA4. Cells within the embryoid-like bodies are typically not adherent to the culture substrate, as are the placental stem cells described herein, but remain attached to the adherent cells during culture. Embryoid-like body cells are dependent upon the adherent placental stem cells for viability, as embryoid-like bodies do not form in the absence of the adherent stem cells. The adherent placental cells thus facilitate the growth of one or more embryoid-like bodies in a population of placental cells that comprise the adherent placental cells. Mesenchymal stem cells, e.g., bone marrow-derived mesenchymal stem cells, do not develop embryoid-like bodies in culture.

5.4.6 Differentiation

The placental cells, useful in the methods of treating pain in an individual, provided herein, in certain embodiments are differentiable into different committed cell lineages. For example, in certain embodiments, the placental cells can be differentiated into cells of an adipogenic, chondrogenic, neurogenic, or osteogenic lineage. Such differentiation can be accomplished, e.g., by any method known in the art for differentiating, e.g., bone marrow-derived mesenchymal stem cells into similar cell lineages, or by methods described elsewhere herein. Specific methods of differentiating placental cells into particular cell lineages are disclosed in, e.g., U.S. Pat. No. 7,311,905, and in U.S. Patent Application Publication No. 2007/0275362, the disclosures of which are hereby incorporated by reference in their entireties.

The placental stem cells provided herein can exhibit the capacity to differentiate into a particular cell lineage in vitro, in vivo, or in vitro and in vivo. In a specific embodiment, the placental stem cells provided herein can be differentiated in vitro when placed in conditions that cause or promote differentiation into a particular cell lineage, but do not detectably differentiate in vivo, e.g., in a NOD-SCID mouse model.

5.5 Methods of Obtaining Placental Stem Cells

5.5.1 Stem Cell Collection Composition

Placental stem cells can be collected and isolated according to the methods provided herein. Generally, placental stem cells are obtained from a mammalian placenta using a physiologically-acceptable solution, e.g., a stem cell collection composition. A stem cell collection composition is described in detail in related U.S. Provisional Application No. 60/754,969, entitled "Improved Composition for Collecting and Preserving Placental cells and Methods of Using the Composition" filed on Dec. 29, 2005.

The stem cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl. etc.), a culture medium (e.g., DMEM, HDMEM, etc.), and the like.

The stem cell collection composition can comprise one or more components that tend to preserve placental stem cells, that is, prevent the placental stem cells from dying, or delay the death of the placental stem cells, reduce the number of placental stem cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The stem cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The stem cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram(+) and/or Gram(−) bacteria, e.g., *Pseudomonas aeruginosa, Staphylococcus aureus*, and the like.

The stem cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 µM to about 100 µM); a reducing agent (e.g., N-acetylcysteine present at about 0.1 mM to about 5 mM); an agent that prevents calcium entry into cells (e.g., verapamil present at about 2 µM to about 25 µM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 µM to about 5 µM).

5.5.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the stem cells harvested therefrom. For example, human placental cells can be used, in light of the medical history, for personalized medicine for the infant associated with the placenta, or for parents, siblings or other relatives of the infant.

Prior to recovery of placental stem cells, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank Inc., Cedar Knolls, N.J., ViaCord, Cord Blood Registry and Cryocell. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. patent application Ser. No. 11/230,760, filed Sep. 19, 2005. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to placental stem cell collection, can be stored under sterile conditions and at either room temperature or at a temperature of 5 to 25° C. (centigrade). The placenta may be stored for a period of longer than forty eight hours, and preferably for a period of four to twenty-four hours prior to perfusing the placenta to remove any residual cord blood. The placenta is preferably stored in an anticoagulant solution at a temperature of 5 to 25° C. (centigrade). Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental cells are collected.

The mammalian placenta or a part thereof, once collected and prepared generally as above, can be treated in any art-known manner, e.g., can be perfused or disrupted, e.g., digested with one or more tissue-disrupting enzymes, to obtain stem cells.

5.5.3 Physical Disruption and Enzymatic Digestion of Placental Tissue

In one embodiment, placental stem cells are collected from a mammalian placenta by physical disruption, e.g., enzymatic digestion, of the organ, e.g., using the stem cell collection composition described in Section 5.6.1, above. For example, the placenta, or a portion thereof, may be, e.g., crushed, sheared, minced, diced, chopped, macerated or the like, while in contact with, e.g., a buffer, medium or a stem cell collection composition, and the tissue subsequently digested with one or more enzymes. The placenta, or a portion thereof, may also be physically disrupted and digested with one or more enzymes, and the resulting material then immersed in, or mixed into, a buffer, medium or a stem cell collection composition. Any method of physical disruption can be used, provided that the method of disruption leaves a plurality, more preferably a majority, and more preferably at least 60%, 70%, 80%, 90%, 95%, 98%, or 99% of the cells in said organ viable, as determined by, e.g., trypan blue exclusion.

Typically, placental cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume.

Enzymatic digestion can be performed using single enzymes or combinations of enzymes. In one embodiment, enzymatic digestion of placental tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes that can be used to disrupt placenta tissue include papain, deoxyribonucleases, serine proteases, such as trypsin, chymotrypsin, or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping stem cells within the viscous digest.

Typical concentrations for tissue digestion enzymes include, e.g., 50-200 U/mL for collagenase I and collagenase IV, 1-10 U/mL for dispase, and 10-100 U/mL for elastase. Proteases can be used in combination, that is, two or more proteases in the same digestion reaction, or can be used sequentially in order to liberate placental cells. For example, in one embodiment, a placenta, or part thereof, is digested first with an appropriate amount of collagenase I at 2 mg/ml for 30 minutes, followed by digestion with trypsin, 0.25%, for 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the placental stem cells with the stem cell collection composition.

It will be appreciated that where an entire placenta, or portion of a placenta comprising both fetal and maternal cells (for example, where the portion of the placenta comprises the chorion or cotyledons) is digested to obtain placental stem cells, the placental cells collected will comprise a mix of placental cells derived from both fetal and maternal sources. Where a portion of the placenta that comprises no, or a negligible number of, maternal cells (for example, amnion) is used to obtain placental stem cells, the placental stem cells collected will comprise almost exclusively fetal placental stem cells.

5.5.4 Placental Perfusion

Placental stem cells can also be obtained by perfusion of the mammalian placenta. Methods of perfusing mammalian placenta to obtain stem cells are disclosed, e.g., in Hariri, U.S. Application Publication No. 2002/0123141, and in related U.S. Provisional Application No. 60/754,969, entitled "Improved Composition for Collecting and Preserving Placental Cells and Methods of Using the Composition" filed on Dec. 29, 2005.

Placental stem cells can be collected by perfusion, e.g., through the placental vasculature, using, e.g., a stem cell collection composition as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid, e.g., the stem cell collection composition provided herein, through the placental vasculature, or through the placental vasculature and surrounding tissue. In one embodiment, the umbilical artery and the umbilical vein are connected simultaneously to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. In another embodiment, the perfusion solution is passed through the umbilical veins and collected from the umbilical artery, or is passed through the umbilical artery and collected from the umbilical veins.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood; this portion of the perfusion can be discarded. The perfusion fluid becomes more colorless as perfusion proceeds and the residual cord blood cells are washed out of the placenta.

The volume of perfusion liquid used to collect placental stem cells may vary depending upon the number of placental stem cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with the stem cell collection composition, or a standard perfusion solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., f-mercaptoethanol (0.1 mM); antibiotics such as streptomycin (e.g., at 40-100 µg/ml), penicillin (e.g., at 40 U/ml), amphotericin B (e.g., at 0.5 µg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., stem cell collection composition, is repeated until the number of recovered nucleated cells falls below 100 cells/ml. The perfusates at different time points can be further processed individually to recover time-dependent populations of placental stem cells. Perfusates from different time points can also be pooled.

Without wishing to be bound by any theory, after exsanguination and a sufficient time of perfusion of the placenta, placental stem cells are believed to migrate into the exsanguinated and perfused microcirculation of the placenta where they are collectable, preferably by washing into a collecting vessel by perfusion. Perfusing the isolated placenta not only serves to remove residual cord blood but also provide the placenta with the appropriate nutrients, including oxygen. The placenta may be cultivated and perfused with a similar solution which was used to remove the residual cord blood cells, preferably, without the addition of anticoagulant agents.

Stem cells can be isolated from placenta by perfusion with a solution comprising one or more proteases or other tissue-disruptive enzymes. In a specific embodiment, a placenta or portion thereof is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The placental stem cells are washed after several minutes with a cold (e.g., 4° C.) stem cell collection composition described elsewhere herein.

Perfusion using the pan method, that is, whereby perfusate is collected after it has exuded from the maternal side of the placenta, results in a mix of fetal and maternal cells. As a result, the cells collected by this method comprise a mixed population of placental stem cells of both fetal and maternal origin. In contrast, perfusion solely through the placental vasculature, whereby perfusion fluid is passed through one or two placental vessels and is collected solely through the remaining vessel(s), results in the collection of a population of placental stem cells almost exclusively of fetal origin.

5.5.5 Isolation, Sorting, and Characterization of Placental Cells

Stem cells from mammalian placenta, whether obtained by perfusion or enyzmatic digestion, can initially be purified from (i.e., be isolated from) other cells by Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In another embodiment, placental perfusate is concentrated to about 200 ml, gently layered over Ficoll, and centrifuged at about 1100×g for 20 minutes at 22° C., and the low-density interface layer of cells is collected for further processing.

Cell pellets can be resuspended in fresh stem cell collection composition, or a medium suitable for stem cell maintenance, e.g., IMDM serum-free medium containing 2 U/ml heparin and 2 mM EDTA (GibcoBRL, NY). The total mononuclear cell fraction can be isolated, e.g., using Lymphoprep (Nycomed Pharma, Oslo, Norway) according to the manufacturer's recommended procedure.

As used herein, "isolating" placental stem cells means removing at least 20%, 30%, 40%, 50%, 60%, 70%, 80%, 90%, 95% or 99% of the cells with which the placental stem cells are normally associated in the intact mammalian placenta.

Placental stem cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because placental stem cells typically detach from plastic surfaces within about five minutes whereas other adherent populations typically require more than 20-30 minutes incubation. The detached placental stem cells can be harvested following trypsinization and trypsin neutralization, using, e.g., Trypsin Neutralizing Solution (TNS, Cambrex).

In one embodiment of isolation of placental stem cells, aliquots of, for example, about $5\text{-}10\times10^6$ placental cells are placed in each of several T-75 flasks, preferably fibronectin-coated T75 flasks. In such an embodiment, the cells can be cultured with commercially available Mesenchymal Stem Cell Growth Medium (MSCGM) (Cambrex), and placed in a tissue culture incubator (37° C., 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34 as compared to, for example, an isotype control; if so, the cell is $CD34^+$. Likewise, if a cell produces enough OCT-4 RNA to be detectable by RT-PCR, or significantly more OCT-4 RNA than a terminally-differentiated cell, the cell is $OCT\text{-}4^+$. Antibodies to cell surface markers (e.g., CD markers such as CD34) and the sequence of stem cell-specific genes, such as OCT-4, are well-known in the art.

Placental cells, particularly cells that have been isolated by Ficoll separation, differential adherence, or a combination of both, may be sorted, e.g., further isolated, using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, placental stem cells can be sorted on the basis of expression of the markers CD34, CD38, CD44, CD45, CD73, CD105, OCT-4 and/or HLA-G, or any of the other markers listed elsewhere herein. This can be accomplished in connection with procedures to select stem cells on the basis of their adherence properties in culture. For example, adherence selection of placental stem cells can be accomplished before or after sorting on the basis of marker expression. In one embodiment, for example, placental stem cells can be sorted first on the basis of their expression of CD34; CD34$^-$ cells are retained, and cells that are CD200$^+$ or HLA-G$^+$, are separated from all other CD34$^-$ cells. In another embodiment, placental stem cells can be sorted based on their expression of CD200 and/or HLA-G, or lack thereof; for example, cells displaying either of these markers can be isolated for further use. Cells that express, e.g., CD200 and/or HLA-G can, in a specific embodiment, be further sorted based on their expression of CD73 and/or CD105, or epitopes recognized by antibodies SH2, SH3 or SH4, or lack of expression of CD34, CD38 or CD45. For example, in one embodiment, placental stem cells are sorted by expression, or lack thereof, of CD200, HLA-G, CD73, CD105, CD34, CD38 and CD45, and placental stem cells that are CD200$^+$, HLA-G$^-$, CD73$^+$, CD105$^+$, CD34$^-$, CD38$^-$ and CD45$^-$ are isolated from other placental cells for further use.

In another embodiment, magnetic beads can be used to separate cells, e.g., separate placental stem cells from other placental cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Placental stem cells can also be characterized and/or sorted based on cell morphology and growth characteristics. For example, placental stem cells can be characterized as having, and/or selected on the basis of, e.g., a fibroblastoid appearance in culture. Placental stem cells can also be characterized as having, and/or be selected, on the basis of their ability to form embryoid-like bodies. In one embodiment, for example, placental cells that are fibroblastoid in shape, express CD73 and CD105, and produce one or more embryoid-like bodies in culture can be isolated from other placental cells. In another embodiment, OCT-4$^+$ placental cells that produce one or more embryoid-like bodies in culture are isolated from other placental cells.

In another embodiment, placental stem cells can be identified and characterized by a colony forming unit assay. Colony forming unit assays are commonly known in the art, such as MESENCULT™ medium (Stem Cell Technologies, Inc., Vancouver British Columbia).

Placental stem cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

Placental stem cells can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

5.6 Culture of Placental Stem Cells

5.6.1 Culture Media

Isolated placental stem cells, or placental cell populations, or cells or placental tissue from which placental cells grow out, can be used to initiate, or seed, cell cultures. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL (BD Discovery Labware, Bedford, Mass.)).

Placental stem cells can be cultured in any medium, and under any conditions, recognized in the art as acceptable for the culture of stem cells. Preferably, the culture medium comprises serum. Placental stem cells can be cultured in, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dextrose, L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 10% FBS, EGF, and heparin; α-MEM (minimal essential medium) comprising 10% FBS, GlutaMAX™ and gentamicin; DMEM comprising 10% FBS, GlutaMAX™ and gentamicin, etc. A preferred medium is DMEM-LG/MCDB-201 comprising 2% FBS, ITS, LA+BSA, dextrose, L-ascorbic acid, PDGF, EGF, and penicillin/streptomycin.

Other media in that can be used to culture placental stem cells include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMEM/F12, RPMI 1640, advanced DMEM (Gibco), DMEM/MCDB201 (Sigma), and CELL-GRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

Any of the culture methods and media disclosed herein can be used to culture and propagate placental stem cells, as well.

5.6.2 Expansion and Proliferation of Placental Stem Cells

Once placental stem cells are isolated (e.g., separated from at least 50% of the placental cells with which the stem cell or population of stem cells is normally associated in vivo), the stem cell or population of stem cells can be proliferated and expanded in vitro. Similarly, once placental stem cells are produced, such cells can also be proliferated and expanded in vitro. For example, placental stem cells can be cultured in tissue culture containers, e.g., dishes, flasks, multiwell plates, or the like, for a sufficient time for the placental stem cells to proliferate to 70-90% confluence, that is, until the placental stem cells and their progeny occupy 70-90% of the culturing surface area of the tissue culture container.

Placental stem cells can be seeded in culture vessels at a density that allows cell growth. For example, the placental stem cells may be seeded at low density (e.g., about 1,000 to about 5,000 cells/cm$^2$) to high density (e.g., about 50,000 or more cells/cm$^2$). In a preferred embodiment, the placental stem cells are cultured at about 0 to about 5 percent by volume $CO_2$ in air. In some preferred embodiments, the placental stem cells are cultured at about 2 to about 25 percent $O_2$ in air, preferably about 5 to about 20 percent $O_2$ in air. The placental stem cells preferably are cultured at about 25° C. to about 40° C., preferably 37° C. The placental stem cells are preferably cultured in an incubator. The culture medium can be static or agitated, for example, using a bioreactor. Placental stem cells are preferably are grown under low oxidative stress (e.g., with addition of glutathione, ascorbic acid, catalase, tocopherol, N-acetylcysteine, or the like).

Once 70%-90% confluence is obtained, the placental stem cells may be passaged. For example, the cells can be enzymatically treated, e.g., trypsinized, using techniques well-known in the art, to separate them from the tissue culture surface. After removing the placental stem cells by pipetting and counting the cells, about 20,000-100,000 stem cells, preferably about 50,000 placental stem cells, are passaged to a new culture container containing fresh culture medium. Typically, the new medium is the same type of medium from which the stem cells were removed. Provided herein are populations of placental stem cells that have been passaged at least 1, 2, 3, 4, 5, 6, 7, 8, 9, 10, 12, 14, 16, 18, or 20 times, or more, and combinations of the same.

5.7 Preservation of Placental Stem Cells

Placental stem cells can be preserved, that is, placed under conditions that allow for long-term storage, or conditions that inhibit cell death by, e.g., apoptosis or necrosis.

Placental stem cells can be preserved using, e.g., a composition comprising an apoptosis inhibitor, necrosis inhibitor and/or an oxygen-carrying perfluorocarbon, as described in U.S. Patent Application Publication No. 2007/0190042.

In one embodiment, provided herein is a method of preserving placental stem cells comprising contacting said placental stem cells with a stem cell collection composition comprising an inhibitor of apoptosis and an oxygen-carrying perfluorocarbon, wherein said inhibitor of apoptosis is present in an amount and for a time sufficient to reduce or prevent apoptosis in the population of placental stem cells, as compared to a population of placental stem cells not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said placental stem cells. In another embodiment, said stem cell collection composition comprises said inhibitor of apoptosis and said oxygen-carrying perfluorocarbon in separate phases. In another embodiment, said stem cell collection composition comprises said inhibitor of apoptosis and said oxygen-carrying perfluorocarbon in an emulsion. In another embodiment, the stem cell collection composition additionally comprises an emulsifier, e.g., lecithin. In another embodiment, said apoptosis inhibitor and said perfluorocarbon are between about 0° C. and about 25° C. at the time of contacting the stem cells. In another more specific embodiment, said apoptosis inhibitor and said perfluorocarbon are between about 2° C. and 10° C., or between about 2° C. and about 5° C., at the time of contacting the stem cells. In another more specific embodiment, said contacting is performed during transport of said placental stem cells. In another more specific embodiment, said contacting is performed during freezing and thawing of said population of stem cells.

In another embodiment, placental stem cells can be preserved by a method comprising contacting said placental stem cells with an inhibitor of apoptosis and an organ-preserving compound, wherein said inhibitor of apoptosis is present in an amount and for a time sufficient to reduce or prevent apoptosis of the placental stem cells, as compared to placental stem cells not contacted with the inhibitor of apoptosis. In a specific embodiment, the organ-preserving compound is UW solution (described in U.S. Pat. No. 4,798,824; also known as ViaSpan; see also Southard et al., *Transplantation* 49(2):251-257 (1990)) or a solution described in Stem et al., U.S. Pat. No. 5,552,267. In another embodiment, said organ-preserving compound is hydroxyethyl starch, lactobionic acid, raffinose, or a combination thereof.

In another embodiment, placental stem cells, to be used to produce placental stem cells, are contacted with a stem cell collection composition comprising an apoptosis inhibitor and oxygen-carrying perfluorocarbon, organ-preserving compound, or combination thereof, during perfusion. In another embodiment, said placental stem cells, to be used to produce placental stem cells, are contacted during a process of tissue disruption, e.g., enzymatic digestion. In another embodiment, placental cells are contacted with said stem cell collection compound after collection by perfusion, or after collection by tissue disruption, e.g., enzymatic digestion.

Typically, during placental stem cell collection, enrichment and isolation, it is preferable to minimize or eliminate cell stress due to hypoxia and mechanical stress. In another embodiment of the method, therefore, placental stem cells, to be used to produce placental stem cells, are exposed to a hypoxic condition during collection, enrichment or isolation for less than six hours during said preservation, wherein a hypoxic condition is a concentration of oxygen that is less than normal blood oxygen concentration. In a more specific embodiment, said placental stem cells are exposed to said hypoxic condition for less than two hours during said preservation. In another more specific embodiment, said placental stem cells are exposed to said hypoxic condition for less than one hour, or less than thirty minutes, or is not exposed to a hypoxic condition, during collection, enrichment or isolation. In another specific embodiment, said placental stem cells are not exposed to shear stress during collection, enrichment or isolation.

The placental stem cells, as well as the placental stem cells to be used to produce placental stem cells, described herein can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 10% (v/v). Cryopreservation medium may comprise additional agents, for example, Plasmalyte, methylcellulose with or without glycerol. The stem cells are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C.

5.8 Uses of Placental Cells

5.8.1 Compositions Comprising Placental Cells

The methods of treatment of pain provided herein can use compositions comprising the placental stem cells, or biomolecules therefrom. In the same manner, the populations of placental stem cells provided herein can be combined with any physiologically-acceptable or medically-acceptable compound, composition or device for use in, e.g., research or therapeutics.

5.8.1.1 Cryopreserved Placental Cells

The placental cells provided herein can be preserved, for example, cryopreserved for later use. Methods for cryopreservation of cells, such as stem cells, are well known in the art. Placental stem cells can be prepared in a form that is easily administrable to an individual. For example, placental stem cells described herein can be contained within a container that is suitable for medical use. Such a container can be, for example, a sterile plastic bag, flask, jar, vial, or other container from which the placental cell population can be easily dispensed. For example, the container can be a blood bag or other plastic, medically-acceptable bag suitable for the intravenous administration of a liquid to a recipient. The container is preferably one that allows for cryopreservation of the placental stem cells.

Cryopreserved placental stem cells can comprise placental stem cells derived from a single donor, or from multiple donors. The placental stem cells can be completely HLA-matched to an intended recipient, or partially or completely HLA-mismatched.

Thus, in one embodiment, provided herein is a composition comprising placental stem cells in a container. In a specific embodiment, the placental stem cells are, or have been, cryopreserved. In another specific embodiment, the container is a bag, flask, vial or jar. In more specific embodiment, said bag is a sterile plastic bag. In a more specific embodiment, said bag is suitable for, allows or facilitates intravenous administration of said placental stem cells. The bag can comprise multiple lumens or compartments that are interconnected to allow mixing of the placental stem cells and one or more other solutions, e.g., a drug, prior to, or during, administration. In another specific embodiment, the composition comprises one or more compounds that facilitate cryopreservation of the combined stem cell population. In another specific embodiment, said placental stem cells are contained within a physiologically-acceptable aqueous solution. In a more specific embodiment, said physiologically-acceptable aqueous solution is a 0.9% NaCl solution. In another specific embodiment, said placental stem cells are HLA-matched to a recipient of said placental stem cells. In another specific embodiment, said placental stem cells are at least partially HLA-mismatched to a recipient of said placental stem cells. In another specific embodiment, said placental stem cells are from a plurality of donors.

5.8.1.2 Pharmaceutical Compositions

Populations of isolated placental stem cells, or populations of cells comprising the isolated placental stem cells, can be formulated into pharmaceutical compositions for use in vivo, e.g., in the methods of treatment provided herein. Such pharmaceutical compositions comprise placental stem cells, or a population of cells comprising isolated placental stem cells, in a pharmaceutically-acceptable carrier, e.g., a saline solution or other accepted physiologically-acceptable solution for in vivo administration. Pharmaceutical compositions comprising the isolated placental stem cells described herein can comprise any, or any combination, of the isolated placental stem cells populations, or isolated placental stem cells, described elsewhere herein. The pharmaceutical compositions can comprise fetal, maternal, or both fetal and maternal isolated cells. The pharmaceutical compositions provided herein can further comprise isolated placental stem cells obtained from a single individual, umbilical cord or placenta, or from a plurality of individuals, umbilical cords or placentae. Any of the placental stem cells, described elsewhere herein, can be formulated into pharmaceutical composition, as described below.

The pharmaceutical compositions provided herein can comprise any number of isolated placental stem cells. For example, a single unit dose of isolated placental stem cells can comprise, in various embodiments, about, at least, or no more than $1 \times 10^5$, $5 \times 10^5$, $1 \times 10^6$, $5 \times 10^6$, $1 \times 10^7$, $2 \times 10^7$, $2.5 \times 10^7$, $3 \times 10^7$, $3.5 \times 10^7$, $4 \times 10^7$, $4.5 \times 10^7$, $5 \times 10^7$, $5.5 \times 10^7$, $6 \times 10^7$, $6.5 \times 10^7$, $7 \times 10^7$, $7.5 \times 10^7$, $8 \times 10^7$, $8.5 \times 10^7$, $9 \times 10^7$, $9.5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more isolated cells. In certain embodiments, a single unit dose of isolated placental stem cells can comprise about, at least, or no more than $1 \times 10^5$ to about $1 \times 10^6$, about $1 \times 10^5$ to about $1 \times 10^7$, about $1 \times 10^6$ to about $1 \times 10^7$, about $1 \times 10^6$ to about $1 \times 10^8$, about $1 \times 10^7$ to about $1 \times 10^8$, about $1 \times 10^7$ to about $1 \times 10^9$, about $1 \times 10^8$ to about $1 \times 10^{10}$, about $1 \times 10^9$ to about $1 \times 10^{10}$, or about $1 \times 10^{10}$ to about $1 \times 10^{11}$ placental stem cells. In particular embodiments, the placental stem cells are present in a pharmaceutical composition suitable for systemic, e.g., intravenous (IV) administration. In other particular embodiments, the placental stem cells are present in a pharmaceutical composition suitable for local administration.

Pharmaceutical compositions comprising single or multiple unit doses of isolated placental stem cells can be administered in connection with the methods described herein. In one embodiment, administration can comprise administration of a single unit dose of placental stem cells. In another embodiment, administration can comprise administration of multiple unit doses of placental stem cells. Administration can be achieved via, for example, individual or multiple injections, e.g., 1, 5, 10, 15, 20, 25, 30, 35, 40, 45, or 50 local or systemic injections.

The pharmaceutical compositions provided herein comprise populations of cells that comprise 50% viable cells or more (that is, at least 50% of the cells in the population are functional or living). Preferably, at least 60% of the cells in the population are viable. More preferably, at least 70%, 80%, 90%, 95%, or 99% of the cells in the population in the pharmaceutical composition are viable.

The pharmaceutical compositions provided herein can comprise one or more compounds that, e.g., facilitate engraftment (e.g., anti-T-cell receptor antibodies, an immunosuppressant, or the like); stabilizers such as albumin, dextran 40, gelatin, hydroxyethyl starch, plasmalyte, and the like.

When formulated as an injectable solution, in one embodiment, the pharmaceutical composition comprises about 1% to 1.5% HSA and about 2.5% dextran. In a preferred embodiment, the pharmaceutical composition comprises from about $5 \times 10^6$ cells per milliliter to about $2 \times 10^7$ cells per milliliter in a solution comprising 5% HSA and 10% dextran, optionally comprising an immunosuppressant, e.g., cyclosporine A at, e.g., 10 mg/kg.

In other embodiments, the pharmaceutical composition, e.g., a solution, comprises a plurality of cells, e.g., isolated placental stem cells, wherein said pharmaceutical composition comprises between about $1.0 \pm 0.3 \times 10^6$ cells per milliliter to about $5.0 \pm 1.5 \times 10^6$ cells per milliliter. In other embodiments, the pharmaceutical composition comprises between about $1.5 \times 10^6$ cells per milliliter to about $3.75 \times 10^6$ cells per milliliter. In other embodiments, the pharmaceutical composition comprises between about $1 \times 10^6$ cells/mL to about $50 \times 10^6$ cells/mL, about $1 \times 10^6$ cells/mL to about $40 \times 10^6$ cells/mL, about $1 \times 10^6$ cells/mL to about $30 \times 10^6$ cells/mL, about $1 \times 10^6$ cells/mL to about $20 \times 10^6$ cells/mL, about $1 \times 10^6$ cells/mL to about $15 \times 10^6$ cells/mL, or about $1 \times 10^6$ cells/mL to about $10 \times 10^6$ cells/mL. In certain embodiments, the pharmaceutical composition comprises no visible cell clumps (i.e., no macro cell clumps), or substantially no such visible clumps. As used herein, "macro cell clumps" means an aggregation of cells visible without magnification, e.g., visible to the naked eye, and generally refers to a cell aggregation larger than about 150 microns. In some embodiments, the pharmaceutical composition comprises about 2.5%, 3.0%, 3.5%, 4.0%, 4.5%, 5.0%, 5.5%, 6.0%, 6.5%, 7.0%, 7.5% 8.0%, 8.5%, 9.0%, 9.5% or 10% dextran, e.g., dextran-40. In a specific embodiment, said composition comprises about 7.5% to about 9% dextran-40. In a specific embodiment, said composition comprises about 5.5% dextran-40. In certain embodiments, the pharmaceutical composition comprises from about 1% to about 15% human serum albumin (HSA). In specific embodiments, the pharmaceutical composition comprises about 1%, 2%, 3%, 4%, 5%, 65, 75, 8%, 9%, 10%, 11%, 12%, 13%, 14% or 15% HSA. In a specific embodiment, said cells have been cryopreserved and thawed. In another specific embodiment, said cells have been filtered through a 70 μM to 100 μM filter. In another specific embodiment, said composition comprises no visible cell clumps. In another specific embodiment, said composition comprises fewer than about 200 cell clumps per $10^6$ cells, wherein said cell clumps are visible only under a microscope, e.g., a light microscope. In another specific embodiment, said composition comprises fewer than about 150 cell clumps per $10^6$ cells, wherein said cell clumps are visible only under a microscope, e.g., a light microscope. In another specific embodiment, said composition comprises fewer than about 100 cell clumps per $10^6$ cells, wherein said cell clumps are visible only under a microscope, e.g., a light microscope.

In a specific embodiment, the pharmaceutical composition comprises about $1.0 \pm 0.3 \times 10^6$ cells per milliliter, about 5.5% dextran-40 (w/v), about 10% HSA (w/v), and about 5% DMSO (v/v).

In other embodiments, the pharmaceutical composition comprises a plurality of cells, e.g., a plurality of isolated placental stem cells in a solution comprising 10% dextran-40, wherein the pharmaceutical composition comprises between about $1.0 \pm 0.3 \times 10^6$ cells per milliliter to about $5.0 \pm 1.5 \times 10^6$ cells per milliliter, and wherein said composition comprises no cell clumps visible with the unaided eye (i.e., comprises no macro cell clumps). In some embodiments, the pharmaceutical composition comprises between about $1.5 \times 10^6$ cells per milliliter to about $3.75 \times 10^6$ cells per milliliter. In a specific embodiment, said cells have been cryopreserved and thawed. In another specific embodiment, said cells have been filtered through a 70 μM to 100 μM filter. In another specific embodiment, said composition comprises fewer than about 200 micro cell clumps (that is, cell clumps visible only with magnification) per $10^6$ cells. In another specific embodiment, the pharmaceutical composition comprises fewer than about 150 micro cell clumps per $10^6$ cells. In another specific embodiment, the pharmaceutical composition comprises fewer than about 100 micro cell clumps per $10^6$ cells. In another specific embodiment, the pharmaceutical composition comprises less than 15%, 14%, 13%, 12%, 11%, 10%, 9%, 8%, 7%, 6%, 5%, 4%, 3%, or 2% DMSO, or less than 1%, 0.9%, 0.8%, 0.7%, 0.6%, 0.5%, 0.4%, 0.3%, 0.2%, or 0.1% DMSO.

Further provided herein are compositions comprising cells, wherein said compositions are produced by one of the methods disclosed herein. For example, in one embodiment, the pharmaceutical composition comprises cells, wherein the pharmaceutical composition is produced by a method comprising filtering a solution comprising placental stem cells to form a filtered cell-containing solution; diluting the filtered cell-containing solution with a first solution to about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter, e.g., prior to cryopreservation; and diluting the resulting filtered cell-containing solution with a second solution comprising dextran, but not comprising human serum albumin (HSA) to produce said composition. In certain embodiments, said diluting is to no more than about $15 \times 10^6$ cells per milliliter. In certain embodiments, said diluting is to no more than about $10 \pm 3 \times 10^6$ cells per milliliter. In certain embodiments, said diluting is to no more than about $7.5 \times 10^6$ cells per milliliter. In other certain embodiments, if the filtered cell-containing solution, prior to the dilution, comprises less than about $15 \times 10^6$ cells per milliliter, filtration is optional. In other certain embodiments, if the filtered cell-containing solution, prior to the dilution, comprises less than about $10 \pm 3 \times 10^6$ cells per milliliter, filtration is optional. In other certain embodiments, if the filtered cell-containing solution, prior to the dilution, comprises less than about $7.5 \times 10^6$ cells per milliliter, filtration is optional.

In a specific embodiment, the cells are cryopreserved between said diluting with a first dilution solution and said diluting with said second dilution solution. In another specific embodiment, the first dilution solution comprises dextran and HSA. The dextran in the first dilution solution or second dilution solution can be dextran of any molecular weight, e.g., dextran having a molecular weight of from about 10 kDa to about 150 kDa. In some embodiments, said dextran in said first dilution solution or said second solution is about 2.5%, 3.0%, 3.5%, 4.0%, 4.5%, 5.0%, 5.5%, 6.0%, 6.5%, 7.0%, 7.5% 8.0%, 8.5%, 9.0%, 9.5% or 10% dextran. In another specific embodiment, the dextran in said first dilution solution or said second dilution solution is dextran-40. In another specific embodiment, the dextran in said first dilution solution and said second dilution solution is dextran-40. In another specific embodiment, said dextran-40 in said first dilution solution is 5.0% dextran-40. In another specific embodiment, said dextran-40 in said first dilution solution is 5.5% dextran-40. In another specific embodiment, said dextran-40 in said second dilution solution is 10% dextran-40. In another specific embodiment, said HSA in said solution comprising HSA is 1 to 15% HSA. In another specific embodiment, said HSA in said solution comprising HSA is about 1%, 2%, 3%, 4%, 5%, 6%, 7%, 8%, 9%, 10%, 11%, 12%, 13%, 14% or 15% HSA. In another specific embodiment, said HSA in said solution comprising HSA is 10% HSA. In another specific embodiment, said first dilution solution comprises HSA. In a more specific embodiment, said HSA in said first dilution solution is 10% HSA. In another specific embodiment, said first dilution solution comprises a cryoprotectant. In a more specific embodiment, said cryoprotectant is DMSO. In another specific embodiment, said dextran-40 in said second dilution solution is about 10% dextran-40. In another specific embodiment, said composition comprising cells comprises about 7.5% to about 9% dextran. In another specific embodiment, the pharmaceutical composition comprises from about $1.0\pm0.3\times10^6$ cells per milliliter to about $5.0\pm1.5\times10^6$ cells per milliliter. In another specific embodiment, the pharmaceutical composition comprises from about $1.5\times10^6$ cells per milliliter to about $3.75\times10^6$ cells per milliliter.

In another embodiment, the pharmaceutical composition is made by a method comprising (a) filtering a cell-containing solution comprising placental stem cells prior to cryopreservation to produce a filtered cell-containing solution; (b) cryopreserving the cells in the filtered cell-containing solution at about 1 to $50\times10^6$, 1 to $40\times10^6$, 1 to $30\times10^6$, 1 to $20\times10^6$, 1 to $15\times10^6$, or 1 to $10\times10^6$ cells per milliliter; (c) thawing the cells; and (d) diluting the filtered cell-containing solution about 1:1 to about 1:11 (v/v) with a dextran-40 solution. In certain embodiments, if the number of cells is less than about $10\pm3\times10^6$ cells per milliliter prior to step (a), filtration is optional. In a more specific embodiment, the cells in step (b) are cryopreserved at about $10\pm3\times10^6$ cells per milliliter. In a more specific embodiment, the cells in step (b) are cryopreserved in a solution comprising about 5% to about 10% dextran-40 and HSA. In certain embodiments, said diluting in step (b) is to no more than about $15\times10^6$ cells per milliliter.

In another embodiment, the pharmaceutical composition is made by a method comprising: (a) suspending PDAC™ in a 5.5% dextran-40 solution that comprises 10% HSA to form a cell-containing solution; (b) filtering the cell-containing solution through a 70 μM filter; (c) diluting the cell-containing solution with a solution comprising 5.5% dextran-40, 10% HSA, and 5% DMSO to about 1 to $50\times10^6$, 1 to $40\times10^6$, 1 to $30\times10^6$, 1 to $20\times10^6$, 1 to $15\times10^6$, or 1 to $10\times10^6$ cells per milliliter; (d) cryopreserving the cells; (e) thawing the cells; and (f) diluting the cell-containing solution 1:1 to 1:11 (v/v) with 10% dextran-40. In certain embodiments, said diluting in step (c) is to no more than about $15\times10^6$ cells per milliliter. In certain embodiments, said diluting in step (c) is to no more than about $10\pm3\times10^6$ cells/mL. In certain embodiments, said diluting in step (c) is to no more than about $7.5\times10^6$ cells/mL.

In another embodiment, the composition comprising cells is made by a method comprising: (a) centrifuging a plurality of placental stem cells, to collect the cells; (b) resuspending the cells in 5.5% dextran-40; (c) centrifuging the cells to collect the cells; (d) resuspending the cells in a 5.5% dextran-40 solution that comprises 10% HSA; (e) filtering the cells through a 70 μM filter; (f) diluting the cells in 5.5% dextran-40, 10% HSA, and 5% DMSO to about 1 to $50\times10^6$, 1 to $40\times10^6$, 1 to $30\times10^6$, 1 to $20\times10^6$, 1 to $15\times10^6$, or 1 to $10\times10^6$ cells per milliliter; (g) cryopreserving the cells; (h) thawing the cells; and (i) diluting the cells 1:1 to 1:11 (v/v) with 10% dextran-40. In certain embodiments, said diluting in step (f) is to no more than about $15\times10^6$ cells per milliliter. In certain embodiments, said diluting in step (f) is to no more than about $10\pm3\times10^6$ cells/mL. In certain embodiments, said diluting in step (f) is to no more than about $7.5\times10^6$ cells/mL. In other certain embodiments, if the number of cells is less than about $10\pm3\times10^6$ cells per milliliter, filtration is optional.

The compositions, e.g., pharmaceutical compositions comprising the isolated placental cells, described herein can comprise any of the isolated placental stem cells described herein.

Other injectable formulations, suitable for the administration of cellular products, may be used.

In certain embodiments, the placental stem cells can be encapsulated in, e.g., alginate, either before or after cryopreservation. In certain other embodiments, the placental stem cells can be combined with platelet-rich plasma, e.g., for local injection or local administration applications. In specific embodiments, the platelet rich plasma is autologous platelet rich plasma, e.g., autologous to the individual having pain to whom the placental stem cells are administered. In other specific embodiments, the platelet-rich plasma is allogeneic to the individual having pain to whom the placental stem cells are administered. In another specific embodiment, said platelet rich plasma is derived from placental perfusate. In other specific embodiments, the volume to volume ratio of placental stem cells to platelet rich plasma in the composition, or the ratio between numbers of placental stem cells and numbers of platelets, is between about 10:1 and 1:10; between about 100:1 and 1:100; or is about 1:1.

In one embodiment, the pharmaceutical composition comprises isolated placental cells or PDAC™ that are substantially, or completely, non-maternal in origin, that is, have the fetal genotype; e.g., at least about 90%, 95%, 98%, 99% or about 100% are non-maternal in origin.

In a specific embodiment, the pharmaceutical composition additionally comprises stem cells that are not obtained from a placenta.

Isolated placental stem cells in the compositions, e.g., pharmaceutical compositions, provided herein, can comprise placental stem cells derived from a single donor, or from multiple donors. The isolated placental cells can be completely HLA-matched to an intended recipient, or partially or completely HLA-mismatched.

5.9 Placental Stem Cell Conditioned Media

The placental stem cells (including umbilical cord stem cells) provided herein can be used to produce conditioned medium, e.g., for the treatment of an individual having pain, or the amelioration of pain in an individual. In various embodiments, the conditioned medium comprises medium in which placental stem cells have grown for at least 1, 2, 3, 4, 5, 6, 7, 8, 9, 10, 11, 12, 13, 14 or more days. In other embodiments, the conditioned medium comprises medium in which placental stem cells have grown to at least 30%, 40%, 50%, 60%, 70%, 80%, 90% confluence, or up to 100% confluence. In another embodiment, the conditioned medium comprises medium in which placental stem cells and non-placental, non-umbilical cord stem cells have been cultured.

5.10 Matrices Comprising Placental Cells

Further provided herein are matrices, hydrogels, scaffolds, and the like that comprise placental stem cells. The placental stem cells provided herein can be seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20% $H_2O$) amniotic membrane, chorionic membrane, substantially dry chorionic membrane, substantially dry amniotic and chorionic membrane, and the like. Preferred placental biomaterials on which placental stem cells can be seeded are described in Hariri, U.S. Application Publication No. 2004/0048796.

Placental cells provided herein can be suspended in a hydrogel solution suitable for, e.g., injection. Suitable hydrogels for such compositions include self-assembling peptides, such as RAD16. Placental stem cells can also be combined with, e.g., alginate or platelet-rich plasma, or other fibrin-containing matrices, for local injection. In one embodiment, a hydrogel solution comprising placental stem cells can be allowed to harden, for instance in a mold, to form a matrix having the cells dispersed therein for implantation. Placental stem cells in such a matrix can also be cultured so that the cells are mitotically expanded prior to implantation. The hydrogel can be, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix is biodegradable.

In some embodiments, the matrix comprises an in situ polymerizable gel (see., e.g., U.S. Patent Application Publication 2002/0022676; Anseth et al., *J. Control Release*, 78(1-3):199-209 (2002); Wang et al., *Biomaterials*, 24(22): 3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The placental stem cells can be seeded onto a three-dimensional framework or scaffold and implanted in vivo. Such a framework can be implanted in combination with any one or more growth factors, cells, drugs or other components that stimulate tissue formation or otherwise enhance or improve the practice of the methods of treatment described elsewhere herein.

Examples of scaffolds that can be used in the methods of treatment described herein include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(ε-caprolactone)/poly(glycolic acid) (PCL/PGA) copolymer, formed by processes such as freeze-drying, or lyophilization (see, e.g., U.S. Pat. No. 6,355,699), can also be used as scaffolds.

In another embodiment, the scaffold is, or comprises, a nanofibrous scaffold, e.g., an electrospun nanofibrous scaffold. In a more specific embodiment, said nanofibrous scaffold comprises poly(L-lactic acid) (PLLA), type I collagen, a copolymer of vinylidene fluoride and trifluoroethylene (PVDF-TrFE), poly(-caprolactone), poly(L-lactide-co-ε-caprolactone) [P(LLA-CL)] (e.g., 75:25), and/or a copolymer of poly(3-hydroxybutyrate-co-3-hydroxyvalerate) (PHBV) and type I collagen. Methods of producing nanofibrous scaffolds, e.g., electrospun nanofibrous scaffolds, are known in the art. See, e.g., Xu et al., *Tissue Engineering* 10(7):1160-1168 (2004); Xu et al., *Biomaterials* 25:877-886 (20040; Meng et al., *J. Biomaterials Sci., Polymer Edition* 18(1):81-94 (2007).

The placental stem cells described herein can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (CanMedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS®, RHAKOSS™, and CORTOSS® (Orthovita, Malvern, Pa.). The framework can be a mixture, blend or composite of natural and/or synthetic materials.

In another embodiment, placental stem cells can be seeded onto, or contacted with, a felt, which can be, e.g., composed of a multifilament yarn made from a bioabsorbable material such as PGA, PLA, PCL copolymers or blends, or hyaluronic acid.

The placental stem cells described herein can, in another embodiment, be seeded onto foam scaffolds that may be composite structures. Such foam scaffolds can be molded into a useful shape. In some embodiments, the framework is treated, e.g., with 0.1M acetic acid followed by incubation in polylysine, PBS, and/or collagen, prior to inoculation of the placental cells in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with placental stem cells.

5.10.1 Genetically Modified Placental Stem Cells

In another aspect, provided herein are placental cells that are genetically modified, e.g., to produce a nucleic acid or polypeptide of interest. Genetic modification can be accomplished, e.g., using virus-based vectors including, but not limited to, non-integrating replicating vectors, e.g., papilloma virus vectors, SV40 vectors, adenoviral vectors; integrating viral vectors, e.g., retrovirus vector or adeno-associated viral vectors; or replication-defective viral vectors. Other methods of introducing DNA into cells include the use of liposomes, electroporation, a particle gun, direct DNA injection, or the like.

Stem cells can be, e.g., transformed or transfected with DNA controlled by or in operative association with, one or more appropriate expression control elements, for example, promoter or enhancer sequences, transcription terminators, polyadenylation sites, internal ribosomal entry sites. Preferably, such a DNA incorporates a selectable marker. Following the introduction of the foreign DNA, engineered stem cells can be, e.g., grown in enriched media and then switched to selective media. In one embodiment, the DNA used to engineer a placental cell comprises a nucleotide sequence encoding a polypeptide of interest, e.g., a cytokine, growth factor, differentiation agent, or therapeutic polypeptide.

The DNA used to engineer the stem cell can comprise any promoter known in the art to drive expression of a nucleotide sequence in mammalian cells, e.g., human cells. For example, promoters include, but are not limited to, CMV promoter/enhancer, SV40 promoter, papillomavirus promoter, Epstein-Barr virus promoter, elastin gene promoter, and the like. In a specific embodiment, the promoter is regulatable so that the nucleotide sequence is expressed only when desired. Promoters can be either inducible (e.g., those associated with metallothionein and heat shock proteins) or constitutive.

In another specific embodiment, the promoter is tissue-specific or exhibits tissue specificity. Examples of such promoters include but are not limited to: myelin basic protein gene control region (Readhead et al., 1987, *Cell* 48:703) (oligodendrocyte cells); elastase I gene control region (Swit et al., 1984, *Cell* 38:639; Ornitz et al., 1986, *Cold Spring Harbor Symp. Quant. Biol.* 50:399; MacDonald, 1987, *Hepatology* 7:425) (pancreatic acinar cells); insulin gene control region (Hanahan, 1985, *Nature* 315:115) (pancreatic beta cells); myosin light chain-2 gene control region (Shani, 1985, *Nature* 314:283) (skeletal muscle).

Placental cells may be engineered to "knock out" or "knock down" expression of one or more genes. The expression of a gene native to a cell can be diminished by, for example, inhibition of expression by inactivating the gene completely by, e.g., homologous recombination. In one embodiment, for example, an exon encoding an important region of the protein, or an exon 5' to that region, is interrupted by a positive selectable marker, e.g., neo, preventing the production of normal mRNA from the target gene and resulting in inactivation of the gene. A gene may also be inactivated by creating a deletion in part of a gene or by deleting the entire gene. By using a construct with two regions of homology to the target gene that are far apart in the genome, the sequences intervening the two regions can be deleted (Mombaerts et al., 1991, *Proc. Nat. Acad. Sci. U.S.A.* 88:3084). Antisense, DNAzymes, small interfering RNA, and ribozyme molecules that inhibit expression of the target gene can also be used to reduce the level of target gene activity in the stem cells. For example, antisense RNA molecules which inhibit the expression of major histocompatibility gene complexes (HLA) have been shown to be most versatile with respect to immune responses. Triple helix molecules can be utilized in reducing the level of target gene activity. See, e.g., L. G. Davis et al. (eds), 1994, BASIC METHODS IN MOLECULAR BIOLOGY, 2nd ed., Appleton & Lange, Norwalk, Conn., which is incorporated herein by reference.

In a specific embodiment, placental cells can be genetically modified with a nucleic acid molecule comprising a nucleotide sequence encoding a polypeptide of interest, wherein expression of the polypeptide of interest is controllable by an exogenous factor, e.g., polypeptide, small organic molecule, or the like. Such a polypeptide can be a therapeutic polypeptide. In a more specific embodiment, the polypeptide of interest is IL-12 or interleukin-1 receptor antagonist (IL-1Ra). In another more specific embodiment, the polypeptide of interest is a fusion of interleukin-1 receptor antagonist and dihydrofolate reductase (DHFR), and the exogenous factor is an antifolate, e.g., methotrexate. Such a construct is useful in the engineering of placental cells that express IL-1Ra, or a fusion of IL-1Ra and DHFR, upon contact with methotrexate. Such a construct can be used, e.g., in the treatment of rheumatoid arthritis. In this embodiment, the fusion of IL-1Ra and DHFR is translationally upregulated upon exposure to an antifolate such as methotrexate. Therefore, in another specific embodiment, the nucleic acid used to genetically engineer a placental cell can comprise nucleotide sequences encoding a first polypeptide and a second polypeptide, wherein said first and second polypeptides are expressed as a fusion protein that is translationally upregulated in the presence of an exogenous factor. The polypeptide can be expressed transiently or long-term (e.g., over the course of weeks or months).

Such a nucleic acid molecule can additionally comprise a nucleotide sequence encoding a polypeptide that allows for positive selection of engineered stem cells, or allows for visualization of the engineered stem cells. In another more specific embodiment, the nucleotide sequence encodes a polypeptide that is, e.g., fluorescent under appropriate visualization conditions, e.g., luciferase (Luc). In a more specific embodiment, such a nucleic acid molecule can comprise IL-1Ra-DHFR-IRES-Luc, where IRES is an internal ribosomal entry site.

5.10.2 Immortalized Placental Stem Cell Lines

Placental stem cells can be conditionally immortalized by transfection with a vector containing a growth-promoting gene, that is, a gene encoding a protein that, under appropriate conditions, promotes growth of the placental stem cells, such that the production and/or activity of the growth-promoting protein is regulatable by an external factor. In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus.

External regulation of the growth-promoting protein can be achieved by placing the growth-promoting gene under the control of an externally-regulatable promoter, e.g., a promoter the activity of which can be controlled by, for example, contacting the cells with a compound to which the promoter is responsive. In one embodiment, a tetracycline (tet)-controlled gene expression system can be employed (see Gossen et al., *Proc. Natl. Acad. Sci. USA* 89:5547-5551, 1992; Hoshimaru et al., *Proc. Natl. Acad. Sci. USA* 93:1518-1523, 1996). In the absence of tet, a tet-controlled transactivator (tTA) within this vector strongly activates transcription from $ph_{CMV^{*}-1}$, a minimal promoter from human cytomegalovirus fused to tet operator sequences. tTA is a fusion protein of the repressor (tetR) of the transposon-10-derived tet resistance operon of *Escherichia coli* and the acidic domain of VP 16 of herpes simplex virus. Low, non-toxic concentrations of tet (e.g., 0.01-1.0 µg/mL) almost completely abolish transactivation by tTA.

In one embodiment, the vector further contains a gene encoding a selectable marker, e.g., a protein that confers drug resistance. The bacterial neomycin resistance gene ($neo^R$) is one such marker that may be employed within the methods described herein. Cells carrying $neo^R$ may be selected by means known to those of ordinary skill in the art, such as the addition of, e.g., 100-200 µg/mL G418 to the growth medium.

Transfection can be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a placental cell culture prepared as described above may be infected after, e.g., five days in vitro by incubation for about 20 hours in one volume of conditioned medium and two volumes of DMEM/F12 containing N2 supplements. Transfected cells carrying a selectable marker may then be selected as described above.

Following transfection, cultures are passaged onto a surface that permits proliferation, e.g., allows at least 30% of the cells to double in a 24 hour period. Preferably, the substrate is a polyornithine/laminin substrate, consisting of tissue culture plastic coated with polyornithine (10 µg/mL) and/or laminin (10 µg/mL), a polylysine/laminin substrate or a surface treated with fibronectin. Cultures are then fed every 3-4 days with growth medium, which may or may not be supplemented with one or more proliferation-enhancing factors. Proliferation-enhancing factors may be added to the growth medium when cultures are less than 50% confluent.

The conditionally-immortalized placental stem cell lines can be passaged using standard techniques, such as by trypsinization, when 80-95% confluent. Up to approximately the twentieth passage, it is, in some embodiments, beneficial to maintain selection (by, for example, the addition of G418 for cells containing a neomycin resistance gene). Cells may also be frozen in liquid nitrogen for long-term storage.

Clonal cell lines can be isolated from a conditionally-immortalized human placental stem cell line prepared as described above. In general, such clonal cell lines may be isolated using standard techniques, such as by limit dilution or using cloning rings, and expanded. Clonal cell lines may generally be fed and passaged as described above.

Conditionally-immortalized human placental stem cell lines, which may, but need not, be clonal, may generally be induced to differentiate by suppressing the production and/or activity of the growth-promoting protein under culture conditions that facilitate differentiation. For example, if the gene encoding the growth-promoting protein is under the control of an externally-regulatable promoter, the conditions, e.g., temperature or composition of medium, may be modified to suppress transcription of the growth-promoting gene. For the tetracycline-controlled gene expression system discussed above, differentiation can be achieved by the addition of tetracycline to suppress transcription of the growth-promoting gene. In general, 1 g/mL tetracycline for 4-5 days is sufficient to initiate differentiation. To promote further differentiation, additional agents may be included in the growth medium.

6. EXAMPLES

6.1 Example 1: Successful Treatment of Neuropathic Pain Using Placental Stem Cells This Example demonstrates that $CD10^+$, $CD34^-$, $CD105^+$, $CD200^+$ placental stem cells (PDAC™) are effective at reducing neuropathic pain.

A rat neuropathic pain model was used. Male Sprague Dawley rats, weighing 175-200 g, were divided into three groups of experimental animals, which received $1\times10^6$, $3\times10^6$, or $1\times10^7$ PDAC™ intravenously. Negative control animals received only vehicle. Positive control animals received either 50 mg/kg or 100 mg/kg gabapentin (a pain reducer) on Day 11, 14, 18, 21, 25, 28 and 35 post-surgery.

Surgical Procedure: On Day 0 (D0), anesthesia was induced by IP injection of Ketamine (85 mg/kg)/xylazine (5 mg/kg) mix. Left paraspinal muscles of the rats were separated from the spinous processes from L4 to S2. The L6 transverse process was carefully removed with a small rongeur to identify visually L4-L6 spinal nerves. The left L5 & L6 spinal nerves were isolated and tightly ligated with 5-0 silk thread. Animals were then allowed to recuperate.

On D7, pain sensitivity for all groups was assessed as a baseline. Pain sensitivity was assessed again for all animals at D11, D14, D18, D21, D25, D28 and D35.

Before the pain inflicting procedure, on D-1, each rat was placed inside a Plexiglas chamber for 10-15 minute acclimation period. The rats were evaluated for sensitivity to a Von Frey Filament Assortment ranging from the thinnest 8 g filament up to the thickest 15 g filament (8, 10, 15 g) as follows. An individual von Frey filament was applied to the test animal from the bottom direction and up and pin point touching the middle of each paw (facing down) of the rat's hind legs either five consecutive times or until a response occurred. The test was repeated with each of the different chosen filaments with a minimum 90 seconds interval. If the rat lifted its paw at least 3 times in a session, it was considered as the minimum pain sensitivity level.

Treatment with gabapentin, and testing of all animals, were performed on days, 11, 14 17, 21, 24 and 28 post-surgery. Gabapentin-receiving animals were treated on each test day and tested two hours after each dosing, at approximately the same time of day. Animals that on day 7-8 demonstrated motor deficits evident by lack of muscle tone in either hind limbs, or lack of withdrawal reflex, were excluded from the study To assess pain sensitivity during the experiment, the rats were placed inside the Plexiglas chamber for a 15-20 minute acclimation period. Subsequently the rats were evaluated for tactile allodynia (pain from stimuli that are not normally painful) using a von Frey Filament ranging from the thinnest 0.6 g filament up to the thickest 15 g (0.6, 1.4, 2, 4, 6, 8, 10, 15 g) as above for establishing the baseline pain threshold, except that initially, the thinnest von Frey filament was touched to the hind paw 5 consecutive times or until a response occurred. If no response occurred, the next thickest filament was applied in the same manner, repeating until a withdrawal response was obtained. Once a withdrawal response was obtained, the paw was retested, with the preceding descending filament(s) until no response was observed. The interval between successive filaments, was held to no more than approximately 90 seconds. Each animal had both hind paws tested in this manner; first the right leg (the injected leg) and then the left leg. The lowest amount of force required to elicit a response is recorded as withdrawal threshold in grams.

Gabapentin (GBP) was administered intraperitoneally (IP) on each testing day (D11, D14, D17, D21, D24, D28 and D35). PDAC™ were administered intravenously (IV) on day 7 or 8.

A time line of testing activities is presented in Table 1, below.

TABLE 1

Time line

| Activity | Day −1 | Day 0 | Day 7-8* | Days 11, 14, 16 or 17, 21, 23 or 24, 28 and 35 |
|---|---|---|---|---|
| VFF inclusion test | X | | | |
| Surgery | | X | | |
| Dosing - GP 50 or 100 MPK of appropriate groups: 2 hrs prior to testing | | | | X |
| Inclusion/exclusion for pain baseline and motor function | | | X | |
| VFF test | | | X | X |
| Group allocation | | | X | |
| Placental stem cells administration | | | X | |

*Can be done on day 7 or 8

Results

Administration of PDAC™ at the 10×10$^7$ dosage level significantly improved sensitivity scores in the assay as compared to vehicle-treated animals, particularly on D21, D28 and D35; that is, the animals displayed reduced allodynia. See FIG. 1. Results for this dosage were comparable to 50 mg/kg GBP. An aggregate pain relief score, termed TOPAR (Total Pain Relief) was calculated as an Area Under the Curve (AUC) of reduction in mechanical sensitivity following treatment. This analysis confirms that PDAC™ significantly improved pain sensitivity scores. See FIG. 2. Thus, these analyses confirm that PDAC™ can be used to treat pain.

6.2 Example 2: Pre-Clinical Study Establishing Effectiveness of PDAC™ in the Treatment of Cancer Pain and Inflammatory Pain This Example describes studies to demonstrate the effectiveness of CD10$^+$, CD34$^-$, CD105$^+$, CD200$^+$ placental stem cells (PDAC™) in the treatment of cancer pain and inflammatory pain.

6.2.1 Bone Cancer Pain

Five-week-old, immunocompromised male mice (CB17-SCRF; Taconic Laboratories) housed in a germ-free barrier are used. At 6 weeks of age, baseline measurements for mechanical and thermal sensitivities are performed. On the following day, the mice are anesthetized with 100 mg/kg ketamine and 20 mg/kg xylazine and inoculated in the left cardiac ventricle with 5×10$^4$ PC3-ML cells in 100 µL serum-free DMEM/F12. This procedure consistently produces skeletal tumors in tibiae and femora of >80% of inoculated mice; however, PC3-ML cells do not metastasize to any soft-tissue organ with the exception of small tumors produced in the adrenal glands. The PC3-ML cells are engineered to stably express a bright variant of Green Fluorescent Protein (eGFP), allowing visualization of the dissemination of the cells to the skeleton by fluorescence microscopy.

Initially, mechanical and thermal hypersensitivities are measured on days 1, 4, 7, 10, 14, 21 and 28 post-PC13-ML cell inoculation to determine a time course of the development and persistence of pain. Once the onset of quantifiable and statistically significant changes in pain sensitivity has been identified, the effects of the placental stem cells are examined. Placental stem cells are administered following the onset of pain, with periodic pain assessments made during the study period. PDAC™ are administered to experimental mice at doses of, e.g., 0.1×10$^6$ cells, 0.6×10$^6$ cells, and 1.5×10$^6$ cells per dose). Control animals receive only vehicle. Thus, for example, if statistically significant changes in pain sensitivity occur on average on day 12 post-inoculation, PDAC™ at one of the three dosages are administered on that day, prior to pain testing, and pain assessments are made on days 13, 16, 23 and 30. Optionally, the study includes a second administration of PDAC™ if there is an initial attenuation in pain hypersensitivity followed by a recurrence.

Mice not demonstrating changes in pain sensitivity in the first phase of the study (that is, administration of PDAC™ following the development of pain) are excluded from the study.

6.2.2 Chemotherapy-Induced Pain

This study demonstrates the effectiveness of CD10$^+$, CD34$^-$, CD105$^+$, CD200$^+$ placental stem cells against neuropathic pain induced by paclitaxel. In the study, mice (C57BL/6J) are injected with paclitaxel as the chemotherapeutic agent. Paclitaxel has been demonstrated to produce neuropathic pain in both humans and animals (see, e.g., Authier et al., "Animal models of chemotherapy-evoked painful peripheral neuropathies," *Neurotherapeutics* 6:620-629 (2009); Gauchan et. al., 2009; Golden and Johnson, 2004).

Baseline sensitivities in mice are determined prior to administration of paclitaxel. Mice are then administered a dose of paclitaxel (5 mg/kg, i.p.) and mechanical and thermal hypersensitivities are measured on 1, 4, 7, 10 and 14 days. Pain sensitivities typically peak at 14 days in this model, and persist up to 35 days. PDAC™ are administered to experimental mice at doses of, e.g., $0.1 \times 10^6$ cells, $0.6 \times 10^6$ cells, and $1.5 \times 10^6$ cells per dose) on day 14, prior to testing. Control animals receive only vehicle. Pain sensitivity assessments for all animals are made on days 15, 21, 28 and 35. Positive control animals receive either gabapentin or morphine, administered at effective doses.

6.2.3 Inflammatory Pain Model

This study demonstrates effectiveness of $CD1^0$, $CD34^-$, $CD10^5$, $CD200^+$ placental stem cells against pain in an inflammatory pain model.

Mice (C57BL/6J) receive a 20 µL subcutaneous injection of an inflammatory dose of Complete Freund's Adjuvant (CFA; 50% dissolved in saline) in the plantar surface of the hindpaw. Pain sensitivities typically peak at 3 hours after CFA injection and can persist up to 14 days. PDAC™ are administered to experimental mice at doses of, e.g., $0.1 \times 10^6$ cells, $0.6 \times 10^6$ cells, and $1.5 \times 10^6$ cells per dose) 3 hours after CFA administration. Positive control mice are administered a pain-reducing-effective dose of a non-steroidal anti-inflammatory drug, e.g., celecoxib (CELEBREX®). Mechanical and thermal hypersensitivities are then measured on days 1, 3, 7 and 14.

For each of the pain studies above, mechanical allodynia are assessed using von Frey filaments as described in Example 1, above. Thermal sensitivity is assessed using the Hargreaves Procedure. The Hargreaves assay measures nociceptive sensitivity in a freely moving animal by focusing a radiant heat source on the plantar surface of an animal's hindpaw as it stands in a Plexiglas chamber, and measuring latency to withdraw its paw from the heat. Cold sensitivity will be assessed using acetone; in this method, a drop of acetone is applied to a hind paw followed by evaporation, and measuring latency to withdrawal of the paw from a surface.

In each of the studies, the PDAC™ are administered IV into the tail vein. Control vehicle in each study is 5% dextran-40 in saline buffer.

6.3 Example 3: Treatment of Neuropathic Pain Using PDAC™

6.3.1 Intravenous Administration

Case 1

An individual presents with neuropathic pain in the extremities related to administration of paclitaxel. The attending oncologist indicates that maintenance of paclitaxel therapy is strongly indicated. An assessment of pain is performed using the Pain Quality Assessment Scale, with the quality of pain indicated on a scale of 0-10 for each indicated type of pain. An aggregate score is also recorded. After pain assessment, the individual is administered $1 \times 10^9$ $CD34^-$, $CD10^+$, $CD105^+$, $CD200^+$ placental stem cells (PDAC™) in normal saline by intravenous infusion. The individual is monitored for the following seven days for any adverse events, and is reassessed for pain on day 7 following administration. The scores for each individual pain quality, and overall aggregate pain score, are compared to the scores prior to administration. If the majority of the pain quality scores, or the aggregate score, is not reduced after administration, the individual is optionally provided a second administration of $1 \times 10^9$ PDAC™ in normal saline by intravenous infusion. The individual is then monitored over the course of paclitaxel therapy, and optionally for six months afterwards; administration of the PDAC™ is repeated at any time paclitaxel-related pain is determined to increase by the Pain Quality Assessment Scale.

Case 2

A 78-year old diabetic individual presents with diabetic neuropathy experienced primarily in the legs, with apparent sciatic nerve involvement, making walking difficult. The individual's pain is assessed using the Numeric Pain Assessment Scale, both while the individual is seated, and while the individual is walking. After pain assessment, the individual is administered $1 \times 10^9$ $CD34^-$, $CD10^+$, $CD105^+$, $CD200^+$ placental stem cells (PDAC™) in normal saline by intravenous infusion. The individual is monitored for the following seven days for any adverse events, and is reassessed for pain on day 7 following administration, again while the individual is seated and while the individual is walking. The administration is considered successful if the individual indicates are reduction in pain while seated, while walking, or both. Optionally, if the individual indicates improvement while seated, or while walking, but not both, the individual may be administered a second dose of PDAC™ equivalent to the first. The individual is then monitored for the following six months every 1-2 weeks, and follow-up administration(s) take place whenever pain according to the Numeric Pain Assessment Scale is determined to worsen.

Case 3

A 62-year old individual presents with postherpetic neuralgia. The individual's medical records confirm a previous case of shingles with accompanying rash and herpetic pustules on the individual's right dorsal area. Pain associated with the shingles, however, has not resolved after one month after healing of the rash and pustules. The individual's pain is assessed using the Numeric Pain Assessment Scale. After pain assessment, the individual is administered $1 \times 10^9$ $CD34^-$, $CD10^+$, $CD105^+$, $CD200^+$ placental stem cells (PDAC™) in normal saline by intravenous infusion. The individual is monitored for the following seven days for any adverse events, and is reassessed for pain on day 7 following administration.

Case 4

An individual presents with neuropathic pain in the extremities related to previous injury. The attending surgeon indicates that narcotics and NSAIDs failed to treat the condition. An assessment of pain is performed using the Pain Quality Assessment Scale, with the quality of pain indicated on a scale of 0-10 for each indicated type of pain. An aggregate score is also recorded. After pain assessment, the individual is administered $1 \times 10^9$ $CD34^-$, $CD10^+$, $CD105^+$, $CD200^+$ placental stem cells (PDAC™) in normal saline by intravenous infusion. The individual is monitored for the following seven days for any adverse events, and is reassessed for pain on day 7 following administration. The scores for each individual pain quality, and overall aggregate pain score, are compared to the scores prior to administration. If the majority of the pain quality scores, or the aggregate score, is not reduced after administration, the individual is optionally provided a second administration of $1 \times 10^9$ PDAC™ in normal saline by intravenous infusion. The individual is then monitored over the course of paclitaxel therapy, and optionally for six months afterwards; administration of the PDAC™ is repeated at any time paclitaxel-related pain is determined to increase by the Pain Quality Assessment Scale.

6.3.2 Local Administration

A 62-year old individual presents with postherpetic neuralgia. The individual's medical records confirm a previous case of shingles with accompanying rash and herpetic pustules. Pain associated with the shingles, however, has not resolved after one month after healing of the rash and pustules. The individual's pain is assessed using the Numeric Pain Assessment Scale. After pain assessment, the individual is administered $3 \times 10^7$ CD34$^-$, CD10$^+$, CD105$^+$, CD200$^+$ placental stem cells (PDAC™) in a solution of platelet-rich plasma in a series of 10 injections adjacent to the nerve trunk servicing the area of the individual affected by the shingles. The individual is monitored for the following seven days for any adverse events, and is reassessed for pain on day 7 following administration.

6.4 Example 4: Treatment of Vulvodynia Using PDAC™

A 41-year old female individual presents with vulvodynia. Prior to treatment, the exact pain sites are determined with cotton tips and gentle digital palpation. The individual's pain is assessed using the Numeric Pain Assessment Scale. After pain assessment, the individual is given $1 \times 10^9$ CD34$^-$, CD10$^+$, CD105$^+$, CD200$^+$ placental stem cells (PDAC™) in a solution of platelet-rich plasma via intravaginal administration to the pain sites. The individual is monitored for the following seven days for any adverse events, and is reassessed for pain on day 7 following administration.

6.5 Example 5: Treatment of Interstitial Cystitis Using PDAC™

A 29-year old female individual is diagnosed with interstitial cystitis. The individual's pain is assessed using the Numeric Pain Assessment Scale. After pain assessment, the individual is given $1 \times 10^9$ CD34$^-$, CD10$^+$, CD105$^+$, CD200$^+$ placental stem cells (PDAC™) in a solution of platelet-rich plasma via intravesical route, on either side of the bladder neck, and other pelvic sites that the individual has identified as tender during the examination. The individual is monitored for the following seven days for any adverse events, and is reassessed for pain on day 7 following administration. The individual is also assessed by urinalysis and biomarkers for interstitial cystitis on day 7 following administration.

6.6 Example 6: Attenuation of Pain on Perineural Inflammation in Rats Using PDAC™

This example describes a study using a rat neuritis model to evaluate the effect of CD34$^-$, CD10$^+$, CD105$^+$, CD200$^+$ placental stem cells (PDAC™) on neuropathic pain and to assess potential ex vivo changes that may mediate the cells effects. The neuritis model is an established model for neuropathic pain driven by perineural inflammation. In this model, perineural inflammation is induced in the sciatic nerve vicinity of rats. Pain develops in the nerve target organ (hind-paw) within 2-3 days and resolves within approximately 8 days.

Experimental Procedure

Three-month-old male Sprague Dawley rats initially weighing approximately 250-300 g were used. Four groups were included in the study: 0.4, 1 or 4 million of PDAC™ and the vehicle control. The minimum and maximum weights of the rats were within the range of ±20%.

While under surgical anesthesia (50 mg/kg ketamine and 7.5 mg/kg xylazine, injected IM), the common sciatic nerve of the rats was exposed at mid thigh and wrapped with sterile biocompatible carrier soaked with 200 μl of 1% lambda carrageenan (Sigma-Aldrich CAS Number: 9064-57-7).

Three days following surgery, animals were assessed for mechanical hypersensitivity as an indirect measure of pain in the hind paws. Tactile allodynia was measured by assessing the withdrawal response to calibrated von Frey fibers. Three fibers according to force application, low (8 g), medium (16 g) and high force fiber (26 g) were employed in this study. Each fiber was applied to the plantar surface of both hind paws 5 times and percent response was calculated.

On Day 4 following the perineural inflammation induction, animals were treated with PDAC™ at the dose of 0.4, 1 or 4 million or vehicle immediately following the assessment of allodynia. The treatment was provided intravenously through the tail vein. At various time points after treatment, animals were assessed for mechanical allodynia by applying the same procedure as on Day 3 post surgery. Pain levels were assessed on days 0, 3, 4, 6 and 8. Tissue samples including sciatic nerve, draining lymph node and plasma were analyzed.

Results

The results demonstrated that PDAC™ at the dose of 4 million and 1 million reduced the pain significantly compared to the vehicle group on Days 4, 6 and 8, while PDAC™ at 0.4 million showed a trend of pain reduction on Day 4. Ex vivo tissue analyses demonstrated that PDAC™ suppressed T-cell priming and activation in draining lymph node by suppressing activation of antigen presenting cells, including dendritic cells and macrophage. PDAC™ reduced interferon gamma, IL-17, while increased IL-10 production in draining lymph node as well as ipsi-lateral sciatic nerve, suggesting that PDAC™ modulates T-cell differentiation. Furthermore, in ipsi-lateral sciatic nerve, significantly less leukocyte infiltration was observed in PDAC™-treated animals.

6.7 Example 7: Production of Placental Stem Cells

This Example demonstrates the isolation of placental stem cells

Summary: Placental tissue is dissected and digested, followed by primary and expansion cultures to achieve an expanded cell product that produces many cell doses. Cells are stored in a two-tiered cell bank and are distributed as a frozen cell product. All cell doses derived from a single donor placenta are defined as a lot, and one placenta lot is processed at a time using sterile technique in a dedicated room and Class 100 laminar flow hood. The cell product is defined as being CD105+, CD200+, CD10+, and CD34−, having a normal karyotype and no or substantially no maternal cell content.

6.7.1 Obtaining Stem Cells

Tissue Dissection and Digestion:

A placenta is obtained less than 24 hours after expulsion. Placental tissue is obtained from amnion, a combination of amnion and chorion, or chorion. The tissue is minced into small pieces, about 1 mm in size. Minced tissue is digested in 1 mg/ml Collagenase 1A for 1 hour at 37° C. followed by Trypsin-EDTA for 30 minutes at 37° C. After three washes in 5% FBS in PBS, the tissue is resuspended in culture medium.

Primary Culture:

The digested tissue is suspended in culture medium and placed into Corning T-flasks, which are incubated in a humidified chamber maintained at 37° C. with 5% $CO_2$. Half of the medium is replenished after 5 days of culture. High-density colonies of cells form by 2 weeks of culture.

Colonies are harvested with Trypsin-EDTA, which is then quenched with 2% FBS in PBS. Cells are centrifuged and resuspended in culture medium for seeding expansion cultures. These cells are defined as Passage 0 cells having doubled 0 times.

Expansion Culture:

Cells harvested from primary culture, harvested from expansion culture, or thawed from the cell bank are used to seed expansion cultures. Cell Factories (NUNC™) are treated with 5% $CO_2$ in air at 50 ml/min/tray for 10 min through a sterile filter and warmed in a humidified incubator maintained at 37° C. with 5% $CO_2$. Cell seeds are counted on a hemacytometer with trypan blue, and cell number, viability, passage number, and the cumulative number of doublings are recorded. Cells are suspended in culture medium to about $2.3 \times 10^4$ cells/ml and 110 ml/tray are seeded in the Cell Factories. After 3-4 days and again at 5-6 days of culture, culture medium is removed and replaced with fresh medium, followed by another treatment with 5% $CO_2$ in air. When cells reach approximately $10^5$ cells/cm$^2$, cells are harvested with Trypsin-EDTA, followed by quenching with 2% FBS in PBS. Cells are then centrifuged and resuspended in culture medium.

Cryopreservation:

Cells to be frozen down are harvested from culture with Trypsin-EDTA, quenched with 2% FBS in PBS, and counted on a hemacytometer. After centrifugation, cells are resuspended with 10% DMSO in FBS to a concentration of about 1 million cells/ml for cells to be used for assembly of a cell bank, and 10 million cells/ml for individual frozen cell doses. The cell solution is transferred to a freezing container, which is placed in an isopropyl alcohol bath in a −80° C. freezer. The following day, cells are transferred to liquid nitrogen.

6.8 Example 8: Identification of Placental Stem Cell-Specific Genes

Gene expression patterns from placental stem cells as prepared in Example 7 from amnion-chorion (AC) and umbilical cord (UC) were compared to gene expression patterns of multipotent bone marrow-derived mesenchymal stem cells (BM) and dermal fibroblasts (DF), the latter of which is considered to be terminally differentiated. Cells were grown for a single passage, an intermediate number of passages, and a large number of passages (including until senescence). Results indicate that the number of population doublings has a major impact on gene expression. A set of genes was identified that are up-regulated in AC and UC, and either down-regulated or absent in BM and DF, and that are expressed independent of passage number. Placental stem cells and umbilical cord stem cells will be referred to collectively hereinafter in this Example as AC/UC stem cells.

6.8.1 Methods and Materials

6.8.1.1 Cells and Cell Culture

BM (Cat #PT-2501) and DF (Cat #CC-2511) were purchased from Cambrex. AC and UC originated from passage 0 tissue culture flasks. AC and UC in the flasks were obtained by digestion from a donor placenta. T-75 culture flasks were seeded at 6000 cells/cm$^2$ and cells were passaged when they became confluent. Population doublings were estimated from trypan blue cell counts. Cultures were assayed for gene expression after 3, 11-14, and 24-38 population doublings.

6.8.1.2 RNA, Microarrays, and Analysis

Cells were lysed directly in their tissue culture flasks, with the exception of one culture that was trypsinized prior to lysis. Total RNA was isolated with the RNeasy kit from QIAGEN. RNA integrity and concentrations were determined with an Agilent 2100 Bioanalyzer. Ten micrograms of total RNA from each culture were hybridized on an Affymetrix GENECHIP® platform. Total RNA was converted to labeled cRNAs and hybridized to oligonucleotide Human Genome U133A 2.0 arrays according to the manufacture's methods. Image files were processed with the Affymetrix MAS 5.0 software, and normalized and analyzed with Agilent GeneSpring 7.3 software.

6.8.2 Results

6.8.2.1 Selection of BM-MSC, AC/UC Stem Cell, and DF Culture Time-Points for Microarray Analyses To establish a gene expression pattern unique to AC/UC stem cells, two stem cell lines, AC(6) and UC(6), were cultured in parallel with BM-MSC and DF. To maximize identifying a gene expression profile attributable to cellular origin and minimize exogenous influences all cells were grown in the same medium, seeded, and sub-cultured using the same criteria. Cells were harvested after 3 population doublings, 11-14 doublings, or 35 doublings or senescence, whichever came first. Genes whose expression in AC/UC stem cells are unchanged by time-in-culture and are up-regulated relative to BM and DF are candidates for AC/UC stem cell-specific genes.

Samples (BM, AC(6), and UC(6)) were collected and harvested after three population doublings; these samples were regarded as being in culture for a "short" period of time. A short-term DF sample was not collected. Intermediate length cultures, 11 to 14 doublings, were collected for all cell types. Long-term cultures were collected from all cell lines at about 35 population doublings or just prior to senescence, whichever came first. Senescence occurred before 15 doublings for BM and at 25 doublings for DF. The purchased BM and DF cells were expanded many times prior to gene analysis, and cannot be considered early-stage. However, operationally, BM grown for three doublings (BM-03) are deemed a short-term culture. Likewise, BM-11 is operationally referred to as an intermediate length culture, but because senescence occurred at 14 doublings, BM-11 is most likely a long-term culture biologically.

6.8.2.2 Hierarchical Clustering Shows Relatedness Between BM, AC/UC Stem Cells, and DF Microarray analysis identifies patterns of gene expression, and hierarchical clustering (HC) attempts to find similarities in the context of two dimensions—genes in the first dimension and different conditions (different RNA samples) in the second. The GeneChips used in this experiment contained over 22,000 probe sets (referred to as the "all genes list"), but many of these sets interrogate genes that are not expressed in any condition. To reduce the all genes list, genes not expressed or expressed at low levels (raw values below 250) in all samples were eliminated to yield a list of 8,215 genes.

6.8.2.3 Filtering Methods Used to Identify AC/UC Stem Cell-Specific Genes

Genes that remain constant across all AC/UC samples, and are down-regulated in BM and DF, are considered AC/UC stem cell-specific. Two filtering methods were combined to create a list of 58 AC/UC stem cell-specific genes (Table 2).

TABLE 2

58 Placental stem cell or Umbilical cord stem cell-specific genes

| Symbol | Gene | Biological Process, Description, and Additional Annotation |
|---|---|---|
| ACTG2 | actin, gamma 2, smooth muscle, enteric | muscle development, cytoskeleton, expressed in umbilical cord artery and prostate epithelia |
| ADARB1 | adenosine deaminase, RNA-specific, B1 (RED1 homolog rat) | RNA processing, central nervous system development |
| AMIGO2 | amphoterin induced gene 2 | homophilic and heterophilic cell adhesion, adhesion molecule with Ig like domain 2 |
| ARTS-1 | type 1 tumor necrosis factor receptor shedding aminopeptidase regulator | proteolysis, antigen processing, angiogenesis, expressed in placenta |
| B4GALT6 | UDP-Gal:betaGlcNAc beta 1,4-galactosyltransferase, polypeptide 6 | carbohydrate metabolism, integral to membrane, may function in intercellular recognition and/or adhesion |
| BCHE | butyrylcholinesterase | cholinesterase activity, serine esterase activity, hydrolase activity |
| C11orf9 | chromosome 11 open reading frame 9 | hypothetical protein, p53-like transcription factor, expressed in retinal pigment epithelium |
| CD200 | CD200 antigen | immunoglobulin-like, surface protein, inhibits macrophage |
| COL4A1 | collagen, type IV, alpha I | ECM, basement membrane, afibrillar collagen, contains arresten domain |
| COL4A2 | collagen, type IV, alpha 2 | ECM, biogenesis, basement membrane, coexpressed with COL 4A1, down-reg. in dysplastic epithelia |
| CPA4 | carboxypeptidase A4 | proteolytic, histone acetylation, maternal imprinted, high expression in prostate cancer cell lines |
| DMD | dystrophin (muscular dystrophy, Duchenne and Becker types) | muscle contraction, cell shape and cell size control, muscle development |
| DSC3 | desmocollin 3 | homophilic cell-cell adhesion, localized to desmosomes |
| DSG2 | desmoglein 2 | homophilic cell-cell adhesion, localized to desmosomes |
| ELOVL2 | elongation of very long chain fatty acids (FEN1/Elo2, SUR4/Elo3, yeast)-like 2 | fatty acid biosynthesis, lipid biosynthesis |
| F2RL1 | coagulation factor II (thrombin) receptor-like 1 | G-protein coupled receptor protein signaling pathway, highly expressed in colon epithelia and neuronal elements |
| FLJ10781 | hypothetical protein FLJ10781 | — |
| GATA6 | GATA binding protein 6 | transcription factor, muscle development |
| GPR126 | G protein-coupled receptor 126 | signal transduction, neuropeptide signaling pathway |
| GPRC5B | G protein-coupled receptor, family C, group 5, member B | G-protein coupled receptor protein signaling pathway, |
| ICAM1 | intercellular adhesion molecule 1 (CD54), human rhino virus receptor | cell-cell adhesion, cell adhesion, transmembrane receptor activity, expressed in conjunctival epithelium |
| IER3 | immediate early response 3 | anti-apoptosis, embryogenesis and morphogenesis, cell growth and/or maintenance |
| IGFBP7 | insulin-like growth factor binding protein 7 | negative regulation of cell proliferation, overexpressed in senescent epithelial cells |
| IL1A | interleukin 1, alpha | immune response, signal transduction, cytokine activity, cell proliferation, differentiation, apoptosis |
| IL1B | interleukin 1, beta | immune response, signal transduction, cytokine activity, cell proliferation, differentiation, apoptosis |
| 1L6 | interleukin 6 (interferon, beta 2) | cell surface receptor linked signal transduction, immune response |
| KRT18 | keratin 18 | morphogenesis, intermediate filament, expressed in placenta, fetal, and epithelial tissues |
| KRT8 | keratin 8 | cytoskeleton organization and biogenesis, phosphorylation, intermediate filament, coexpressed with KRTIB |
| LIPG | lipase, endothelial | lipid metabolism, lipoprotein lipase activity, lipid transporter, phospholipase activity, involved in vascular biology |

TABLE 2-continued

58 Placental stem cell or Umbilical cord stem cell-specific genes

| Symbol | Gene | Biological Process, Description, and Additional Annotation |
|---|---|---|
| LRAP | leukocyte-derived arginine aminopeptidase | antigen processing, endogenous antigen via MHC class I; N-terminal aminopeptidase activity |
| MATN2 | matrilin 2 | widely expressed in cell lines of fibroblastic or epithelial origin, nonarticular cartilage ECM |
| MEST | mesoderm specific transcript homolog (mouse) | paternally imprinted gene, development of mesodermal tissues, expressed in fetal tissues and fibroblasts |
| NFE2L3 | nuclear factor (erythroid-derived 2)-like 3 | transcription co-factor, highly expressed in primary placental cytotrophoblasts but not in placental fibroblasts |
| NUAK1 | NUAK family, SNF1-like kinase, I | protein amino acid phosphorylation, protein serine-threonine kinase activity |
| PCDH7 | BH-protocadherin (brain-heart) | cell-cell adhesion and recognition, containing 7 cadherin repeats |
| PDLIM3 | PDZ and LIM domain 3 | alpha-actinin-2-associated LIM protein, cytoskeleton protein binding, expressed in skeletal muscle |
| PKP2 | plakophilin 2 | cell-cell adhesion, localized to desmosomes, found in epithelia, binds cadherins and intermediate filament |
| RTN1 | reticulon 1 | signal transduction, neuron differentiation, neuroendocrine secretion, membrane trafficking in neuroendocrine cells |
| SERPINB9 | serpin peptidase inhibitor, ciade B (ovalbumin), member 9 | serine protease inhibitor, coagulation, fibrinolysis, complement fixation, matrix remodeling, expressed in placenta |
| ST3GAL6 | sialyltransferase 10 | amino sugar metabolism, protein amino acid glycosylation, glycolipid metabolism, protein-lipoylation |
| ST6GALNAC5 | sialyltransferase 7E | protein amino acid glycosylation, ganglioside biosynthesis |
| SLC12A8 | solute carrier family 12 (sodium/potassium/chloride transporters), member 8 | amino acid-polyamine transporter activity, cation-chloride cotransporter 9, possible role in epithelial immunity (psoriasis) |
| TCF21 | transcription factor 21 | regulation of transcription, mesoderm development, found in epithelial cells of the kidney |
| TGFB2 | transforming growth factor, beta 2 | regulation of cell cycle, signal transduction, cell-cell signaling, cell proliferation, cell growth |
| VTN | vitronectin (serum spreading factor, somatomedin B, complement S-protein) | immune response, cell adhesion, secreted protein, binds ECM |
| ZC3H12A | zinc finger CCCM-type containing 12A | MCP-I treatment-induced protein, nucleic acid binding, hypothetical zinc finger protein |

First, 58 genes were identified by selecting those genes over-expressed≥three-fold in at least seven of eight AC/UC stem cell conditions relative to all BM and DF samples. Filtering on eight of the eight AC/UC stem cell conditions yielded a similar list. The second filtering method used "absent" and "present" calls provided by the Affymetrix MAS 5.0 software. A list was created by identifying genes absent in all BM and DF conditions and present in AC-03, AC-11, UC-03, and UC-11. Gene calls in the later AC/UC stem cell conditions were not stipulated.

The two lists overlapped significantly and were combined. The combined list was trimmed further by eliminating (1) several genes expressed at very low levels in most or all AC/UC stem cell conditions, and (2) genes carried on the Y chromosome. AC and UC cells used in this study were confirmed to be male by FISH analysis, and the BM and DF were derived from a female donor. The resulting list of 46 AC/UC stem cell-specific genes is shown in Table 3.

TABLE 3

AC/UC-Specific Genes Listed by Ontology

Cell Adhesion

AMIGO2
B4GALT6
DSC3
DSG2
ICAM1
PCDH7
PKP2
VTN

Cytoskeletal

ACTG2
DMD
KRT18
KRT8
PDLIM3

TABLE 3-continued

AC/UC-Specific Genes Listed by Ontology

Development

ADARB1
IER3
IGFBP7
IL1A
IL1B
MEST
TGFB2
ECM

COL4A1
COL4A2
MATN2
VTN
Implicated in Epithelia

ACTG2
C11orf9
COL4A1
COL4A2
DSC3
DSG2
F2RL1
ICAM1
IGFBP7
IL6
KRT18
KRT8
MATN2
PKP2
SLC12A8
TCF21
Glycosylation B4GALT6
ST3GAL6
ST6GALNAC5
Response Immune ARTS-1
CD200
IL1A
IL1B
IL6
LRAP
SLC12A8
VTN
Proteolysis ARTS-1
CPA4
LRAP
Signaling F2RL1
GPR126
GPRC5B
IL1A
IL1B
IL6
RTN1
TGFB2
Transcription C11orf9?
GATA6
NFE2L3
TCF21

This list of 46 genes encodes a collection of proteins presenting a number of ontology groups. The most highly represented group, cell adhesion, contains eight genes. No genes encode proteins involved in DNA replication or cell division. Sixteen genes with specific references to epithelia are also listed.

6.8.3 Discussion

An expression pattern specific to placental stem cells, and distinguishable from bone marrow-derived mesenchymal cells, was identified. Operationally, this pattern includes 46 genes that are over expressed in all placental stem cell samples relative to all BM and DF samples.

The experimental design compared cells cultured for short, medium, and long periods of time in culture. For AC and UC cells, each culture period has a characteristic set of differentially expressed genes. During the short-term or early phase (AC-03 and UC-03) two hundred up-regulated genes regress to the mean after eight population doublings.

Gene expression by the intermediate length cultures is defined by rapid cell division and genes differentially expressed at this time are quite different from those differentially expressed during the early phase. Many of the genes up-regulated in AC-11 and UC-11, along with BM-03 and DF-14, are involved in chromosome replication and cell division. Based on gene expression, BM-03 appears biologically to be a mid-term culture. In this middle stage cell type-specific gene expression is overshadowed by cellular proliferation. In addition, almost every gene over expressed in the short-term AC or UC cultures is down-regulated in the middle and later stage conditions. 143 genes were up-regulated≥five-fold during this highly proliferative phase, constituting approximately 1.7% of the expressed genes.

The long-term cultures represent the final or senescent phase. In this phase, cells have exhausted their ability to divide, and, especially for AC and UC, the absolute number of differentially expressed genes is noticeably reduced. This may be the result of cells being fully adapted to their culture environment and a consequently reduced burden to biosynthesize. Surprisingly, late BM and DF cultures do not display this same behavior; a large number of genes are differentially expressed in BM-11 and DF-24 relative to AC and UC and the normalized value of 1. AC and UC are distinguishable from BM and DF most notably in the long-term cultures.

The placental stem cell-specific gene list described here is diverse. COL4A1 and COL4A2 are coordinately regulated, and KRT18 and KRT8 also appear to be co-expressed. Eight of the genes encode proteins involved in cell to cell contact, three of which (DSC3, DSG2, and PKP2) are localized to desmosomes, intercellular contact points anchored to intermediate filament cytoskeleton proteins such as keratin 18 and keratin 8. Tight cell-to-cell contact is characteristic of epithelial and endothelial cells and not typically associated with fibroblasts. Table 3 lists 16 genes, of the 46 total, characteristic to epithelial cells. Placental stem cells are generally described as fibroblast-like small spindle-shaped cells. This morphology is typically distinct from BM and DF, especially at lower cell densities. Also of note is the expression pattern of CD200, which is present in AC/UC stem cell and absent in all BM and DF samples.

This subset of genes of 46 genes constitutes a set of molecular biomarkers that distinguishes AC/UC stem cells from bone marrow-derived mesenchymal stem cells or fibroblasts.

6.9 Example 9: Attenuation of Allodynia and Neuroinflammatory Response Associated with Perineural Inflammation in Rats Using Placental Stem Cells This example demonstrates that placental stem cells reduce neuro-inflammatory pain via a mechanism that potentially comprises suppression of dendritic cell homing, activation and differentiation; induction of IL-10; and T-cell modulation.

6.9.1 Materials and Methods

6.9.1.1 Animals and Surgical Procedure

Studies were performed using male Sprague Dawley rats, 3 months old, approximately 250-300 g at study initiation; the minimum and maximum weights of the group were within a range of ±20% of group mean weight.

For surgical procedures, rats were anaesthetized with ketamine (50 mg/kg) and xylazine (7.5 mg/kg) solution that was administered intraperitoneally. Following verification of the anesthesia, the area of surgery was shaved and subsequently wiped with betadine and alcohol. The surgery was performed as described previously (see Herzberg et al., Pain, 1999, 83:169-82). In brief, the common sciatic nerve was exposed at the mid-thigh level by blunt dissection through the biceps femoris and gently separated from adjacent tissue. The nerve was wrapped in a band (approx. 3 mm wide and 25 mm long) of sterile hemostatic oxidized cellulose (SURGICEL™ 'cotton' type; Ethicon, J&J, NJ, USA). The SURGICEL™ was applied by passing curved forceps beneath the nerve (taking particular care to avoid stretching the nerve), grasping one end of the band and pulling it under the nerve. The end that was grasped was then gently folded over the nerve, and the other end was folded over in the opposite direction. The SURGICEL™ was wrapped loosely around the nerve and so as not to cause any nerve constriction. Prior to application, 0.2 cc of 1% carrageenan was injected into the SURGICEL™ band to induce a local inflammatory reaction. Before the treatment on Day 3, the rats were randomly assigned to each treatment group.

6.9.1.2 Tactile Allodynia Evaluation

Tactile allodynia was measured by assessing the withdrawal response to calibrated Von Frey fibers. Three fibers according to force application, low (8 g), medium (16 g) and high force fiber (26 g), were employed in this study. Each fiber was applied to the paw five times and a percentage score of responses was calculated as described previously (see Flatters et al., Pain, 2004, 109:150-61).

6.9.1.3 Placental Stem Cell Preparation and Administration

CD34−, CD10+, CD200+ and CD105+ placental stem cells were prepared as described in Example 7.

On the third day following exposure of the left sciatic nerve to perineural inflammation, cryopreserved placental stem cells were thawed in a 37° C. water bath. Cell viability was determined by trypan blue, with an average of viability of approximately 95%. The cells were then diluted with Plasmalyte (Baxter Healthcare Corporation) to $4\times10^6$, $1\times10^6$ or $4\times10^5$ cells/ml in a 50 ml conical tube. Cells were subsequently withdrawn into a 1 ml syringe with a 26 G needle. Within 2 hours post-thaw, 1 ml of placental stem cells or vehicle was administered via the tail vein. Pain levels were assessed on days 0, 3, 4, 6 and 8.

6.9.1.4 Animal Tissues

One day after treatment (Day 4), inguinal lymph nodes were collected and snap-frozen for RNA isolation. Sciatic nerves were harvested at Day 8. For gene expression analysis, sciatic nerves were snap-frozen for RNA isolation. For flow cytometry analysis, sciatic nerves were placed in D-PBS on wet ice. Blood was withdrawn via cardiac puncture into EDTA collection tubes. Immediately, blood samples were centrifuged at 1300 RCF for 10 minutes. Plasma was then collected and snap-frozen.

6.9.1.5 RNA Extraction and Quantitative PCR

Frozen rat sciatic nerve and draining lymph nodes were weighed, and homogenized in appropriate volume of lysis buffer per weight using a TissueRuptor from Qiagen. Total RNA was extracted from homogenized rat sciatic nerve and draining lymph node using Qiagen's RNeasy Lipid Tissue Kit according to the manufacture's protocol. The total RNA concentration was determined by NanoDrop ND-1000 (Thermo Fisher Scientific). cDNA was synthesized from isolated RNA using SuperScript III from Invitrogen. For gene expression, individual TaqMan gene expression assays for rat were used for CD11c, CD86, CD80, CD3d, CD69, IL-12, IFN-γ, IL-10, and IL-17. Relative gene expression was normalized using GAPDH expression and fold change was calculated using the 2-ΔΔCt method.

6.9.1.6 Cytokine Measurements

Plasma cytokine measurements were performed using a rat cytokine 10-plex kit from Invitrogen that examined GM-CSF, IFN-γ, IL-1α, IL-1β, IL-2, IL-4, IL-6, IL-10, IL-12, and TNF-α. Plasma samples were run according to the manufacturer's protocol. Briefly, antibody conjugated beads were added to the vacuum filtration plate provided. Beads were subsequently washed with the working wash solution. Standards or animal samples were added to each well and the plate was incubated for 2 hours at room temperature on an orbital shaker protected from light. The wells were washed twice and a biotinylated detection antibody was added. Following 1 hour of incubation at room temperature and washing, R-phycoerythrin conjugated streptavidin was added to the plate for 30 minutes. The plate was washed 3 times and data acquisition was performed on a Luminex 100 using STarStaion 2.3 software. For IL-17 ELISA, sciatic nerves were weighed and placed in 300.25 µl medium containing: 300 µl of Cellytic-MT mammalian tissue lysis/extraction reagent (Sigma Chemical Co.), and 0.25 µl of protease inhibitor cocktail (Sigma Chemical Co.). Samples were then homogenized and centrifuged (12,500×g for 10 min). The supernatant was collected and the IL-17 level was determined by ELISA (R&D Systems Inc.).

6.9.1.7 Sciatic Nerve Single Cell Suspension and Flow Cytometry

Sciatic nerve samples were obtained fresh and placed in D-PBS on wet ice. Nerves were dissociated to single cell suspension using a Papain Neural Dissociation Kit and the gentleMACS homogenizer from Miltenyi Biotech. Briefly, single sciatic nerves were placed in C-Tubes (Miltenyi Biotech) with 1950 µl of 37° C. pre-heated enzyme mix 1. C-tubes were placed on gentleMACS and "m-brain-01" program was run. Tubes were placed on a rotator and incubated at 37° C. for 15 minutes. Sciatic nerves were run on gentleMACS program "m_brain_02". Afterwards, 30 µl of enzyme mix 2 was added. Nerves were incubated with gentle rotation at 37° C. for 10 minutes. Nerve samples were run on gentleMACS "m_brain_03" followed by a 10 minute incubation at 37° C. The resultant suspension was passed through a 40 g cell strainer. Cells were pelleted at 300×g and re-suspended in FACS buffer (PBS-1% FBS). Single cell suspensions were stained using 0.5 µg of FITC Mouse anti-rat CD3 (BD Biosciences) and 0.5 µg of PE-Mouse Anti-Rat Macrophage Subset (ED2-like antigen, BD Biosciences). Matched Isotype controls were used to set the gating.

6.9.1.8 Immunohistochemistry

Immunostaining was preformed following standard protocol for immunohistochemistry and immunofluorescence. Sciatic nerves were harvested bilaterally 8 days after neuritis induction. Briefly, sciatic nerves were fixed in HOPE buffer as described (see Olert J, Wiedorn K H, Goldmann T, Kuhl H, Mehraein Y, Scherthan H, Immunostaining was preformed following standard protocol for immunohistochemistry and immunofluorescence. Sciatic nerves were harvested bilaterally 8 days after neuritis induction. Briefly, sciatic nerves were fixed in HOPE buffer as described (see Olert et al., Pathol Res Pract, 2001, 197:823-6). Histological sections (5 microns) were blocked in blocking solution (PBS containing 1× casein, 0.3% Triton X-100 and 5% Horse serum) for 30 minutes. Sections were then incubated overnight with one or two of the following primary antibodies: CD68 (clone ED1, mouse monoclonal IgG1, Santa Cruz Biotechnology), CD4 (goat polyclonal IgG, Santa Cruz Biotechnology) and CD8 (mouse monoclonal IgG2a, Santa Cruz Biotechnology). After three washes in PBS, slides were incubated in the appropriate secondary antibodies for 30 min at room temperature: goat-anti-mouse IgG2a conjugated with Alexa Fluor 488 (1:500, Invitrogen), goat-anti-mouse IgG1 conjugated with Alexa Fluor 488 (1:500, Invitrogen), donkey anti-goat conjugated with Alexa Fluor 488 (1:500, Invitrogen). For nuclear staining 600 nM DAPI solution (Sigma) was applied for 10 minutes after the last PBS wash. After being washed in PBS, slides were mounted in aqueous media for fluorescence (Vector). Immunohistochemistry images were captured with NIKON Eclipse microscope model E800 equipped with a high-resolution digital camera Nikon DXM1200F connected to PC equipped with NIS Elements software for image capture and archiving.

6.9.1.9 Data Analysis

Data are expressed as mean±SEM. Data were tabulated and analyzed using StatView software version 5.0 (SAS Institute Inc., San Francisco, Calif., USA). Alpha (two tailed) for significance in all analyses were set at 0.05. Behavioral data were analyzed with repeated measurements analysis of variance (ANOVA) followed by post hoc test. For ex vivo analysis, the 2-tailed Student's t-test was used to identify the differences between vehicle and cell treated group.

6.9.2 Results

6.9.2.1 Placental Stem Cells Alleviate Mechanical Allodynia

Figure 3A:
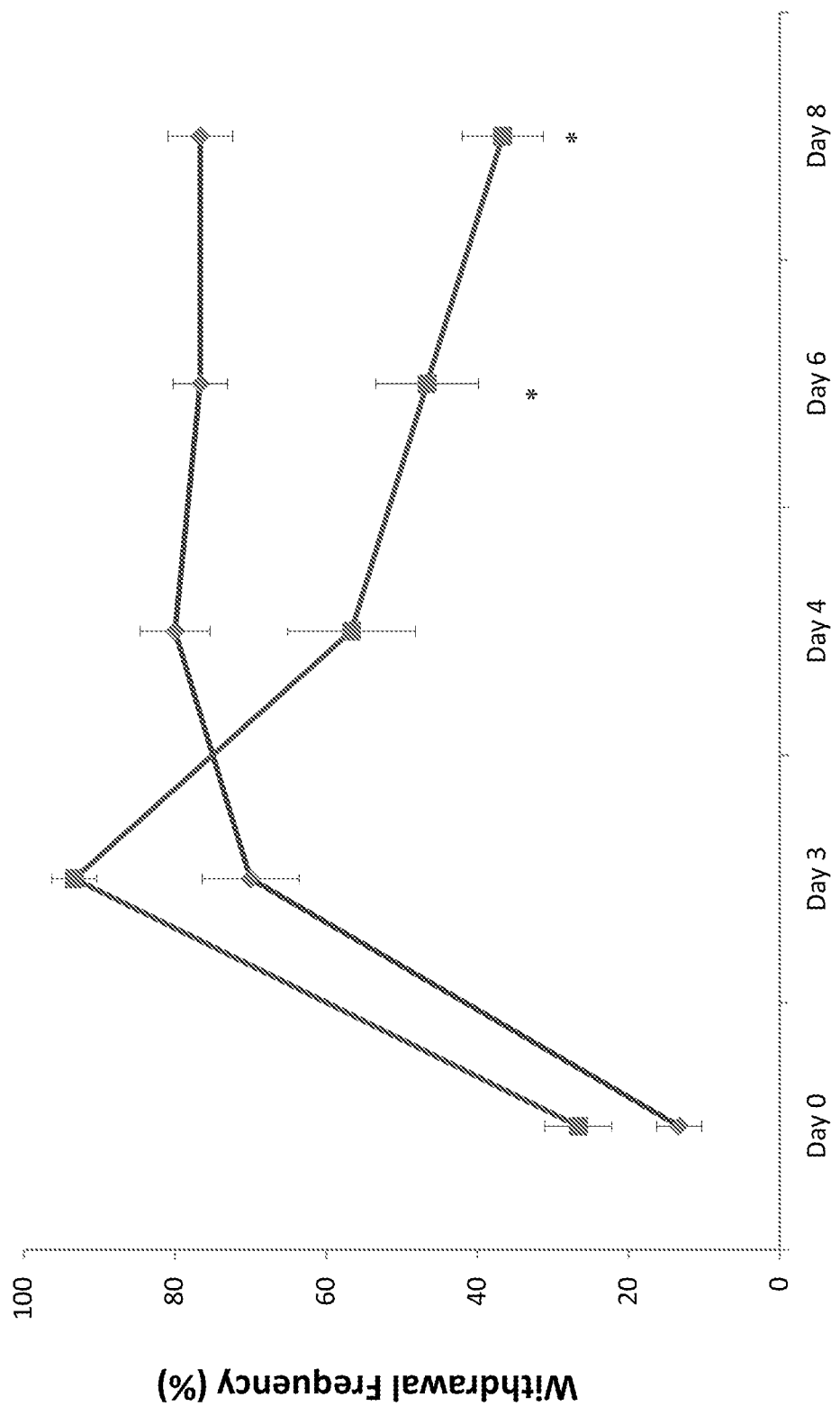
Figure 3B:
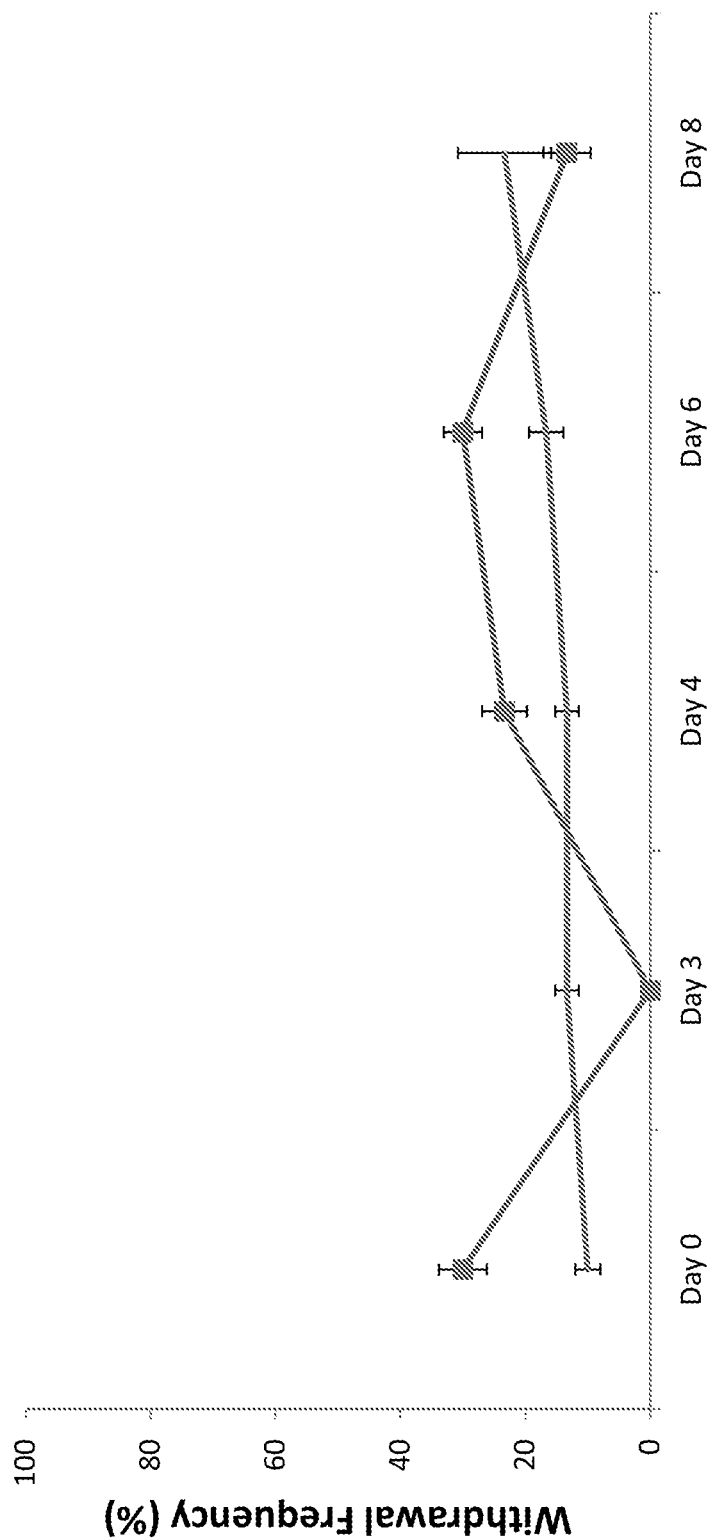

Three different calibrated monofilaments, including 8 g, 16 g, and 26 g, were used to test mechanical allodynia. The response to 16 and 26 g stimuli was consistent and repeatable at day 3 prior to treatment, while scores of the rats did not respond to the 8 g stimuli. Accordingly, only the data gathered from the response to 16 and 26 g stimuli were used for data analysis. As expected, significant increase in the response to stimuli (allodynia) was developed on the 3rd day following the procedure compared to day 0 prior to neuritis induction. No significant difference was observed between vehicle and placental stem cell treated groups at that phase prior to treatment. While the vehicle had no effect on the mechanical sensitivity at 26 g stimuli, the placental stem cell at $4\times10^6$ significantly reduced the hind paw withdrawal from 93.3%±2.98 on day 3 to 46.7%±6.80 and 36.7%±5.37 on days 6 and 8, respectively (FIG. 3A). A similar trend of pain reduction by placental stem cells was observed at 16 g stimuli, where hind paw withdrawal was reduced from 57.8±10.24% to 22.2±7.03% and 26.7±3.33% on days 6 and 8, respectively. No significant effect was observed on the contra-lateral paw (FIG. 3B).

Figure 3C:
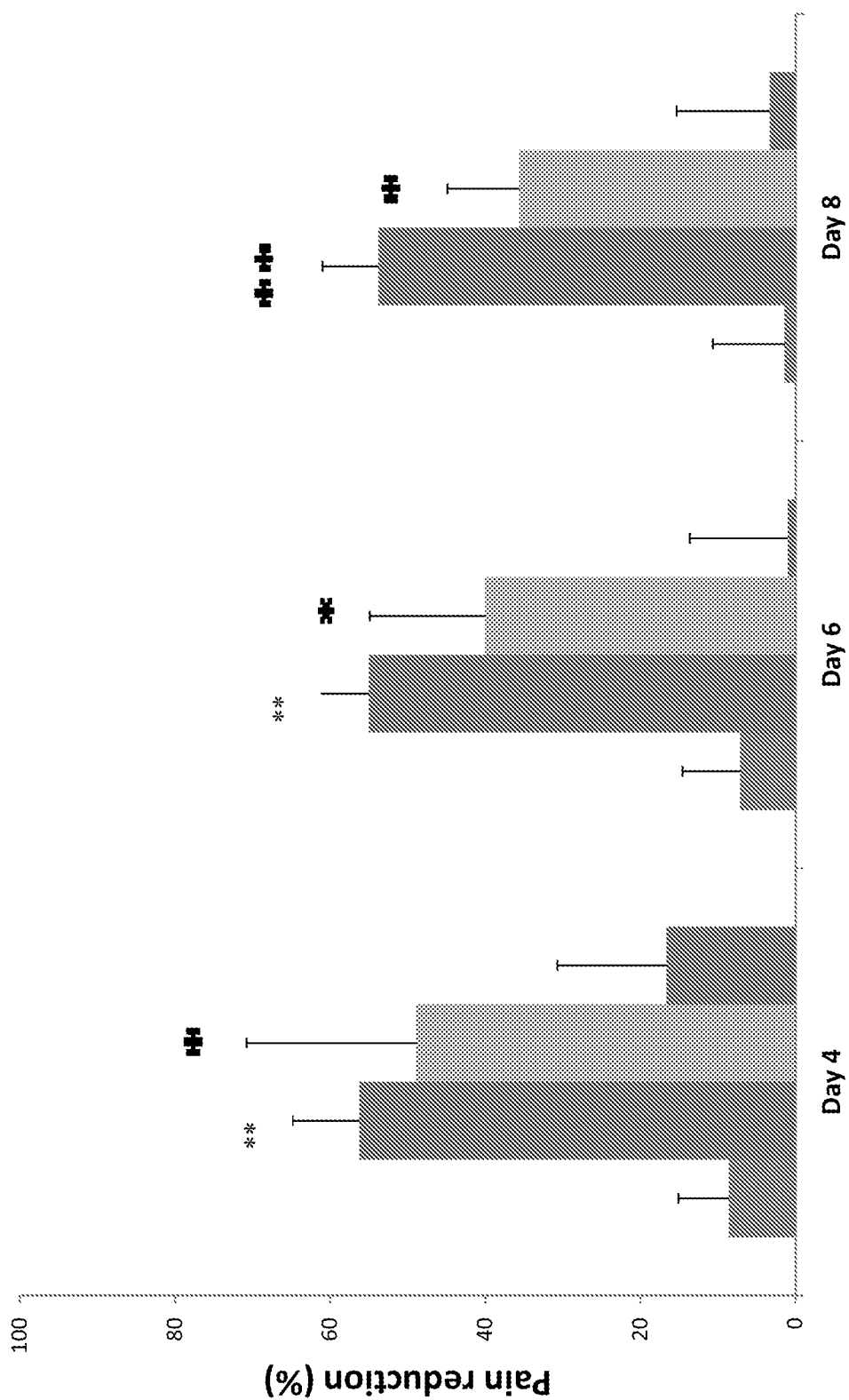
Figure 3D:
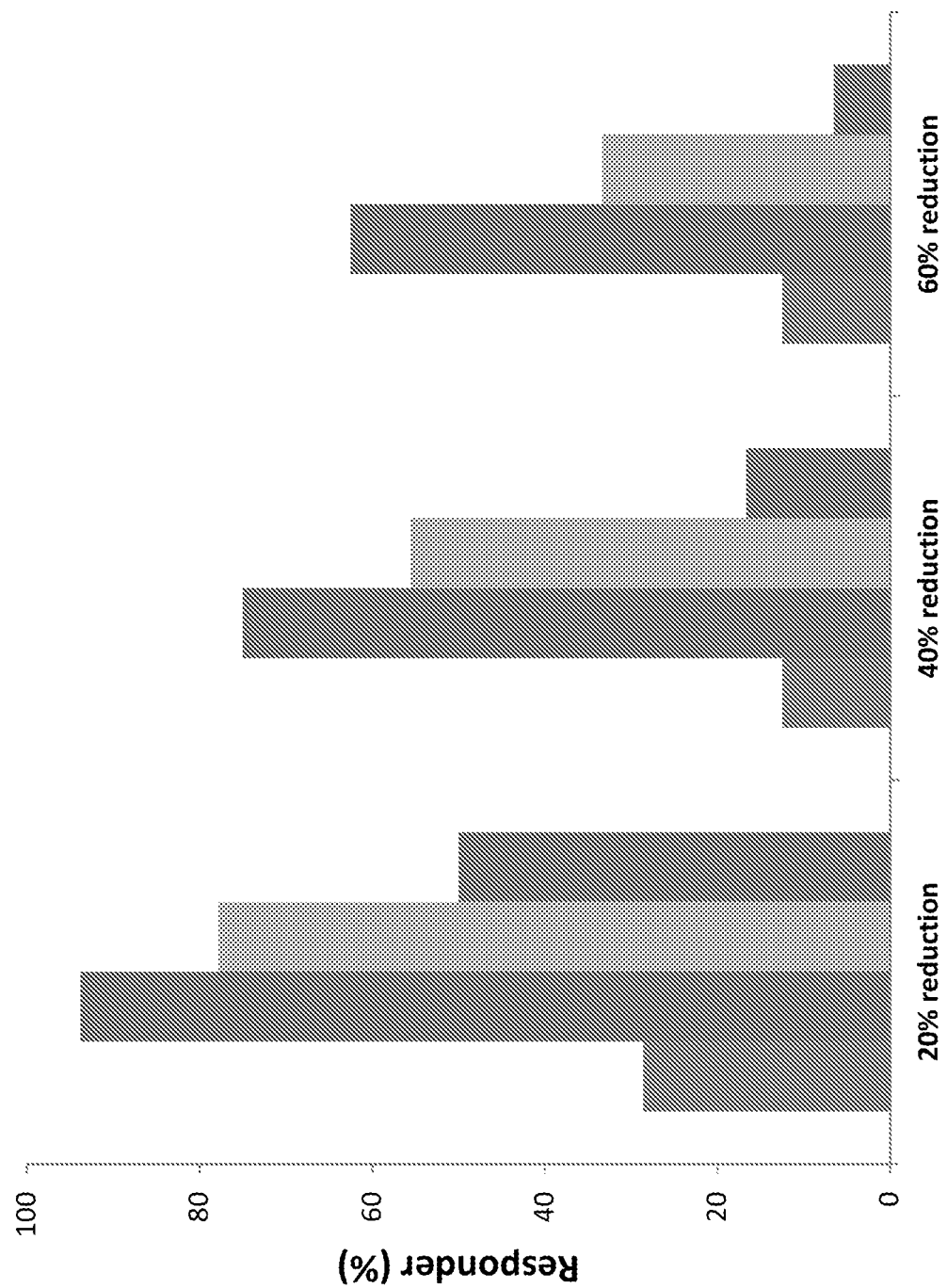

The dose effect of placental stem cells on neuritis-induced mechanical allodynia reduction was further examined. While the placental stem cells at $4\times10^6$ and $1\times10^6$ significantly reduced the mechanical allodynia compared to the vehicle group on Day 4, 6 and 8, the placental stem cells at $4\times10^5$ demonstrated a trend of pain reduction only on Day 4 (FIG. 3C). The percentage of animals responding to placental stem cell treatment demonstrated dose dependence as well (FIG. 3D).

6.9.2.2 Placental Stem Cells Suppress Dendritic Cells Recruitment, Activation and Differentiation In order to elucidate the placental stem cell-mediated anti-neuroinflammatory mechanism, dendritic cells in draining lymph nodes were examined. As shown in FIG. 4A, the placental stem cell treated group had reduced expression of CD11c. Meanwhile, dendritic cell activation markers, CD86 and CD80, were suppressed by placental stem cells. In concert with the suppression of CD11c, CD86 and CD80, the expression of IL-12, a key pro-inflammatory cytokine secreted by differentiated dendritic cells, was also significantly reduced in draining lymph nodes by placental stem cells (FIG. 4B).

6.9.2.3 Placental Stem Cells Suppress T-Cell Priming and Modulate T-Cell Differentiation Given the impaired dendridic cell ability of homing and activation conferred by placental stem cells, we expected that T-cell priming by dendritic cells may be subsequently affected. Indeed, the expression of T-cell receptor, CD3, and T-cell activation marker, CD69, were both significantly lower in the placental stem cell treated group than control group (FIG. 5A), suggesting that T-cell proliferation and activation in draining lymph nodes is suppressed by placental stem cells.

Furthermore, the T-helper cell subpopulation was examined to test whether placental stem cells had an effect on T-cell differentiation. As shown in FIGS. 5B and 5C, placental stem cells significantly suppressed interferon gamma (IFNγ) in draining lymph nodes, suggesting placental stem cells suppress Th-1 T-cell differentiation. In addition, IL-17 expression in draining lymph node (FIG. 5C) as well as ipsi-lateral sciatic nerve (FIGS. 6A and 6B) was down-regulated by placental stem cells. On the other hand, up-regulation of the anti-inflammatory cytokine IL-10 by placental stem cells was observed in draining lymph nodes (FIG. 6C) as well as plasma (Table 4). Among 9 pro-inflammatory cytokines tested in plasma, four pro-inflammatory cytokines, including IFNγ, IL-2, IL-6, and IL-12, were down-regulated by placental stem cells, while no difference of IL-1β was observed between the placental stem cell and vehicle groups (Table 4). Other cytokines, including GM-CSF, IL-1α, IL-4 and TNF-α, were below the level of detection in plasma.

TABLE 4

Plasma cytokine levels (pg/ml) at Day 8 (n = 5)

| Cytokine | Vehicle group | Placental stem cell group |
|---|---|---|
| IFNγ | 14.4 ± 5.16 | 10.9 ± 1.84 |
| IL-1β | 69.6 ± 8.2 | 73.0 ± 9.46 |
| IL-2 | 603.8 ± 57.63 | 419.5 ± 76.78 |
| IL-6 | 43.8 ± 3.52 | 33.9 ± 2.23 |
| IL-10 | 43.1 ± 4.33 | 75.0 ± 7.09* |
| IL-12 | 2976.2 ± 270.9 | 2491.5 ± 190.9 |

*P < 0.05

Figure 7A:
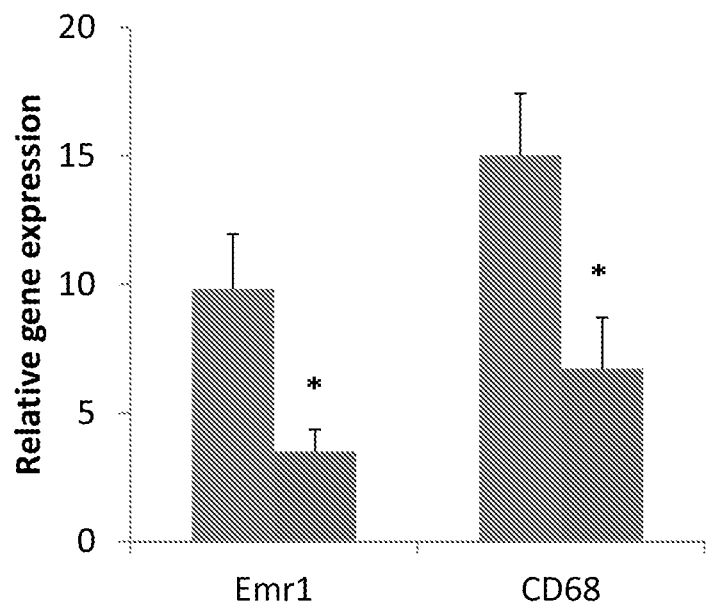
Figure 7B:
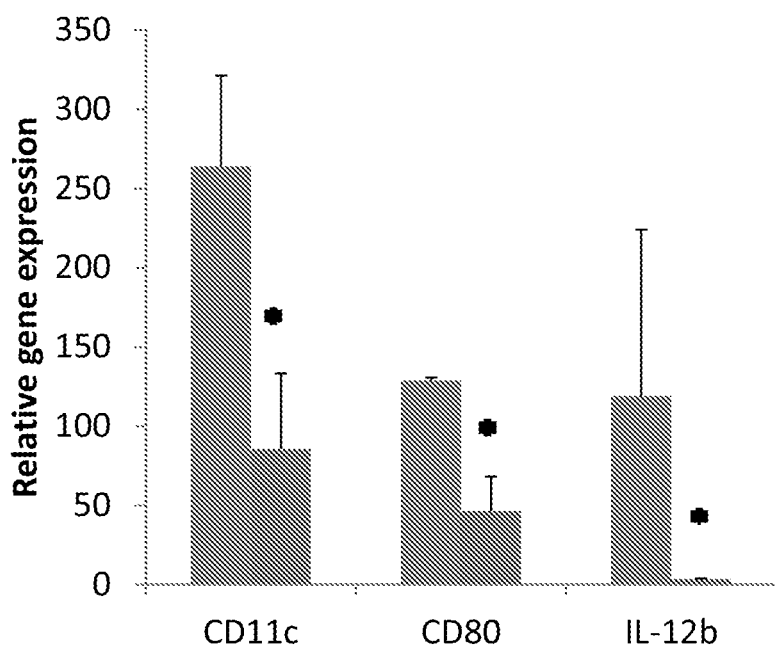
Figure 7C:
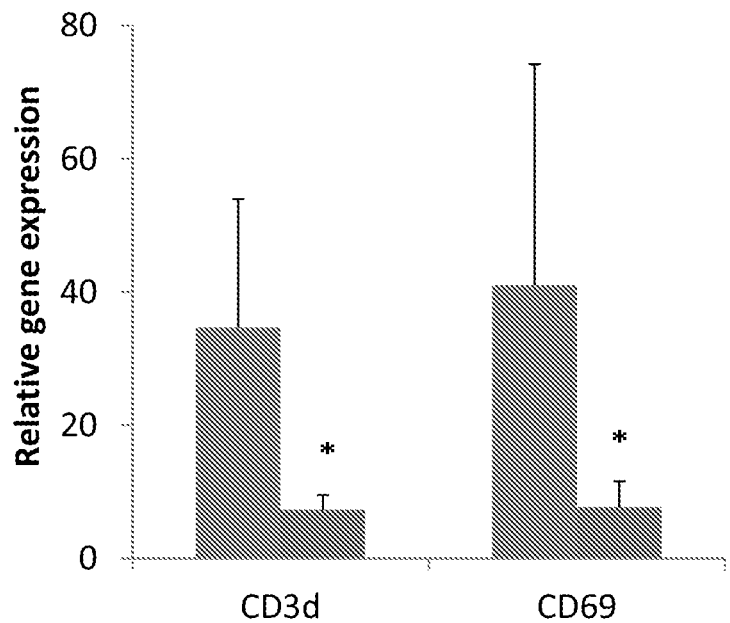
Figure 7D:
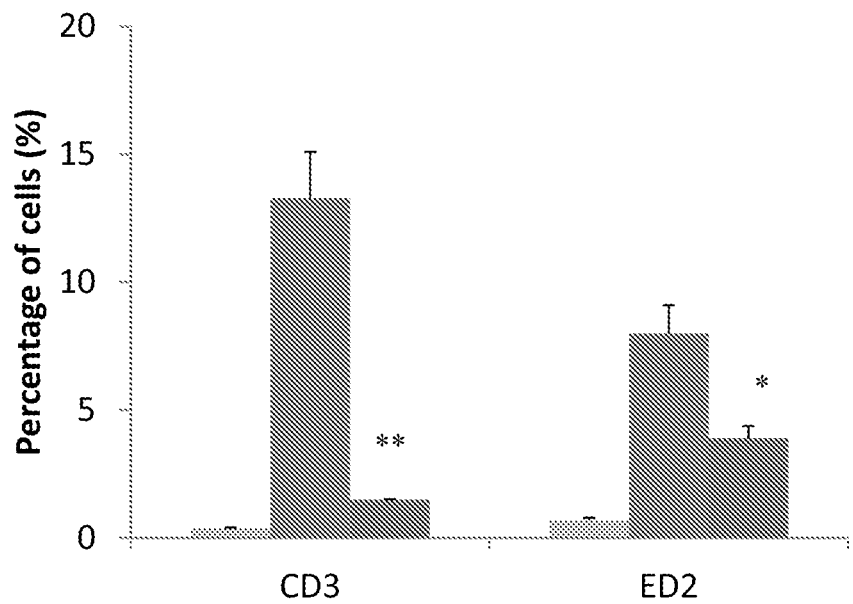

6.9.2.4 Placental Stem Cells Suppress Immune Cell Infiltration in Ipsi-Lateral Sciatic Nerve Next, leukocyte infiltration into the ipsi-lateral sciatic nerve was examined. Macrophage markers, Emr1 and CD68, were down-regulated in the placental stem cell treated group, indicating less macrophage recruitment and activation (FIG. 7A). Dendritic cell infiltration and activation was also suppressed by placental stem cells, evidenced by down-regulation of CD11c, CD80 and IL-12 expression (FIG. 7B). Furthermore, T-cell infiltration and activation was suppressed by placental stem cells as well, indicated by reduced expression of CD3 and CD69 in the placental stem cell treated group (FIG. 7C). Consistent with the above gene expression results, the flow cytometry analysis of a single cell suspension from the ipsi-lateral sciatic nerve showed that only 1.5% CD3+ cells and 3.9% ED2+ cells were detected in the placental stem cell treated group compared with 13.3% CD3+ and 8.0% ED2 cells in the vehicle group (FIG. 7D). H&E staining revealed severe epineural edema and inflammatory infiltrates in the vehicle group compared with normal and placental stem cell treated animals (FIG. 8A-C). The expression of CD68 (FIG. 8D-F), CD8 (FIG. 8G-I), and CD4 (FIG. 8J-L) were all attenuated in the placental stem cell treated group compared with vehicle.

Furthermore, chemokines, including CCL2, CCL12 and CXCL1 were suppressed by placental stem cells in the ipsi-lateral sciatic nerve (FIG. 9).

6.9.2.5 Conclusion

In conclusion, this Example demonstrates that placental stem cells reduce mechanical allodynia induced by perineural inflammation. Moreover placental stem cells suppress T-cell priming, and modulate T-cell differentiation in draining lymph nodes by inhibiting dendritic cell homing to draining lymph nodes and by attenuating the activation of dendritic cells.

6.10 Example 10: Attenuation of Allodynia and Neuroinflammatory Response Associated with Perineural Inflammation in Rats Using Placental Stem Cells This example demonstrates that placental stem cells can reduce neuropathic pain.

6.10.1 Materials and Methods

6.10.1.1 Animals and Surgical Procedure

Seventy seven male Sprague Dawley rats, 3 months old, approximately 200-250 g at study initiation were included in the study. Minimum and maximum weights of the group were within a range of ±20% of group mean weight. Following several days of habituation the rats underwent baseline measurements for pain behavior (tactile-allodynia) and motor sensory assessment (rotarod test). All the rats underwent Sciatic nerve chronic constriction injury (CCI); pain development was verified on the 6th day following the operation and sensory motor behavior on the 7th. On the 8th day following the procedure the rats were assigned randomly to the various treatment groups (Table 5). Pain levels were assessed on the 6th, 10th, 16th, 25th and 30th days following the procedure. Motor sensory coordination was assessed on the 11th, 21st, 26th and 34th days. On the 35th day the rats were euthanized, the sciatic nerves (both sides) were collected and embedded in paraffin. Spleen and lymph nodes underwent snap freezing and the maximum amount of blood that was processed to plasma was collected.

For surgical procedures, rats were anaesthetized with ketamine (50 mg/kg) and xylazine (7.5 mg/kg) solution that was administered IP. Following verification of the anesthesia, the area of surgery was shaved and subsequently sterilized with betadine and alcohol wipe. The rats' eyes were lubricated.

TABLE 5

Treatment groups, volume administrated and number of rats in each group. PSC designates placental stem cells; GBP designates gabapentin.

| Group | Treatment | Volume | N |
|---|---|---|---|
| 1 | vehicle iv | 1.00 cc | 10 |
| 2 | PSC 4 × 10⁶ iv | 1.00 cc | 10 |
| 3 | PSC 1 × 10⁶ iv | 1.00 cc | 9 |
| 4 | vehicle im | 0.25 cc | 10 |
| 5 | PSC 4 × 10⁵ im | 0.25 cc | 10 |
| 6 | PSC 4 × 10⁴ im | 0.25 cc | 10 |
| 7 | GBP 100 mg/ml, ip | 0.25 cc | 9 |
| 8 | PBS (vehicle for GBP,) ip | 0.25 cc | 9 |

6.10.1.2 Placental Stem Cells

CD34−, CD10+, CD200+ and CD105+ placental stem cells were prepared as described in Example 7.

6.10.1.3 Chronic Constriction Injury

The surgery was performed as previously described (see Bennett and Xie, Pain, 1988, 33:87-107). In brief, the common sciatic nerve was exposed at the mid-thigh level by blunt dissection through the biceps femoris and gently separated from adjacent tissue. Proximal to the sciatic trifurcation, the nerve was gently freed of adhering tissue for about 7 mm, and 3 ligatures (4/0 chromic gut) were tied loosely around it with a 1.0-1.5 mm interval between each. The ligatures were tied such that the nerve was barely constricted, and the circulation through the superficial epineural vasculature was not arrested. The incision was closed in layers using 3/0 Vicryl sutures for the muscle and wound clips for the skin.

6.10.1.4 Behavior Test

Pain level was evaluated using a Tactile allodynia test. In this test, the withdrawal response to calibrated Von Frey fibers is measured. Three fibers according to force application—low (8 g), medium (16 g) and high force fiber (26 g) were employed in this study. Each fiber was applied to the paw five times and a percentage score of responses was calculated (see Flatters et al., Pain, 2004, 109:150-161). The most reliable and repeatable score at baseline levels were the response to 26 g; therefore statistical analysis was performed on the 26 g data.

Motor sensory coordination was evaluated with the Rotarod Test. In this test the rodent is placed on a rotating rod and the speed of rotation is gradually increased. The rodent's ability to remain on the rotating rod is recorded (time in seconds). The speed used was 4-40 rpm (max 180 sec), with a drop height less than 30 cm. The purpose of the Rotarod test is to assess the rodent's motor sensory coordination. The test is sensitive to drugs that affect motor function and helps to assess the sedative effect of a medication.

6.10.1.5 Gabapentin

Gabapentin was prepared in Phosphate Buffered Saline (PBS). The dose used was 100 mg/ml and 0.25 ml was injected into the 250 g rats intraperitoneally (IP). The same volume of PBS was injected into the control group IP.

6.10.1.6 Data Analysis

Data were tabulated and analyzed using StatView software version 5.0 (SAS Institute Inc., San Francisco, Calif., USA). Alpha (two tailed) for significance in all analyses were set at 0.05. Behavioral statistics were calculated only for rats with data at all time points. A repeated measurements analysis of variance (ANOVA) followed by post hoc test was used for the pain and motor sensory coordination scores. Pain development was verified by comparison to baseline levels. Effect on pain was made by comparison to pain level on the 6th day following the procedure.

6.10.2 Results

6.10.2.1 Pain Behavior—Tactile Allodynia

As demonstrated in FIG. 10, six days following the procedure, a significant increase in the responses (indicating pain) was demonstrated in all of the groups.

Figure 10A:
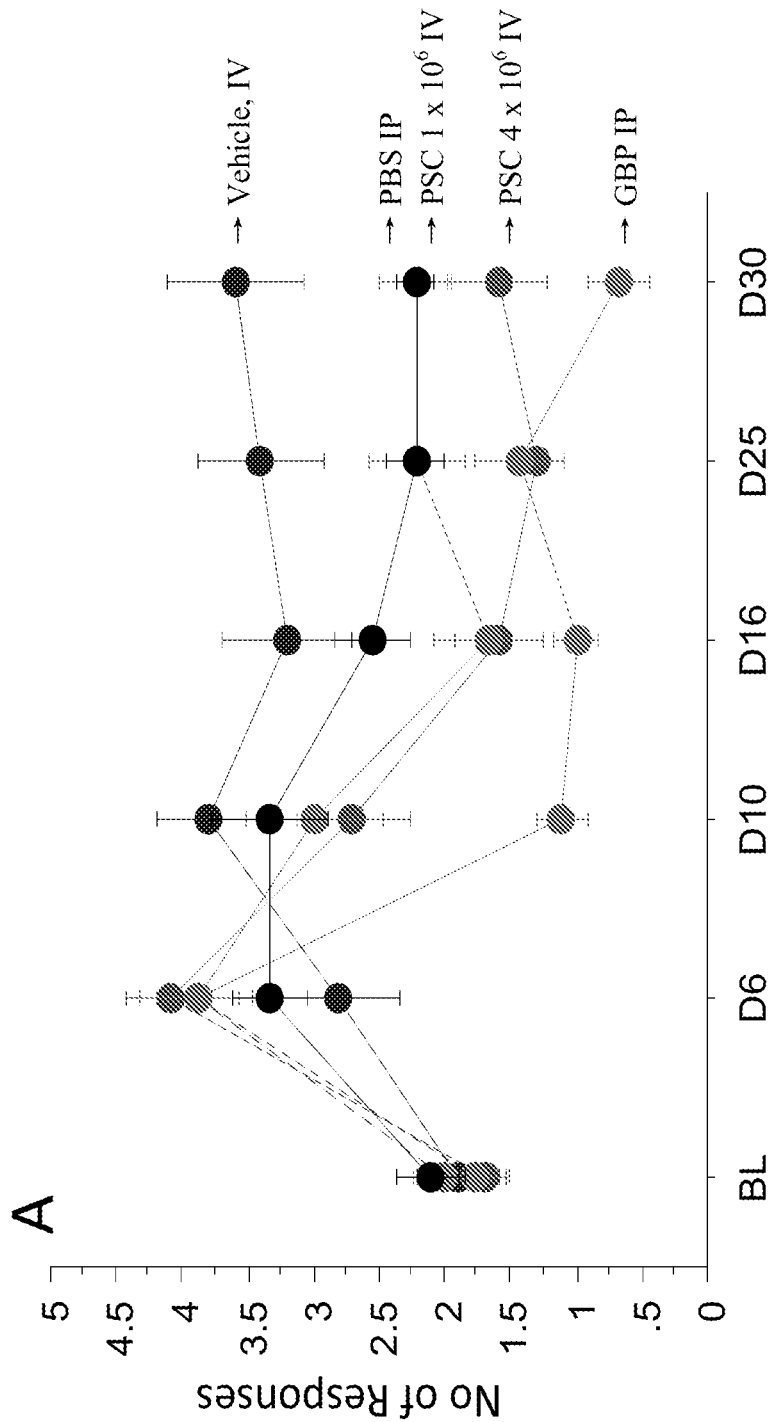
Figure 10B:
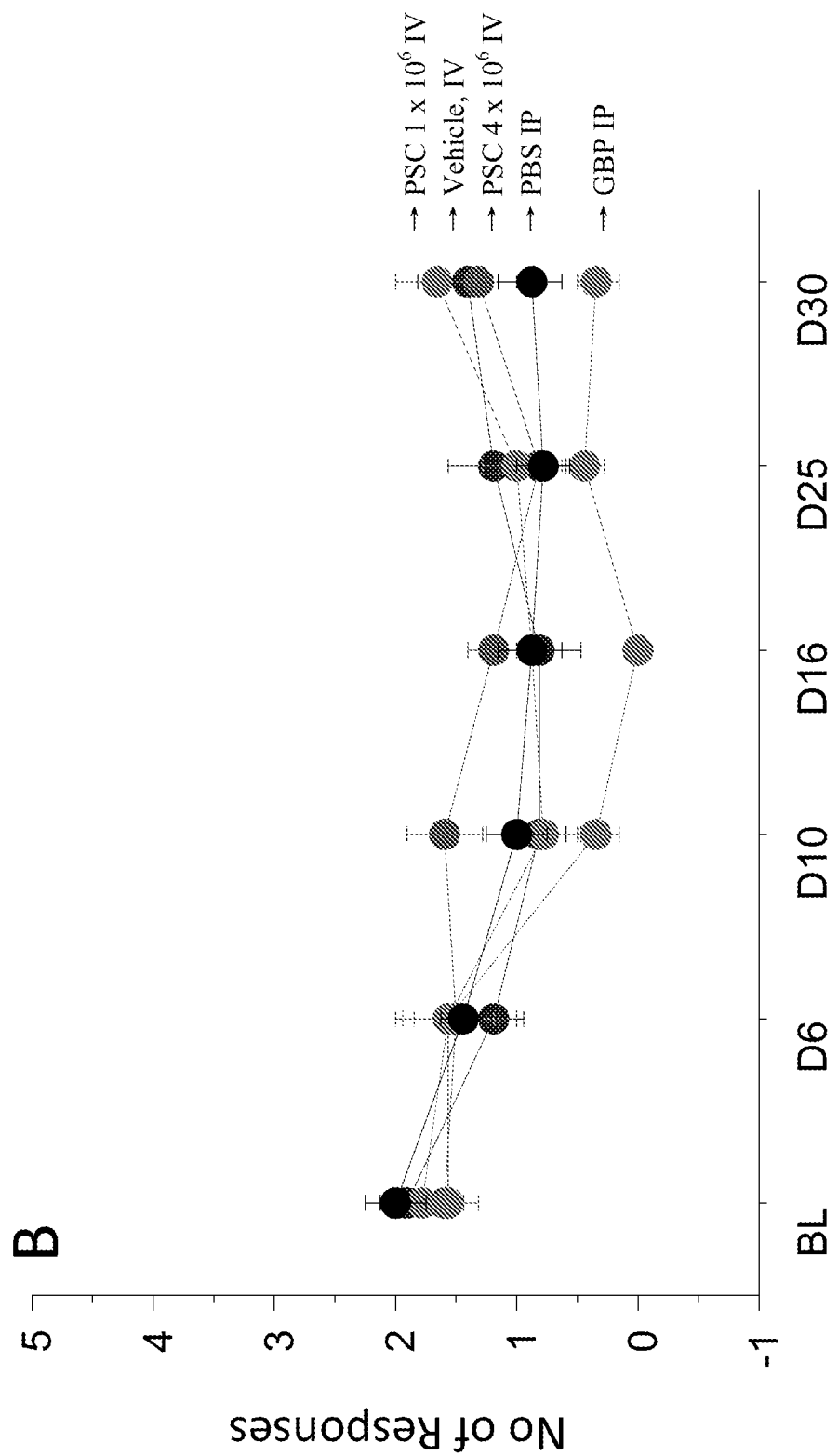
Figure 10C:
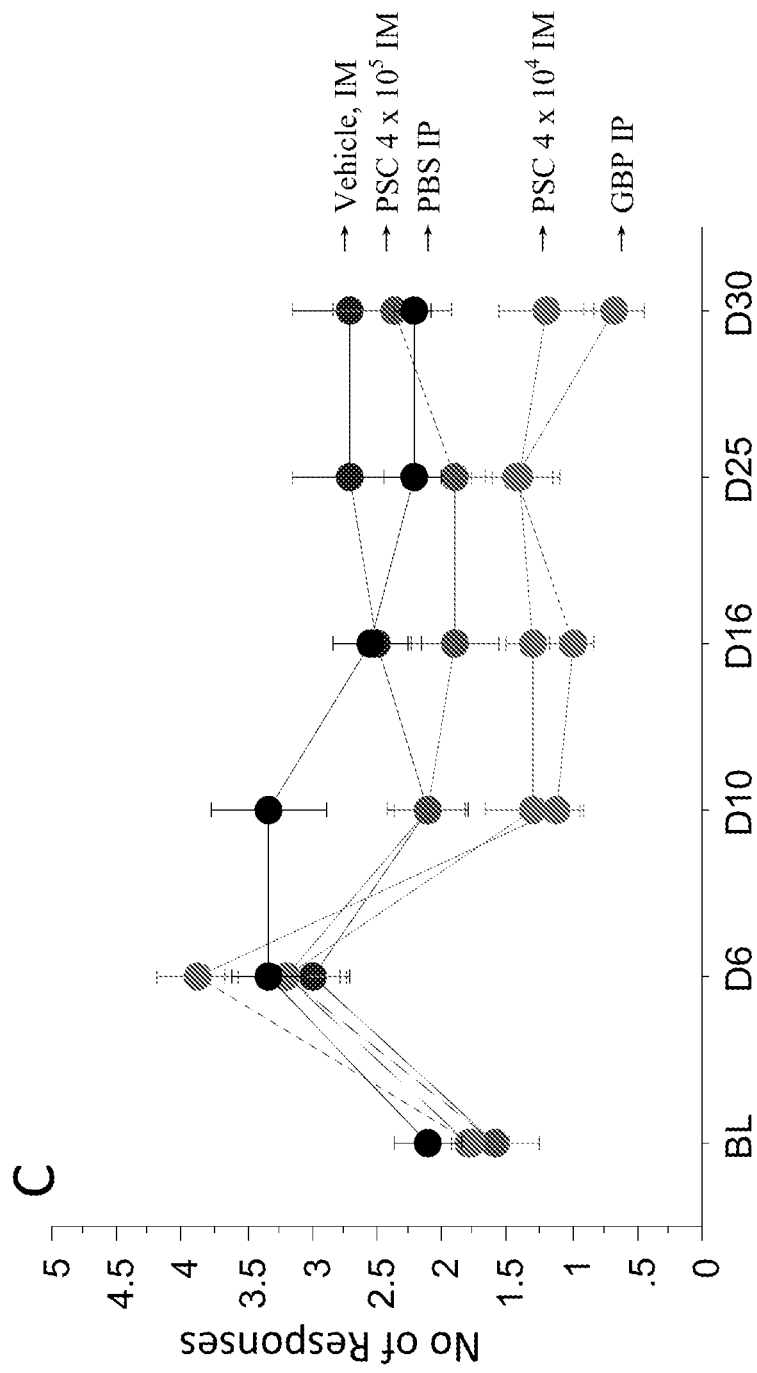
Figure 10D:
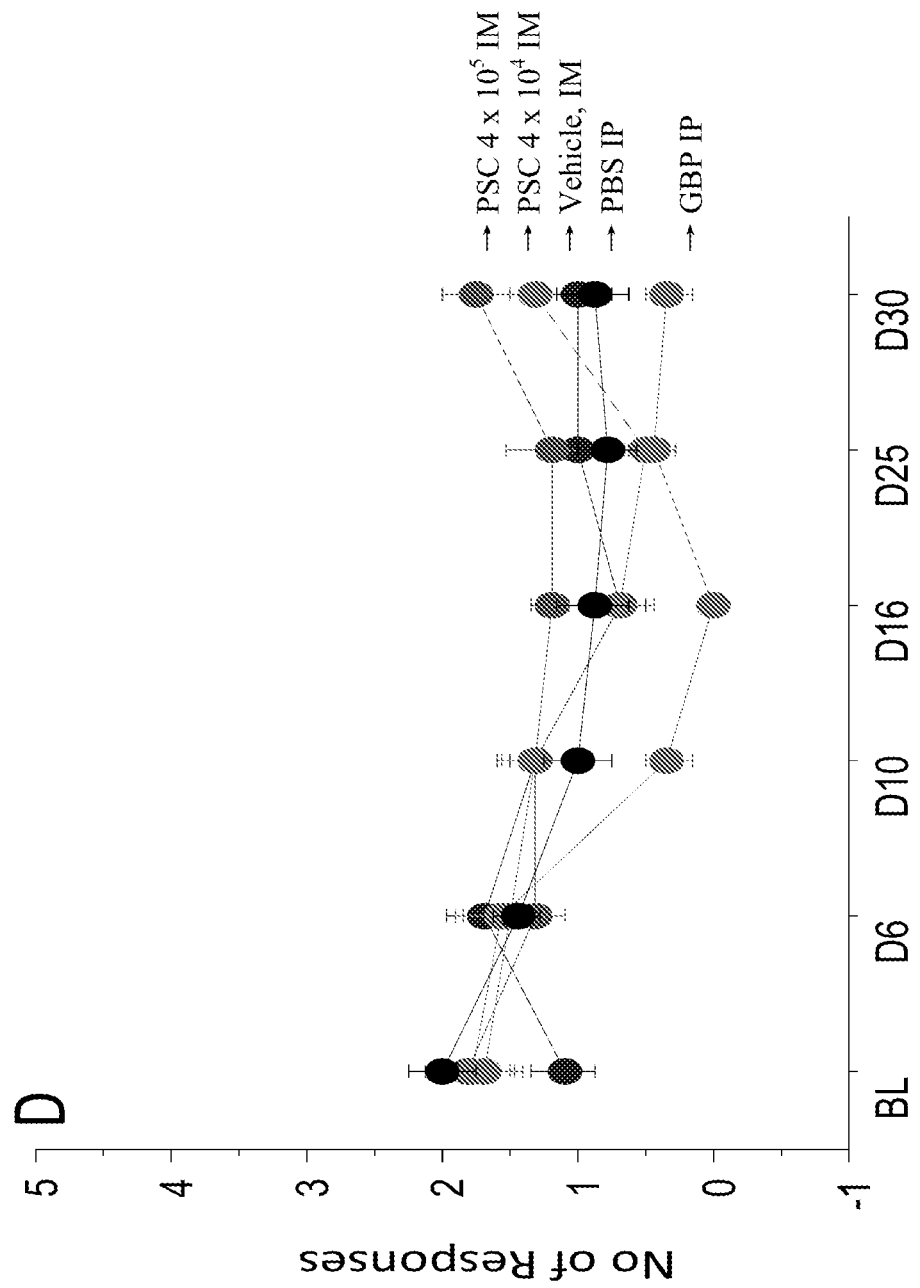

Intramuscular (IM) administration of $4 \times 10^4$ placental stem cells significantly reduced the pain for the duration of the study on days 10, 16, 25 and 30 (FIG. 10C). The intravenous (IV) administration of placental stem cells significantly reduced pain. In particular, IV administration of $4 \times 10^6$ placental stem cells significantly reduced the pain on days 16, 25 and 30; and IV administration of placental stem cells at $1 \times 10^6$ demonstrated a significant pain reduction effect on day 16 (FIG. 10A). As expected, the systemic administration of gabapentin significantly reduced the pain on days 10, 16, 25 and 30 (FIG. 10A, 10C).

6.10.2.2 Motor Sensory Coordination—Rotarod Test

As demonstrated in FIG. 11, the gabapentin treated control group demonstrated a significant reduction in the time spent on the rotarod (altered motor sensory coordination) while the placental stem cell treated group's vehicle motor sensory coordination was (similar to the vehicle-treated group) not affected following IV (FIG. 11A) or IM (FIG. 11B) administration.

6.10.2.3 Conclusion

IV or IM administration of placental stem cells reduces neuropathic pain induced by Sciatic nerve chronic constriction injury. The placental stem cell effect on pain reduction was similar to gabapentin. However, while gabapentin induced significant motor sensory coordination deficiency, the placental stem cells did not.

EQUIVALENTS

The compositions and methods disclosed herein are not to be limited in scope by the specific embodiments described herein. Indeed, various modifications of the compositions and methods in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed is:

1. A method of treating pain in an individual, comprising administering to the individual a therapeutically effective amount of placental stem cells, wherein the therapeutically effective amount is an amount sufficient to cause a detectable improvement in said pain, wherein said pain is a cancer pain or is pain caused by a chemotherapeutic drug or anti-cancer drug.

2. The method of claim 1, wherein said method additionally comprises determining one or more first levels of pain in said individual prior to administration of said placental stem cells, and determining one or more second levels of pain in said individual after administration of said placental stem cells, wherein said therapeutically effective amount of placental stem cells reduces said one or more second levels of said pain as compared to said one or more first level of pain.

3. The method of claim 2, wherein said one or more first levels of pain and said one or more second levels of pain are determined by a pain assessment scale.

4. The method of claim 3, wherein said pain assessment scale is the Numeric Pain Intensity Scale; the Pain Quality Assessment Scale; the Simple Descriptive Pain Intensity Scale; the Visual Analog Scale; the Wong-Baker FACES Pain Rating Scale; the FLACC scale; the CRIES scale; the COMFORT scale; or evoked pain measure induced by subjecting the patient to cold, heat or mechanical stimuli.

5. The method of claim 1, wherein said method additionally comprises determining a first level of one or more physiological indicia of pain in said individual prior to administration of said placental stem cells, and determining a second level of one or more physiological indicia of pain in said individual after administration of said placental stem cells, wherein said therapeutically effective amount of placental stem cells reduces said second level as compared to said first level.

6. The method of claim 5, wherein said physiological indicium of pain is heart rate in the individual.

7. The method of claim 6, wherein said heart rate in said individual is lower after said administration compared to said heart rate in said individual before said administration.

8. The method of claim 5, wherein said physiological indicium of pain is the systolic of said individual.

9. The method of claim 8, wherein said systolic of said individual is lower after said administration compared to said systolic in said individual before said administration.

10. The method of claim 5, wherein said physiological indicium of pain is the diastolic of said individual.

11. The method of claim 10, wherein said diastolic of said individual is lower after said administration compared to said diastolic in said individual before said administration.

12. The method of claim 1, wherein said placental stem cells are $CD10^+$, $CD200^+$, $CD34^-$, $CD105^+$ placental stem cells.

13. The method of claim 1, wherein said placental stem cells express the ELOVL2, ST3GAL6, ST6GALNAC5, and/or SLC12A8 gene at a detectably higher level than an equivalent number of bone marrow-derived mesenchymal stem cells (BM-MSCs).

14. The method of claim 13, wherein said placental stem cells express the ARTS-I, IER3, IL6, KRT18, LRAP, MEST, NFE2L3, and/or TGFB2 gene at a detectably higher level than an equivalent number of BM-MSCs.

15. The method of claim 1, wherein said placental stem cells are formulated to be administered locally, systemically, intravenously or intraarterially.

* * * * *